(12) United States Patent
Gupta et al.

(10) Patent No.: US 11,497,874 B2
(45) Date of Patent: Nov. 15, 2022

(54) PLENUM CHAMBER INSERT FOR PATIENT INTERFACE

(71) Applicant: RESMED PTY LTD, Bella Vista (AU)

(72) Inventors: Tumul Gupta, Sydney (AU); Michael Christopher Hogg, Sydney (AU); Luke Andrew Stanislas, Sydney (AU); Lang Eng Siang Teh, Sydney (AU); Christer Engstrom, Sydney (AU); Lorenz Eberl, Sydney (AU); Adrian Apalakis, Sydney (AU); Balint Franko, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/421,177

(22) PCT Filed: Mar. 18, 2020

(86) PCT No.: PCT/IB2020/052459
§ 371 (c)(1),
(2) Date: Jul. 7, 2021

(87) PCT Pub. No.: WO2020/188495
PCT Pub. Date: Sep. 24, 2020

(65) Prior Publication Data
US 2022/0054783 A1    Feb. 24, 2022

Related U.S. Application Data

(60) Provisional application No. 62/820,098, filed on Mar. 18, 2019, provisional application No. 62/969,747, filed on Feb. 4, 2020.

(51) Int. Cl.
*A61M 16/06* (2006.01)
*A61M 16/08* (2006.01)
(Continued)

(52) U.S. Cl.
CPC .... *A61M 16/0622* (2014.02); *A61M 16/0683* (2013.01); *A61M 16/0875* (2013.01);
(Continued)

(58) Field of Classification Search
CPC .......... A61M 16/0622; A61M 16/0683; A61M 16/0875; A61M 16/1045; A61M 2205/42; A61M 2210/0618; A62B 9/003
See application file for complete search history.

(56) References Cited

U.S. PATENT DOCUMENTS

| 1,679,839 A | 4/1928 | Mitchell |
| 2,435,721 A | 2/1948 | Lehman |

(Continued)

FOREIGN PATENT DOCUMENTS

| WO | WO 98/004310 A1 | 2/1998 |
| WO | WO 98/034665 A1 | 8/1998 |

(Continued)

OTHER PUBLICATIONS

International Preliminary Report on Patentability dated May 14, 2020 issued in International Application No. PCT/IB2020/052459 (5 pages).
(Continued)

*Primary Examiner* — Colin W Stuart
*Assistant Examiner* — Douglas Y Sul
(74) *Attorney, Agent, or Firm* — Nixon & Vanderhye P.C.

(57) ABSTRACT

A patient interface includes: a plenum chamber; a seal-forming structure; a positioning and stabilising structure; a plenum chamber insert configured to be positioned and retained within the plenum chamber; and a vent structure; wherein the plenum chamber insert has a plenum chamber insert port; wherein the plenum chamber insert has an exterior surface configured to be positioned adjacent to an interior surface of the plenum chamber; wherein when the
(Continued)

plenum chamber insert is positioned and retained within the plenum chamber, a radial channel is formed by the interior surface of the plenum chamber and the exterior surface of the plenum chamber insert such that gas is able to pass between a patient-proximal side plenum chamber insert and a patient-distal side of the plenum chamber insert via the radial channel during use.

40 Claims, 126 Drawing Sheets

(51) Int. Cl.
    *A61M 16/10*      (2006.01)
    *A62B 9/00*      (2006.01)
    *G16H 20/40*      (2018.01)
    *G16H 40/60*      (2018.01)

(52) U.S. Cl.
    CPC ........ *A61M 16/1045* (2013.01); *G16H 20/40* (2018.01); *G16H 40/60* (2018.01); *A61M 2205/42* (2013.01); *A61M 2210/0618* (2013.01); *A62B 9/003* (2013.01)

(56) References Cited

U.S. PATENT DOCUMENTS

| | | | |
|---|---|---|---|
| 2,845,927 | A | 8/1958 | Hill |
| 4,200,094 | A | 4/1980 | Gedeon et al. |
| 4,269,183 | A | 5/1981 | Hunt |
| 4,782,832 | A | 11/1988 | Trimble et al. |
| 4,944,310 | A | 7/1990 | Sullivan |
| 5,390,668 | A * | 2/1995 | Lehman ............ B01D 46/0028 96/108 |
| 5,460,172 | A * | 10/1995 | Eckerbom ........... A61M 16/085 128/205.12 |
| 5,687,715 | A | 11/1997 | Landis |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,485,189 | B2 | 7/2013 | Wallnewitz et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 9,038,634 | B2 | 5/2015 | Brambilla et al. |
| 2006/0118117 | A1* | 6/2006 | Berthon-Jones ............................ A61M 16/0057 128/206.27 |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2011/0108036 | A1 | 5/2011 | Loescher |
| 2011/0232646 | A1* | 9/2011 | Ho ..................... A61M 16/1055 128/206.24 |
| 2011/0253147 | A1 | 10/2011 | Gusky et al. |
| 2011/0297152 | A1* | 12/2011 | Duveen ................. A61M 16/06 128/203.29 |
| 2012/0325205 | A1* | 12/2012 | Allum ............... A61M 16/0622 128/205.24 |
| 2013/0220327 | A1* | 8/2013 | Barlow ............. A61M 16/0683 128/205.25 |
| 2015/0328421 | A1* | 11/2015 | Stephenson ....... A61M 16/0633 128/205.25 |
| 2015/0335846 | A1 | 11/2015 | Romagnoli et al. |
| 2016/0158475 | A1* | 6/2016 | Harrison ........... A61M 16/0057 128/205.12 |
| 2016/0175552 | A1* | 6/2016 | Harrington ....... A61M 16/0057 128/201.13 |
| 2017/0035978 | A1* | 2/2017 | Holley .................. A61M 16/22 |
| 2018/0071083 | A1* | 3/2018 | Fahl ......................... A61F 2/20 |
| 2018/0133426 | A1* | 5/2018 | Hallett ............. A61M 16/0683 |
| 2018/0200467 | A1 | 7/2018 | Finch |

FOREIGN PATENT DOCUMENTS

| | | | |
|---|---|---|---|
| WO | WO 2000/078381 A1 | 12/2000 | |
| WO | WO 2004/073778 A1 | 9/2004 | |
| WO | WO 2005/063328 A1 | 7/2005 | |
| WO | WO 2006/074513 A1 | 7/2006 | |
| WO | WO 2006/130903 A1 | 12/2006 | |
| WO | WO 2009/052560 A1 | 4/2009 | |
| WO | WO 2010/070495 A1 | 6/2010 | |
| WO | WO 2010/135785 A1 | 12/2010 | |
| WO | WO 2012/171072 A1 | 12/2012 | |
| WO | WO 2013/020167 A1 | 2/2013 | |
| WO | 2015/013761 A1 | 2/2015 | |
| WO | WO 2015/052681 A1 | 4/2015 | |
| WO | WO 2015/161345 A1 | 10/2015 | |
| WO | WO 2017/011864 A1 | 1/2017 | |
| WO | WO-2017011864 A1 * | 1/2017 | ............ A61M 16/06 |
| WO | WO 2018/053589 A1 | 3/2018 | |
| WO | WO 2018/126295 A1 | 7/2018 | |
| WO | WO 2018/176094 A1 | 10/2018 | |

OTHER PUBLICATIONS

"*Respiratory Physiology*", by John B. West, Lippincott Williams & Wilkins, 9th edition published 2012 (8 pages).
International Search Report dated May 14, 2020 issued in International Application No. PCT/IB2020/052459 (6 pages).
Written Opinion dated May 14, 2020 issued in International Application No. PCT/IB2020/052459 (4 pages).
Extended European Search Report dated May 10, 2022 issued in European Application No. 20774485.5 (9 pages).

* cited by examiner

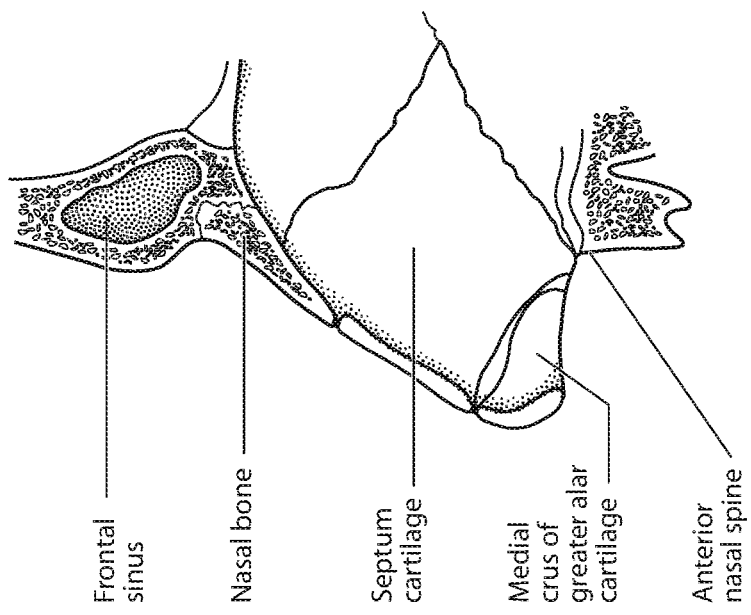
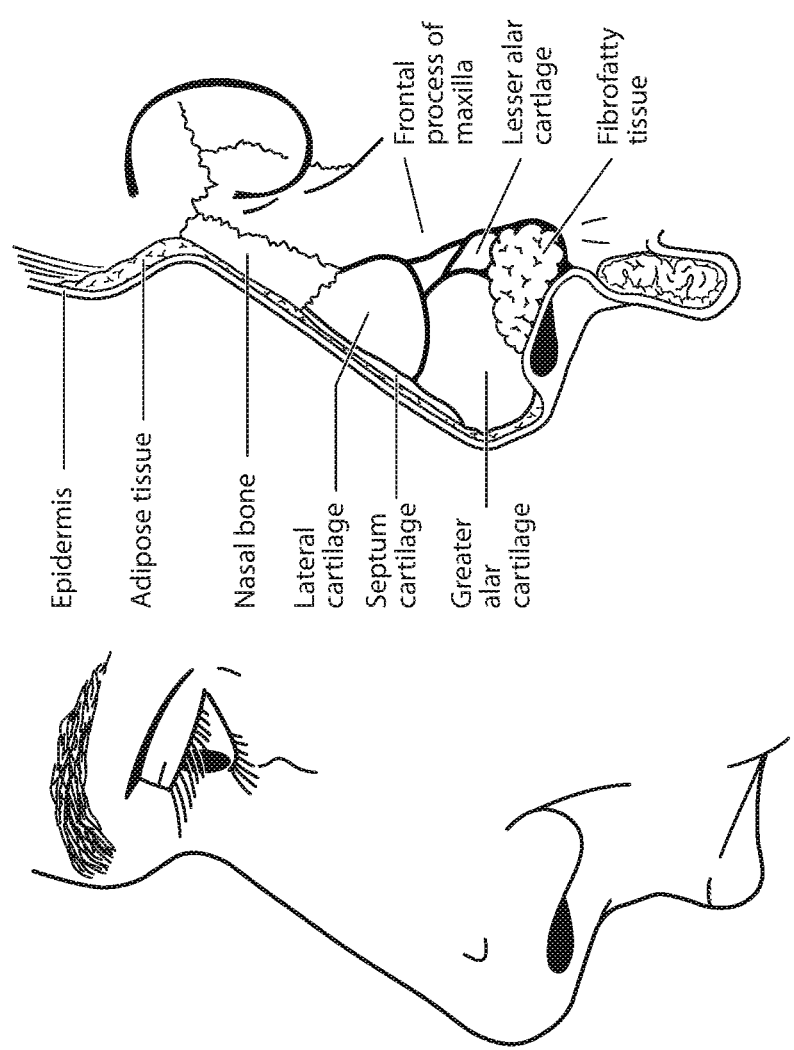
FIG. 2I
FIG. 2H
FIG. 2G

Relatively Large Positive Curvature

Relatively Small Positive Curvature

Zero Curvature

Relatively Small Negative Curvature

Relatively Large Negative Curvature

Copyright 2015 ResMed Limited

Copyright 2015 ResMed Limited

Left-hand rule
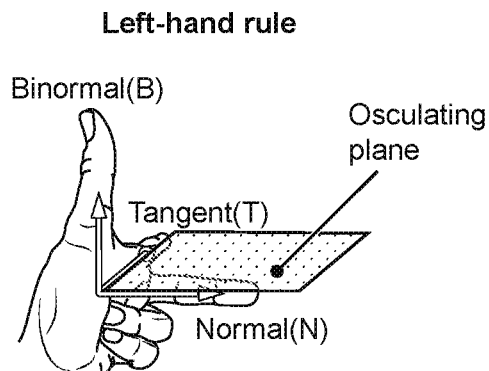
FIG. 3O
Right-hand rule
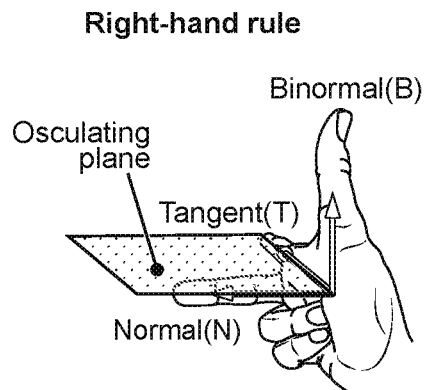
FIG. 3P
Left ear helix
Right ear helix
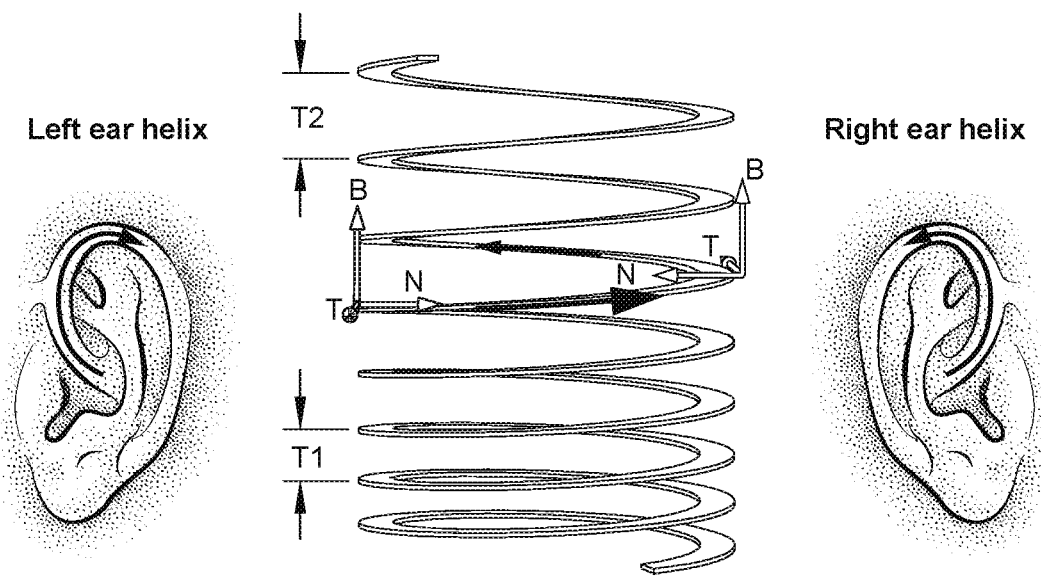
FIG. 3Q
Right-hand helix
Right-hand positive
FIG. 3S
FIG. 3R
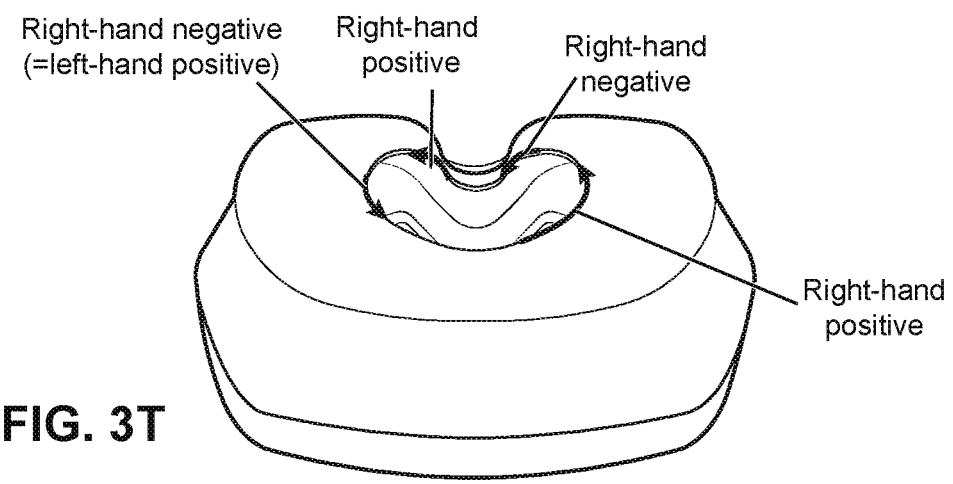
FIG. 3T
Copyright 2015 ResMed Limited

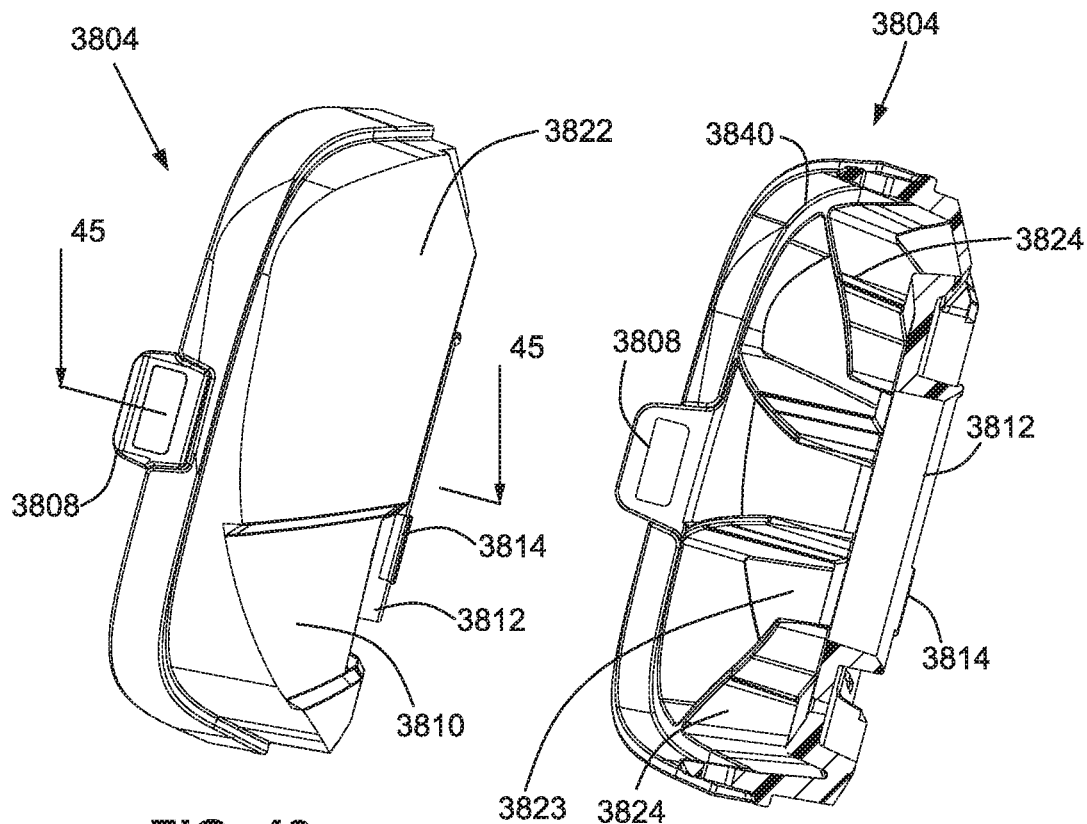
FIG. 43
FIG. 44
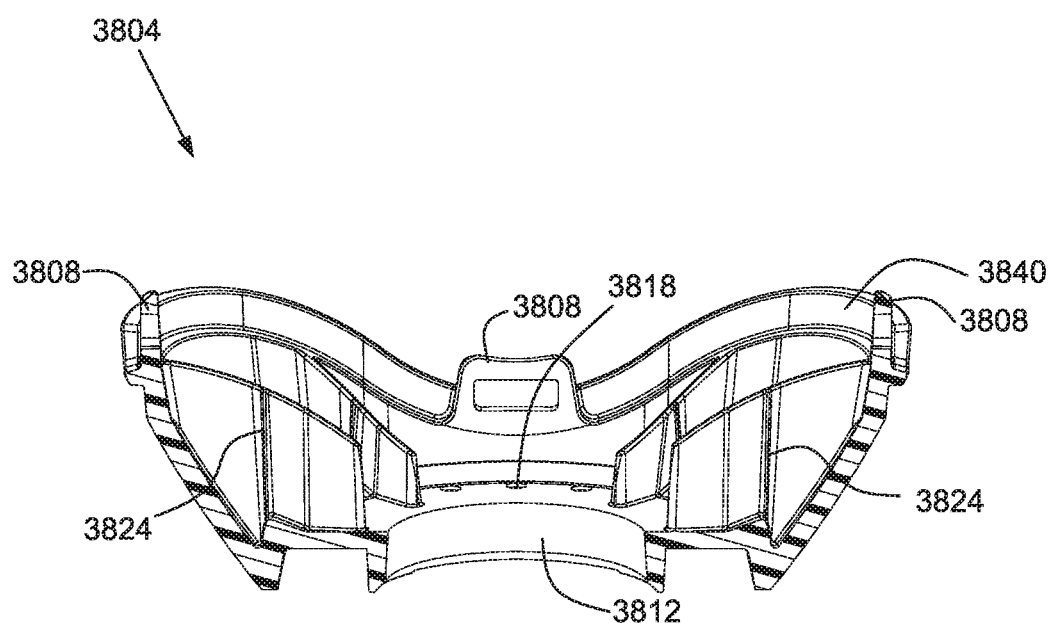
FIG. 45

PLENUM CHAMBER INSERT FOR PATIENT INTERFACE

1 CROSS-REFERENCE TO RELATED APPLICATIONS

This application is the U.S. national phase of International Application No. PCT/IB2020/052459 filed Mar. 18, 2020 which designated the U.S. and claims priorities to U.S. Provisional Patent Application No. 62/820,098 filed Mar. 18, 2019, and 62/969,747 filed Feb. 4, 2020, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cm $H_2O$ relative to ambient pressure. For other forms of therapy, such as the delivery of oxygen, the patient interface may not include a seal sufficient to facilitate delivery to the airways of a supply of gas at a positive pressure of about 10 cm $H_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004310; WO 2006/074513; WO 2010/135785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT FX nasal pillows mask and MIRAGE LIBERTY™ full-face mask. The following patent applications, assigned to ResMed Limited, describe examples of nasal pillows masks: International Patent Application WO2004/073778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063328 and WO 2006/130903 (describing amongst other things aspects of the ResMed Limited MIRAGE LIBERTY™ full-face mask); International Patent Application WO 2009/052560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMedée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034665; International Patent Application Publication No. WO 2000/078381; U.S. Pat. No. 6,581,594; US Patent Application Publication No. US 2009/0050156; US Patent Application Publication No. 2009/0044808.

Table of noise of prior masks
(ISO 17510-2:2007, 10 cmH₂O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH₂O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.7 Heat and Moisture Exchanger (HMX) Technology

A patient may be susceptible to drying of the internal airways passages while undergoing various forms of respiratory therapy as described elsewhere herein. For example, CPAP therapy entails providing the patient with a flow of air pressurized at a pressure greater than ambient continuously, and this continuous flow of air, particularly at an elevated level in conjunction with the positive air pressure, may causing drying of the patient's airways. That drying may cause discomfort, which in turn may negatively impact the patient's compliance with therapy.

To minimize the drying effect of these forms of respiratory therapy, the flow of air provided to the patient may be humidified before it reaches the patient. Certain forms of humidification technology actively provide humid air to the patient to reduce the drying effect by heating a reservoir of water and passing air over its surface to increase the absolute humidity of the air, i.e., the air receives water vapour from the reservoir. The humidified air is then passed to the patient via the air circuit. The air circuit may also be heated to prevent condensation, also known as rainout, of the water vapour within the air circuit during transport to the patient. These forms of technology typically involve filling the reservoir with water before therapy, and then the reservoir is provided to the RPT system so that the water can be heated to humidify the air for therapy. The reservoir typically requires regular cleaning, there is a risk of spillage, which may be particularly problematic in the context of electrical components, and the reservoir requires refilling by the patient before use.

Eliminating the need for a pre-supplied water source, such as a water-filled reservoir, and input electrical power to heat the water may provide several benefits. For example, the RPT device could be made smaller because it would not require space for the water reservoir and heating plate. Since no electrical energy is consumed in heating of the water, electricity costs may be reduced. Also, fewer electrical components may be needed in the RPT device, which reduces its cost and complexity. Also, the RPT device may be easier to use because there is no water reservoir to fill, empty, and clean. Risk of spillage may be reduced as well. Also, operation of the RPT device may be simplified because there are no humidification settings to operate.

In operation, the patient breathes out (exhalation) air that has been heated within the patient's body and that has received water vapour from the patient's airways. The heat and moisture in the exhaled air is captured by the HMX material(s), i.e., the HMX material(s) are heated by the relatively warm exhaled air and the HMX material(s) receives water vapour from the relatively humid exhaled air, as the exhaled air passes through HMX material(s) prior to being vented to atmosphere. During inhalation, the flow of pressurized air passes through the HMX material(s) in the opposite direction to exhalation to reach the patient's airways, and the source of the incoming air is typically ambient air. Thus, the flow of pressurized air, as it passes through the HMX material(s) prior to reaching the patient's airways, receives moisture in the form of water vapour as it is desorbed from the HMX material(s) and the flow of pressurized air is heated by heat released from the HMX material(s).

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

An aspect of the present technology relates to apparatus used in the screening, diagnosis, monitoring, amelioration, treatment or prevention of a respiratory disorder.

Another aspect of the present technology is directed to a patient interface that may comprise: a plenum chamber; a seal-forming structure; and a positioning and stabilising structure. The patient interface may further comprise a vent structure. The patient may further be configured to leave the patient's mouth uncovered, or if the seal-forming structure is configured to seal around the patient's nose and mouth, the patient interface may be further configured to allow the patient to breath from ambient in the absence of a flow of pressurised air through the plenum chamber inlet port.

Another aspect of the present technology is directed to a patient interface comprising: a plenum chamber pressurisable to a therapeutic pressure of at least 4 cm H2O above ambient air pressure, said plenum chamber including a plenum chamber inlet port sized and structured to receive a flow of air at the therapeutic pressure for breathing by a patient; a seal-forming structure constructed and arranged to seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; a positioning and stabilising structure configured to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure configured to allow a continuous flow of gases exhaled by the patient from an interior of the plenum chamber to ambient, said vent structure being sized and shaped to maintain the therapeutic pressure in the plenum chamber in use; wherein the patient interface is configured to leave the patient's mouth uncovered, or if the seal-forming structure is configured to seal around the patient's nose and mouth, the patient interface is configured to allow the patient to breath from ambient in the absence of a flow of pressurised air through the plenum chamber inlet port.

Another aspect of the present technology relates to a plenum chamber insert configured to be positioned and retained within a plenum chamber; wherein the plenum chamber insert has a plenum chamber insert port; wherein the plenum chamber insert has an exterior surface configured to be positioned adjacent to an interior surface of the plenum chamber; wherein when the plenum chamber insert is positioned and retained within the plenum chamber, a radial channel is formed by the interior surface of the plenum chamber and the exterior surface of the plenum chamber insert such that gas is able to pass between a patient-proximal side of the plenum chamber insert and a patient-distal side of the plenum chamber insert via the radial channel during use.

Another aspect of the present technology relates to a patient interface that includes a plenum chamber; a seal-forming structure; a positioning and stabilising structure; a plenum chamber insert configured to be positioned and retained within the plenum chamber; and a vent structure; wherein the plenum chamber insert has a plenum chamber insert port; wherein the plenum chamber insert has an exterior surface configured to be positioned adjacent to an interior surface of the plenum chamber; wherein when the plenum chamber insert is positioned and retained within the plenum chamber, a radial channel is formed by the interior surface of the plenum chamber and the exterior surface of the plenum chamber insert such that gas is able to pass between a patient-proximal side of the plenum chamber insert and a patient-distal side of the plenum chamber insert via the radial channel during use.

Another aspect of the present technology relates to a patient interface that includes a plenum chamber; a seal-forming structure; a positioning and stabilising structure; a plenum chamber insert configured to be positioned and retained within the plenum chamber; and a vent structure; wherein the plenum chamber insert has a plenum chamber insert port.

The aspect of the preceding paragraph may further include: (a) the plenum chamber insert having an exterior surface configured to be positioned adjacent to an interior surface of the plenum chamber; and/or (b) when the plenum chamber insert is positioned and retained within the plenum chamber, a radial channel is formed by the interior surface of the plenum chamber and the exterior surface of the plenum chamber insert such that gas is able to pass between a patient-proximal side of the plenum chamber insert and a patient-distal side of the plenum chamber insert via the radial channel during use.

Another aspect of the present technology relates to a patient interface that includes a plenum chamber pressurisable to a therapeutic pressure of at least 4 cm $H_2O$ greater than ambient air pressure, said plenum chamber including a plenum chamber port sized and structured to receive a flow of air at the therapeutic pressure for breathing by a patient; a seal-forming structure constructed and arranged to contact and seal against a region of the patient's face surrounding an entrance to the patient's airways, said seal-forming structure having a hole therein such that the flow of air at said therapeutic pressure is delivered to at least the patient's nares, the seal-forming structure constructed and arranged to maintain said therapeutic pressure in the plenum chamber throughout the patient's respiratory cycle in use; a positioning and stabilising structure configured to hold the seal-forming structure in a therapeutically effective position on the patient's head, the positioning and stabilising structure comprising a tie, the tie being constructed and arranged so that at least a portion of the tie overlies a region of the patient's head superior to the patient's corresponding otobasion superior in use; a plenum chamber insert configured to be positioned and retained within the plenum chamber and between the entrance to the patient's airways and the plenum chamber port; and a vent structure configured to allow a continuous flow of gases exhaled by the patient from an interior of the plenum chamber to ambient, said vent structure being sized and shaped to maintain the therapeutic pressure in the plenum chamber in use; wherein the plenum chamber insert has a plenum chamber insert port configured to be positioned in pneumatic communication with the plenum chamber port such that the flow of air at the therapeutic pressure passes through the plenum chamber insert port after passing through the plenum chamber port; wherein the plenum chamber insert has an exterior surface configured to be positioned adjacent to an interior surface of the plenum chamber; wherein when the plenum chamber insert is positioned and retained within the plenum chamber, a radial channel is formed by the interior surface of the plenum chamber and the exterior surface of the plenum chamber insert such that gas is able to pass between a patient-proximal side of the plenum chamber insert and a patient-distal side of the plenum chamber insert via the radial channel during use; and wherein the patient interface is configured to allow the patient to breath from ambient through their mouth in the absence of a flow of pressurised air through the plenum chamber inlet port, or the patient interface is configured to leave the patient's mouth uncovered.

In examples of the aspects described in the five preceding paragraphs, (a) the seal-forming structure may be constructed and arranged to be positioned against the patient's face and surround the patient's nares and mouth in use such that the flow of air at said therapeutic pressure is delivered to the patient's nares and mouth through the hole, and the patient interface may be configured to allow the patient to breath from ambient through their mouth in the absence of a flow of pressurised air through the plenum chamber inlet port, (b) the seal-forming structure and the plenum chamber may have a generally triangular profile to cover the patient's nose and mouth while not covering the patient's eyes in use, (c) the plenum chamber insert may further comprise three radial channels positioned circumferentially around the plenum chamber insert port and oriented to direct air inside of the seal-forming structure and the plenum chamber from a corresponding corner region of the generally triangular profile of the seal-forming structure and the plenum chamber from the patient-proximal side of the plenum chamber insert to the patient-distal side of the plenum chamber insert, (d) the plenum chamber insert may further comprise a plurality of radial channels positioned circumferentially around the plenum chamber insert port and oriented to direct air inside of the seal-forming structure and the plenum chamber from the patient-proximal side of the plenum chamber insert to the patient-distal side of the plenum chamber insert, (e) the plenum chamber insert may further comprise a heat and moisture exchanger (HMX) material, the HMX material configured to receive and retain water from gas exhaled by the patient and to desorb the retained water into the flow of air at the therapeutic pressure passing through the HMX material, while the flow of air at the therapeutic pressure is provided to the plenum chamber port, (f) the plenum chamber insert may be permanently connect to the plenum chamber, (g) the plenum chamber insert may be removably connected to the plenum chamber, (h) the plenum chamber insert may further comprise an insert frame configured to secure the HMX material in an operable position within the plenum chamber, (i) the insert frame may be permanently connected to the plenum chamber, (j) the insert frame may be removably connected to the plenum chamber, (k) the insert frame may further comprise an anterior insert frame and a posterior insert frame configured to be attached to one another, and the HMX material may be secured between the anterior insert frame and the posterior insert frame when the anterior insert frame and the posterior insert frame are attached together, (l) the plenum chamber insert port may be formed through the anterior frame, (m) the anterior insert frame may comprise an anterior insert frame wall, and the radial channel may be recessed into the anterior frame wall, or when the plenum chamber insert further comprises the three radial channels, the three radial channels may be recessed into the anterior frame wall, or wherein when the plenum chamber insert further comprises the plurality of radial channels, the plurality of radial channels may be recessed into the anterior frame wall, (n) the posterior insert frame may further comprise a plurality of posterior insert frame openings such that at least a portion of the HMX material is exposed in a posterior direction that faces the patient during use, (o) the posterior insert frame may further comprise an orientation indicator configured to visually and/or tactilely indicate the orientation of the plenum chamber insert, when the plenum chamber insert is assembled and when the plenum chamber insert is positioned and retained within the plenum chamber, (p) the anterior insert frame may further comprise at least one anterior insert frame spacer extending from the anterior insert frame wall, the anterior insert frame spacer configured to contact and space the HMX material away from the anterior insert frame wall such that a gap is formed between the anterior insert frame wall and the HMX material, (q) at least one posterior insert frame protrusion may extend from the posterior insert frame, the posterior insert frame protrusion configured to contact and hold the HMX material in position between the anterior insert frame and the posterior insert frame, (r) the anterior insert frame may further comprise a catch or a detent and the posterior insert frame further comprises the other of the catch or the detent, the catch and the detent configured to retain the anterior insert frame and the posterior insert frame together, (s) the anterior insert frame may further comprise a plurality of catches or a plurality of detents and the posterior insert frame may further comprise an equal number of corresponding catches or detents, (t) the anterior insert frame may further comprise a rim surrounding the insert frame port and extending in anterior direction therefrom, (u) the anterior insert frame may further comprise an annular channel surrounding the rim and recessed into the anterior insert frame wall, (v) a frame assembly may be configured to attach to the plenum chamber and join the positioning and stabilising structure to the plenum chamber and the rim may further comprise one or more tabs to releasably connect the plenum chamber insert to the frame assembly through the plenum chamber port, (w) a frame assembly may be configured to attach to the plenum chamber and join the positioning and stabilising structure to the plenum chamber and the anterior insert frame may further comprise one or more tabs extending from the annular channel to releasably connect the plenum chamber insert to the frame assembly through the plenum chamber port, (x) one or more annular channel vent holes may be formed through the anterior insert frame at the annular channel, (y) an elbow assembly may have a first end configured to be releasably attached to the frame assembly or the plenum chamber and a second end configured to be releasably attached to an air circuit to provide the flow of air at the therapeutic pressure to the plenum chamber, the elbow assembly including the vent structure such that the vent structure is positioned opposite the patient's airways relative to the plenum chamber insert, (z) one or more radial channel vent holes may be formed through the anterior insert frame at the radial channel, or when the plenum chamber insert further comprises the three radial channels, the anterior insert frame may include one or more radial channel vent holes formed through the anterior insert frame at one or more of the three radial channels, or when the plenum chamber insert further comprises the plurality of radial channels, the anterior insert frame may include one or more radial channel vent holes formed through the anterior insert frame at one or more of the plurality of radial channels, (aa) the plenum chamber insert may be concave on the patient-proximal side to avoid contact with the patient's face during use, (bb) the HMX material may comprise foam, (cc) the HMX material may comprise open-cell foam having a salt applied thereto, (dd) the HMX material may comprise paper, (ee) the HMX material may comprise a corrugated structure constructed from paper, the corrugated structure forming flow channels through the HMX material, (ff) the flow channels may be oriented to allow air to flow therethrough in a generally anterior-posterior direction during use, (gg) the HMX material may be shaped to substantially correspond to a shape of the interior of the insert frame, (hh) the HMX material may be configured to be deformed to substantially correspond to a shape of the interior of the insert frame, (ii) the HMX material may have a substantially consistent thickness, and/or (jj) the HMX material may have a thickness that varies in at least one direction.

Another aspect of the present technology is directed to a patient interface system comprising: the patient interface of any of the aspects and examples described in the preceding paragraphs; a respiratory pressure therapy device configured to pressurize the flow of air at the therapeutic pressure; and an air circuit configured to direct the flow of air from the respiratory pressure therapy device to the patient interface.

In further examples, the patient interface system may not include a humidifier, and the air circuit may include a tube with a heating element configured to heat the flow of air or the tube may not include a heating element.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device 4000 is humidified in a humidifier 5000, and passes along an air circuit 4170 to the patient 1000. The patient is sleeping in a side sleeping position.

4.2 Respiratory System and Facial Anatomy

Figure 1A:
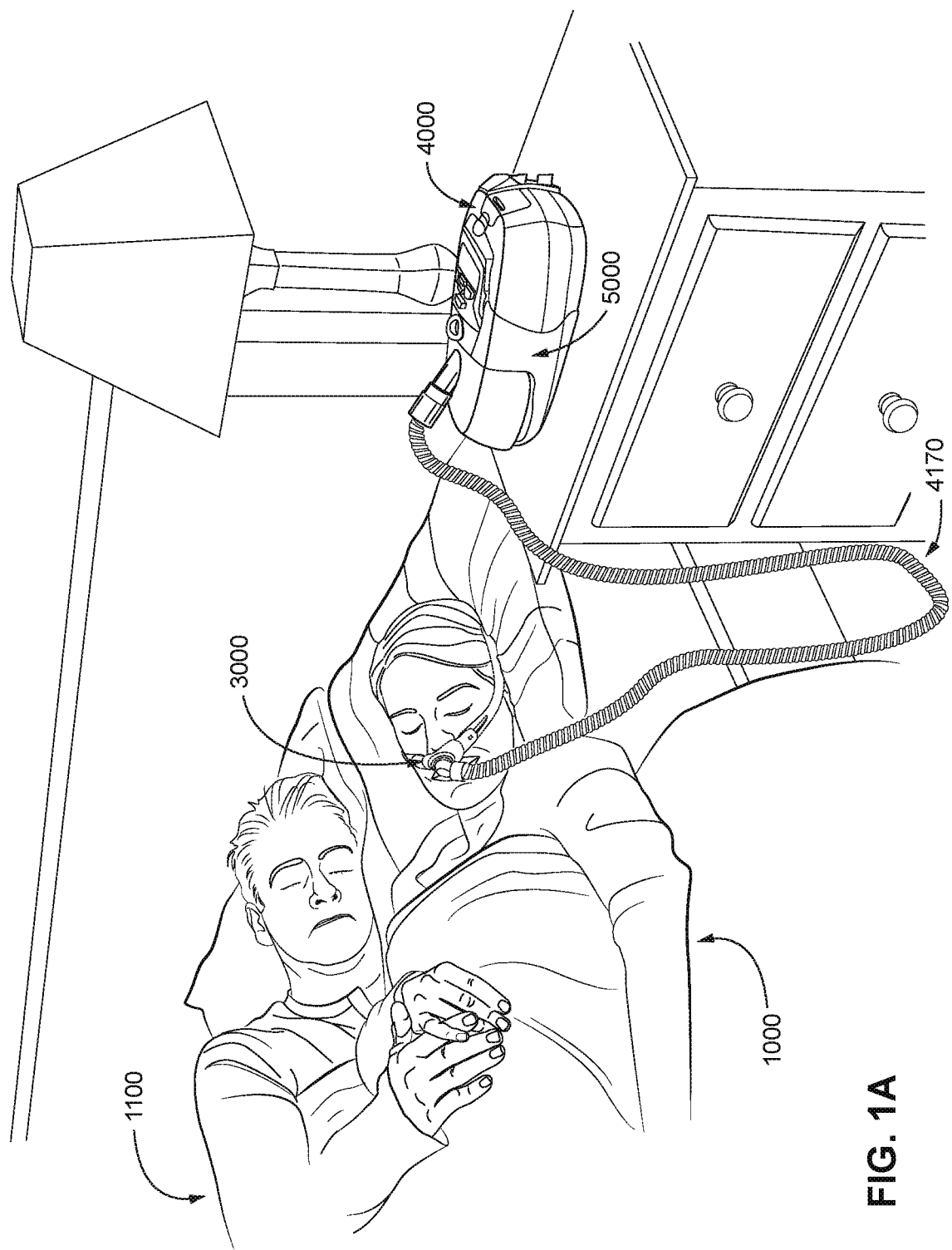
Figure 1B:
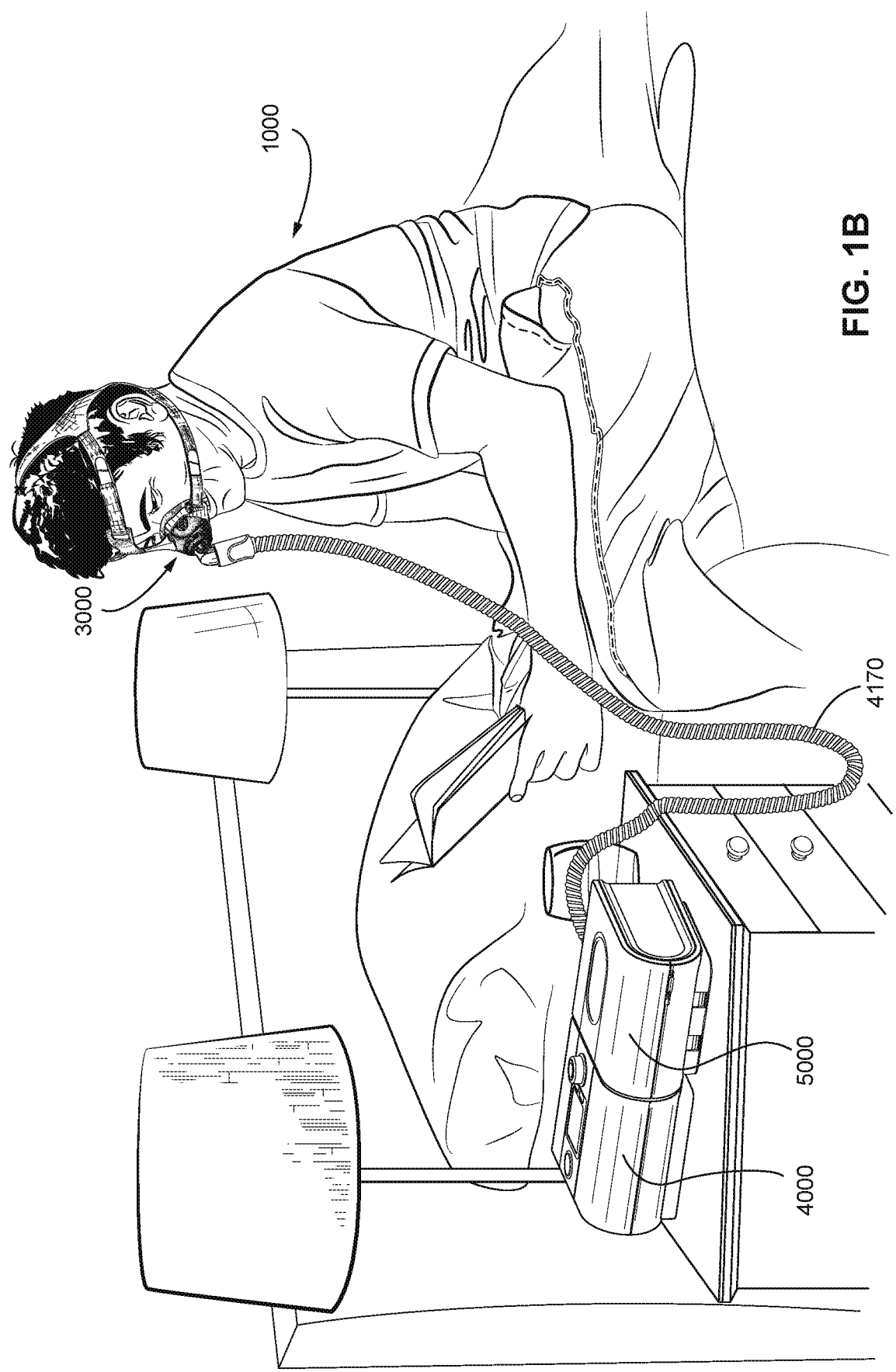
Figure 1C:
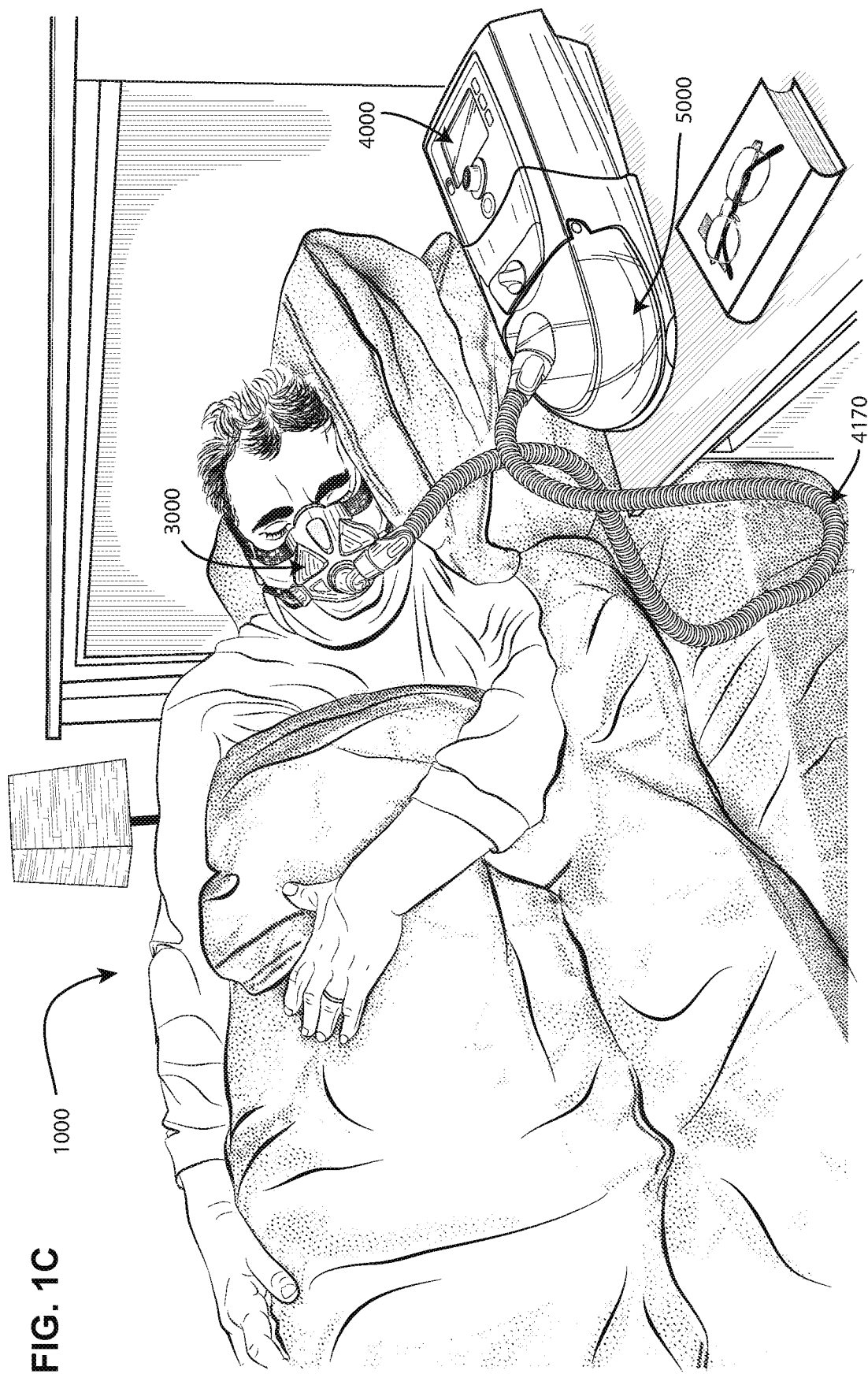
Figure 2A:
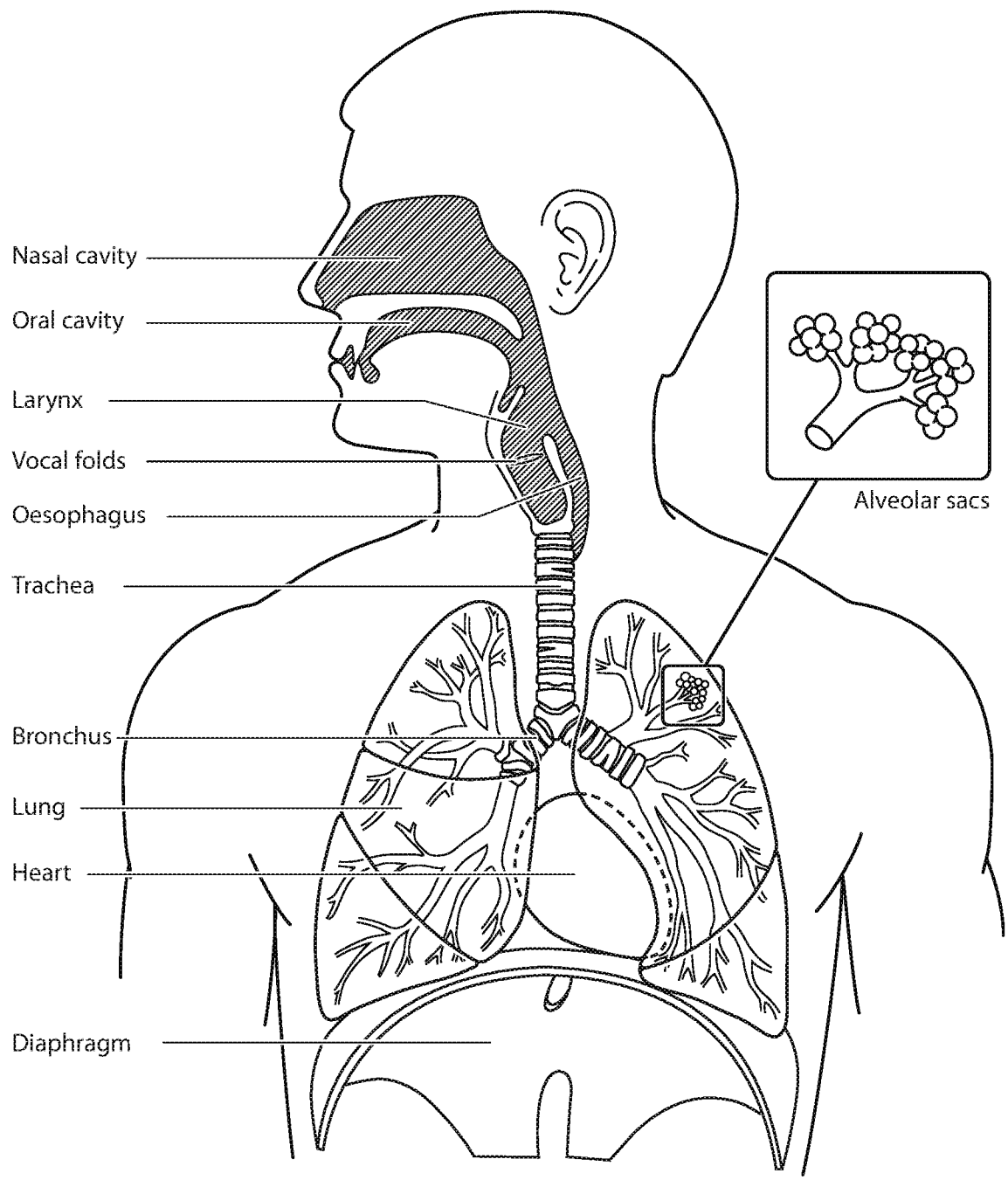
FIG. 2A shows an overview of a human respiratory system including the nasal and oral cavities, the larynx, vocal folds, oesophagus, trachea, bronchus, lung, alveolar sacs, heart and diaphragm.
Figure 2B:
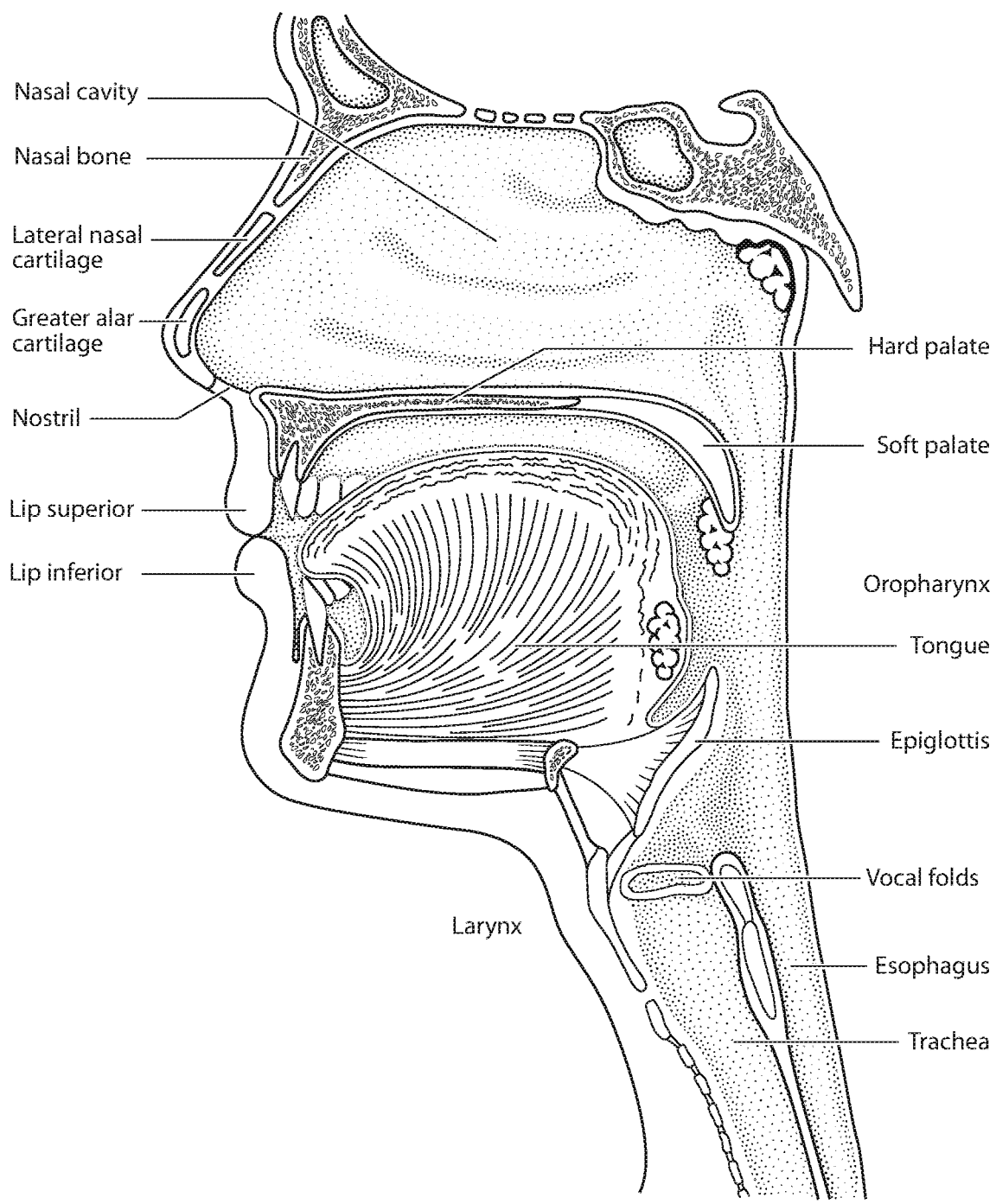
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
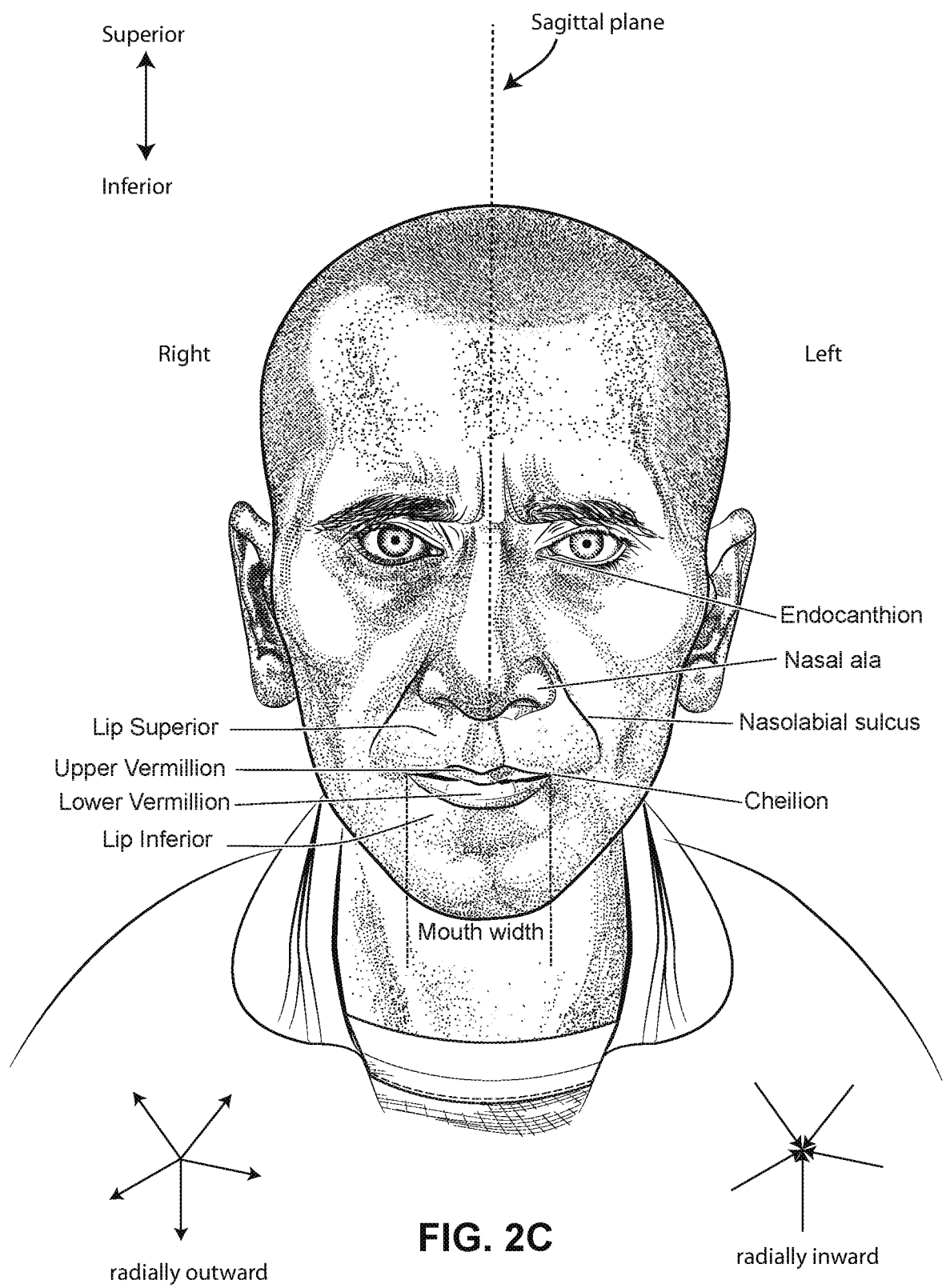
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
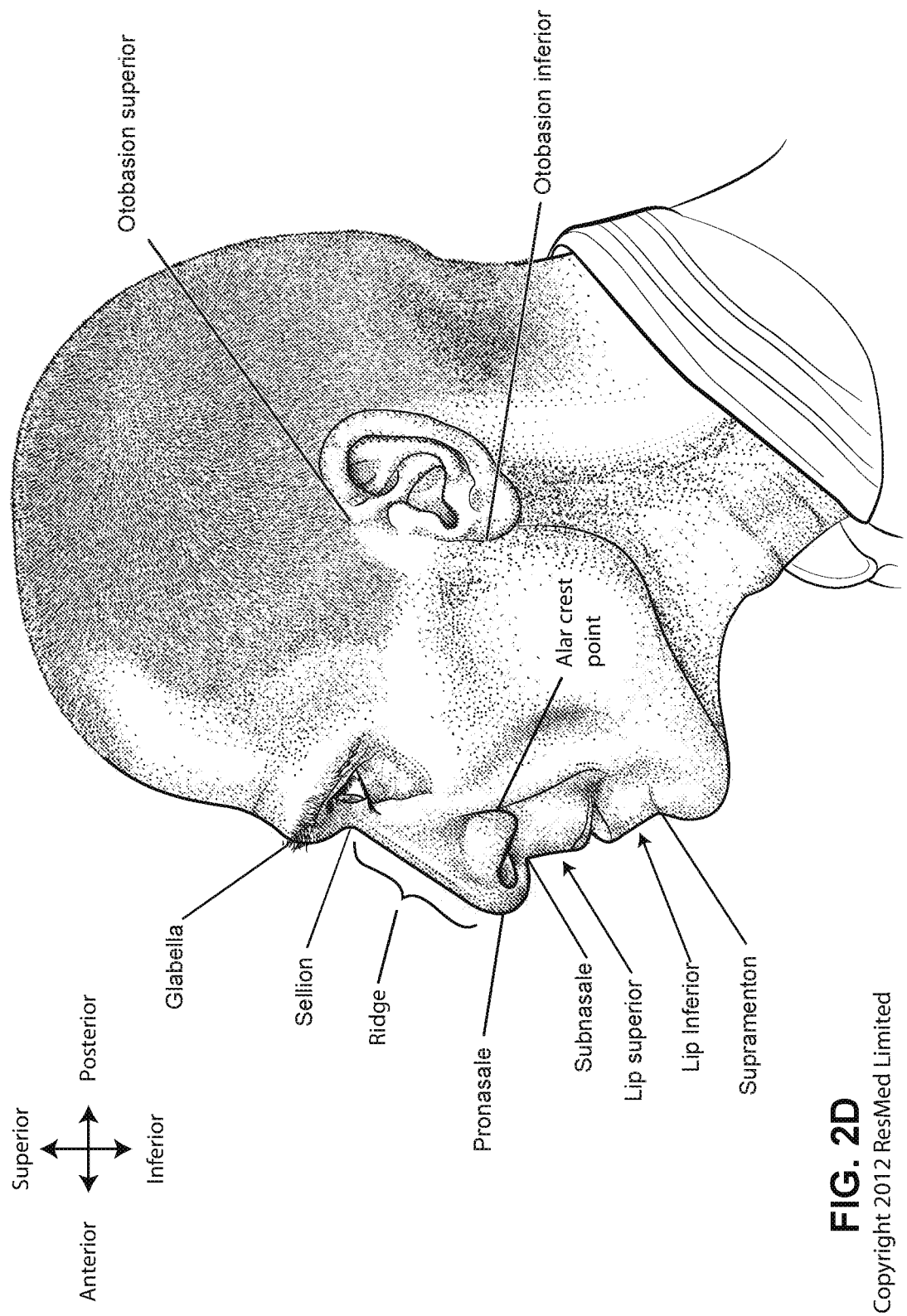
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
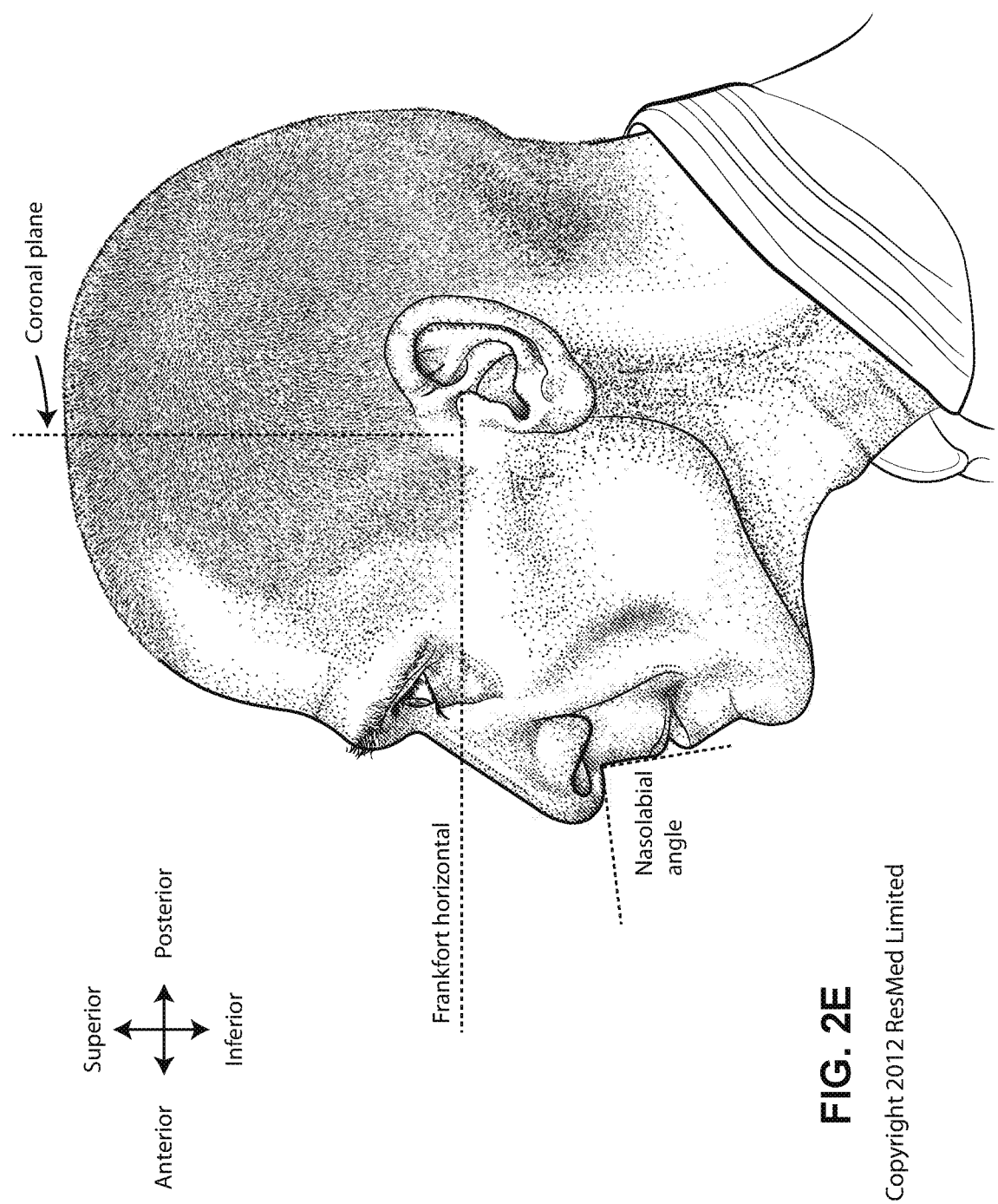

FIG. 2E is a further side view of a head. The approximate locations of the Frankfort horizontal and nasolabial angle are indicated. The coronal plane is also indicated.

Figure 2F:
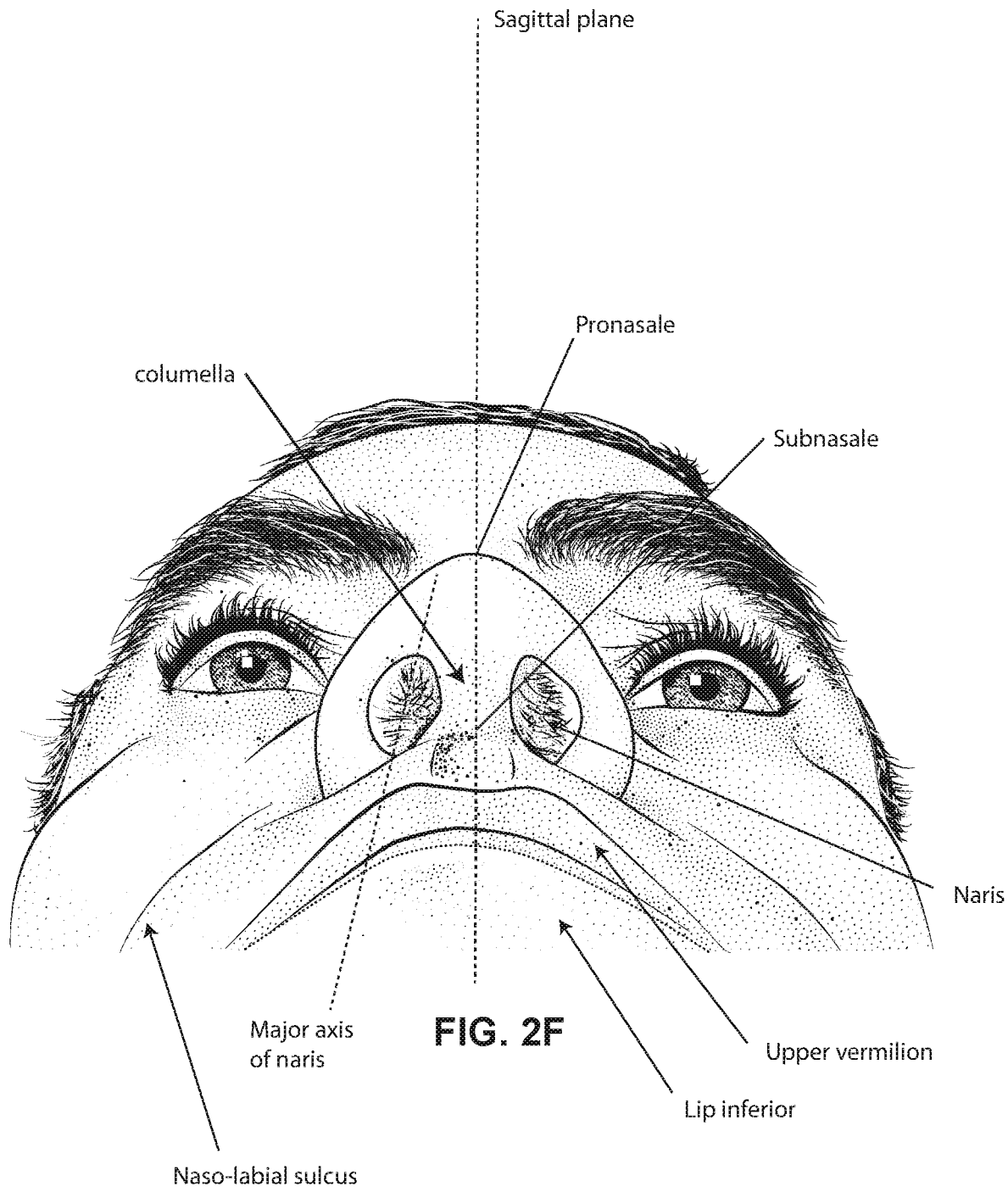

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
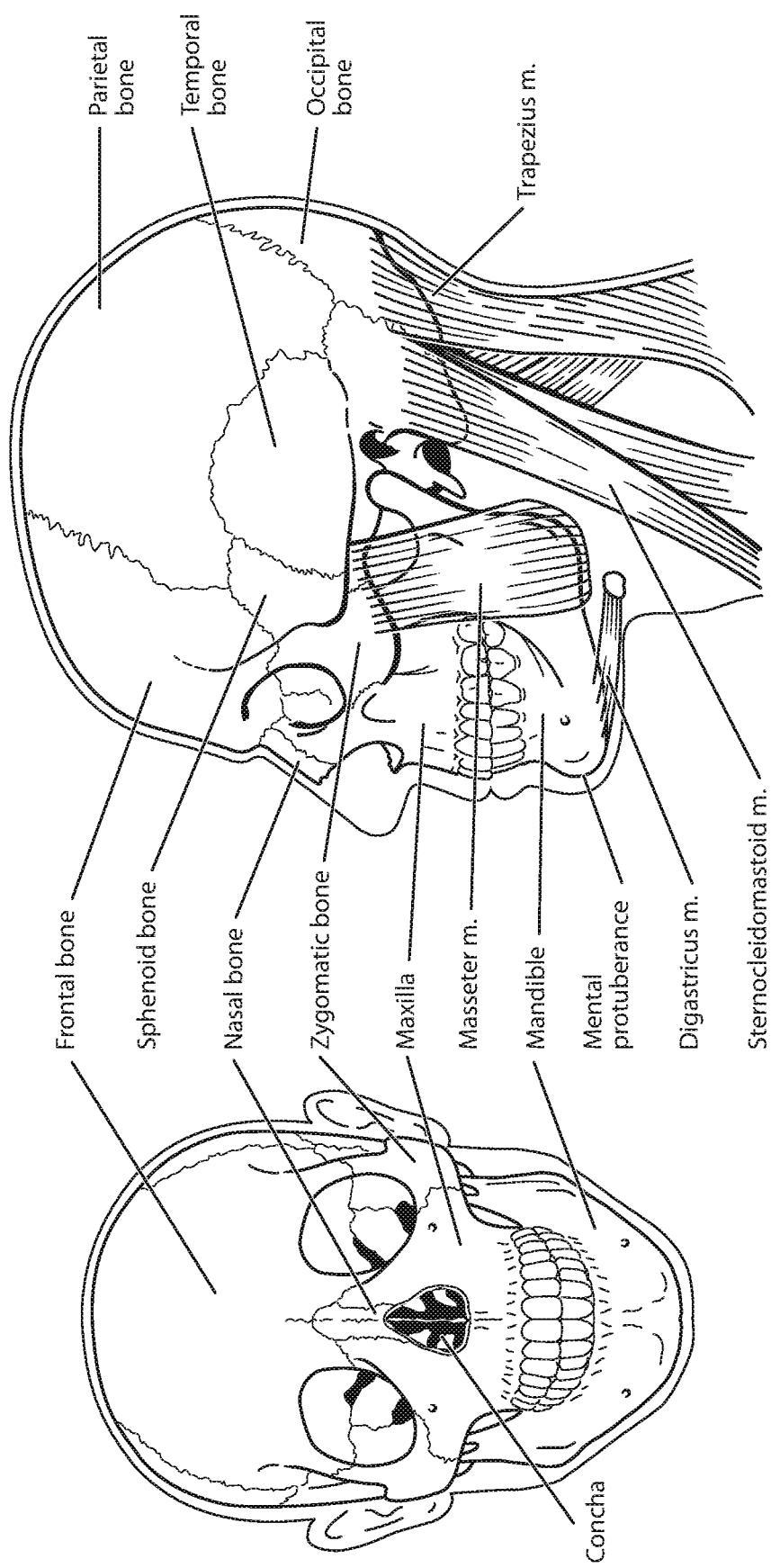

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
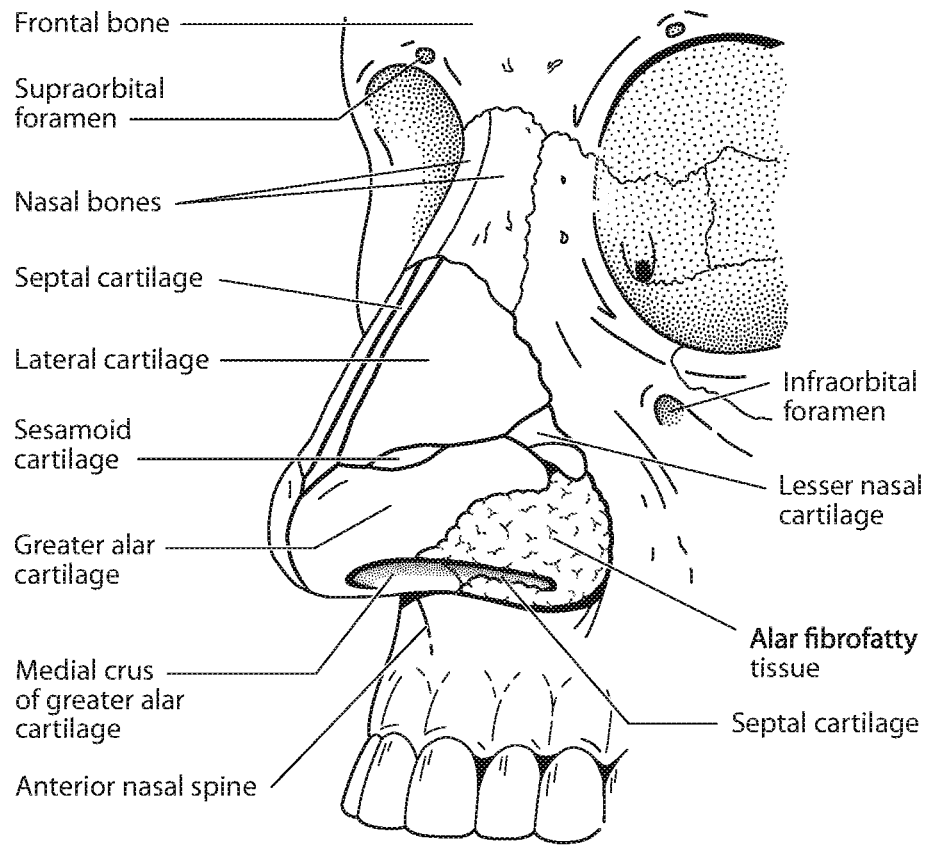

FIG. 2L shows an anterolateral view of a nose.

4.3 Patient Interface

Figure 3A:
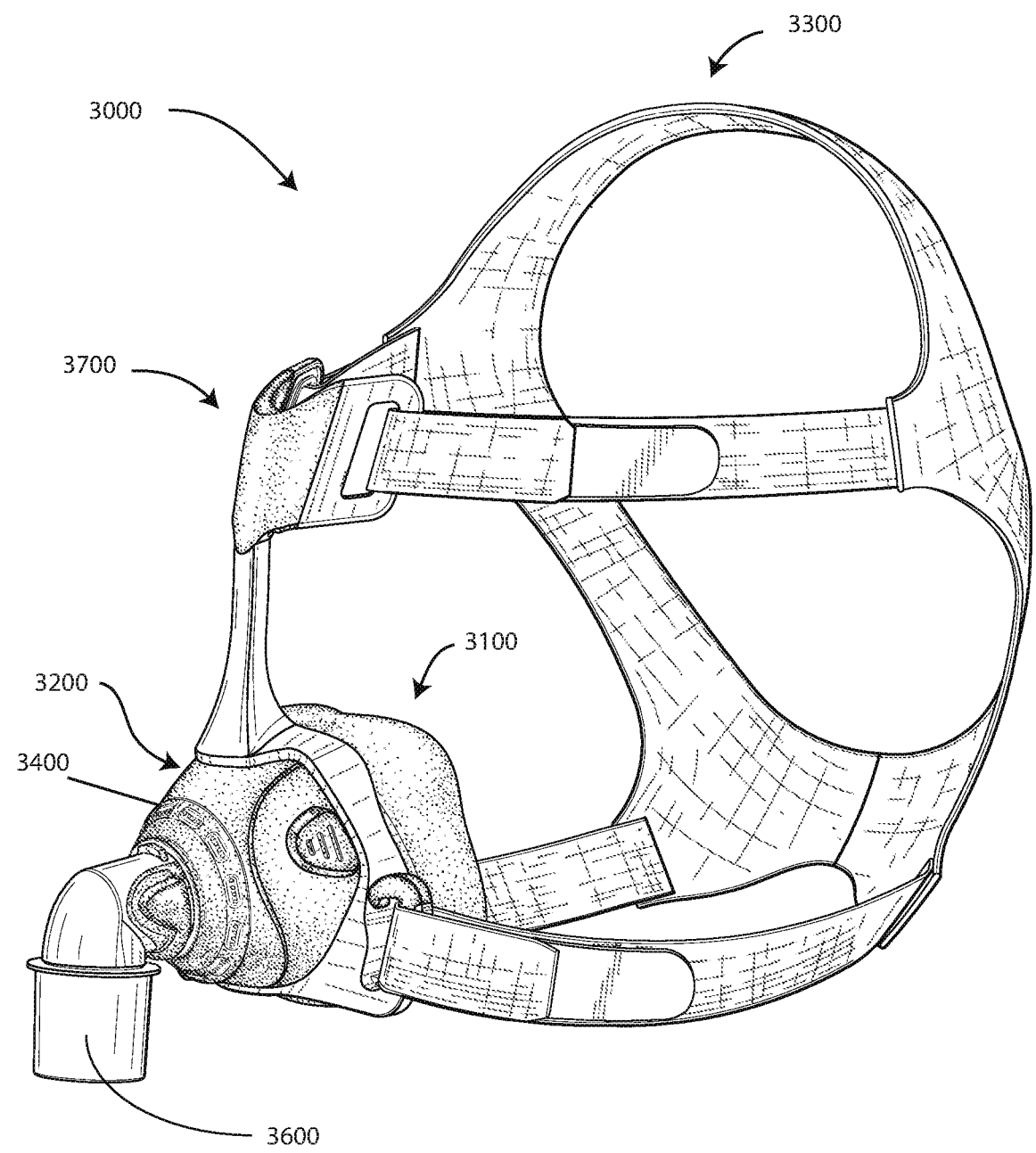

FIG. 3A shows a patient interface in the form of a nasal mask in accordance with one form of the present technology.

Figure 3B:
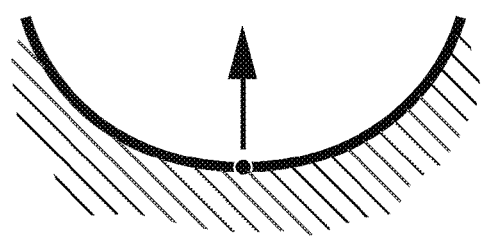

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
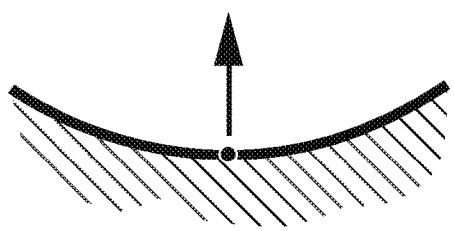

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
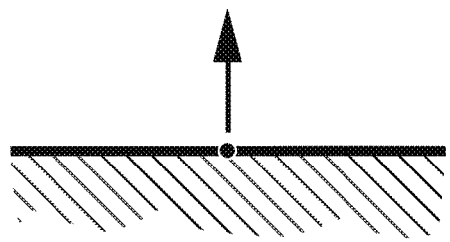

FIG. 3D shows a schematic of a cross-section through a structure at a point. An outward normal at the point is indicated. The curvature at the point has a value of zero.

Figure 3E:
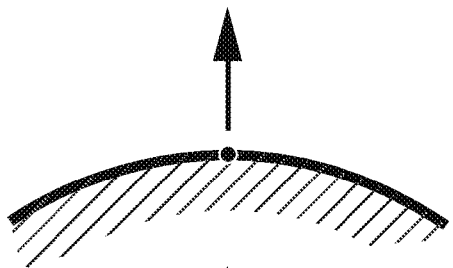

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
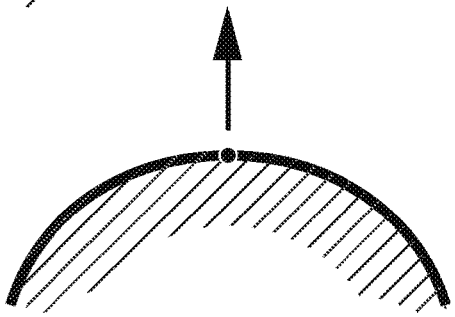

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
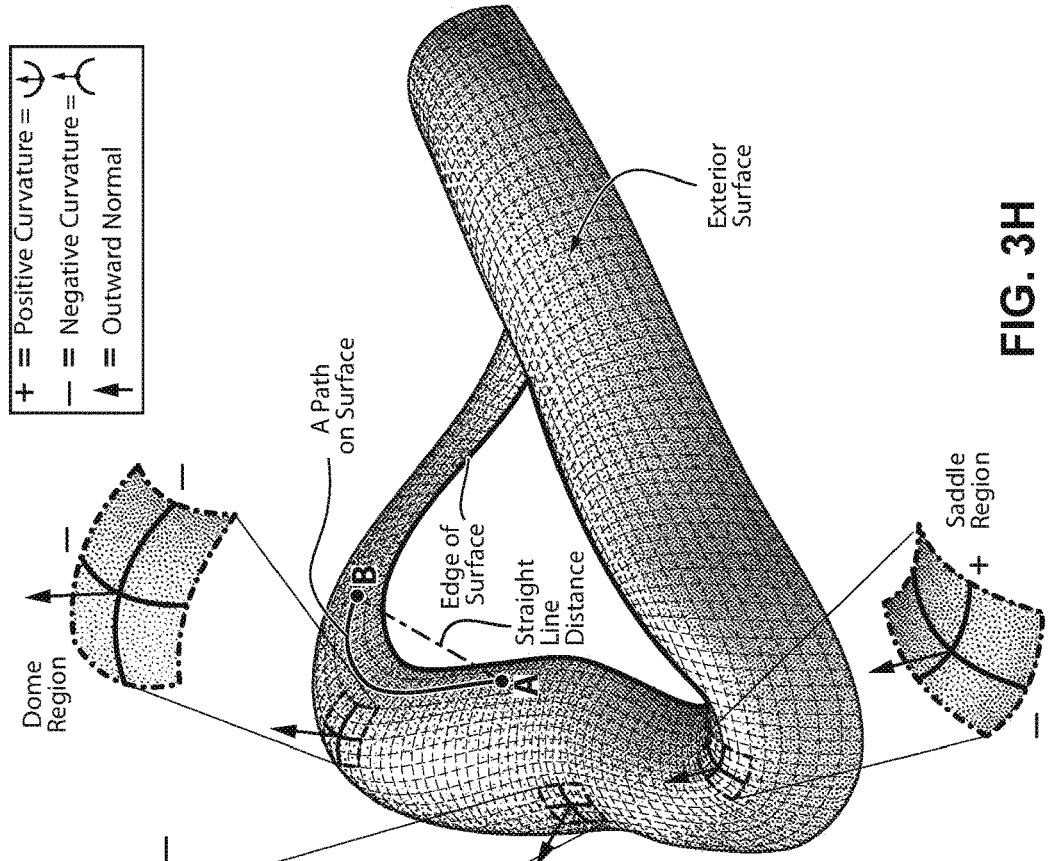
Figure 3G:
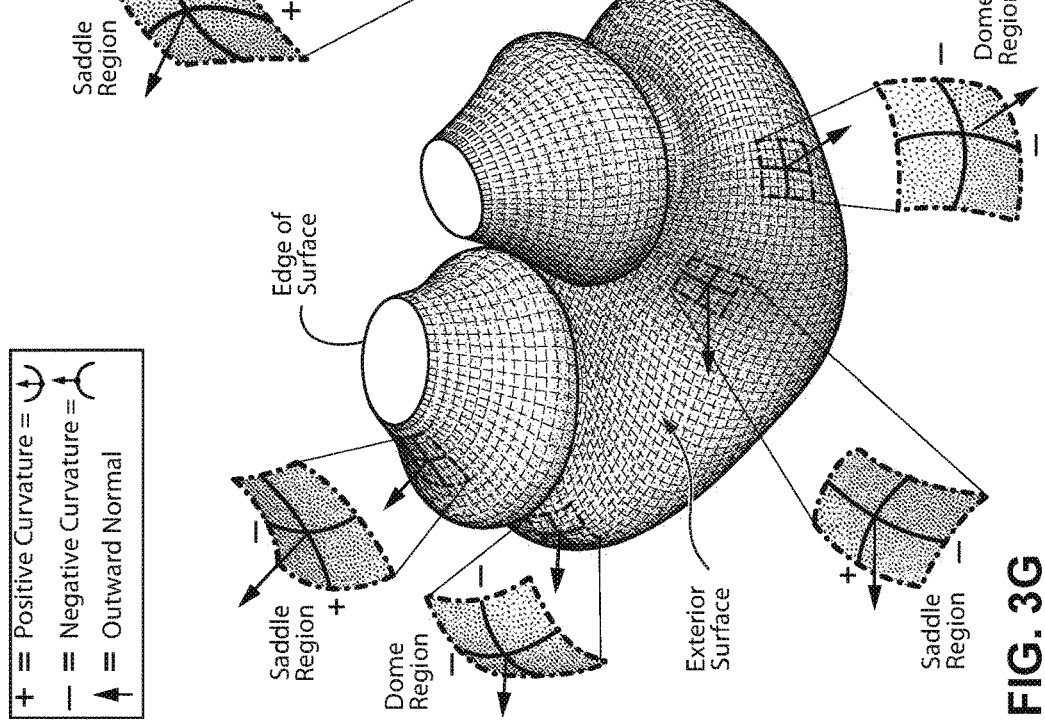

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
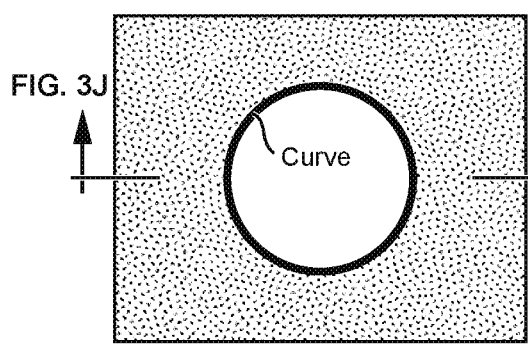

FIG. 3I shows the surface of a structure, with a one dimensional hole in the surface. The illustrated plane curve forms the boundary of a one dimensional hole.

Figure 3K:
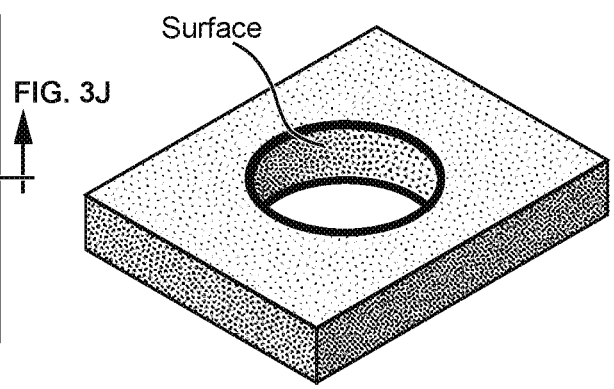
Figure 3J:
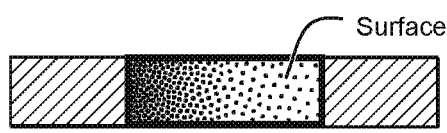

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
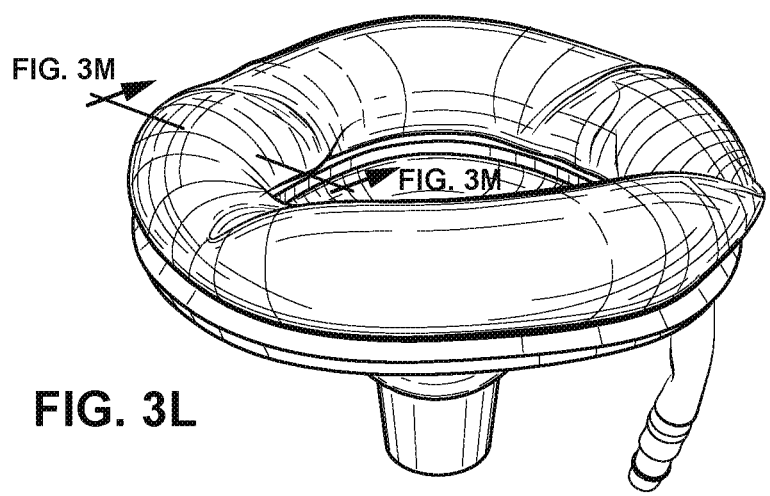

FIG. 3L shows a mask having an inflatable bladder as a cushion.

Figure 3M:
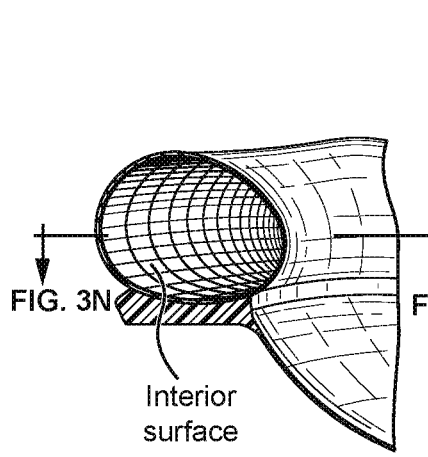

FIG. 3M shows a cross-section through the mask of FIG. 3L, and shows the interior surface of the bladder. The interior surface bounds the two dimensional hole in the mask.

Figure 3N:
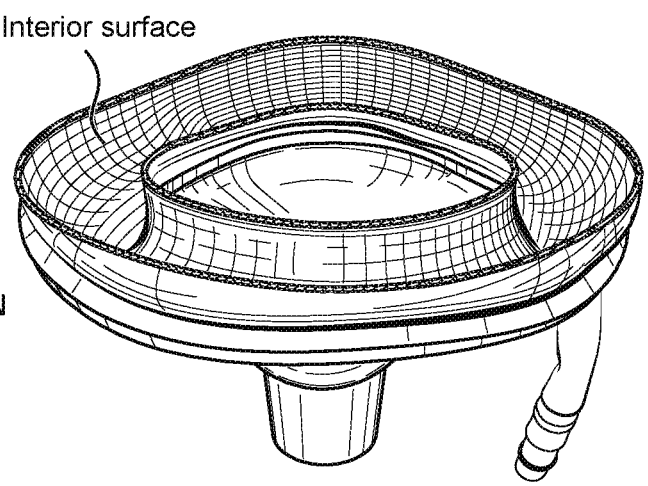

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figure 3U:
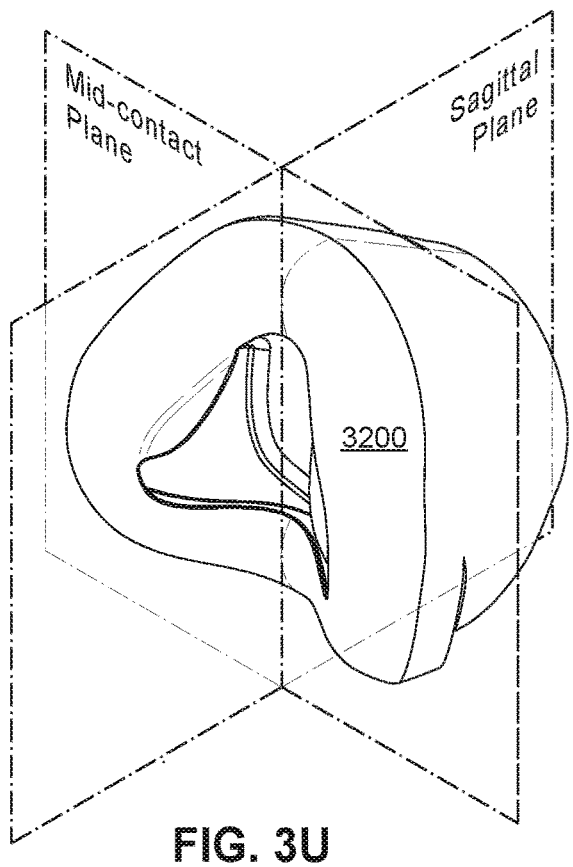

FIG. 3U shows a view of a plenum chamber 3200 showing a sagittal plane and a mid-contact plane.

Figure 3V:
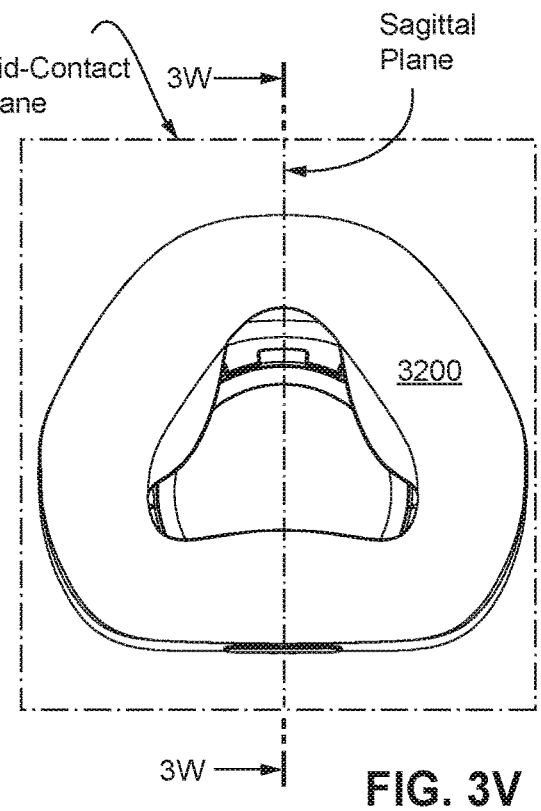

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
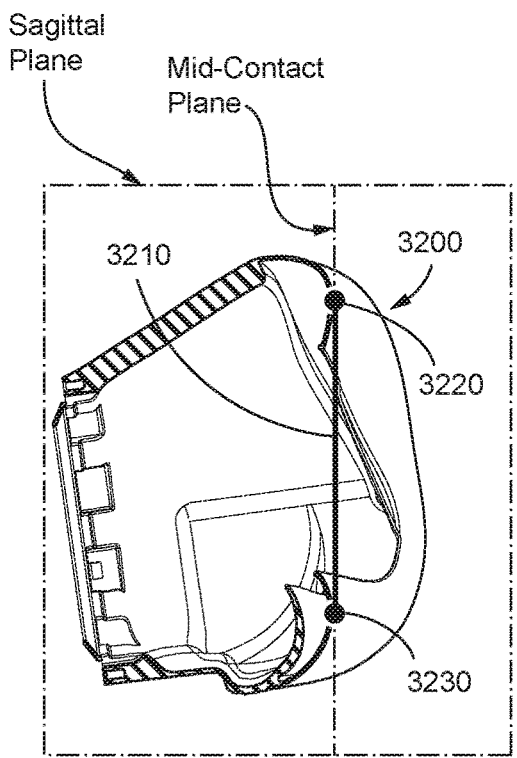

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
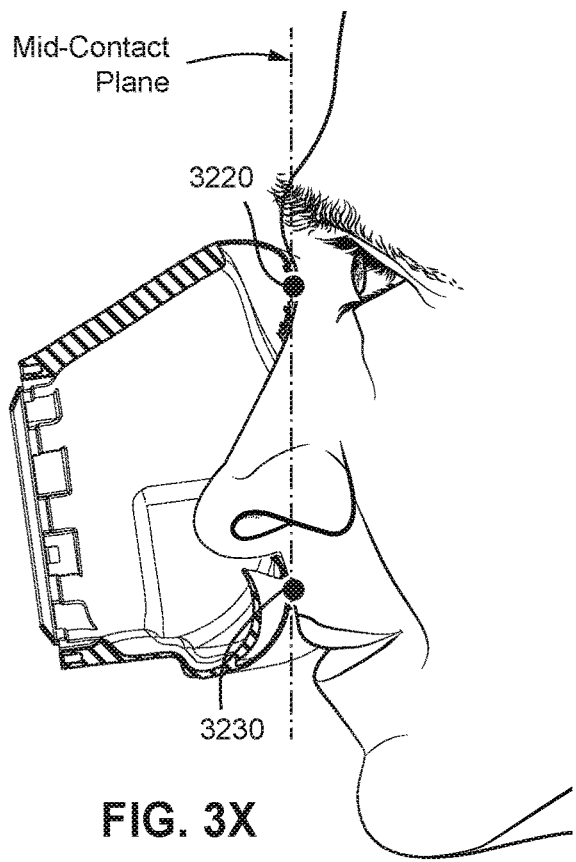

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
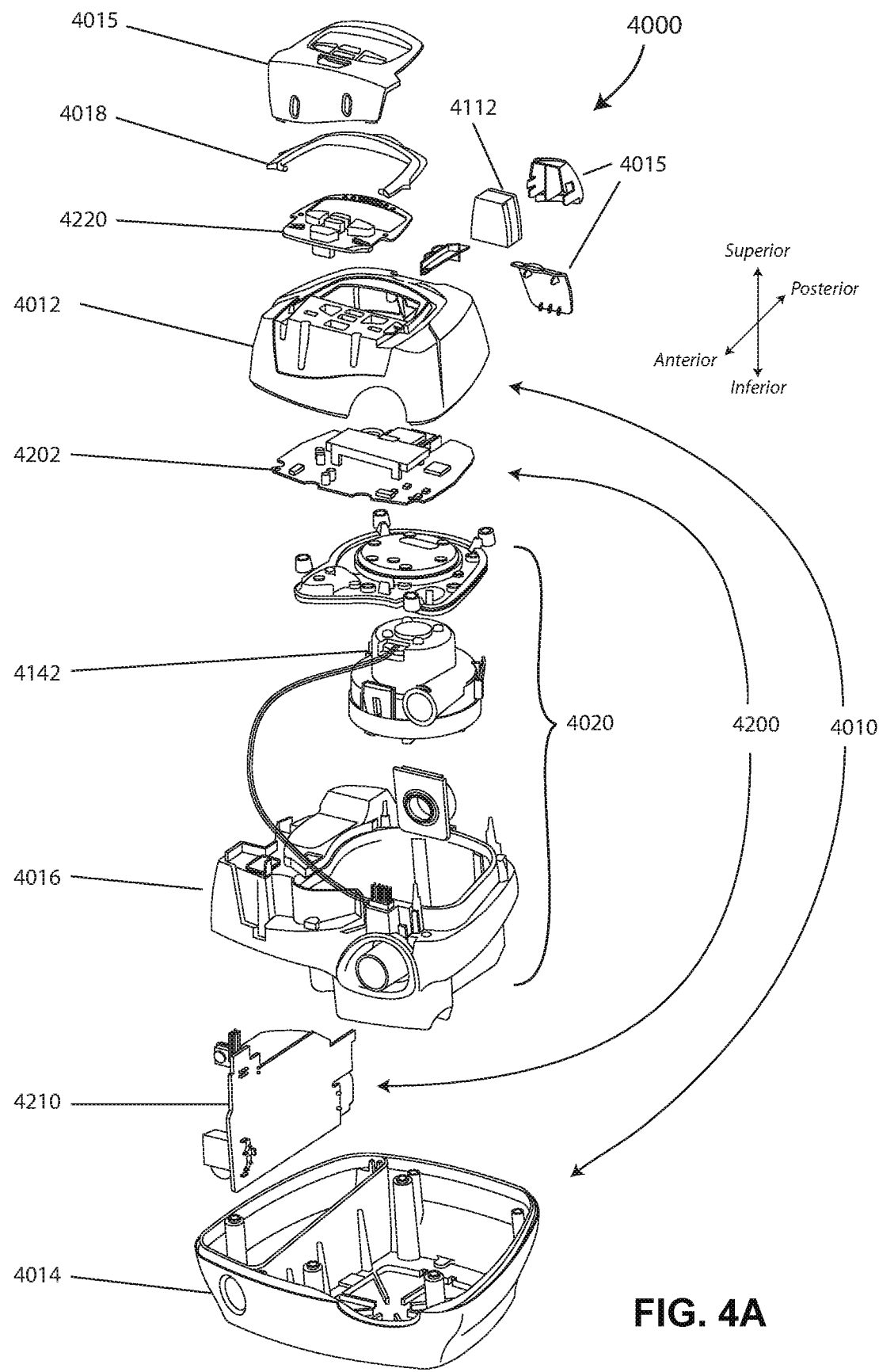

FIG. 4A shows an RPT device in accordance with one form of the present technology.

Figure 4B:
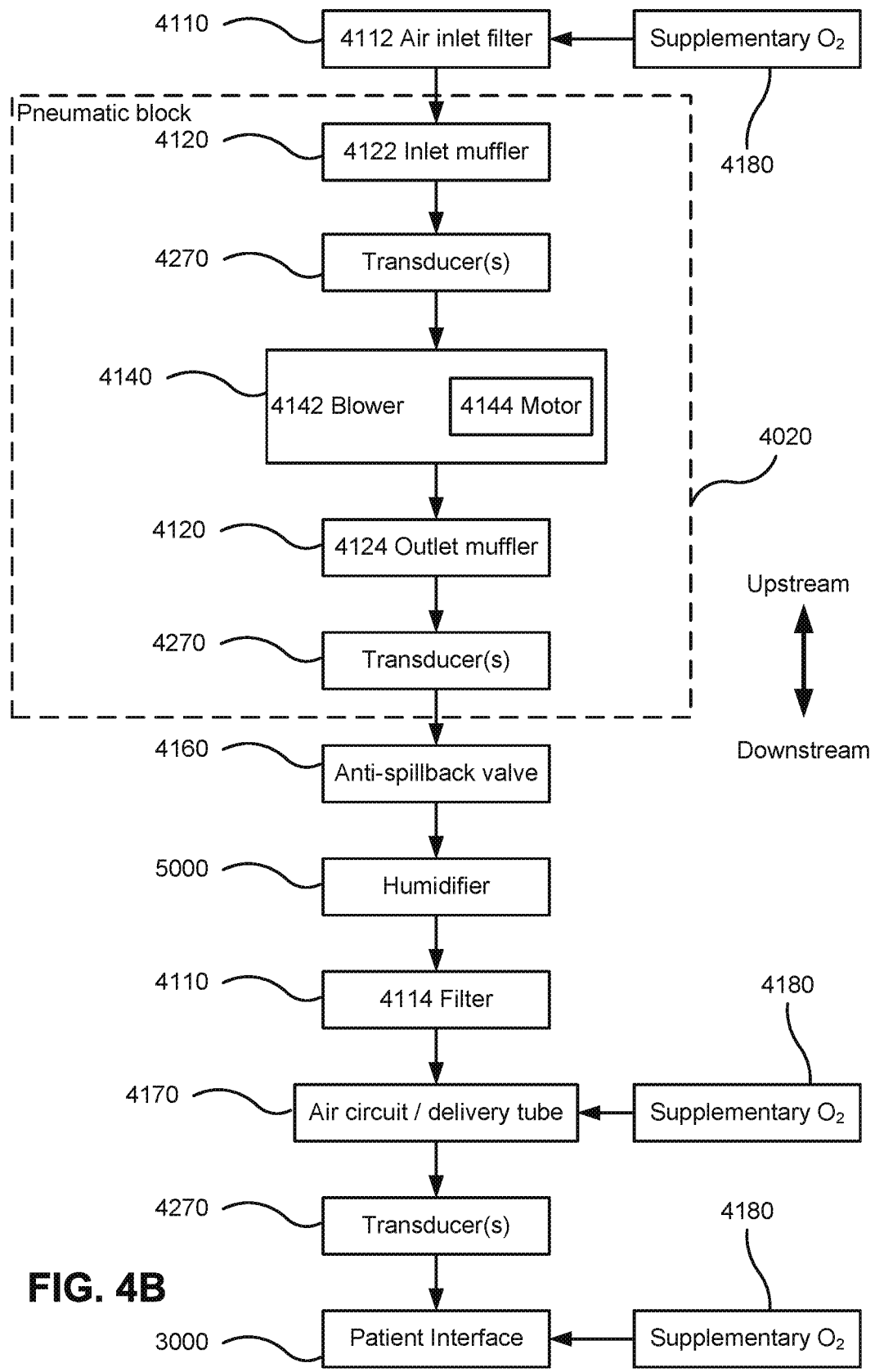

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
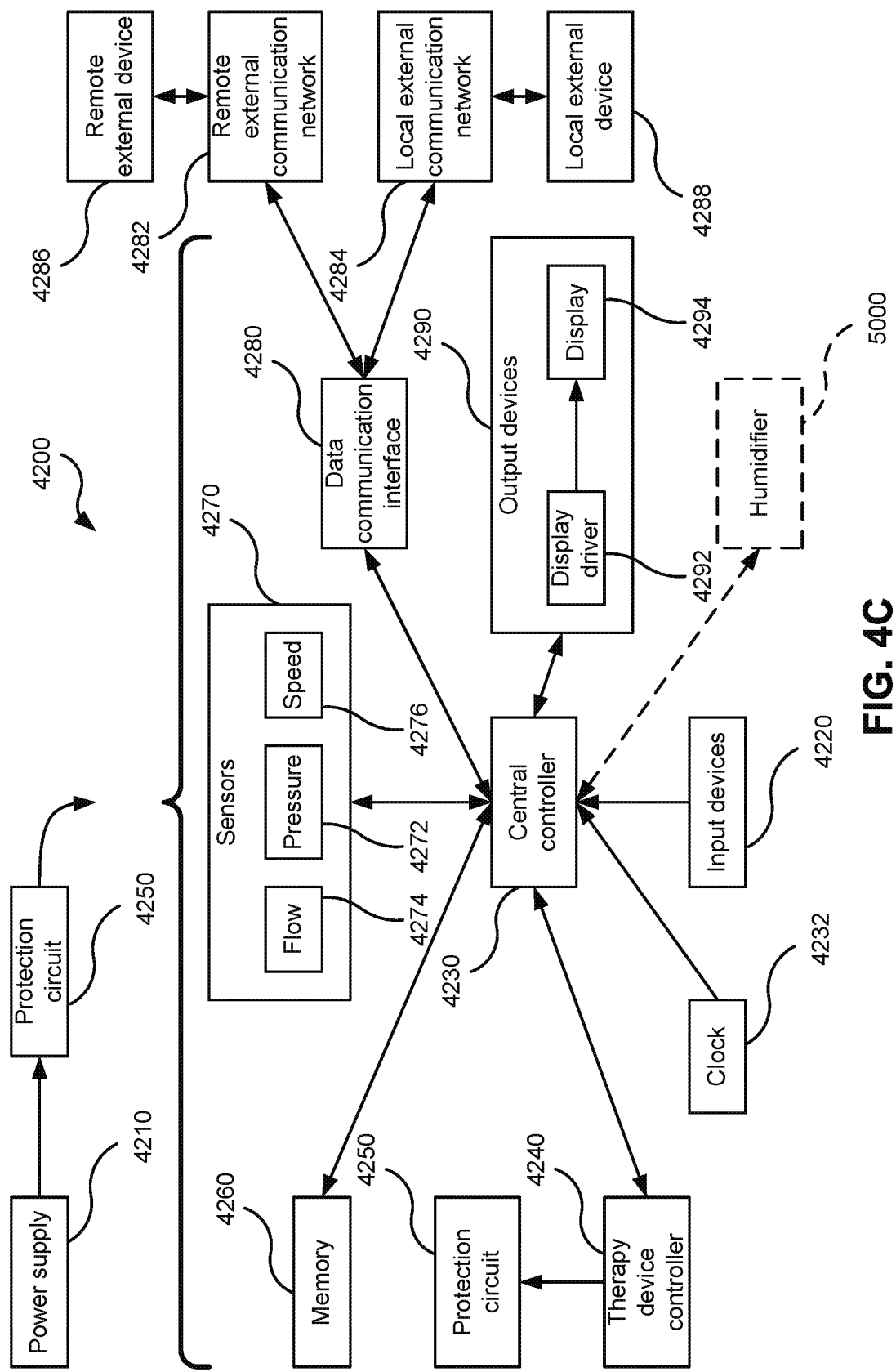

FIG. 4C is a schematic diagram of the electrical components of an RPT device in accordance with one form of the present technology.

4.5 Humidifier

Figure 5A:
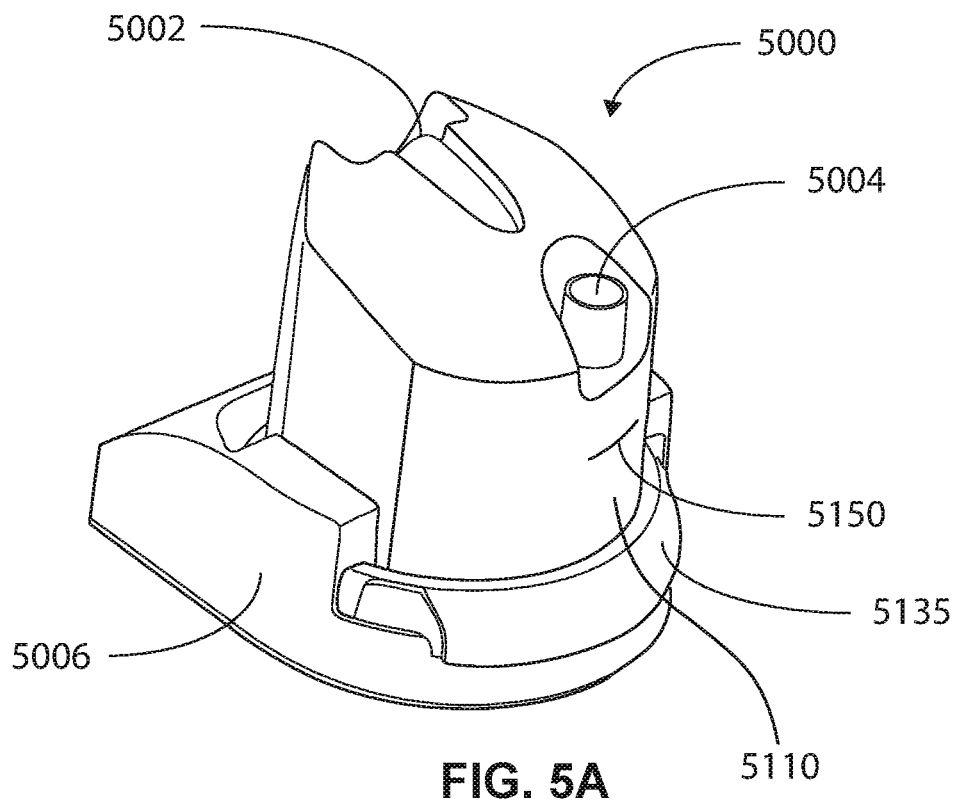

FIG. 5A shows an isometric view of a humidifier in accordance with one form of the present technology.

Figure 5B:
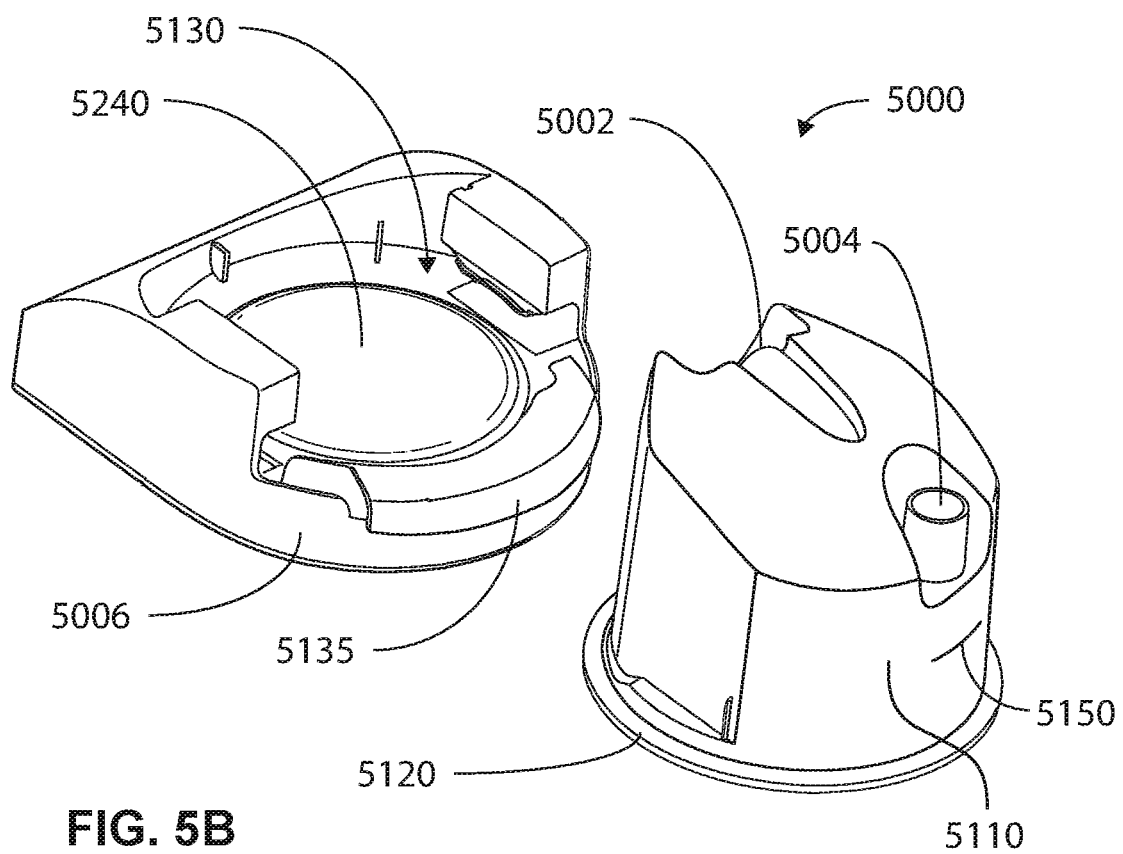

FIG. 5B shows an isometric view of a humidifier in accordance with one form of the present technology, showing a humidifier reservoir 5110 removed from the humidifier reservoir dock 5130.

Figure 5C:
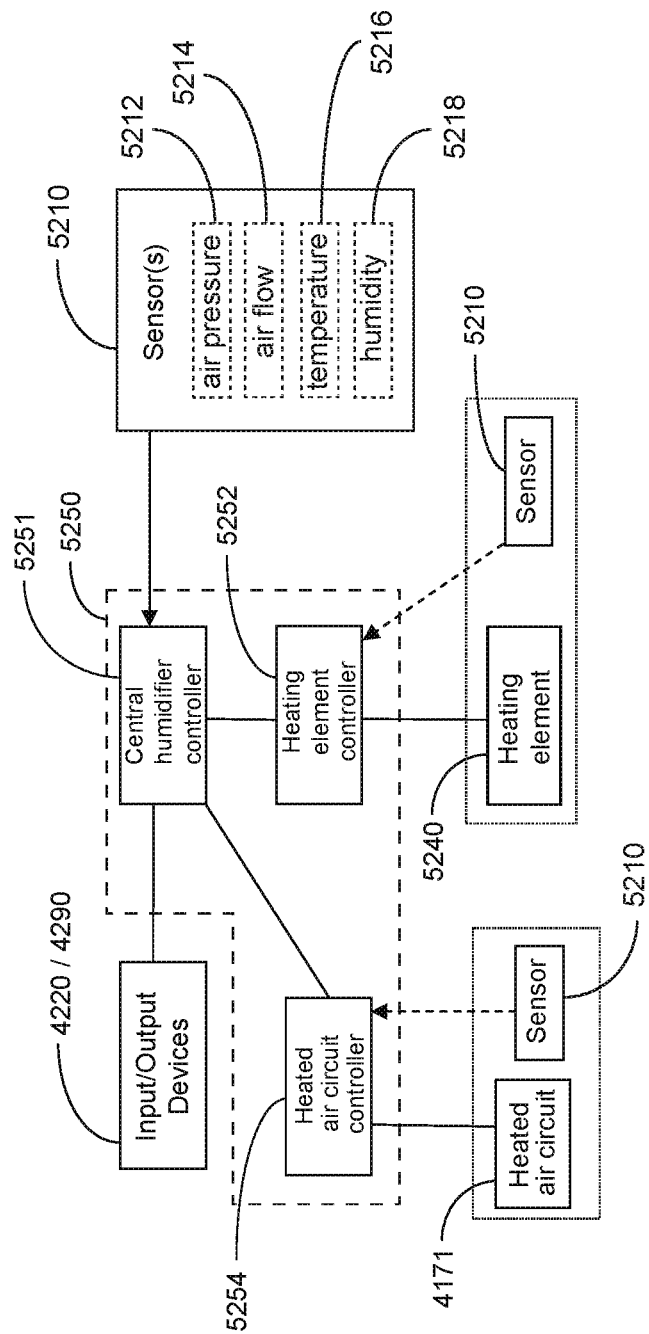

FIG. 5C shows a schematic of a humidifier in accordance with one form of the present technology.

4.6 Breathing Waveforms

Figure 6:
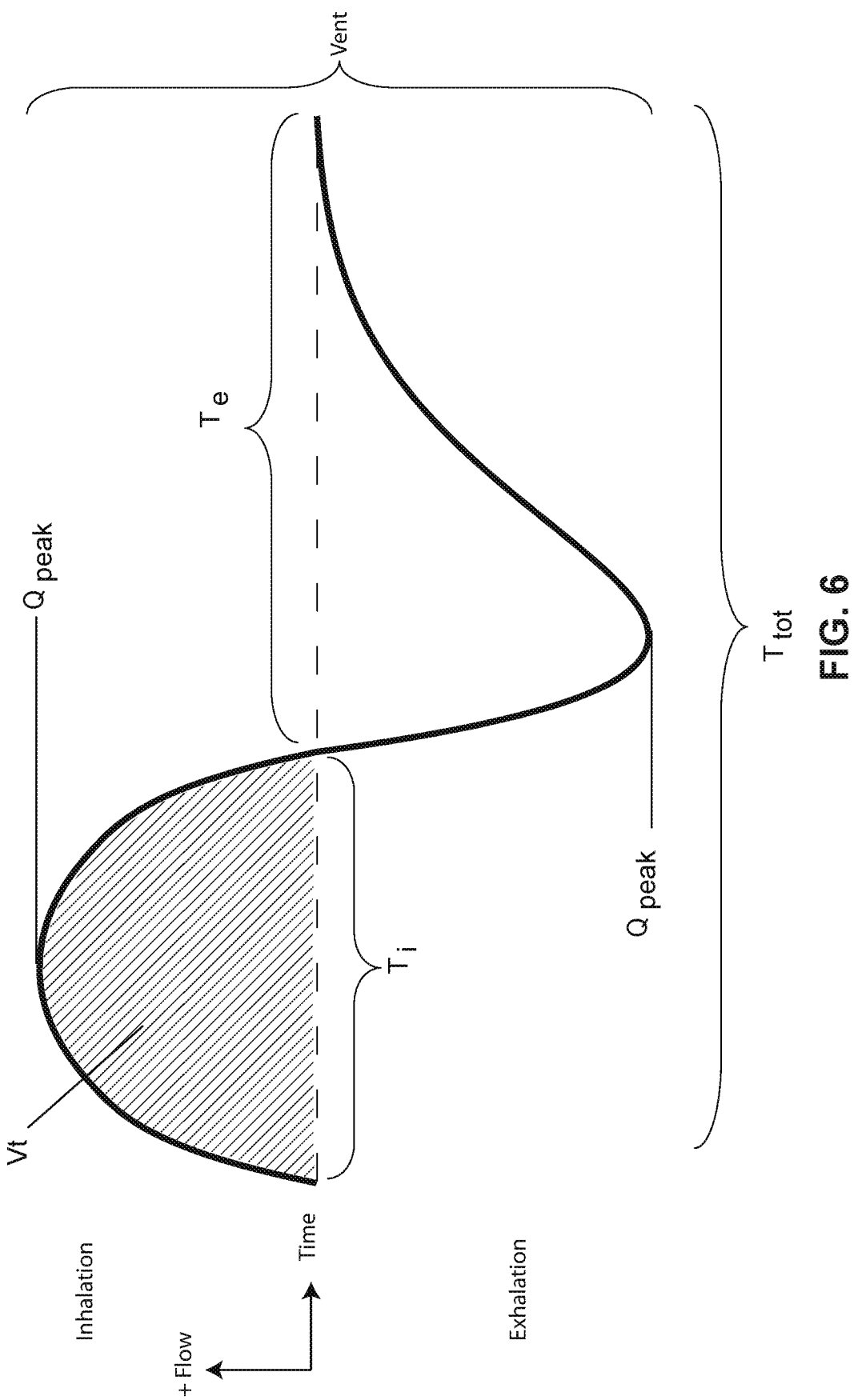

FIG. 6 shows a model typical breath waveform of a person while sleeping.

4.7 Patient Interface of Present Technology

Figure 7:
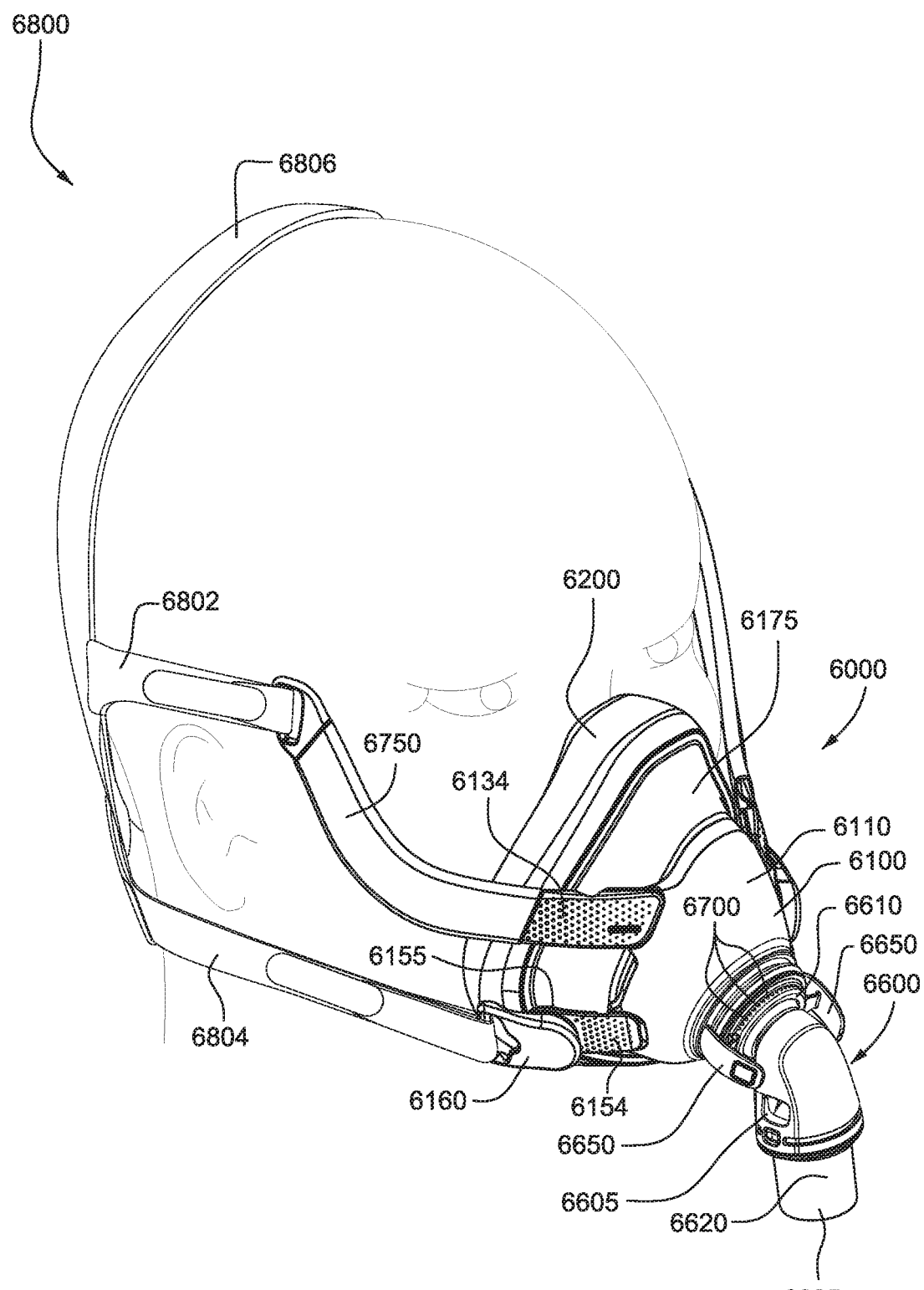

FIG. 7 is a perspective view of a patient interface shown on a patient's head according to an example of the present technology.

Figure 8:
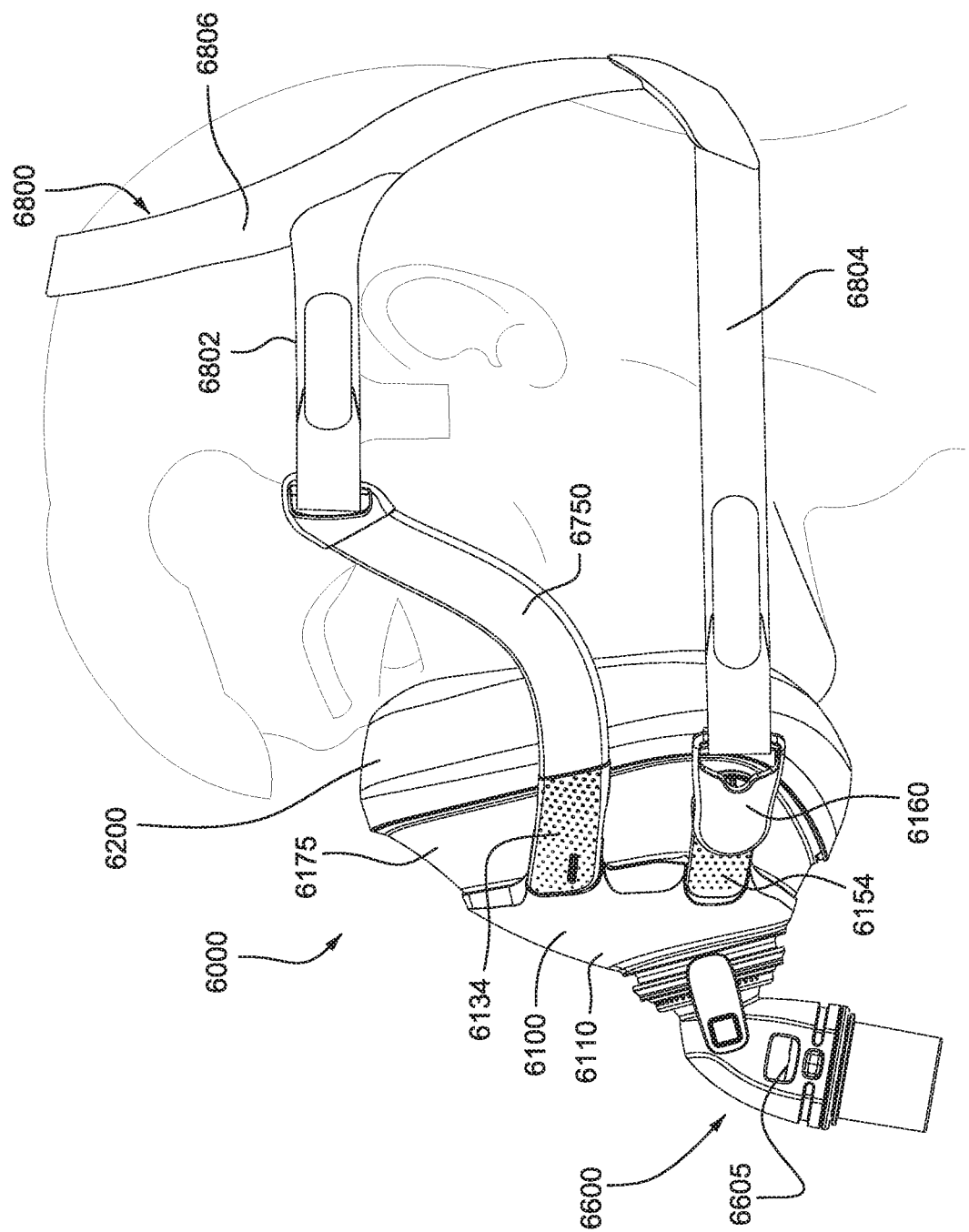

FIG. 8 is a side view of the patient interface shown in FIG. 7.

Figure 9:
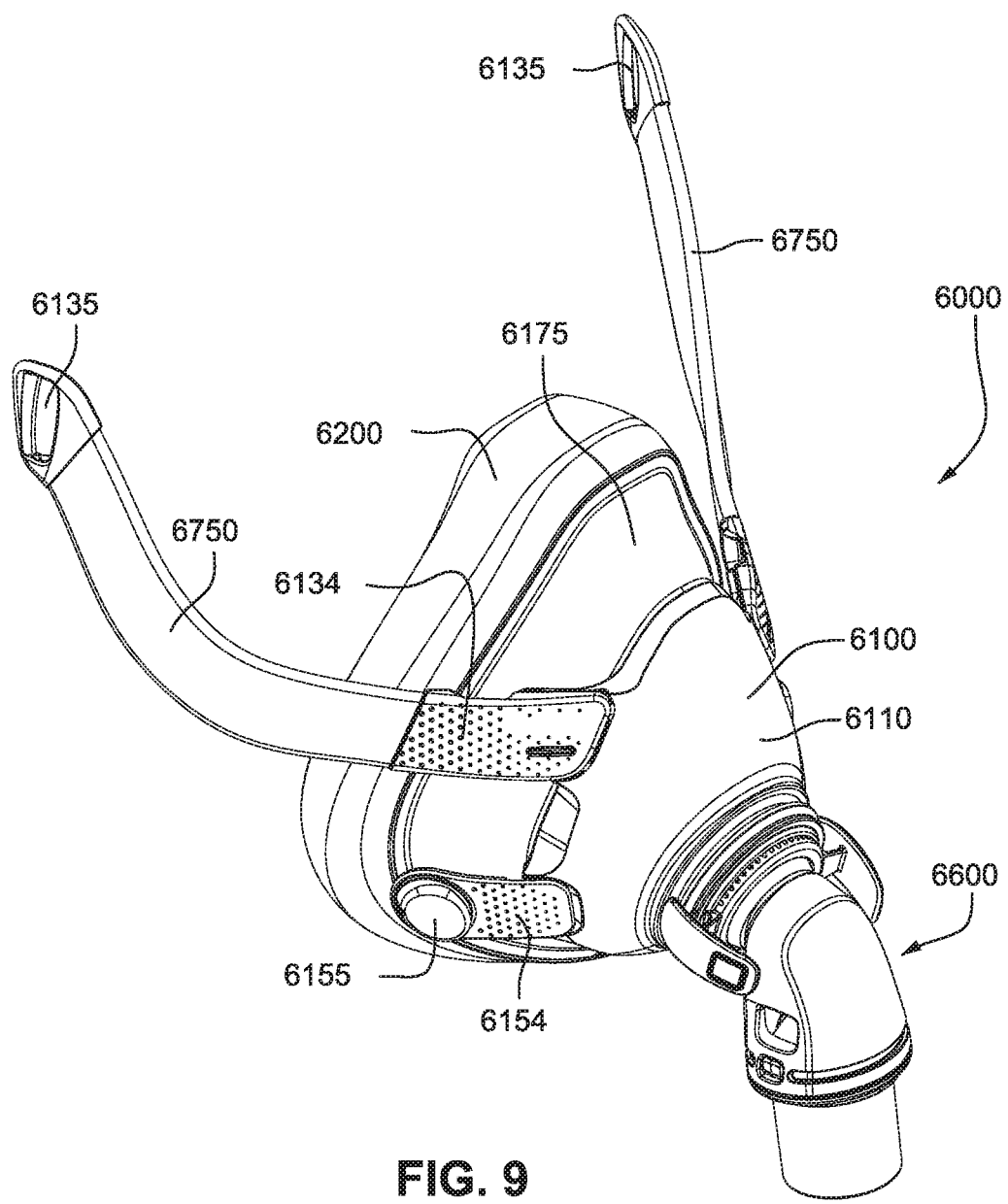

FIG. 9 is a perspective view of a patient interface according to an example of the present technology, the patient interface being shown with headgear removed.

Figure 10:
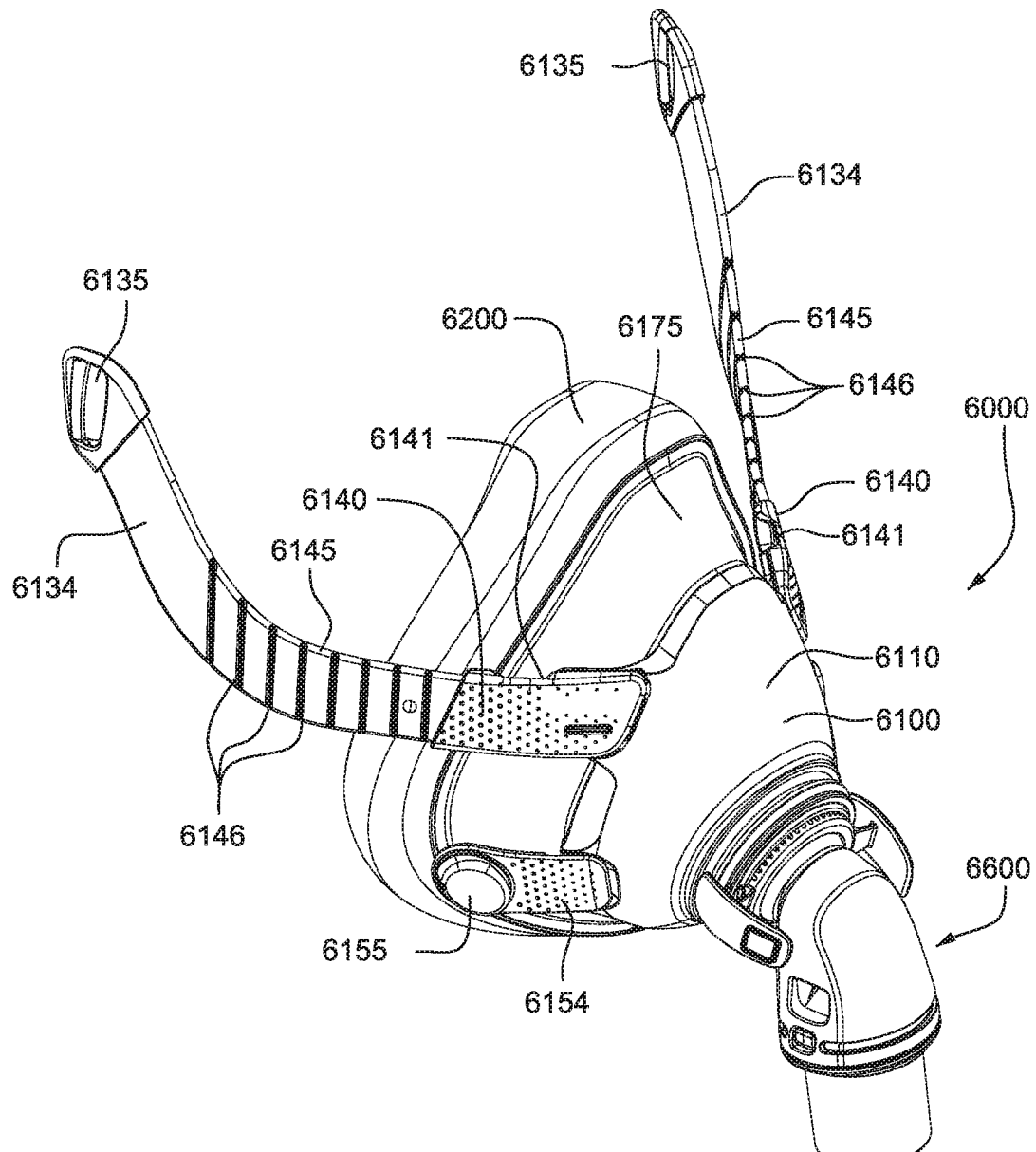

FIG. 10 is a perspective view of the patient interface shown in FIG. 9 with arm covers for upper arms of the frame assembly removed.

Figure 11:
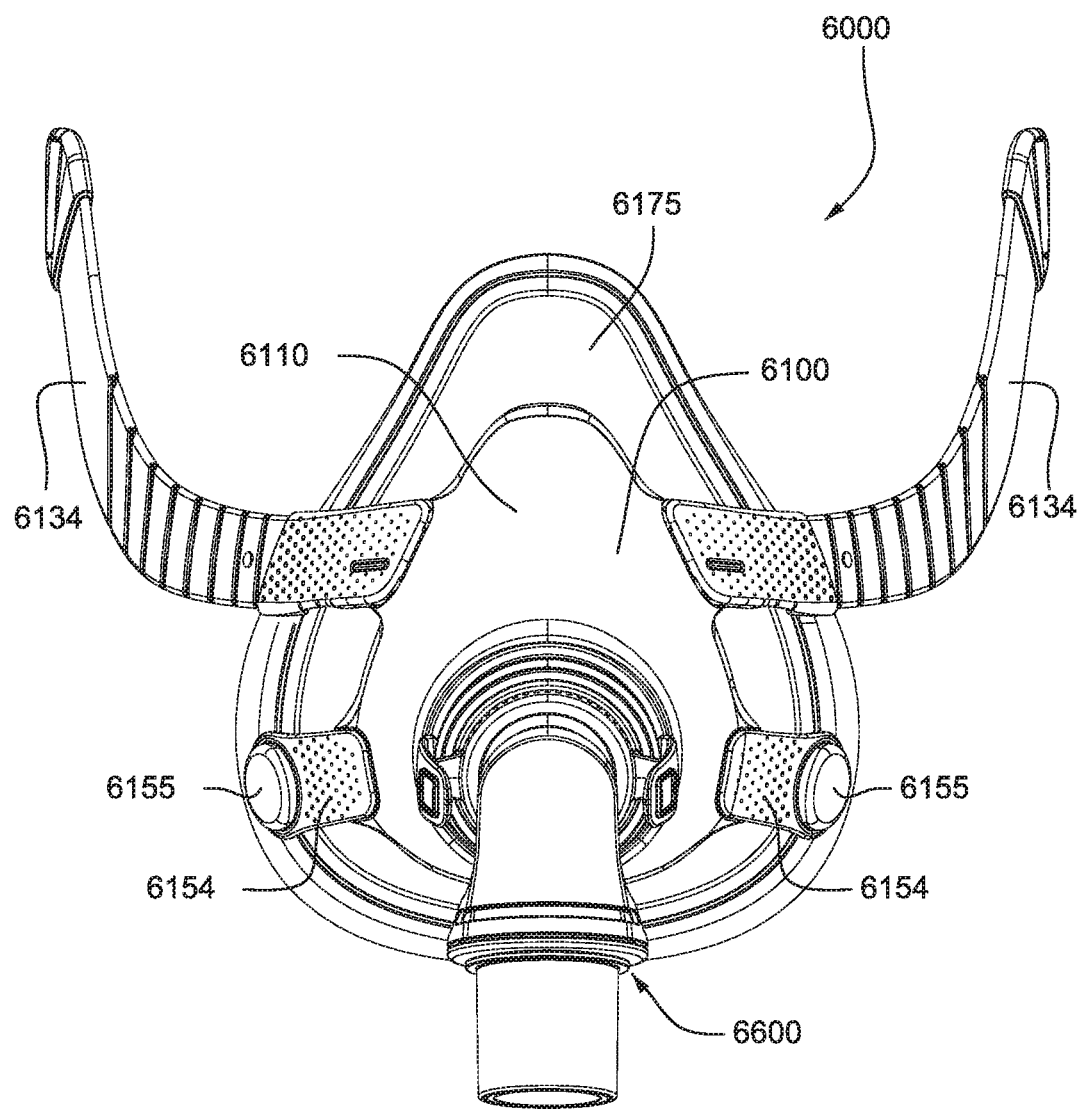

FIG. 11 is a front view of the patient interface shown in FIG. 10.

Figure 12:
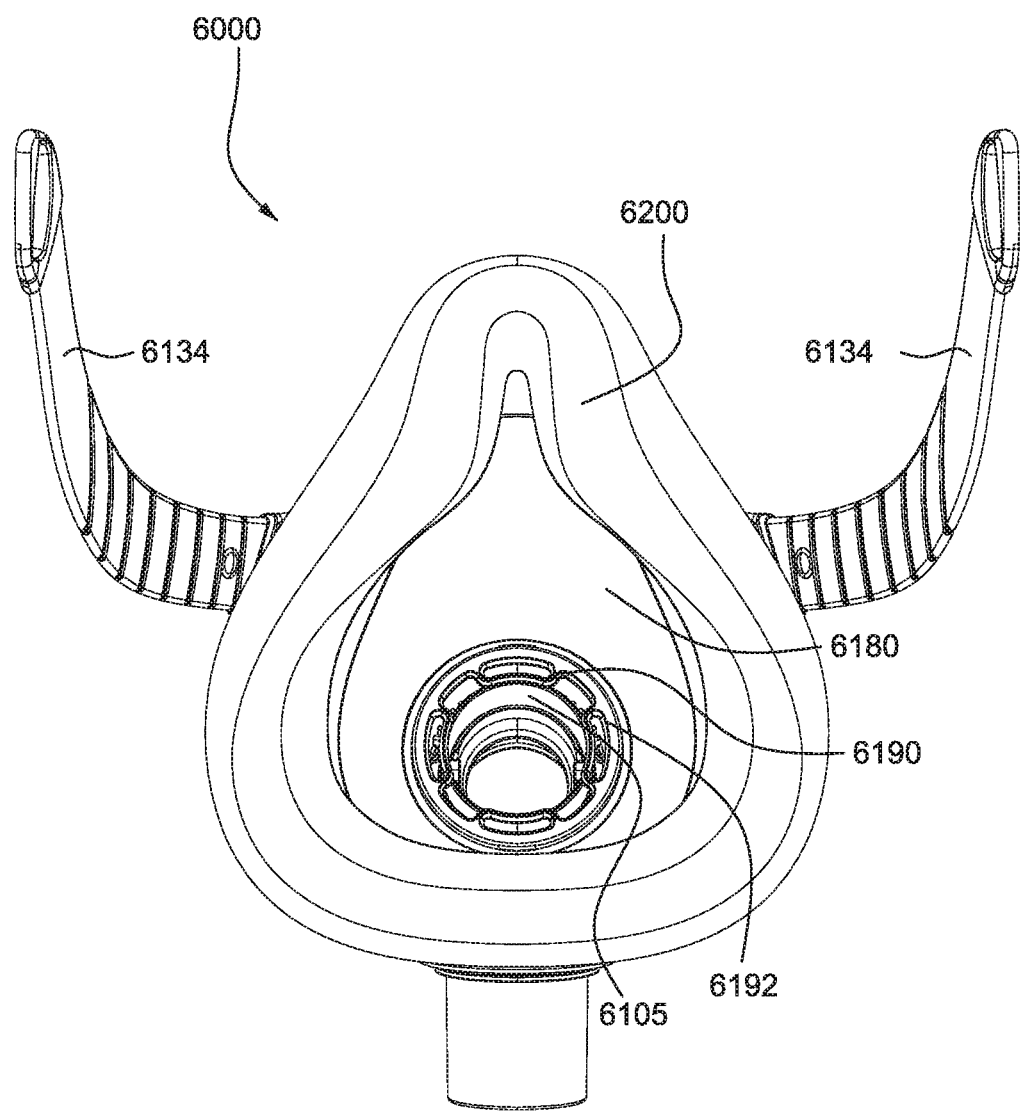

FIG. 12 is a rear view of the patient interface shown in FIG. 10.

Figure 13:
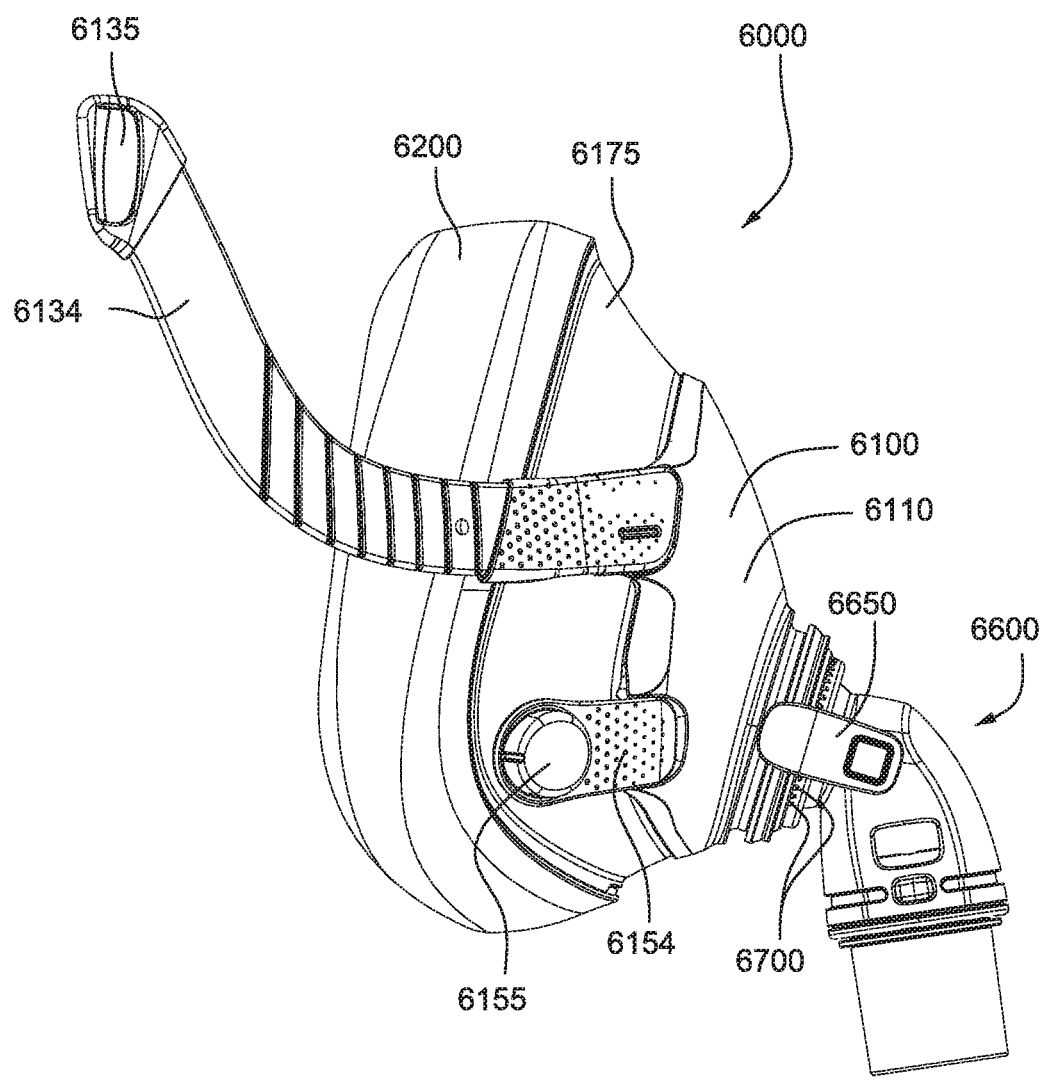

FIG. 13 is a side view of the patient interface shown in FIG. 10.

Figure 14:
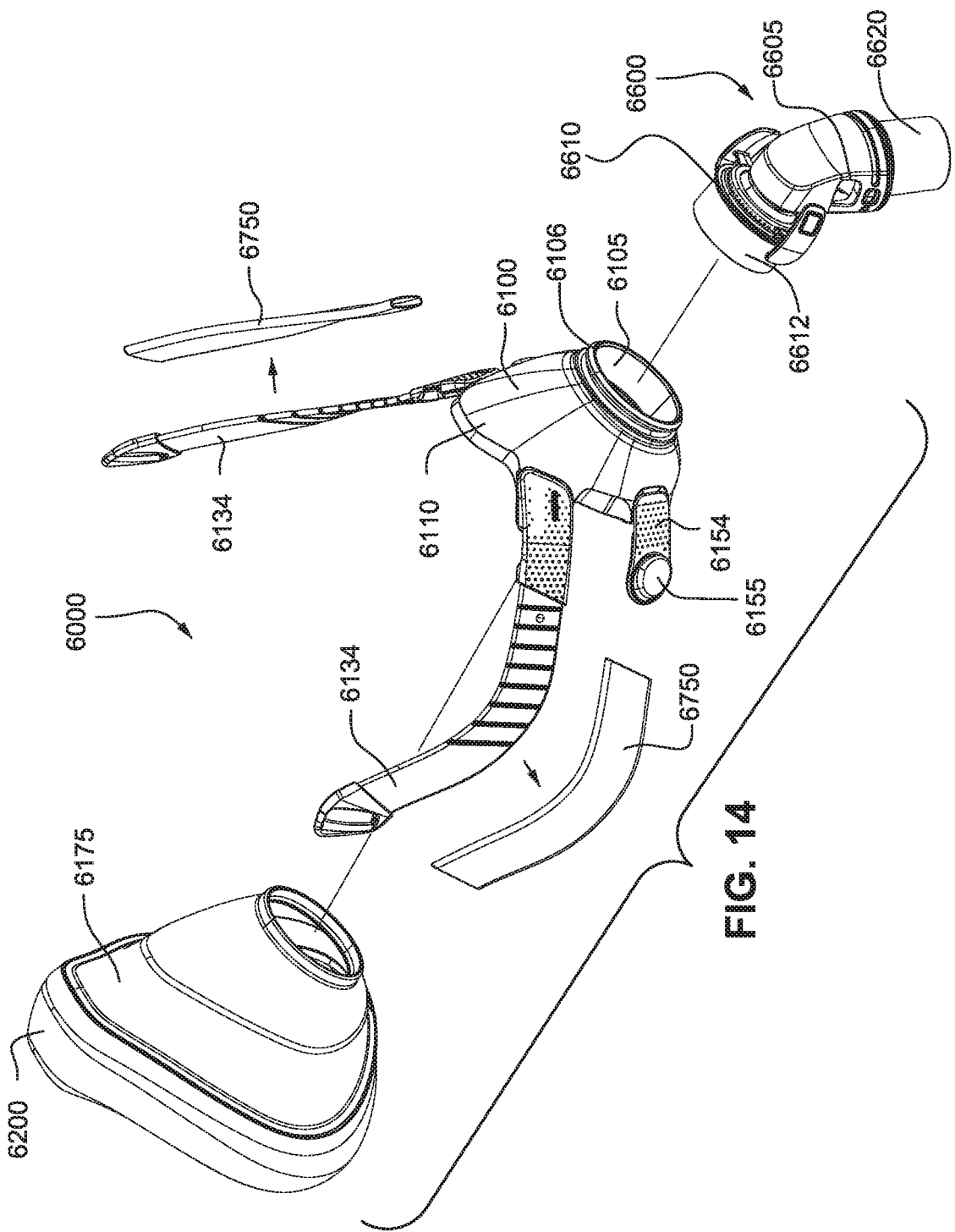

FIG. 14 is an exploded view of the patient interface shown in FIG. 9 showing the cushion assembly, frame assembly, arm covers, and elbow assembly.

Figure 15:
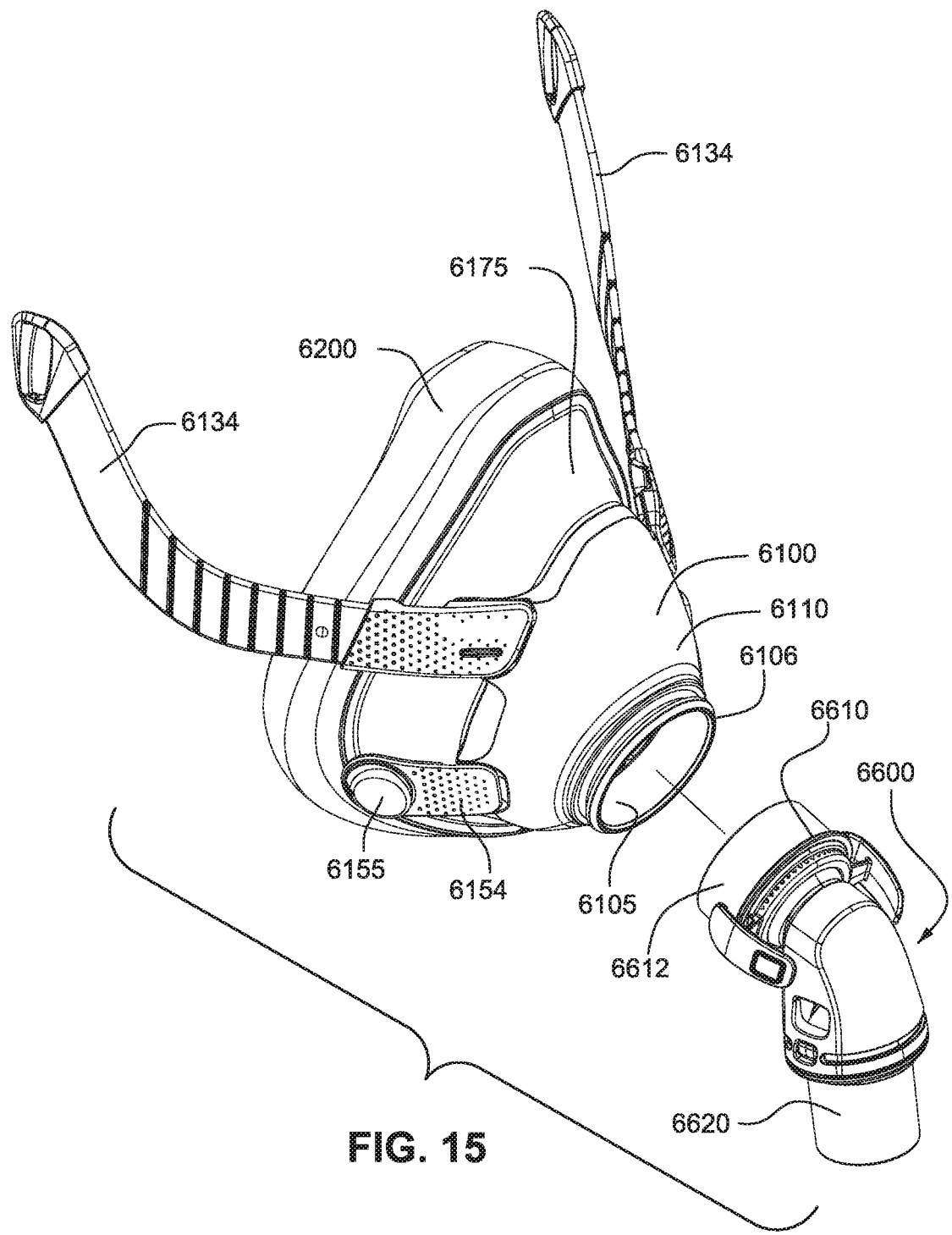

FIG. 15 is an exploded view of the patient interface shown in FIG. 10 showing the cushion assembly and frame assembly removably connected with the elbow assembly removed.

Figure 16:
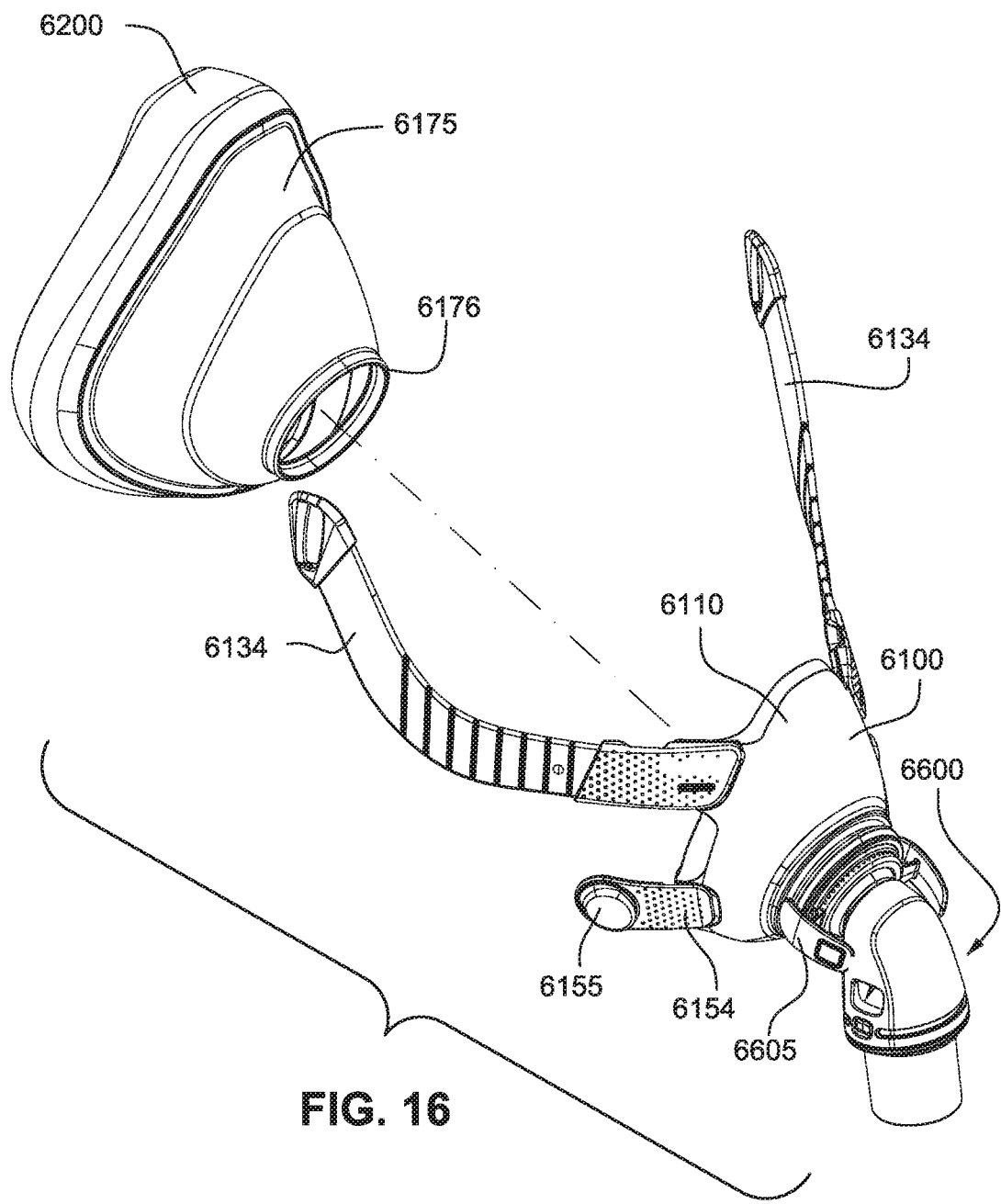

FIG. 16 is an exploded view of a patient interface shown in FIG. 10 showing the frame assembly and elbow assembly removably connected with the cushion assembly removed.

Figure 17:
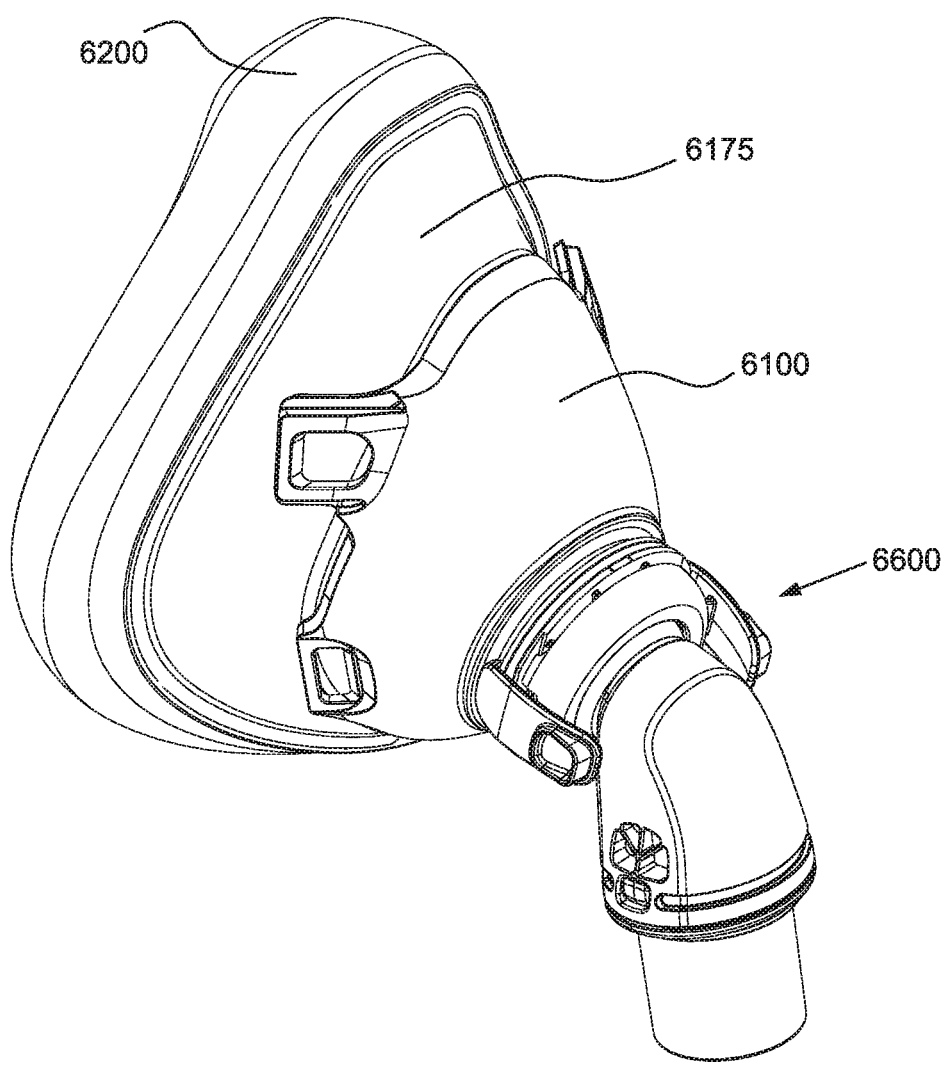

FIG. 17 is a perspective view of components of a patient interface assembled together according to an example of the present technology.

Figure 18:
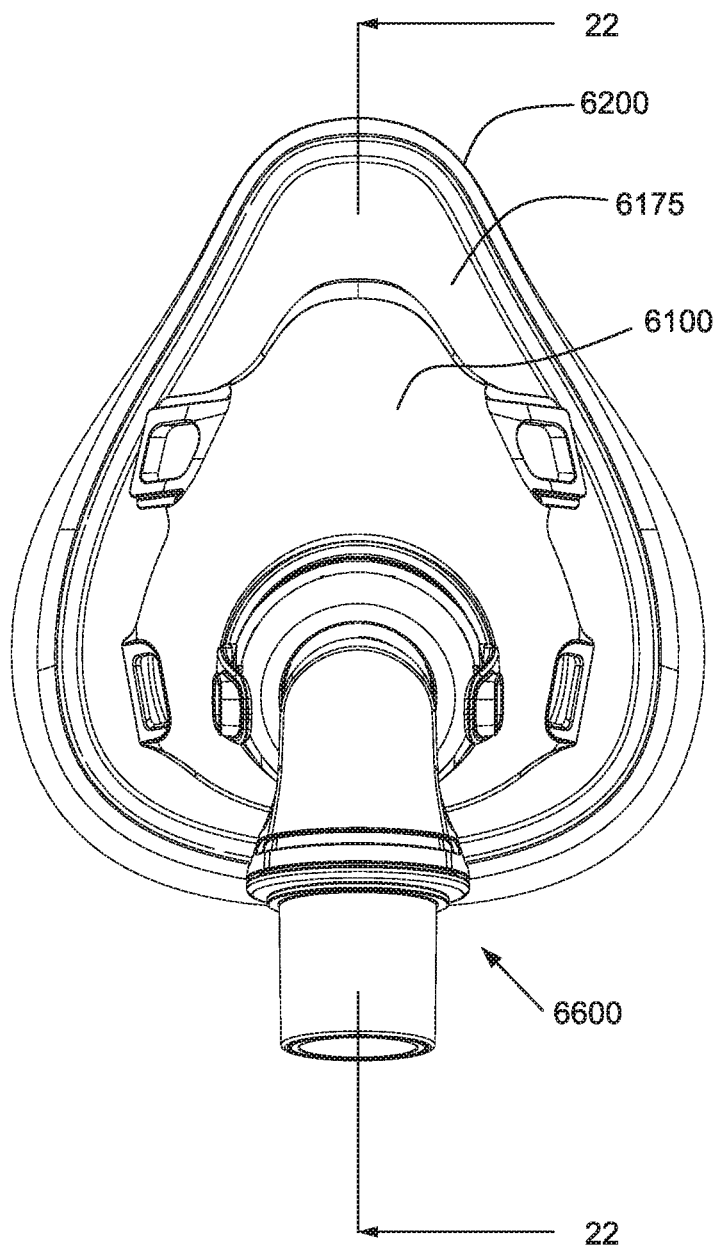

FIG. 18 is anterior view of components of a patient interface assembled together according to an example of the present technology.

Figure 19:
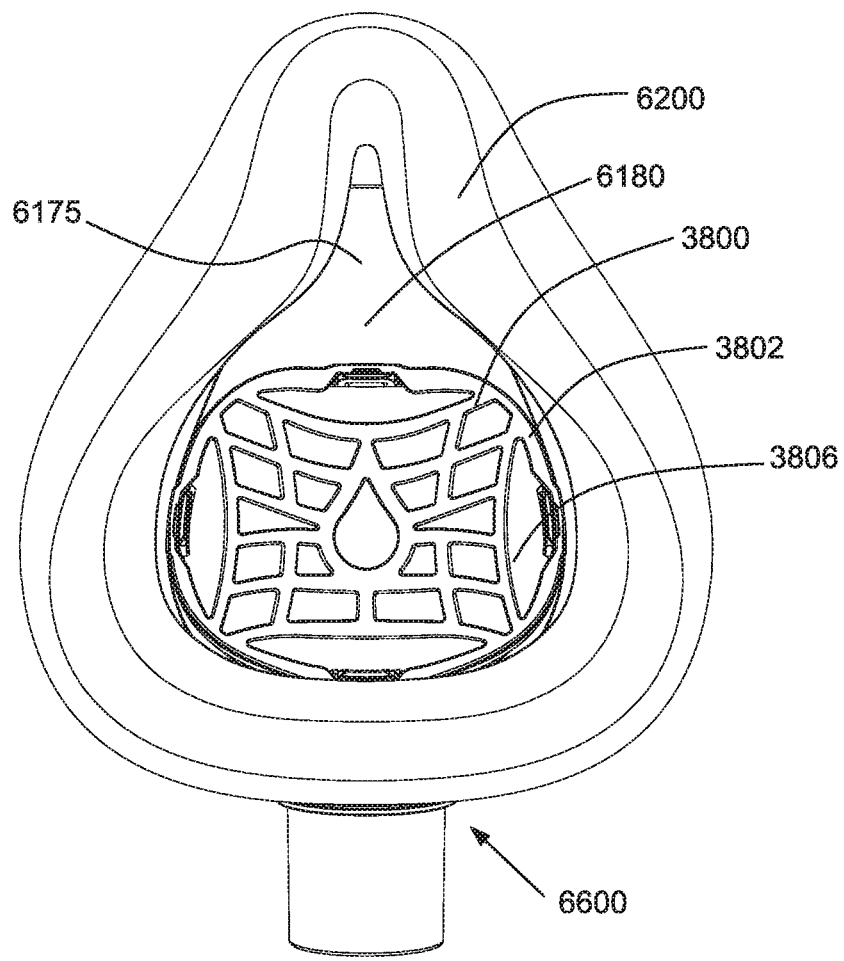

FIG. 19 is a posterior view of components of a patient interface, including a plenum chamber insert, assembled together according to an example of the present technology.

Figure 20:
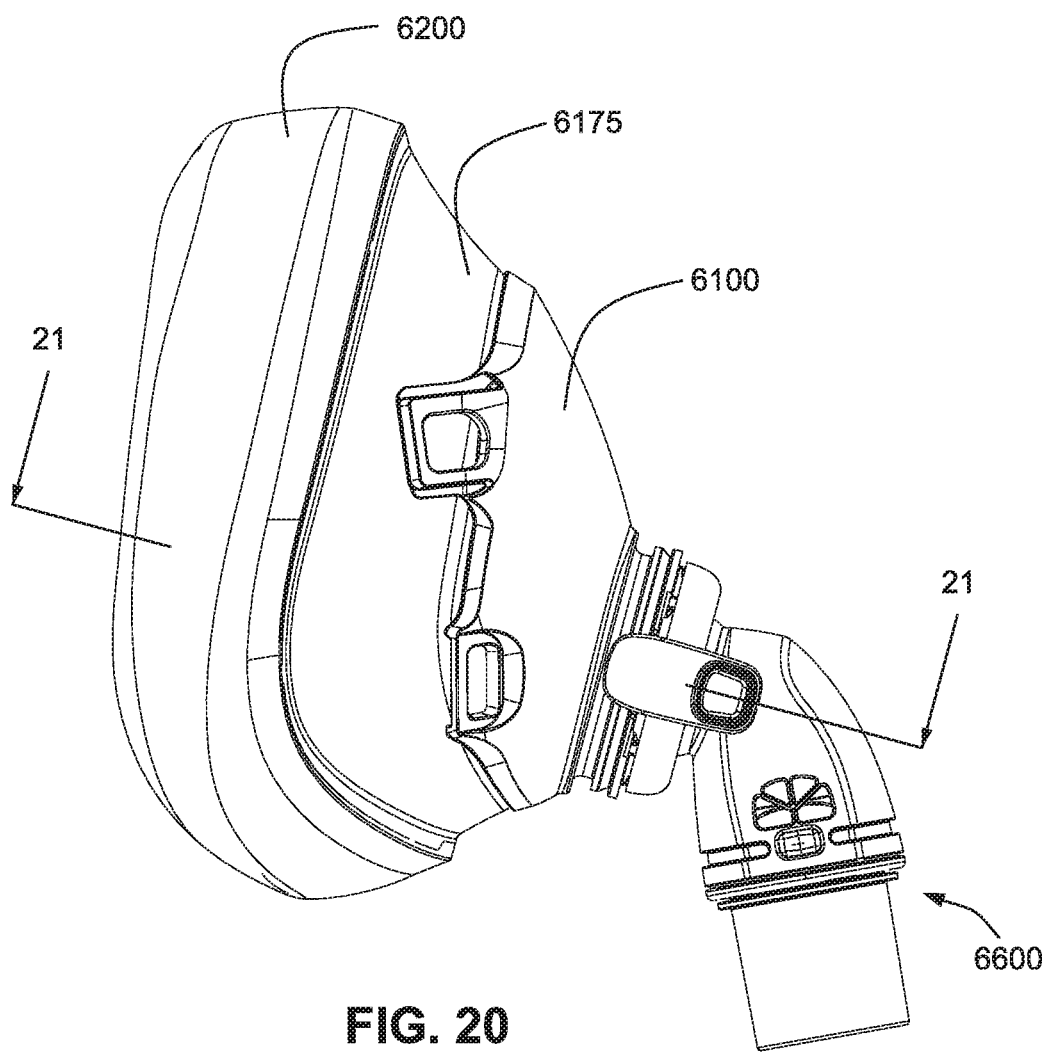

FIG. 20 is a lateral view of components of a patient interface assembled together according to an example of the present technology.

Figure 21:
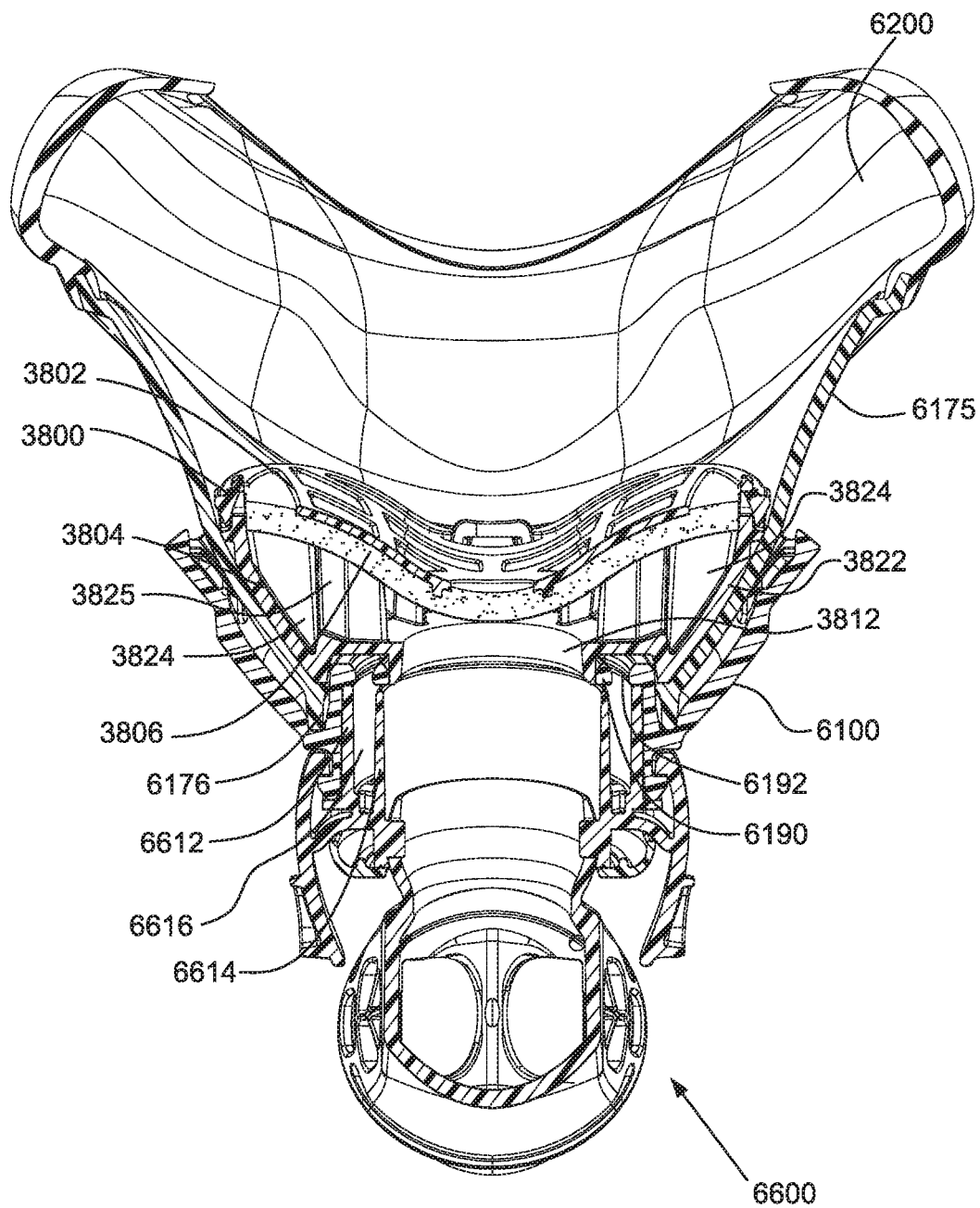

FIG. 21 is a cross-sectional view, taken through line 21-21 of FIG. 20, of components of a patient interface, including a plenum chamber insert, assembled together according to an example of the present technology.

Figure 22:
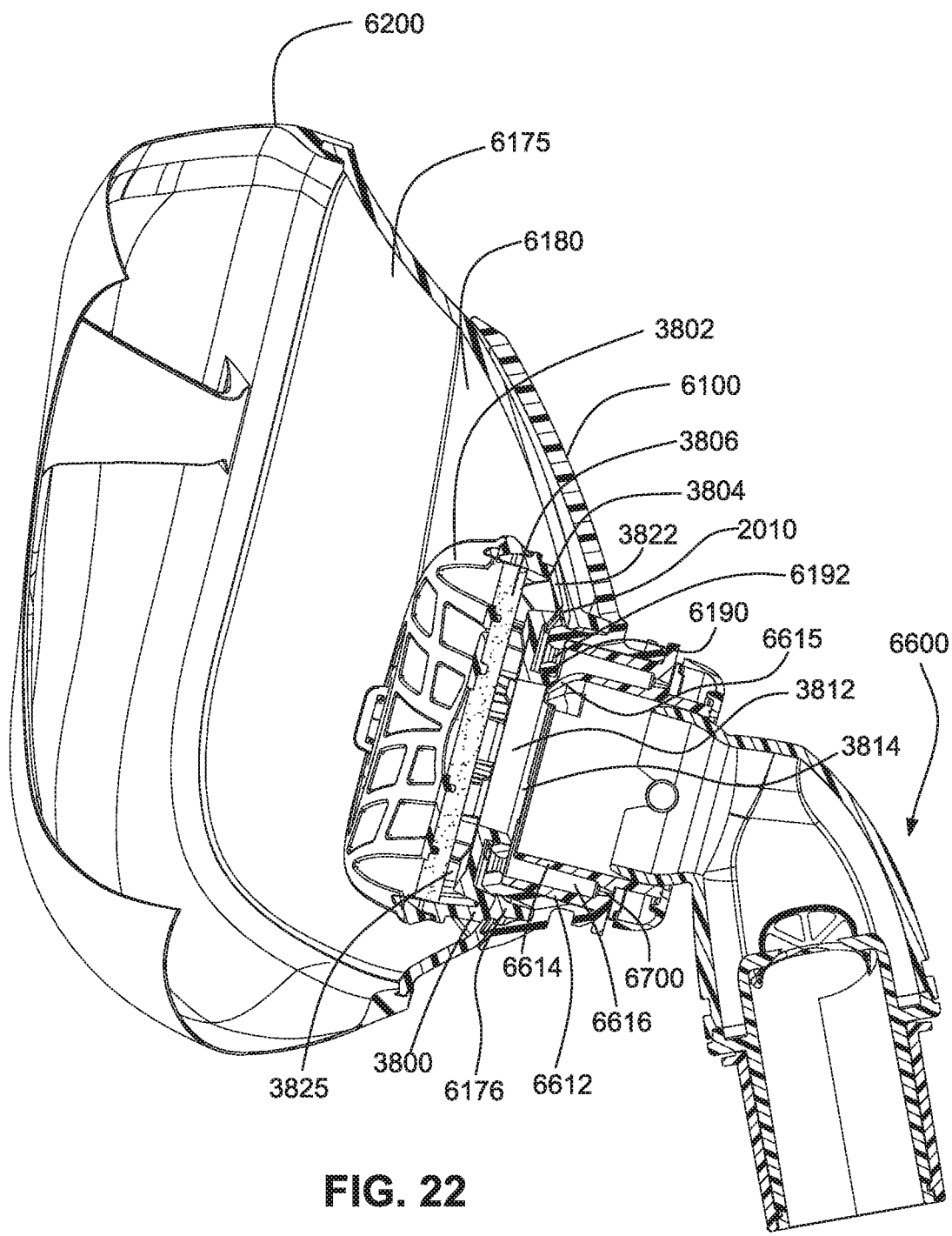

FIG. 22 is a cross-sectional view, taken through line 22-22 of FIG. 18, of components of a patient interface, including a plenum chamber insert, assembled together according to an example of the present technology.

Figure 23:
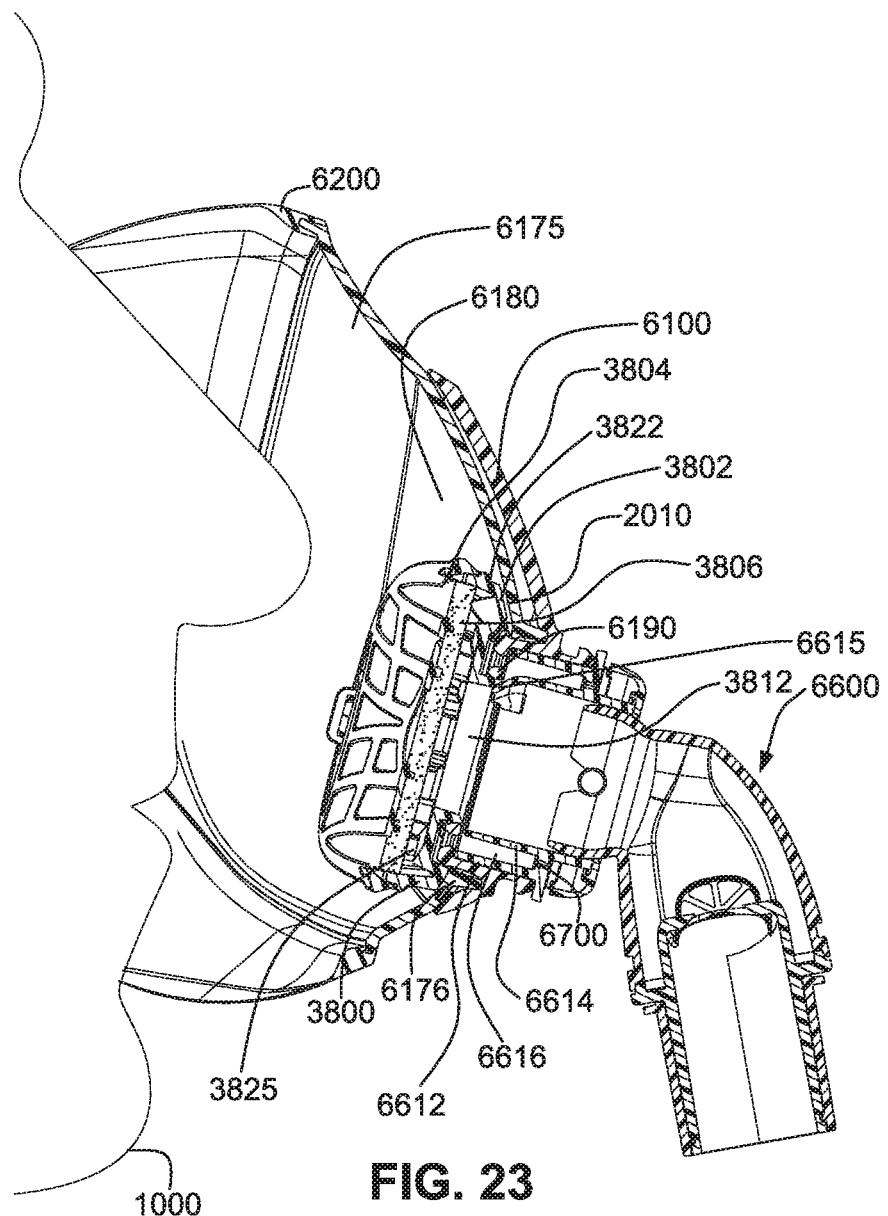

FIG. 23 is the cross-sectional view of FIG. 22 with the system against a patient's face.

Figure 24:
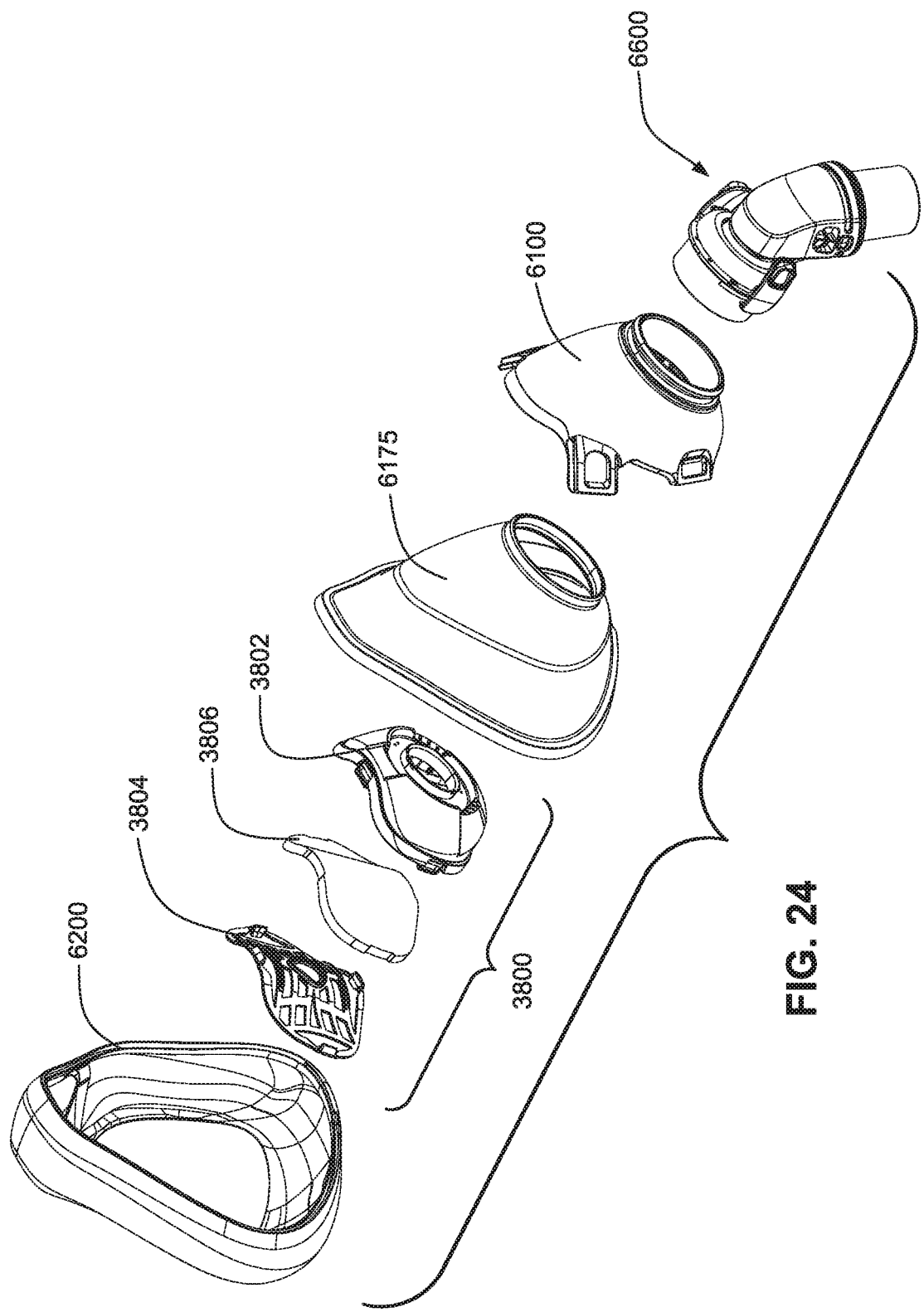

FIG. 24 is an exploded view of a seal-forming structure, a chassis, a plenum chamber insert, a frame assembly, and an elbow assembly according to an example of the present technology.

Figure 25:
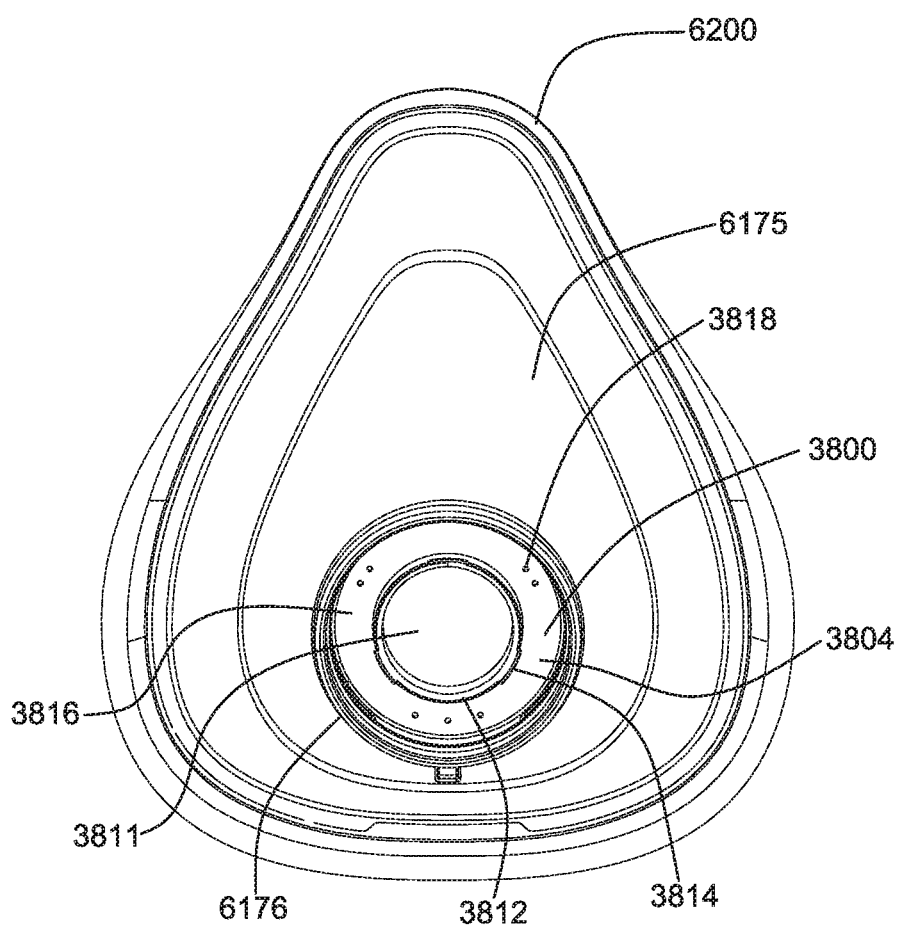

FIG. 25 is an anterior view of a seal-forming structure, a chassis, and a plenum chamber insert according to an example of the present technology.

Figure 26:
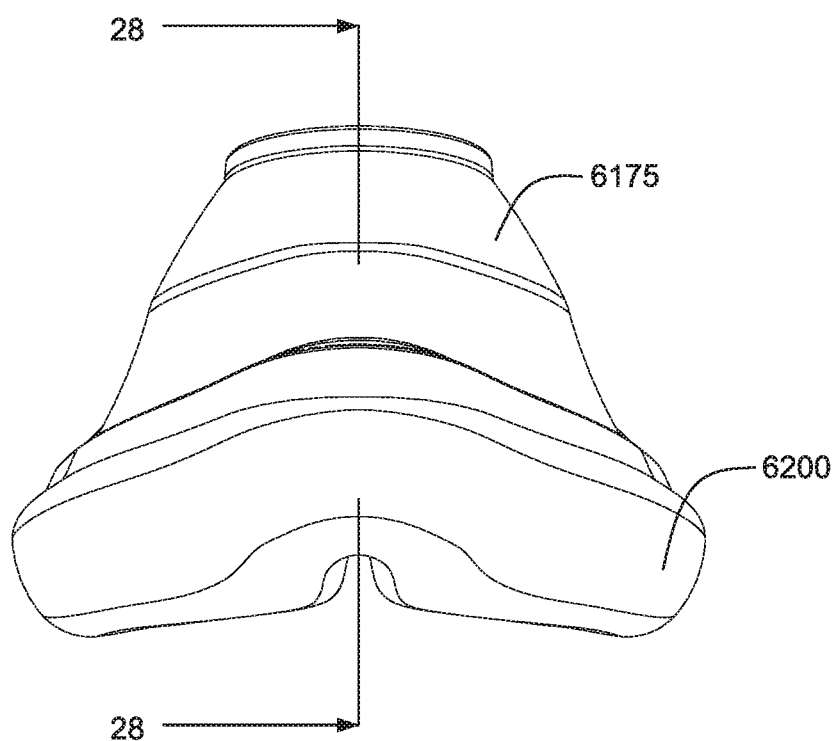

FIG. 26 is a superior view of a seal-forming structure, a chassis, and a plenum chamber insert according to an example of the present technology.

Figure 27:
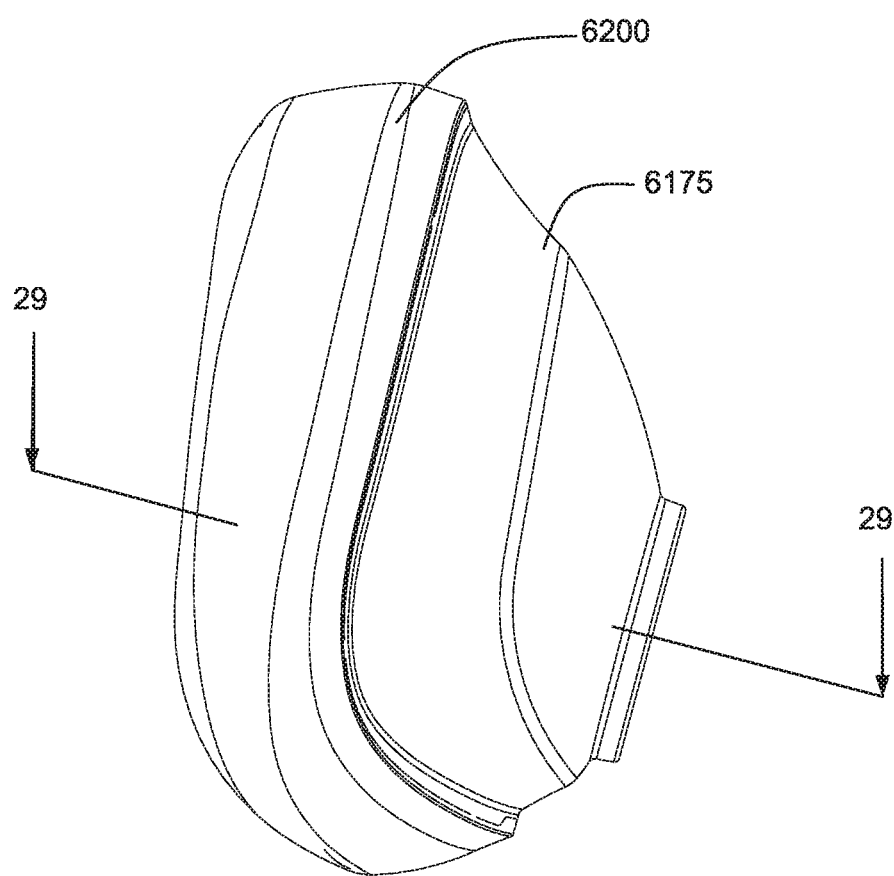

FIG. 27 is a lateral view of a seal-forming structure, a chassis, and a plenum chamber insert according to an example of the present technology.

Figure 28:
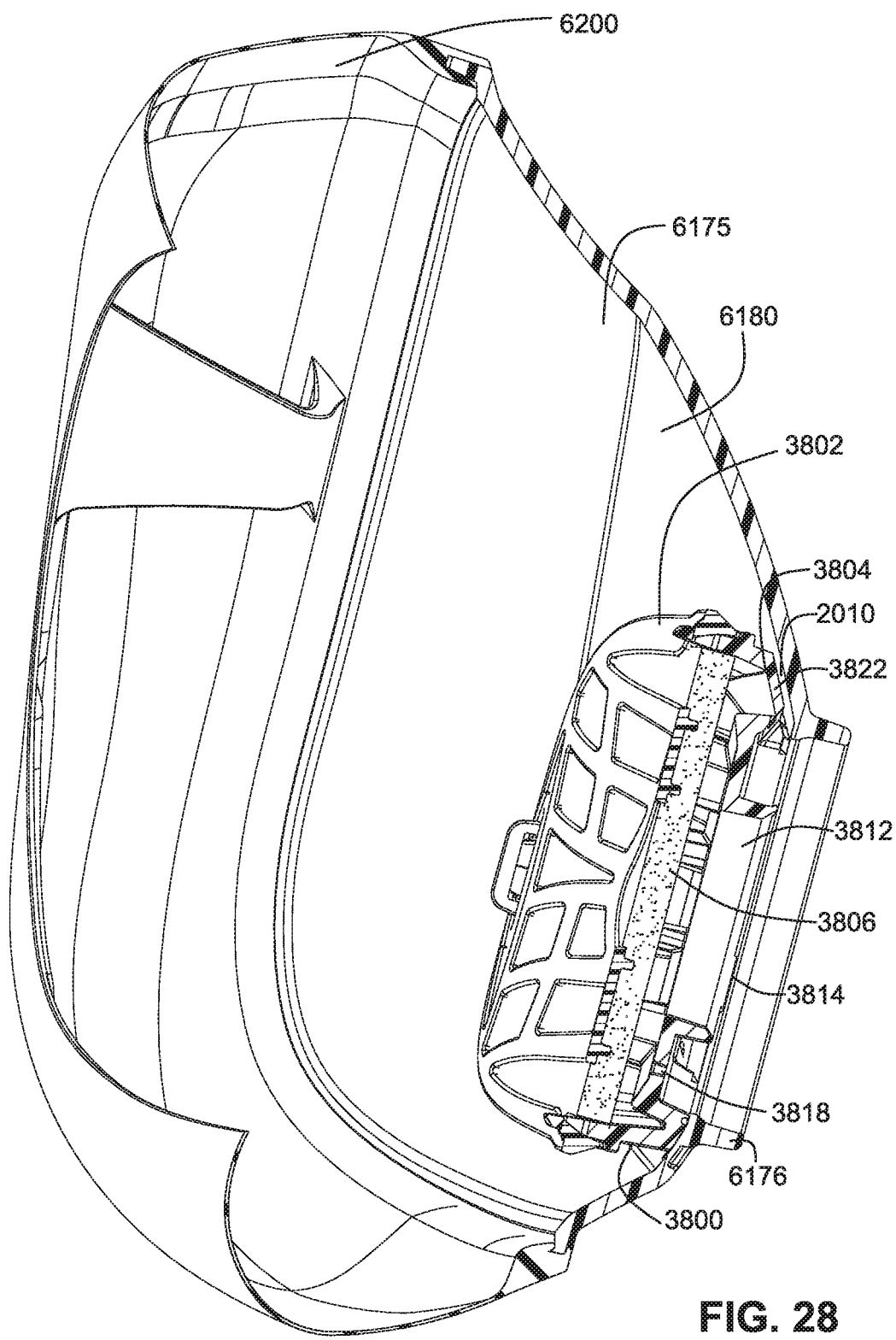

FIG. 28 is a cross-sectional view of a seal-forming structure, a chassis, and a plenum chamber insert taken through line 28-28 of FIG. 26 according to an example of the present technology.

Figure 29:
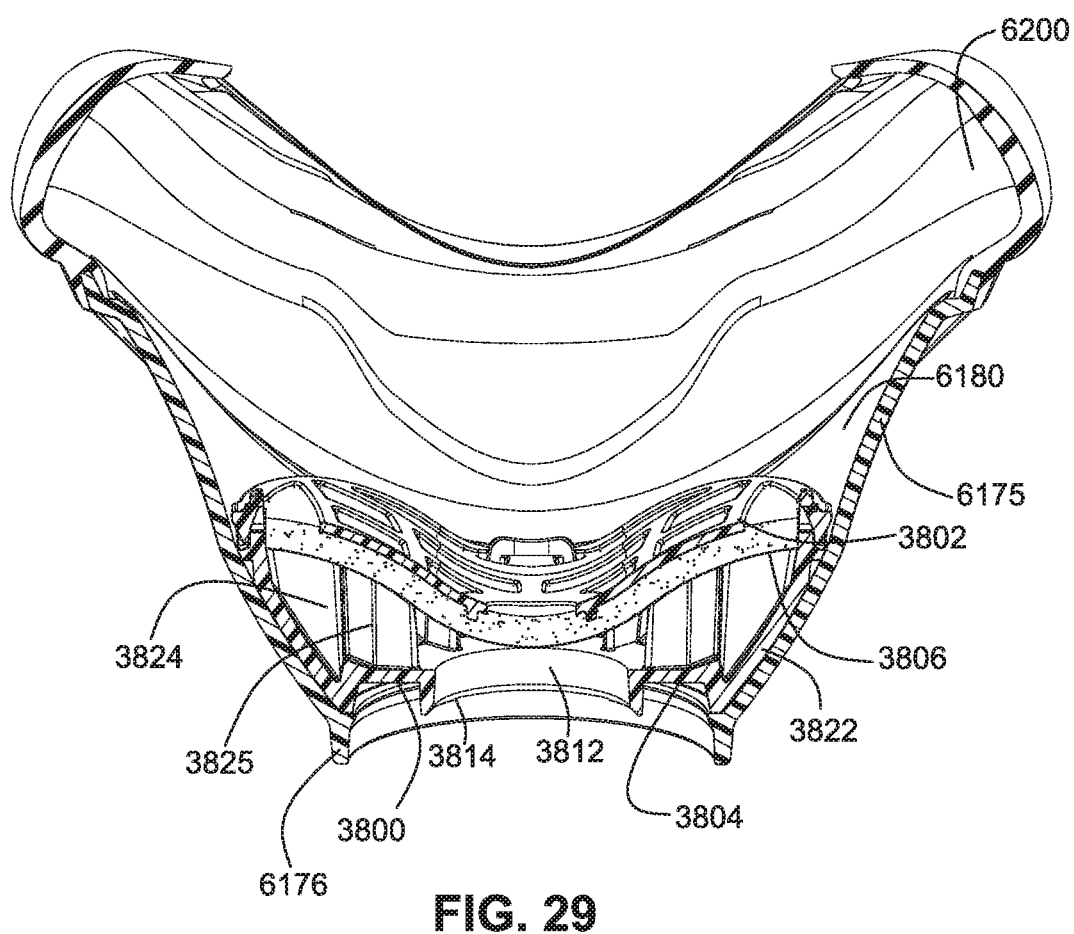

FIG. 29 is a cross-sectional view of a seal-forming structure, a chassis, and a plenum chamber insert taken through line 29-29 of FIG. 27 according to an example of the present technology.

Figure 30:
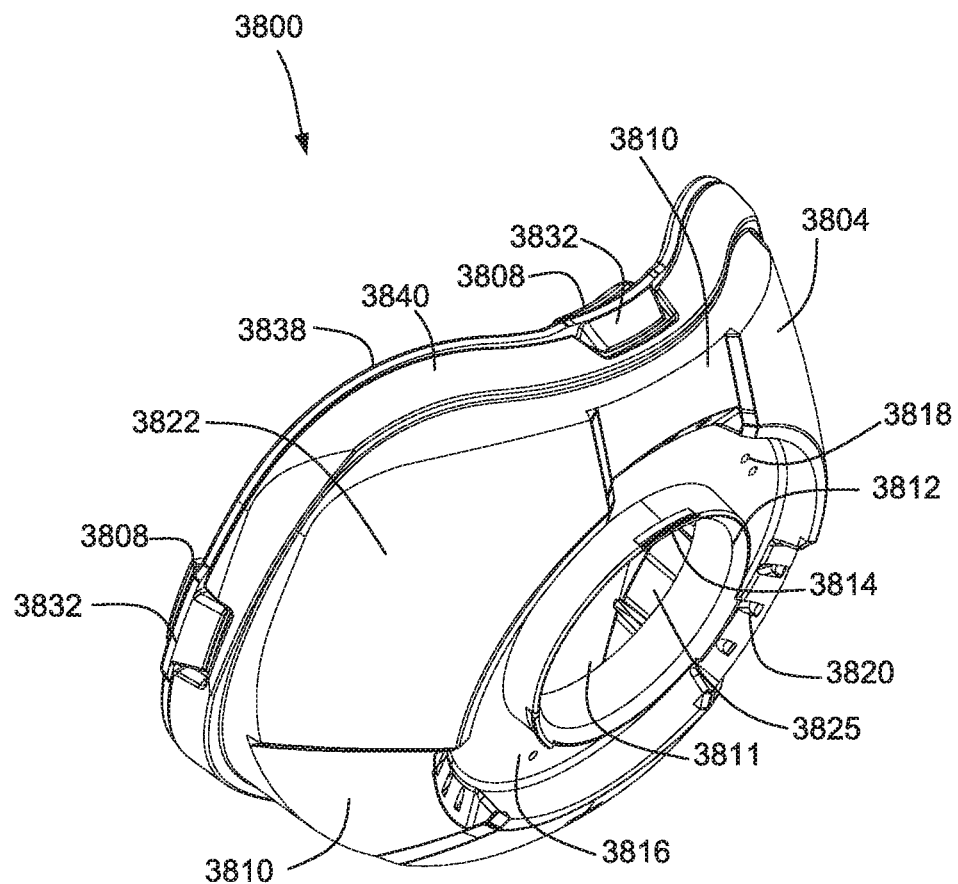

FIG. 30 is an anterior perspective view of a plenum chamber insert according to an example of the present technology.

Figure 31:
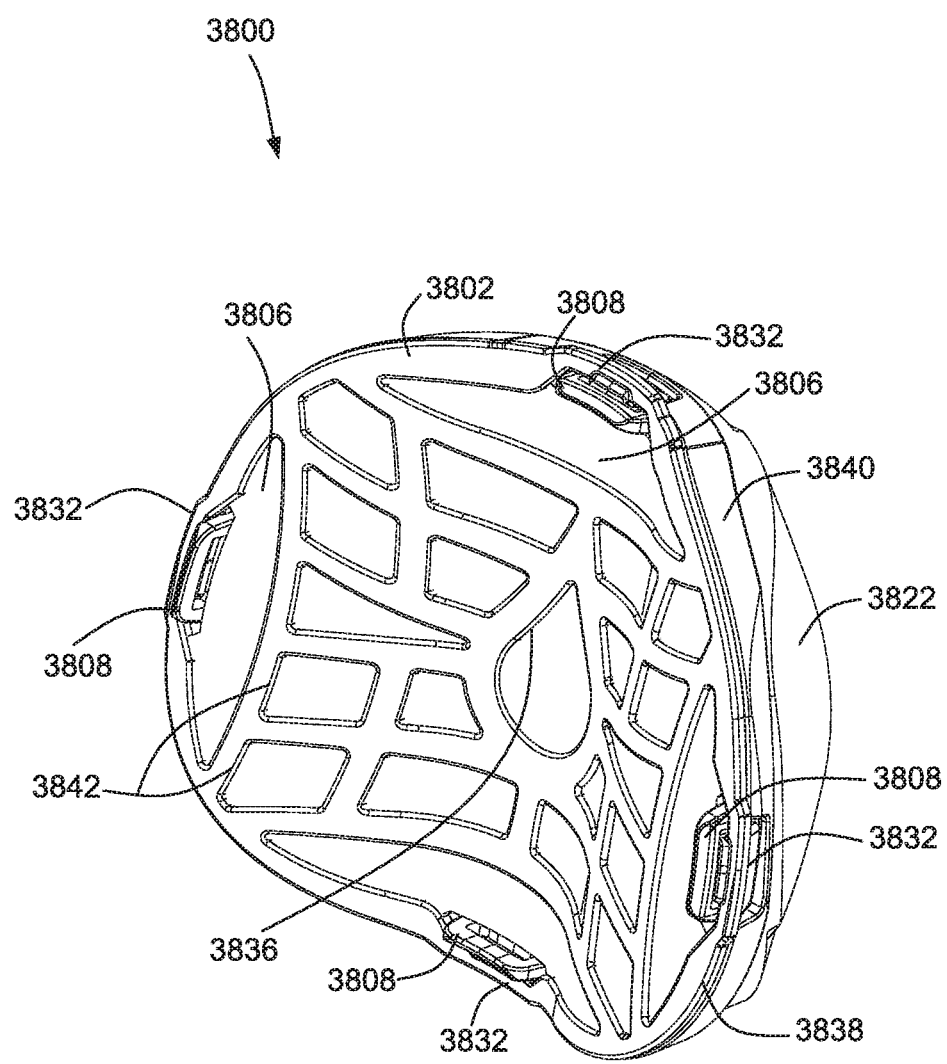

FIG. 31 is a posterior perspective view of a plenum chamber insert according to an example of the present technology.

Figure 32:
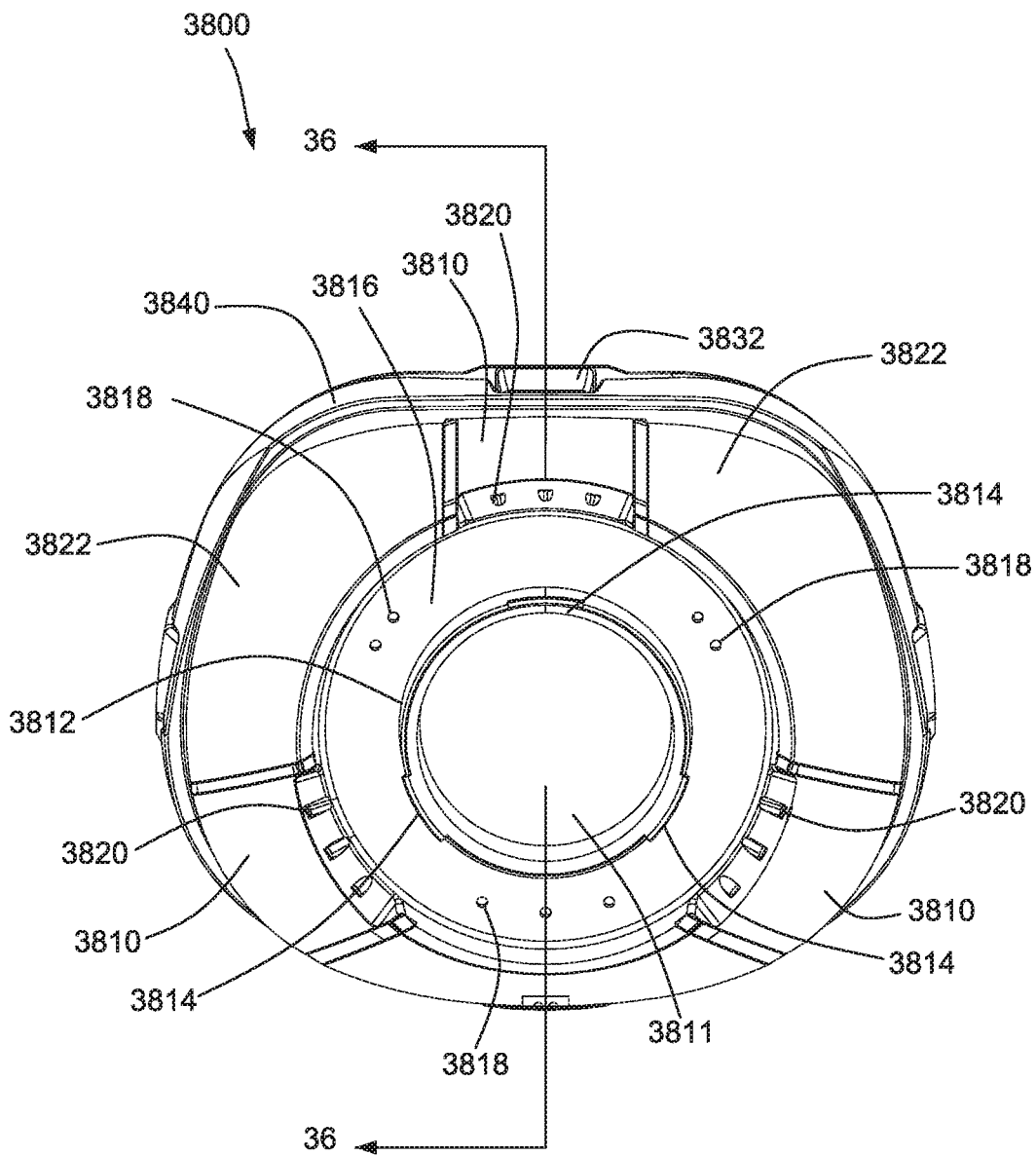

FIG. 32 is an anterior view of a plenum chamber insert according to an example of the present technology.

Figure 33:
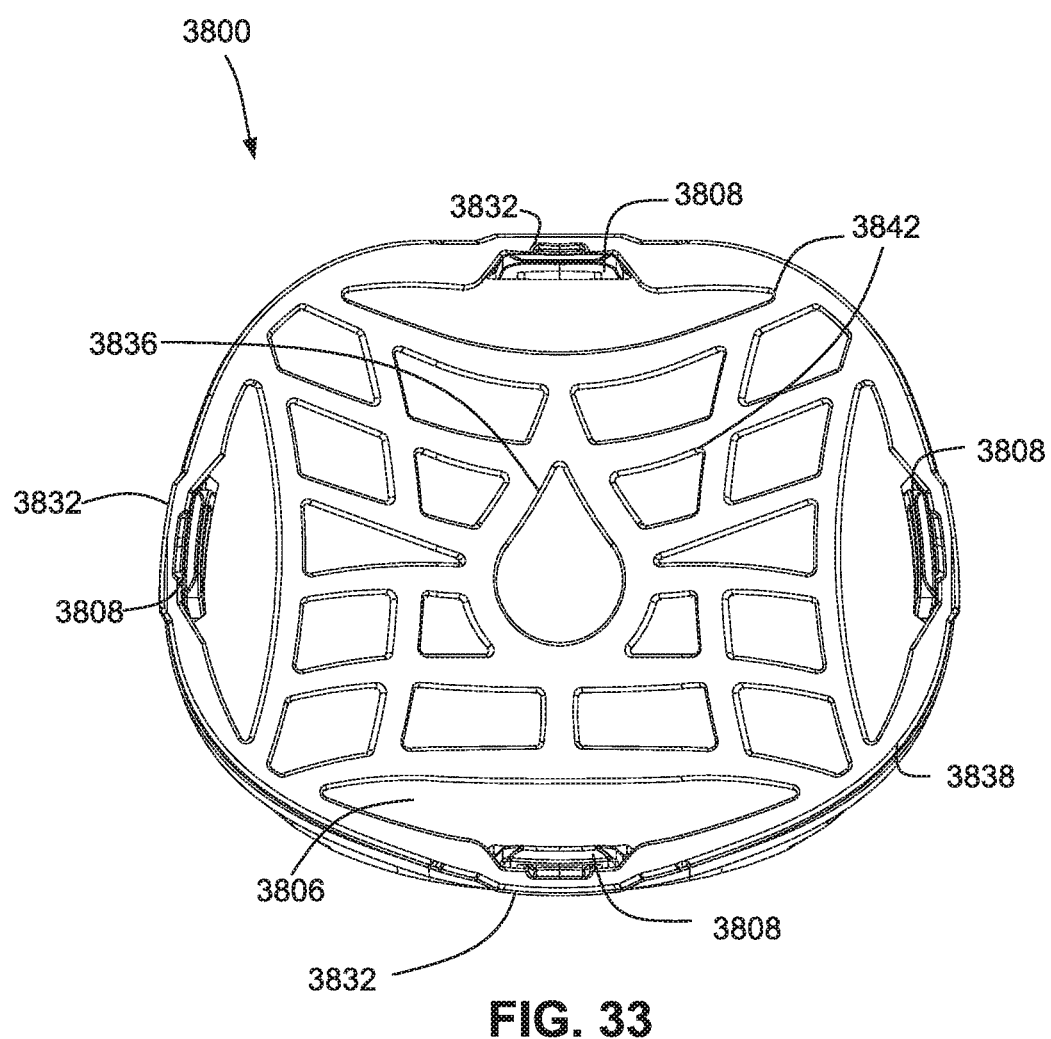

FIG. 33 is a posterior view of a plenum chamber insert according to an example of the present technology.

Figure 34:
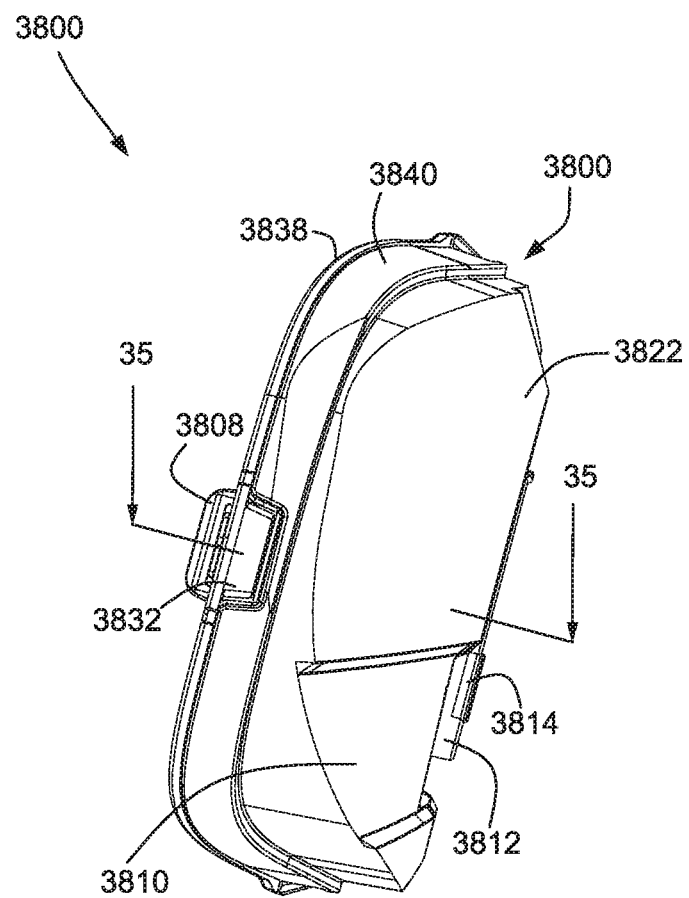

FIG. 34 is a lateral view of a plenum chamber insert according to an example of the present technology.

Figure 35:
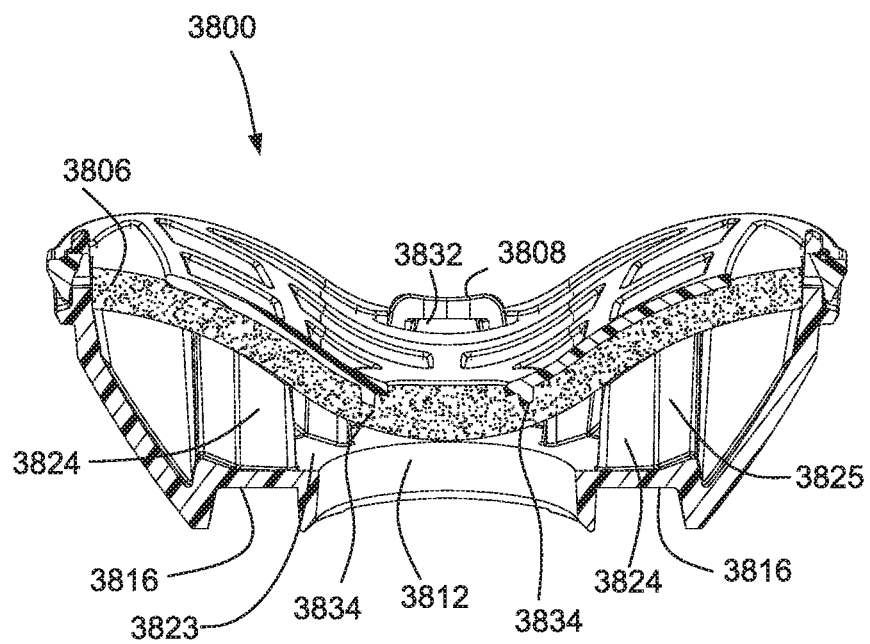

FIG. 35 is a cross-sectional view of a plenum chamber insert taken through line 35-35 of FIG. 34 according to an example of the present technology.

Figure 36:
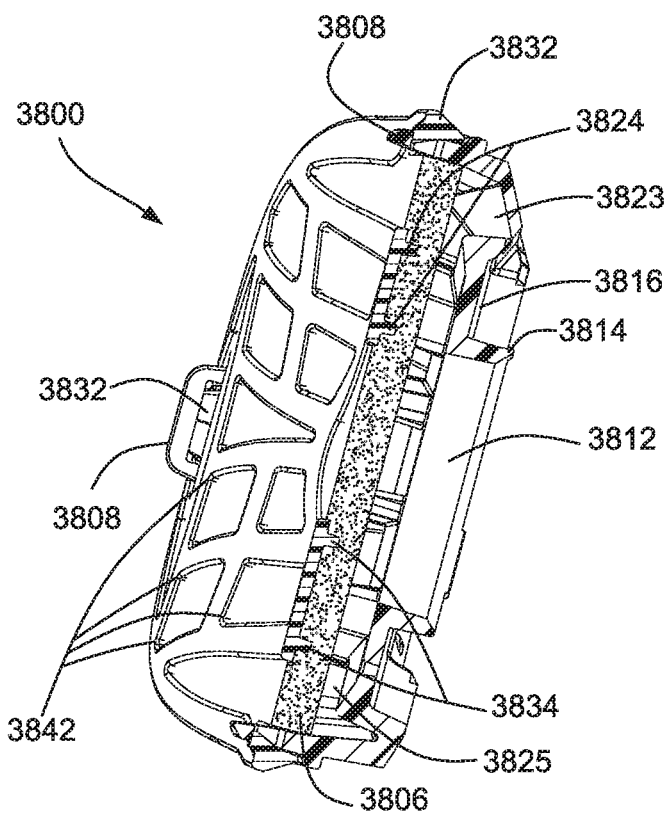

FIG. 36 is a cross-sectional view of a plenum chamber insert taken through line 36-36 of FIG. 32 according to an example of the present technology.

Figure 37:
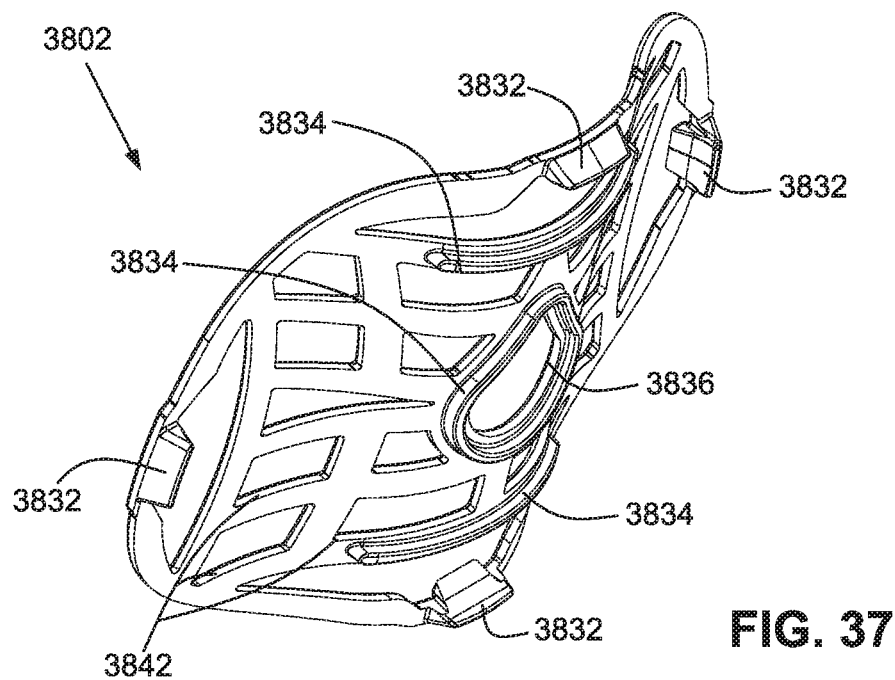

FIG. 37 is an anterior perspective view of a posterior insert frame of a plenum chamber insert according to an example of the present technology.

Figure 38:
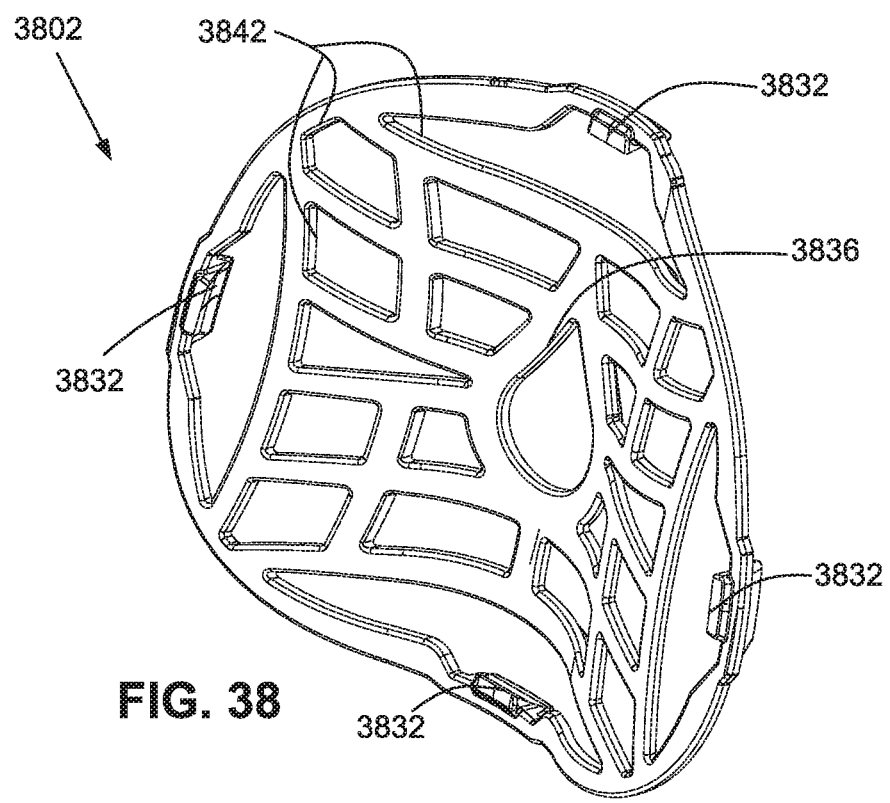

FIG. 38 is a posterior perspective view of a posterior insert frame of a plenum chamber insert according to an example of the present technology.

Figure 39:
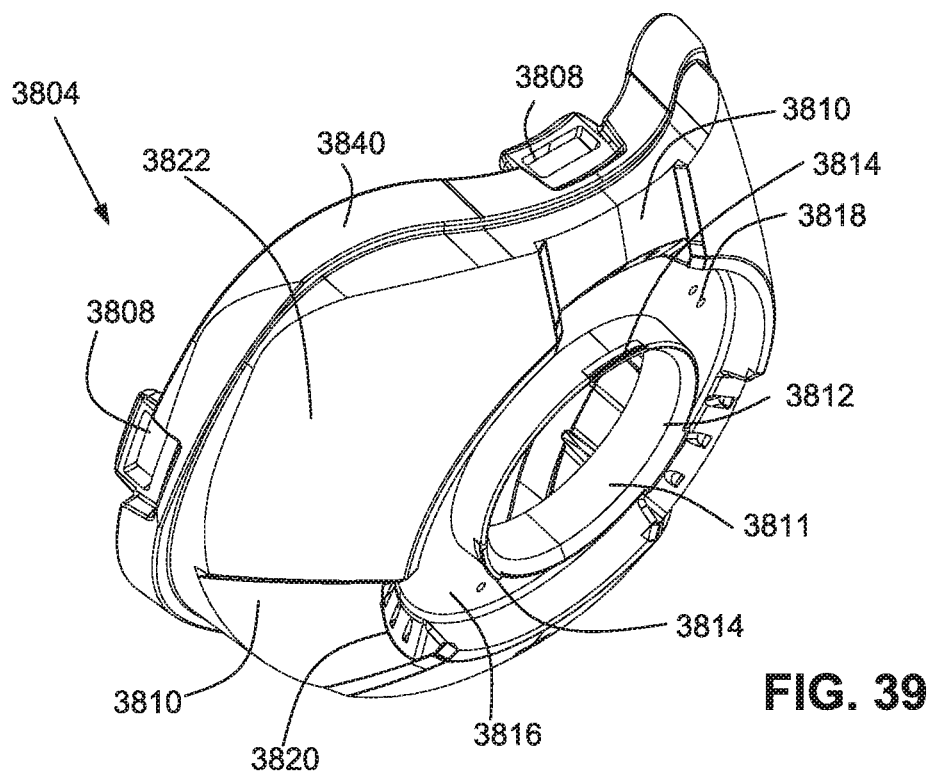

FIG. 39 is an anterior perspective view of an anterior insert frame of a plenum chamber insert according to an example of the present technology.

Figure 40:
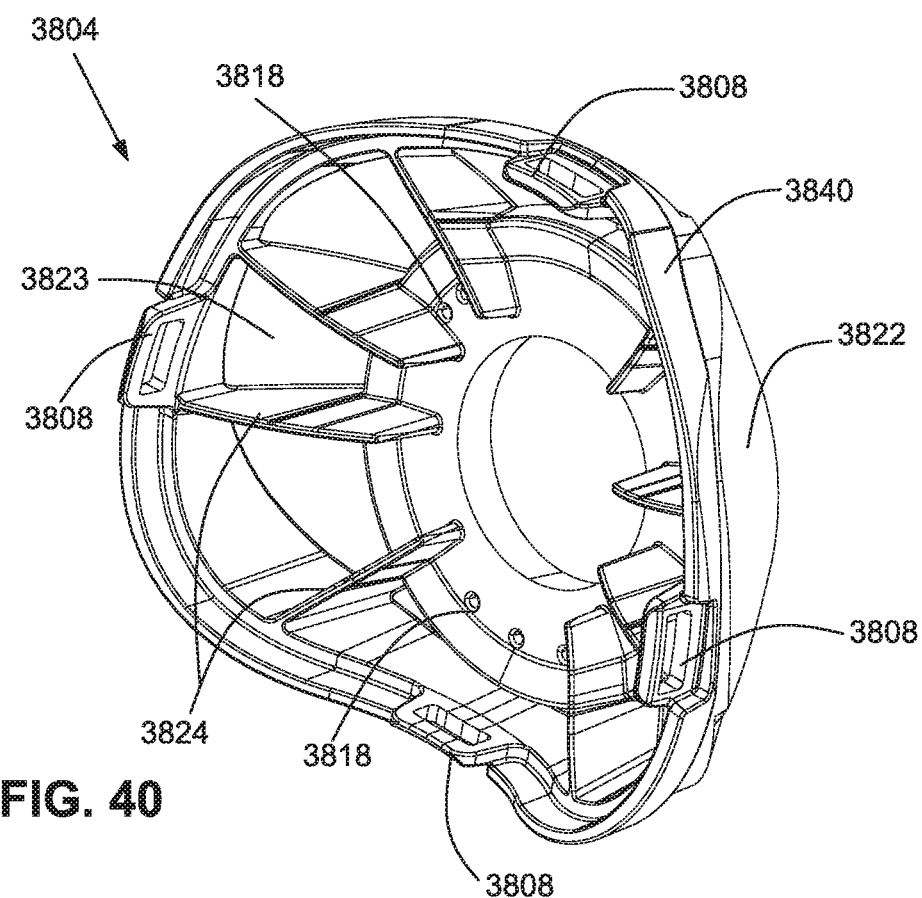

FIG. 40 is a posterior perspective view of an anterior insert frame of a plenum chamber insert according to an example of the present technology.

Figure 41:
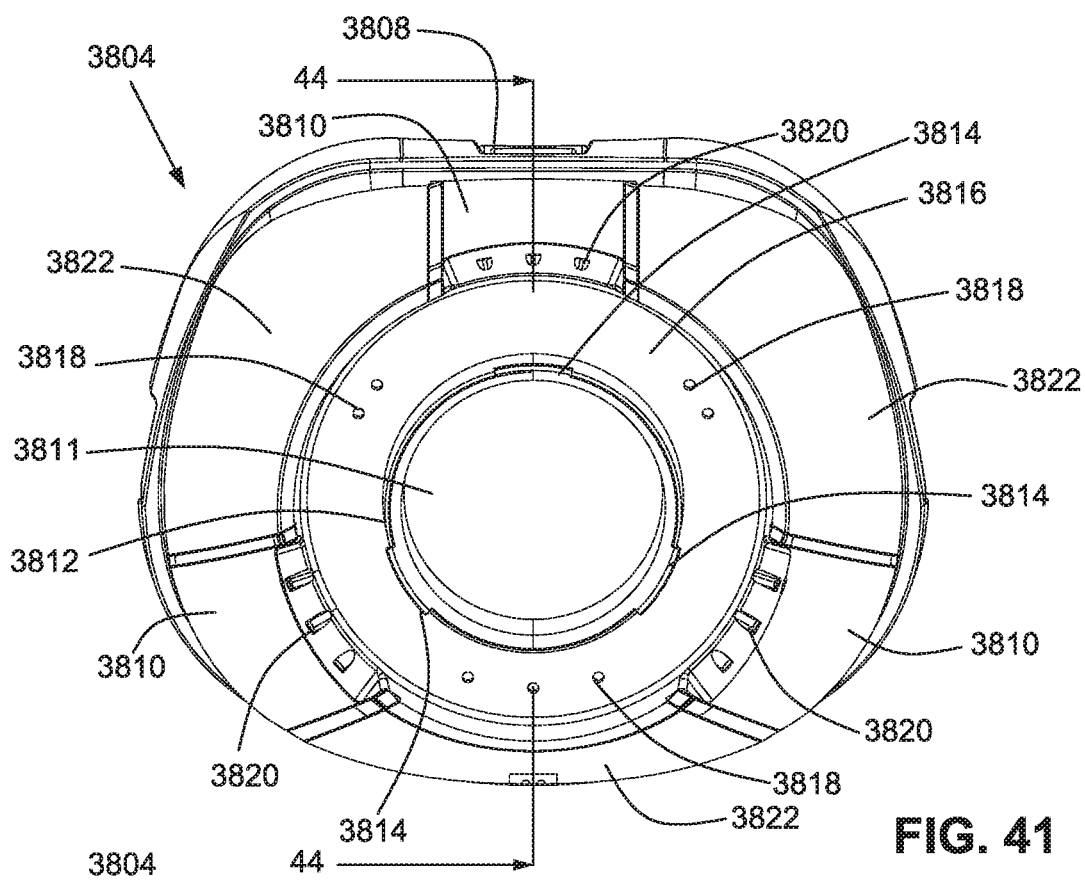

FIG. 41 is an anterior view of an anterior insert frame of a plenum chamber insert according to an example of the present technology.

Figure 42:
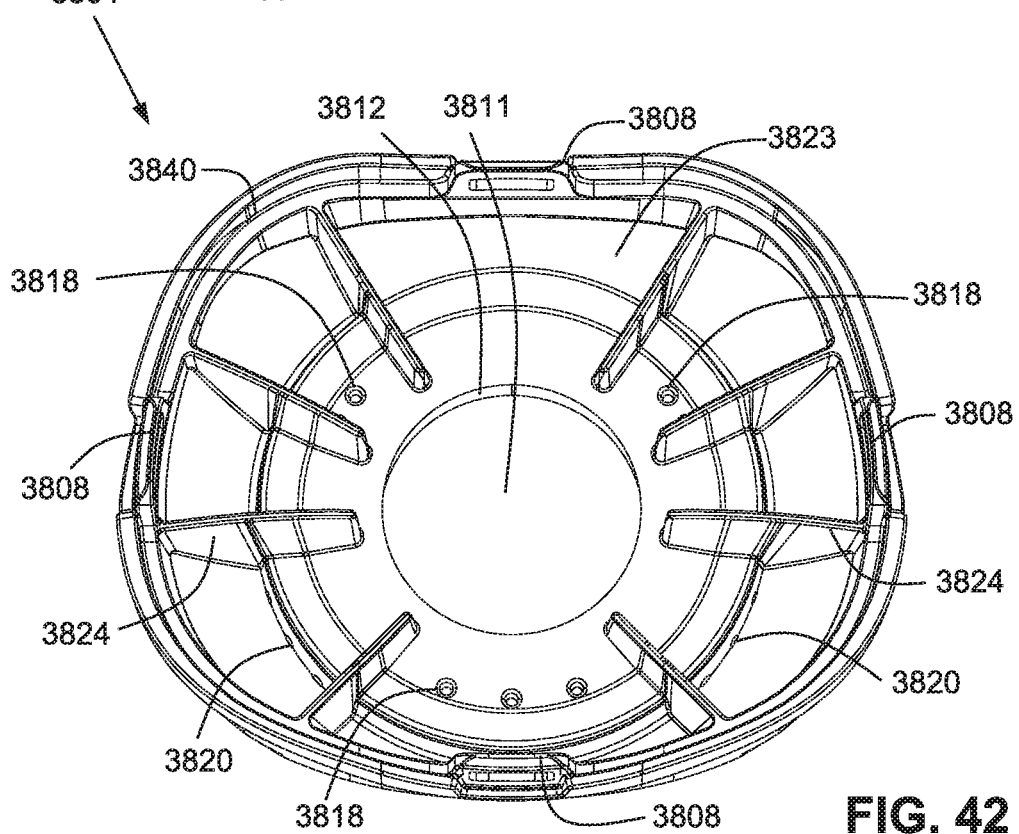

FIG. 42 is a posterior view of an anterior insert frame of a plenum chamber insert according to an example of the present technology.

FIG. 43 is a lateral view of an anterior insert frame of a plenum chamber insert according to an example of the present technology.

FIG. 44 is a cross-sectional view of an anterior insert frame of a plenum chamber insert taken through line 44-44 of FIG. 41 according to an example of the present technology.

FIG. 45 is a cross-sectional view of an anterior insert frame of a plenum chamber insert taken through line 45-45 of FIG. 43 according to an example of the present technology.

Figure 46:
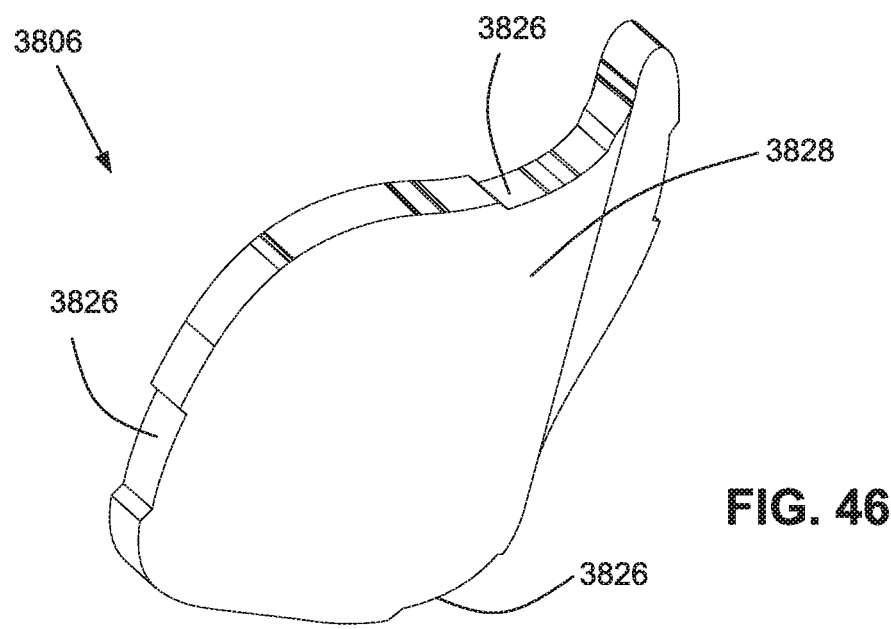

FIG. 46 is an anterior perspective view of heat and moisture exchanger (HMX) material of a plenum chamber insert according to an example of the present technology.

Figure 47:
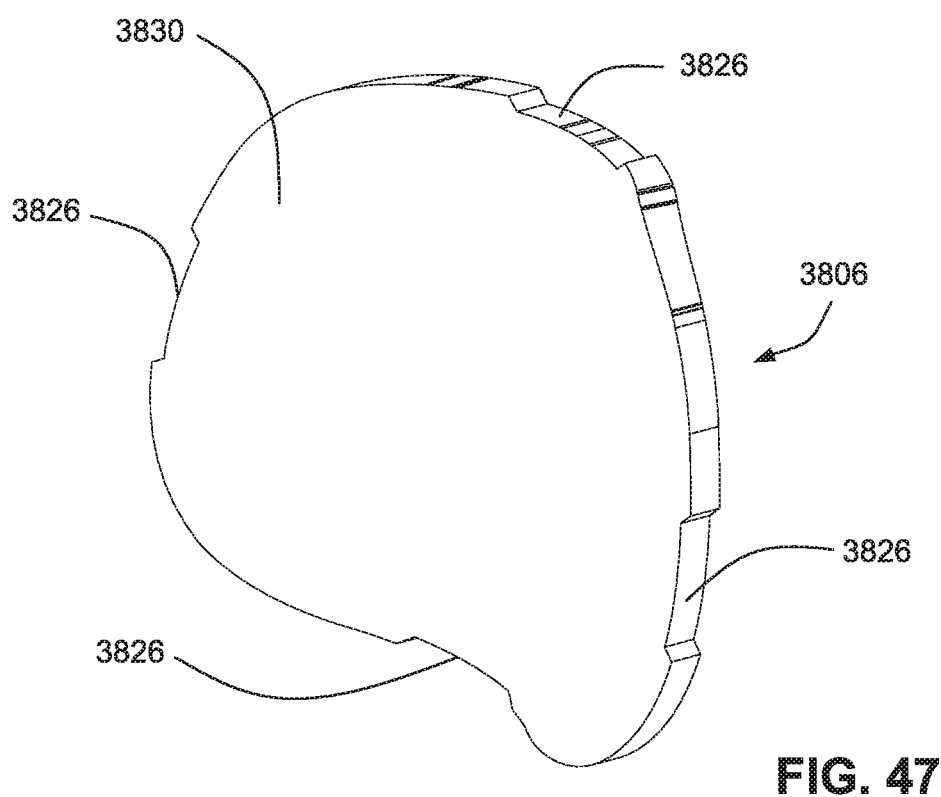

FIG. 47 is a posterior perspective view of heat and moisture exchanger (HMX) material of a plenum chamber insert according to an example of the present technology.

Figure 48:
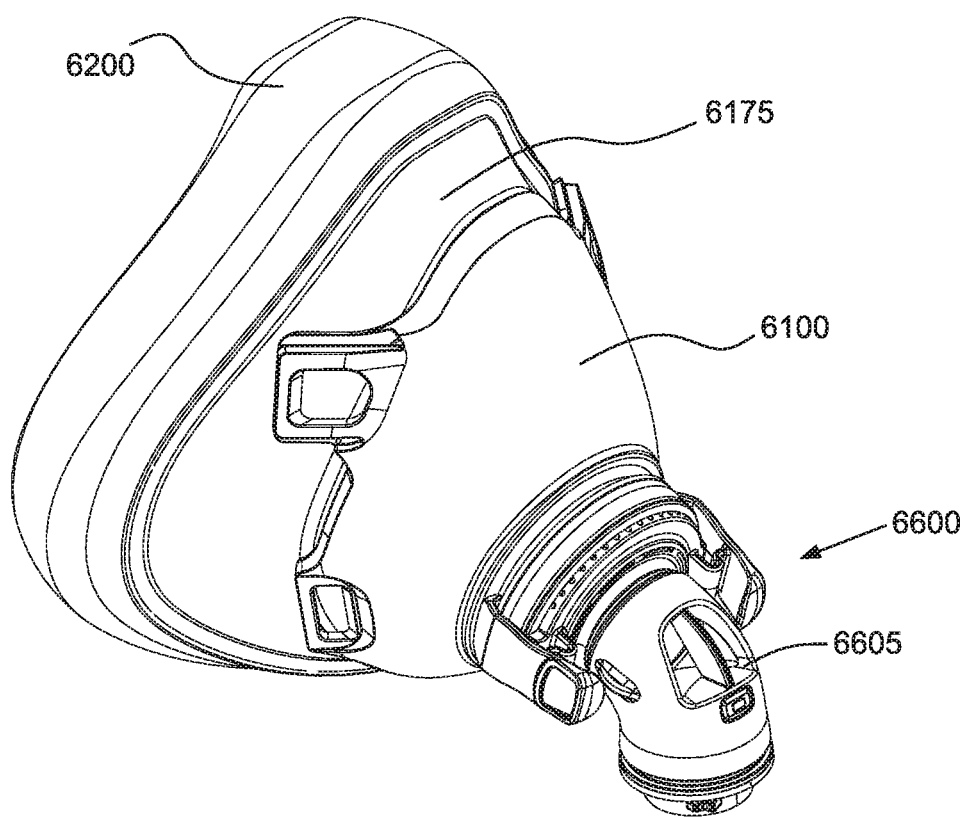

FIG. 48 is an anterior perspective view of a seal-forming structure, a chassis, a frame assembly, and an elbow assembly according to an example of the present technology.

Figure 49:
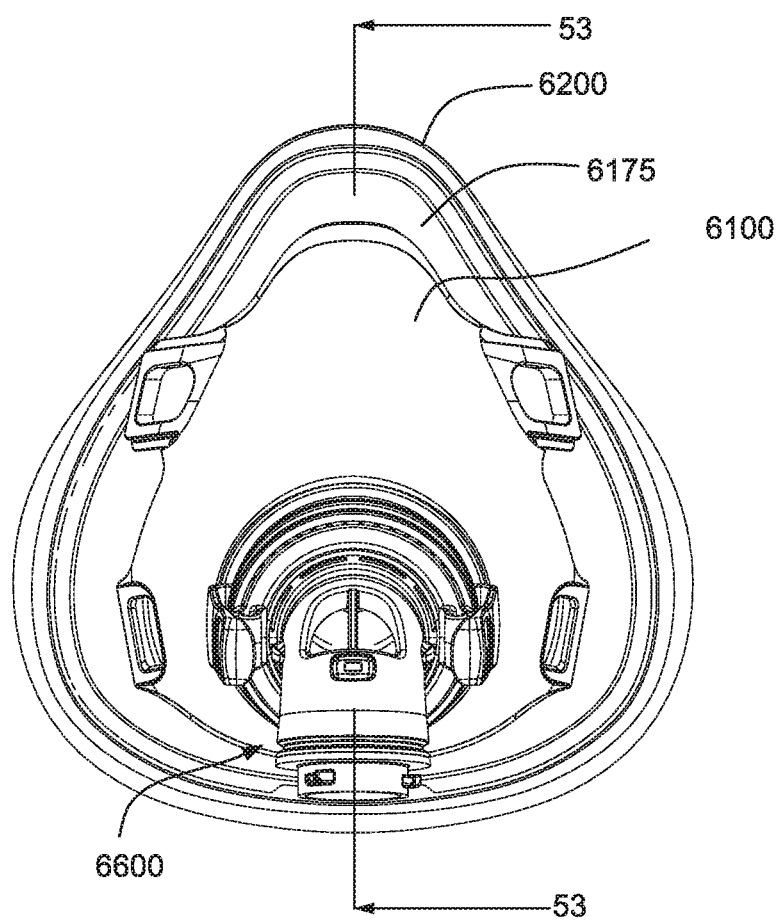

FIG. 49 is an anterior view of a seal-forming structure, a chassis, a frame assembly, and an elbow assembly according to an example of the present technology.

Figure 50:
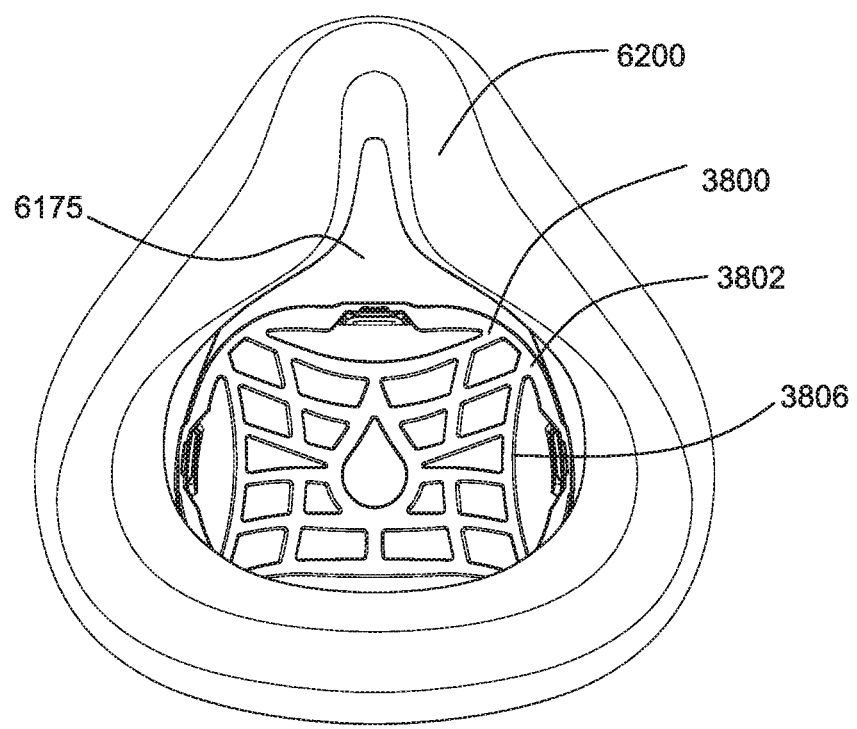

FIG. 50 is a posterior view of a seal-forming structure, a chassis, and a plenum chamber insert according to an example of the present technology.

Figure 51:
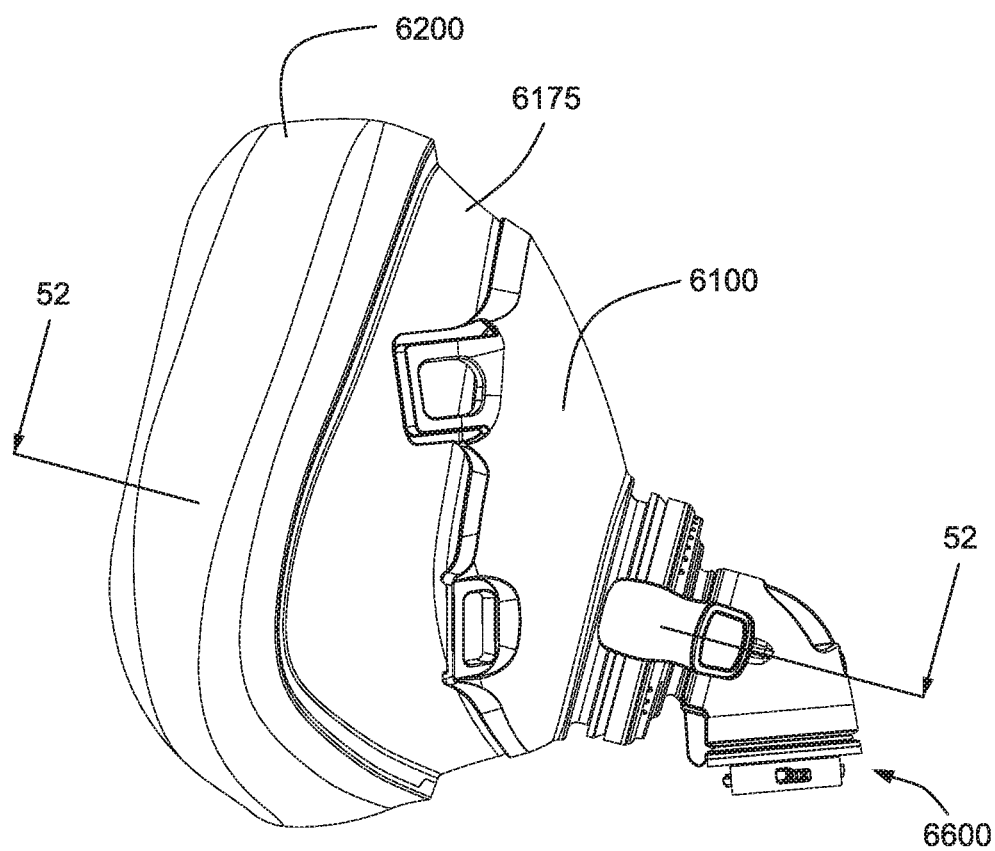

FIG. 51 is a lateral view of a seal-forming structure, a chassis, a frame assembly, and an elbow assembly according to an example of the present technology.

Figure 52:
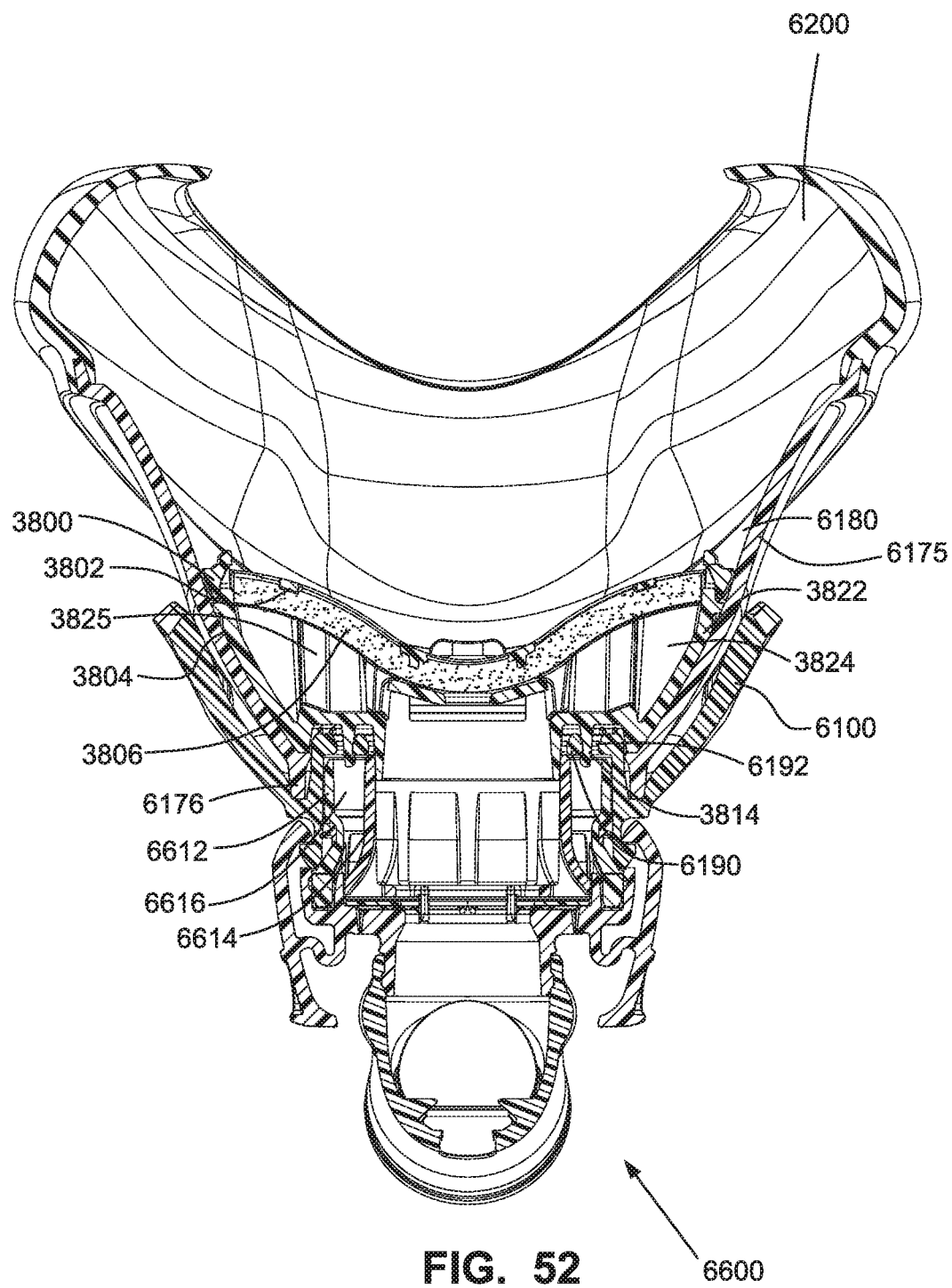

FIG. 52 is a cross-sectional view of a seal-forming structure, a chassis, a frame assembly, an elbow assembly, and a plenum chamber insert taken through line 52-52 of FIG. 51 according to an example of the present technology.

Figure 53:
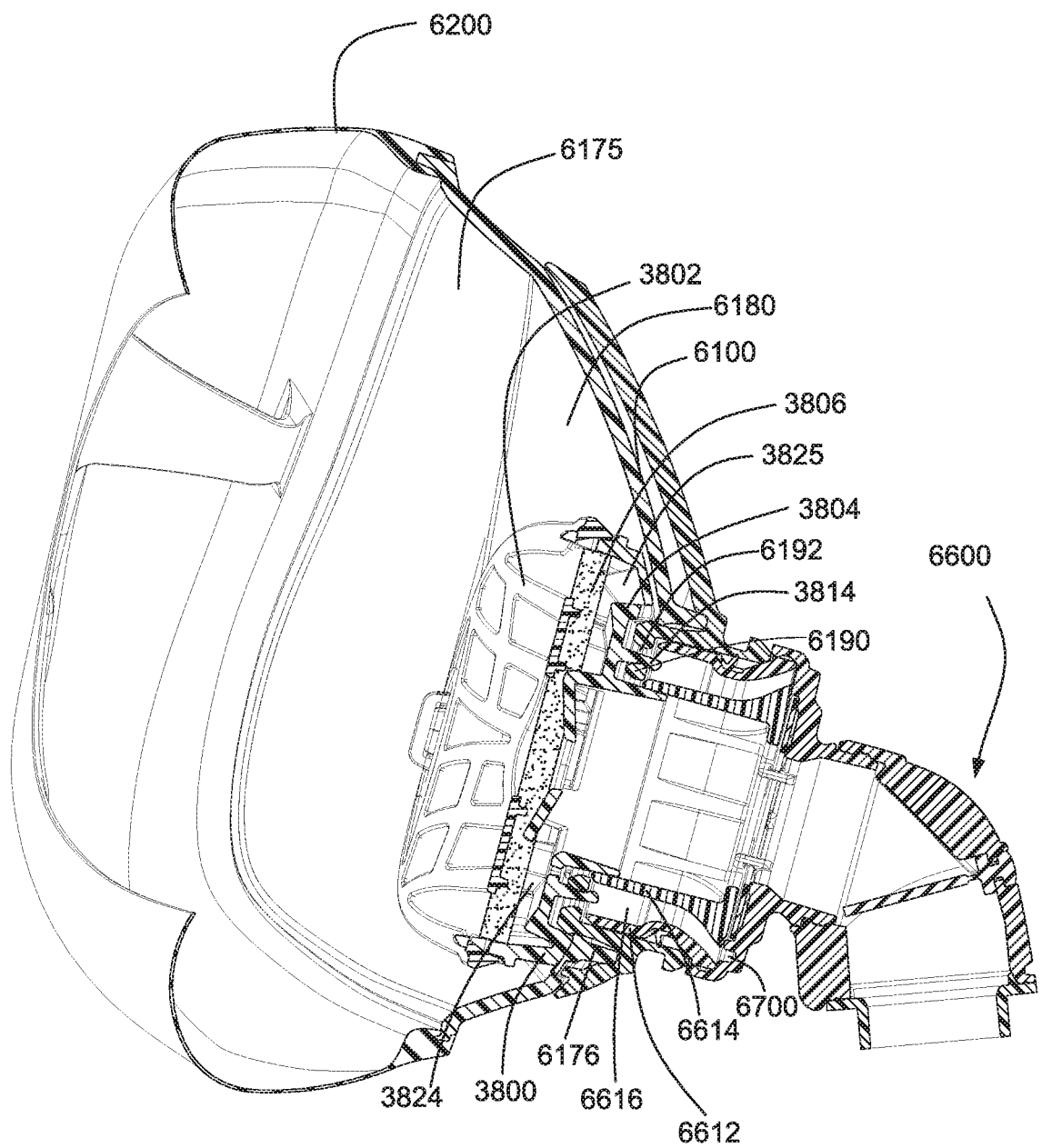

FIG. 53 is a cross-sectional view of a seal-forming structure, a chassis, a frame assembly, an elbow assembly, and a plenum chamber insert taken through line 53-53 of FIG. 49 according to an example of the present technology.

Figure 54:
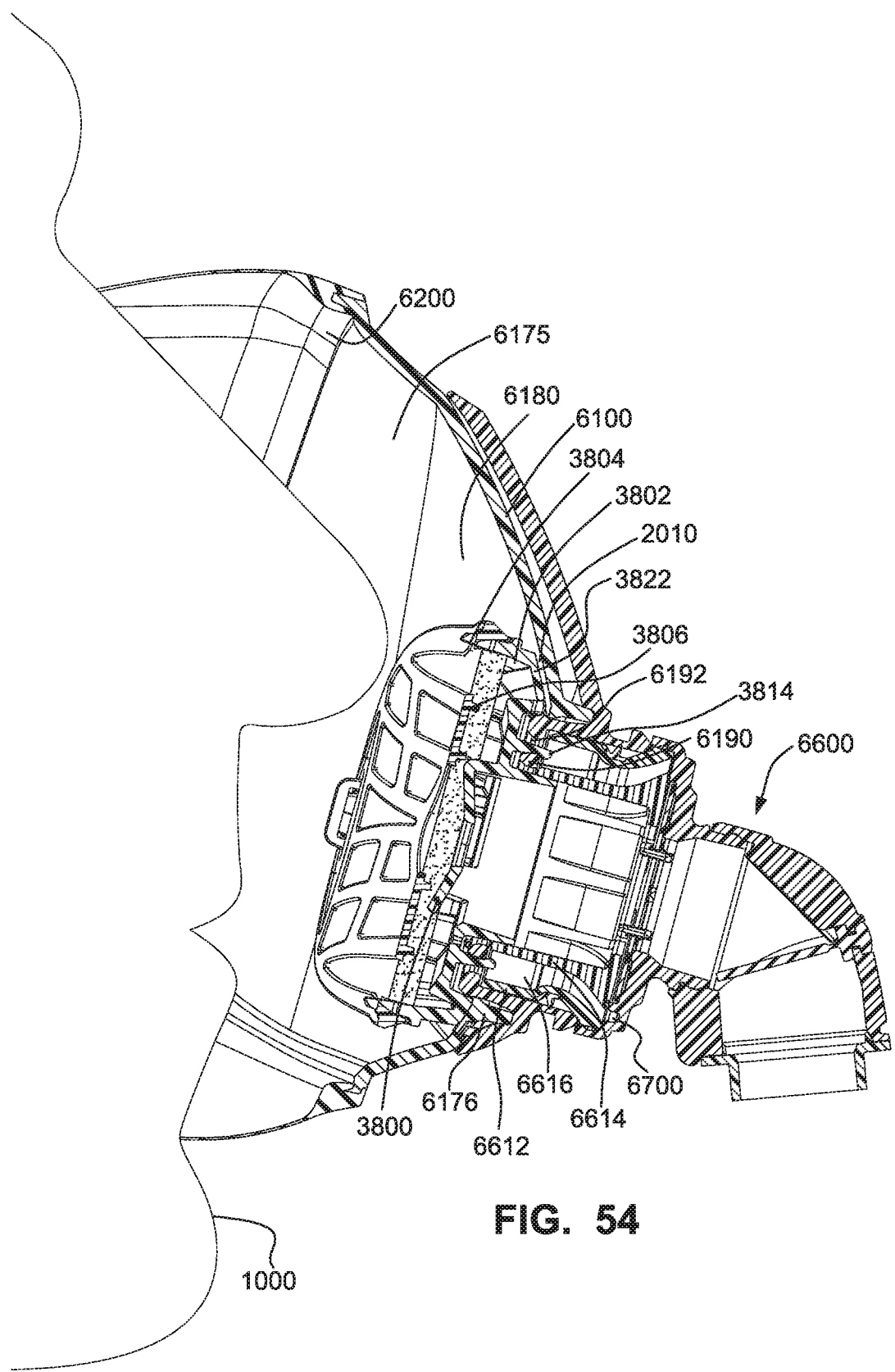

FIG. 54 is the cross-sectional view of FIG. 53 with the system against a patient's face.

Figure 55:
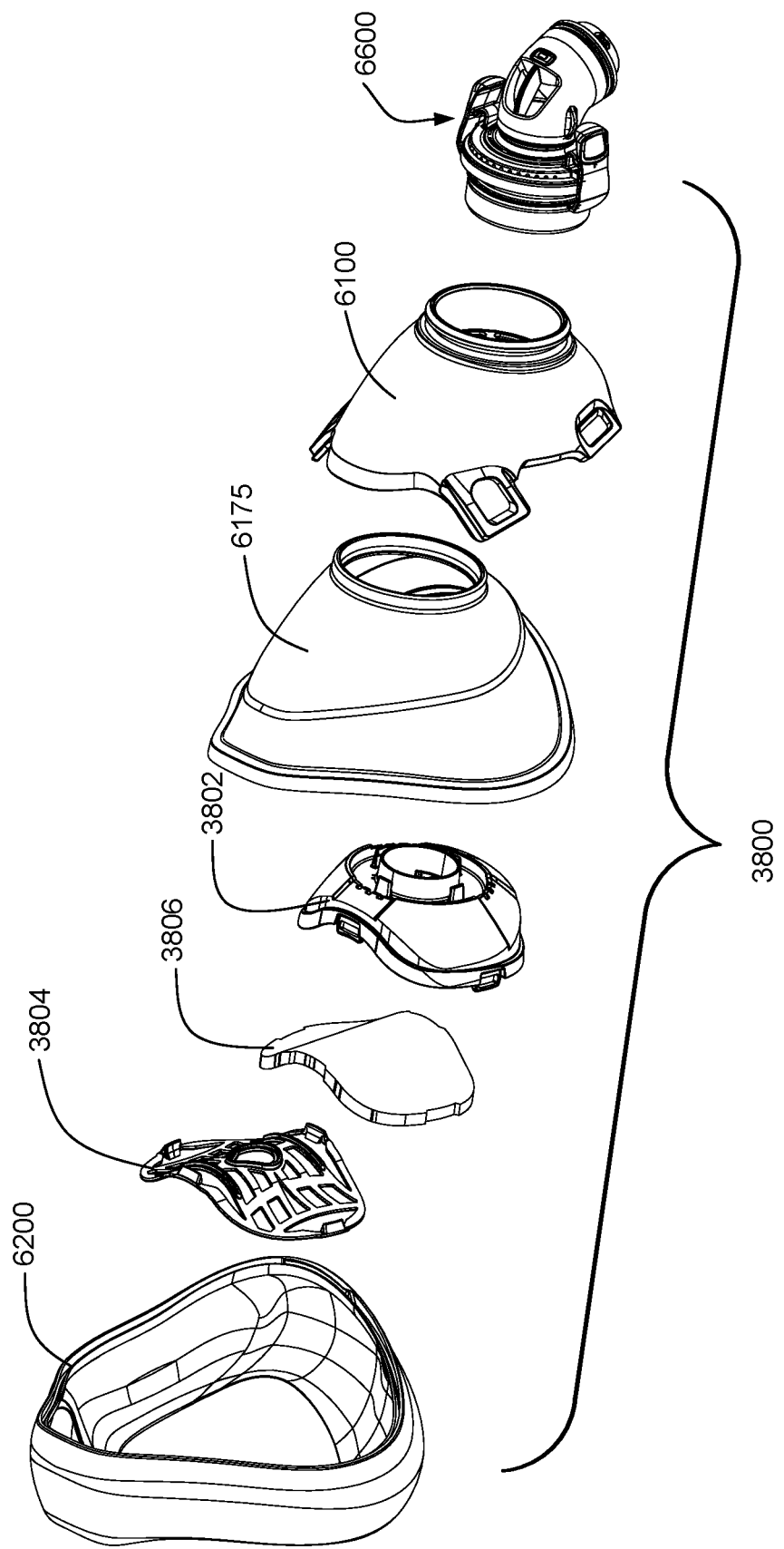

FIG. 55 is an exploded view of a seal-forming structure, a chassis, a plenum chamber insert, a frame assembly, and an elbow assembly according to an example of the present technology.

Figure 56:
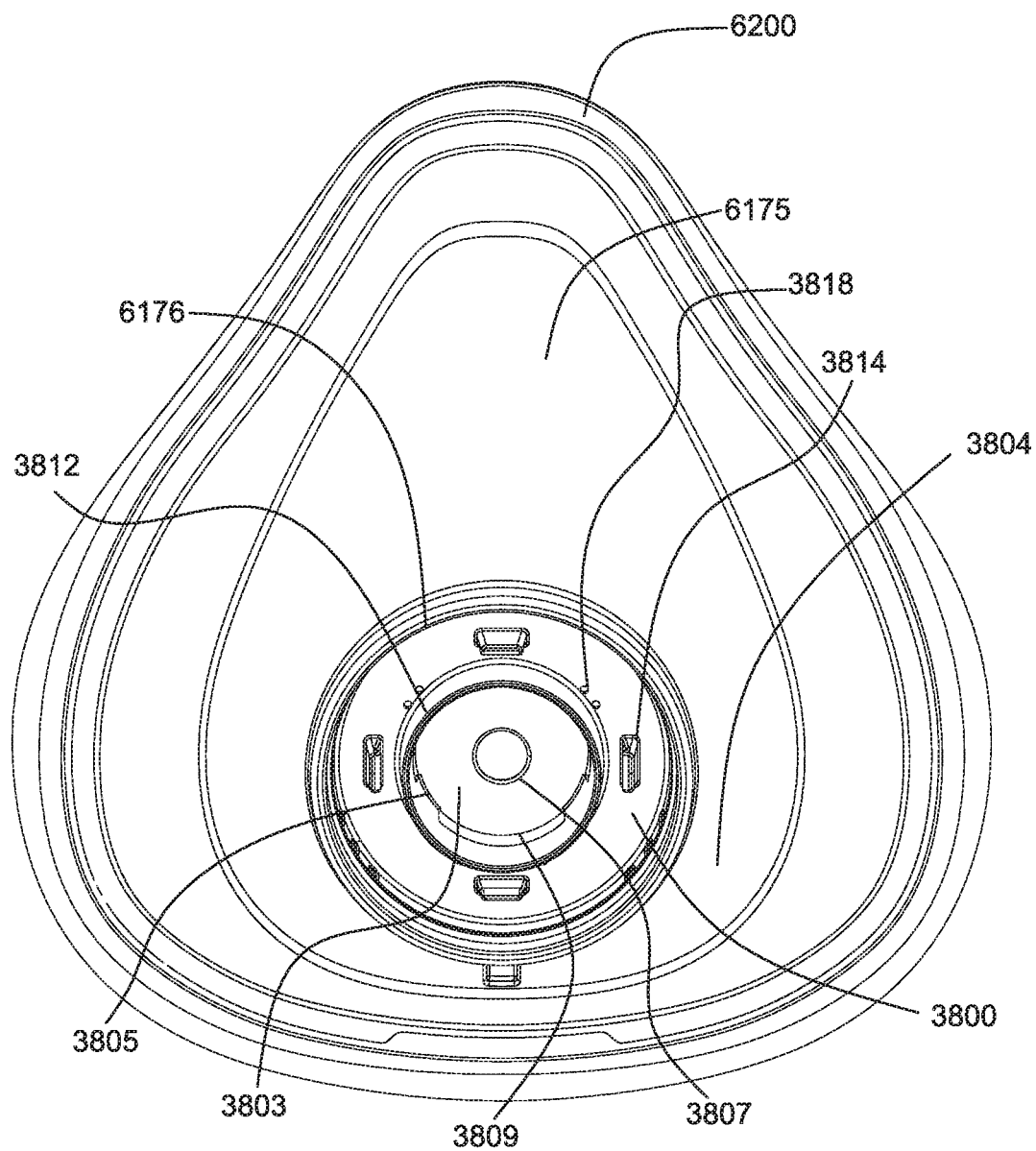

FIG. 56 is an anterior view of a seal-forming structure, a chassis, and a plenum chamber insert according to an example of the present technology.

Figure 57:
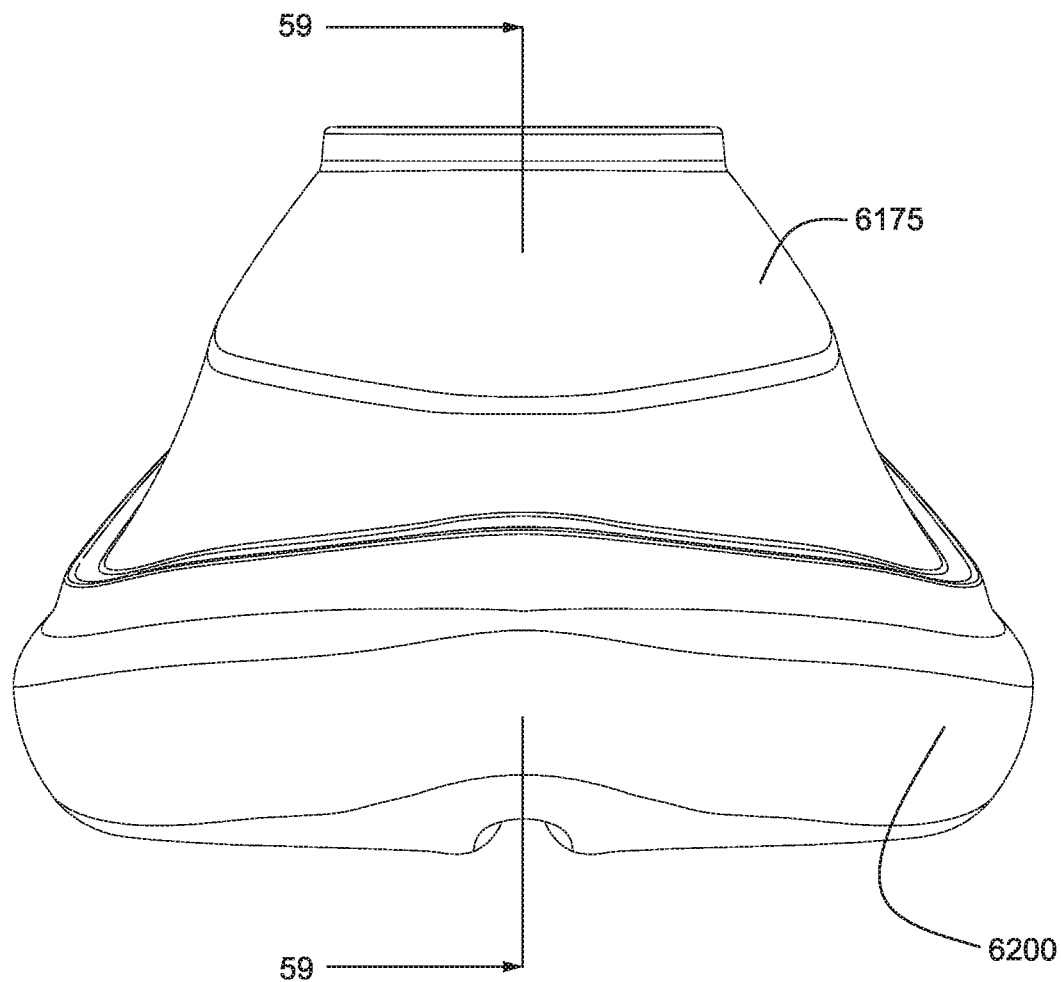

FIG. 57 is a superior view of a seal-forming structure and a chassis according to an example of the present technology.

Figure 58:
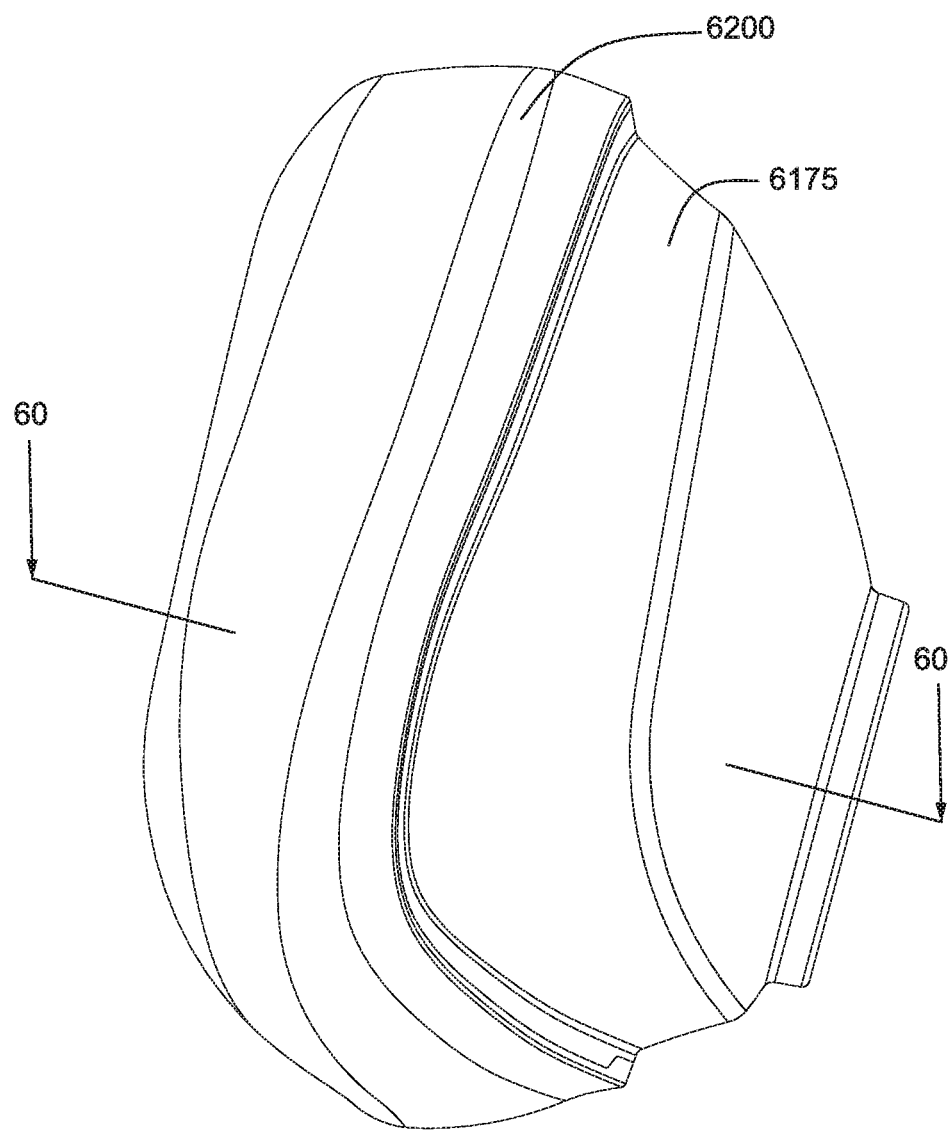

FIG. 58 is a lateral view of a seal-forming structure and a chassis according to an example of the present technology.

Figure 59:
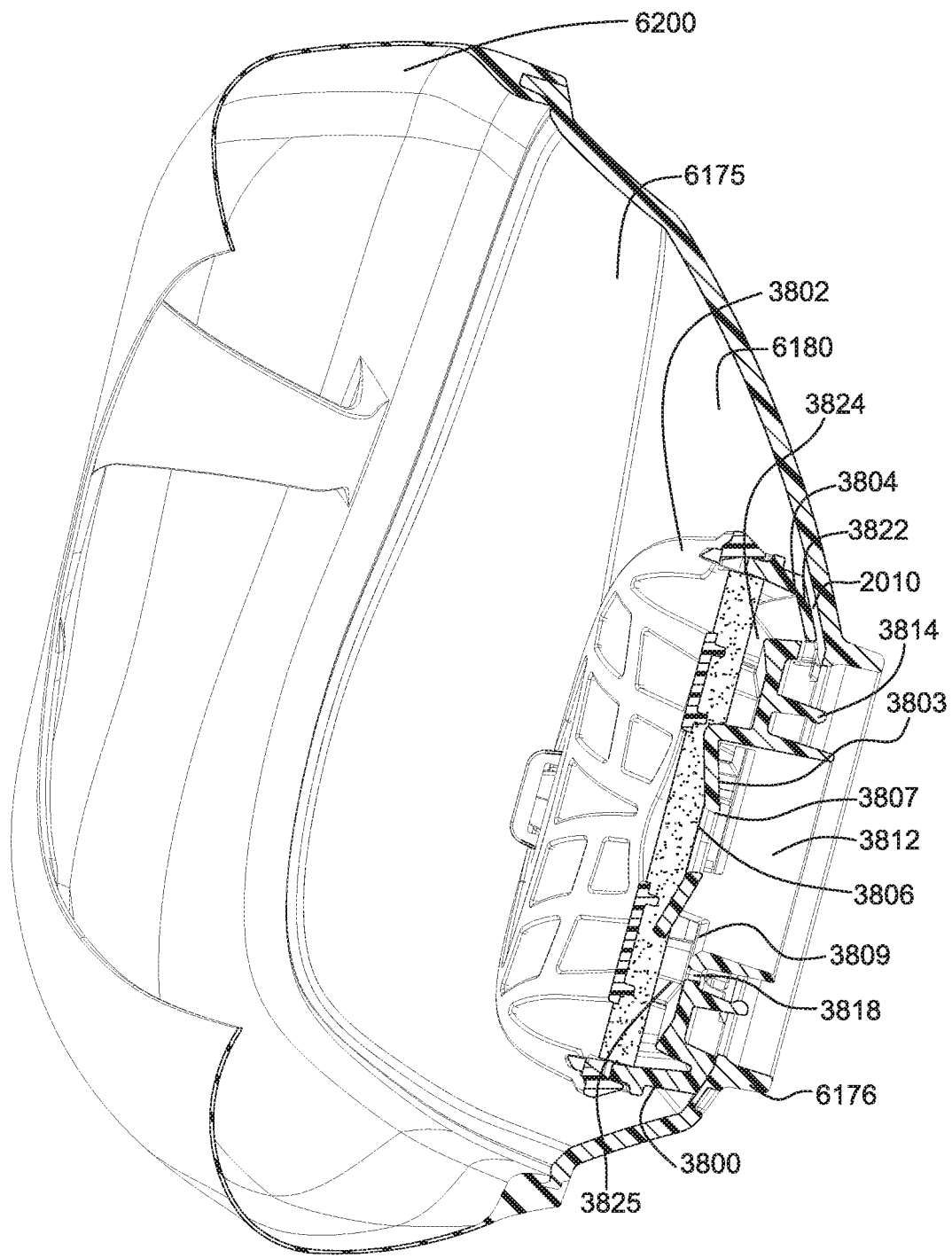

FIG. 59 is a cross-sectional view of a seal-forming structure, a chassis, and a plenum chamber insert taken through line 59-59 of FIG. 57 according to an example of the present technology.

Figure 60:
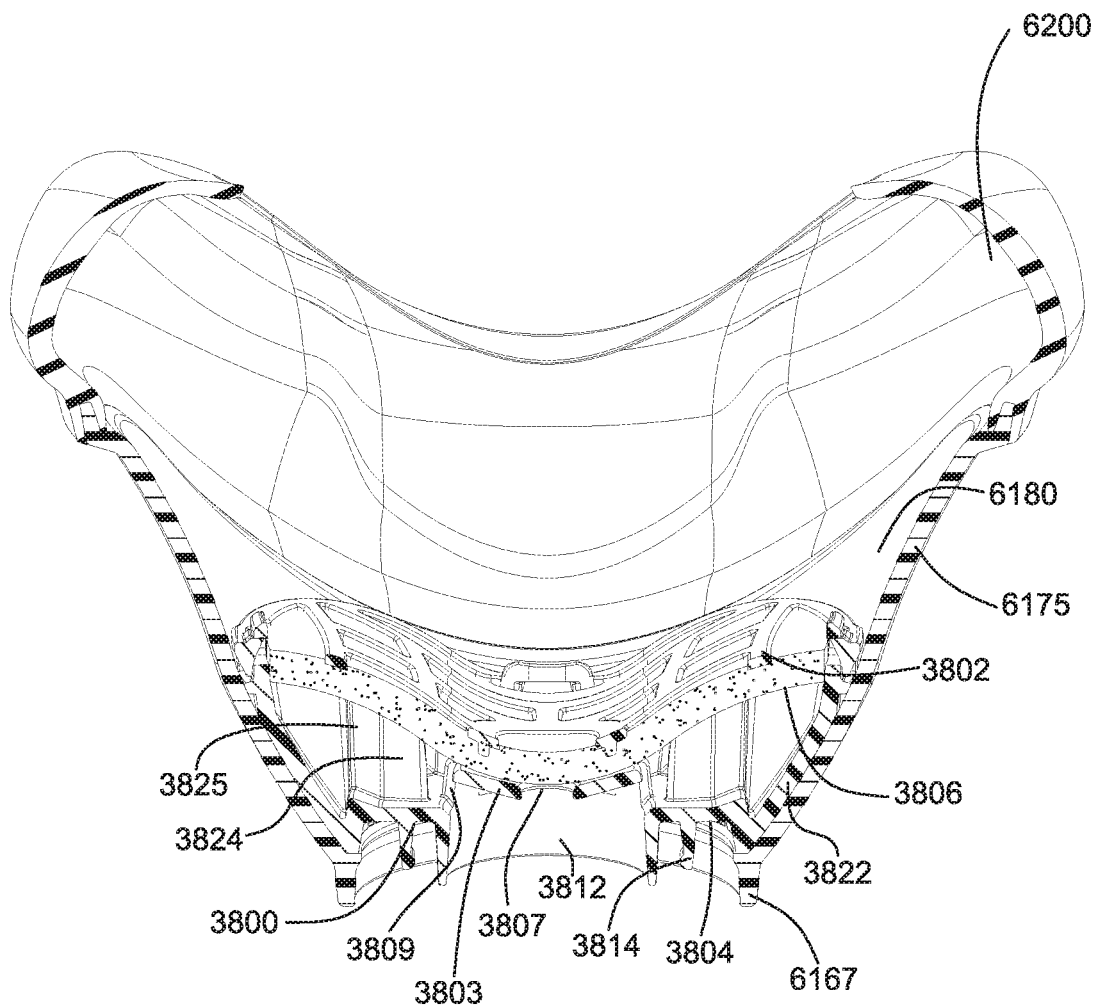

FIG. 60 is a cross-sectional view of a seal-forming structure, a chassis, and a plenum chamber insert taken through line 60-60 of FIG. 58 according to an example of the present technology.

Figure 61:
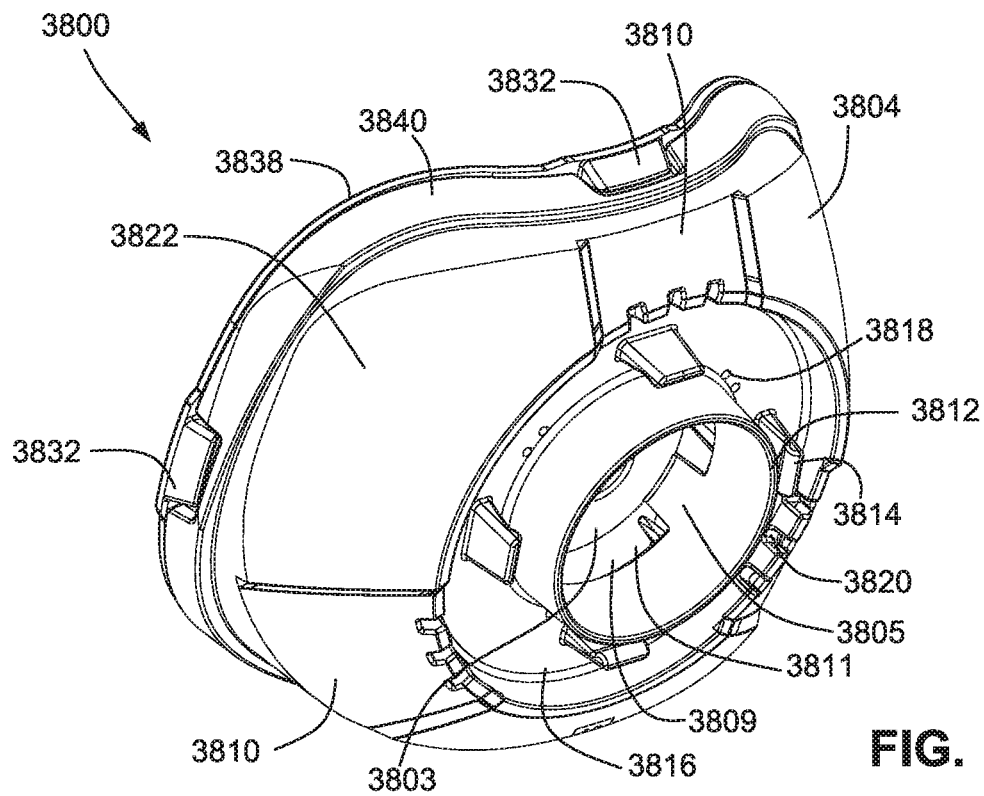

FIG. 61 is an anterior perspective view of a plenum chamber insert according to an example of the present technology.

Figure 62:
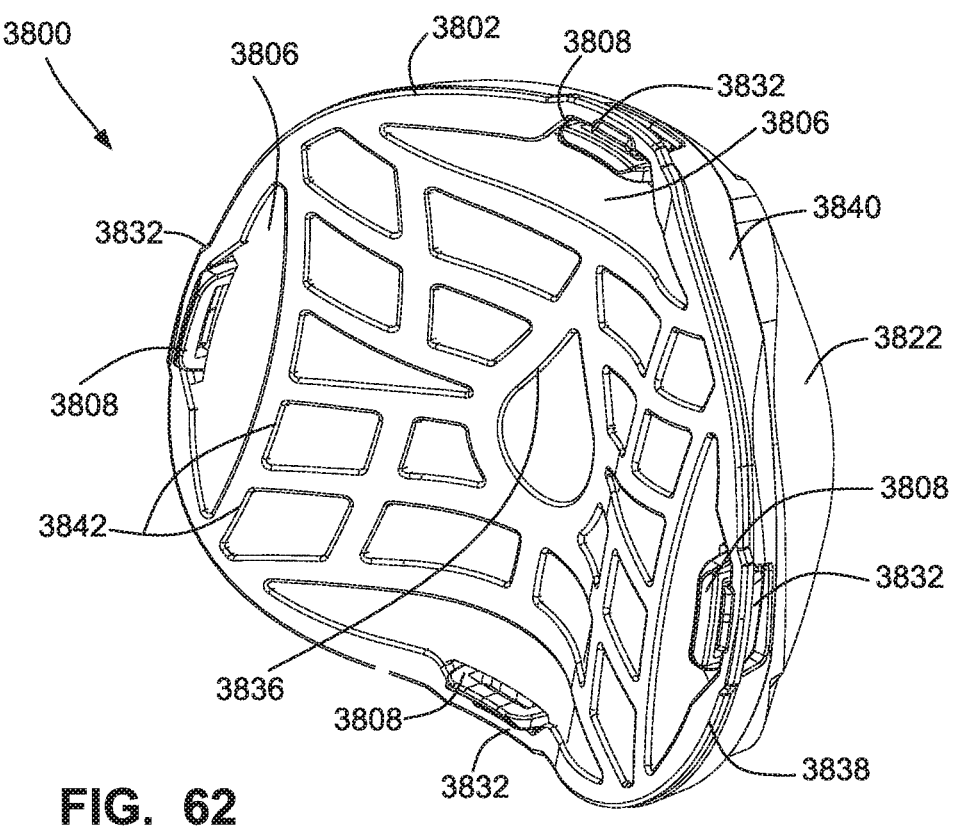

FIG. 62 is a posterior perspective view of a plenum chamber insert according to an example of the present technology.

Figure 63:
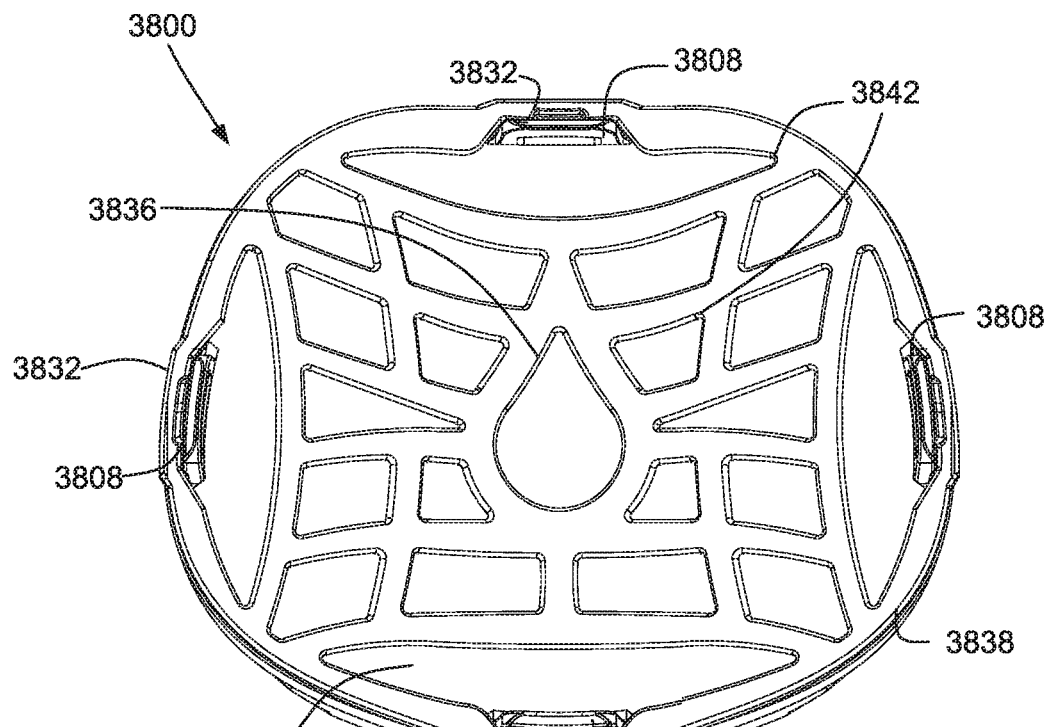

FIG. 63 is a posterior view of a plenum chamber insert according to an example of the present technology.

Figure 64:
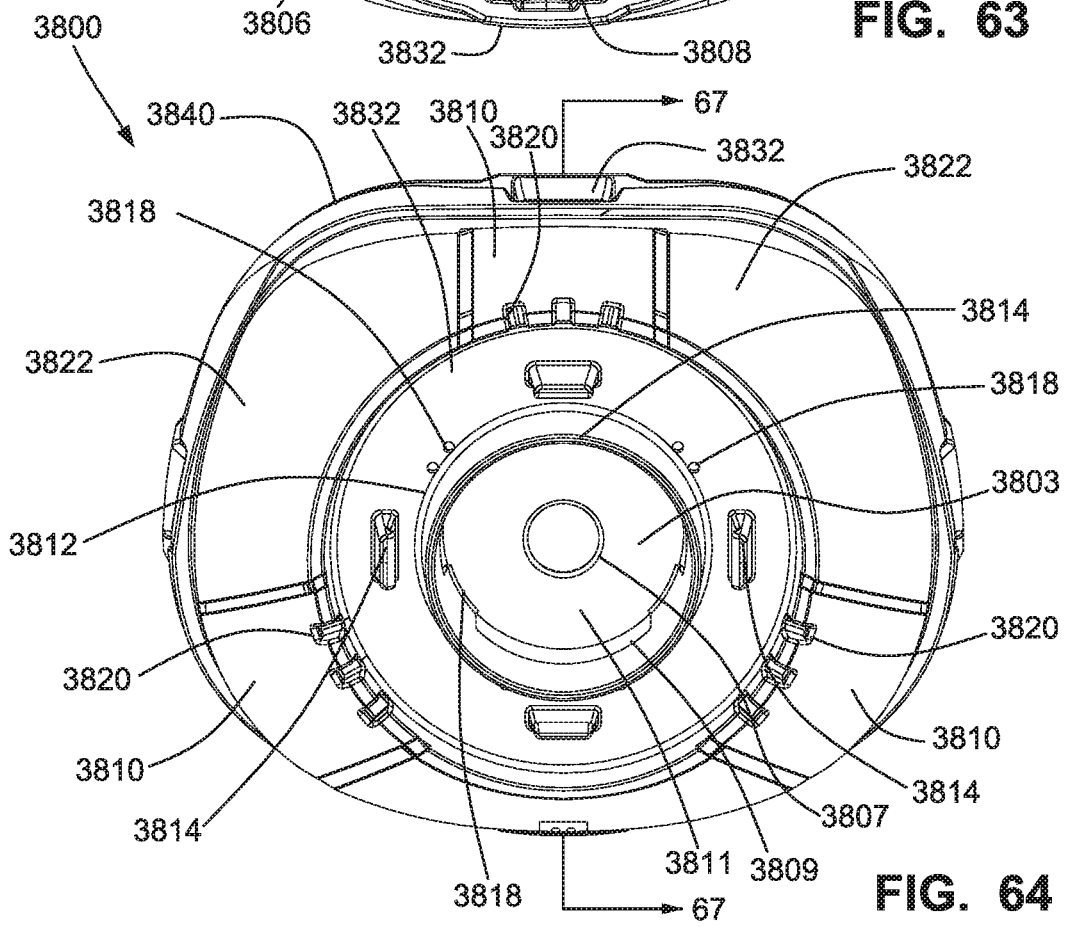

FIG. 64 is an anterior view of a plenum chamber insert according to an example of the present technology.

Figure 65:
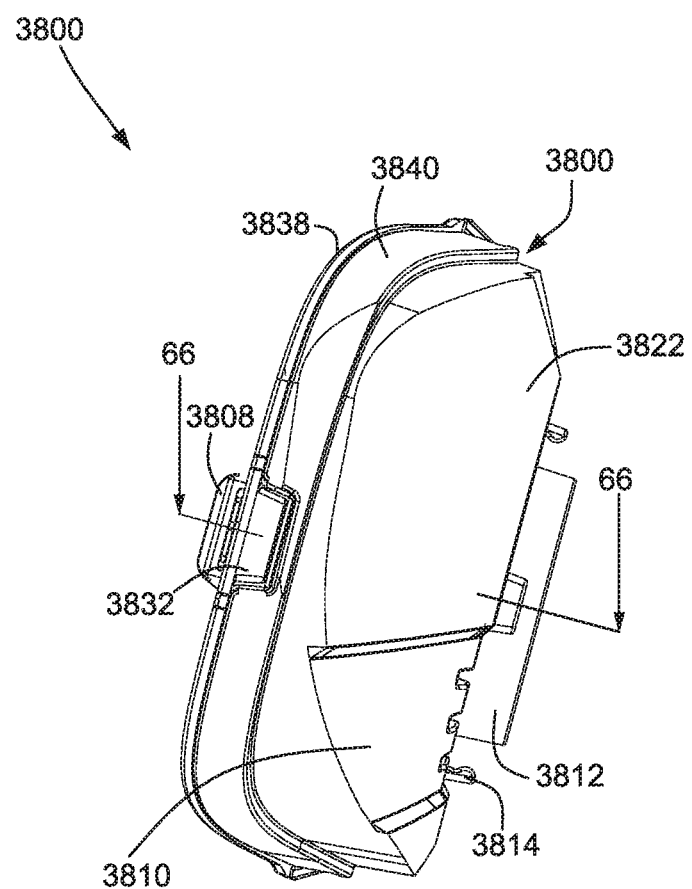

FIG. 65 is a lateral view of a plenum chamber insert according to an example of the present technology.

Figure 66:
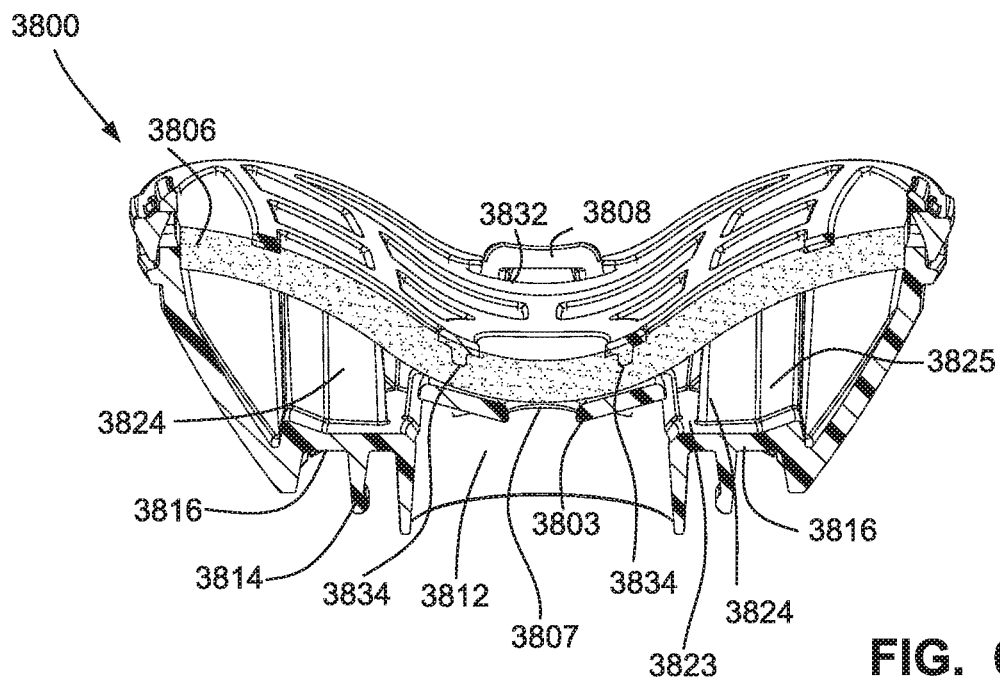

FIG. 66 is a cross-sectional view of a plenum chamber insert taken through line 66-66 of FIG. 65 according to an example of the present technology.

Figure 67:
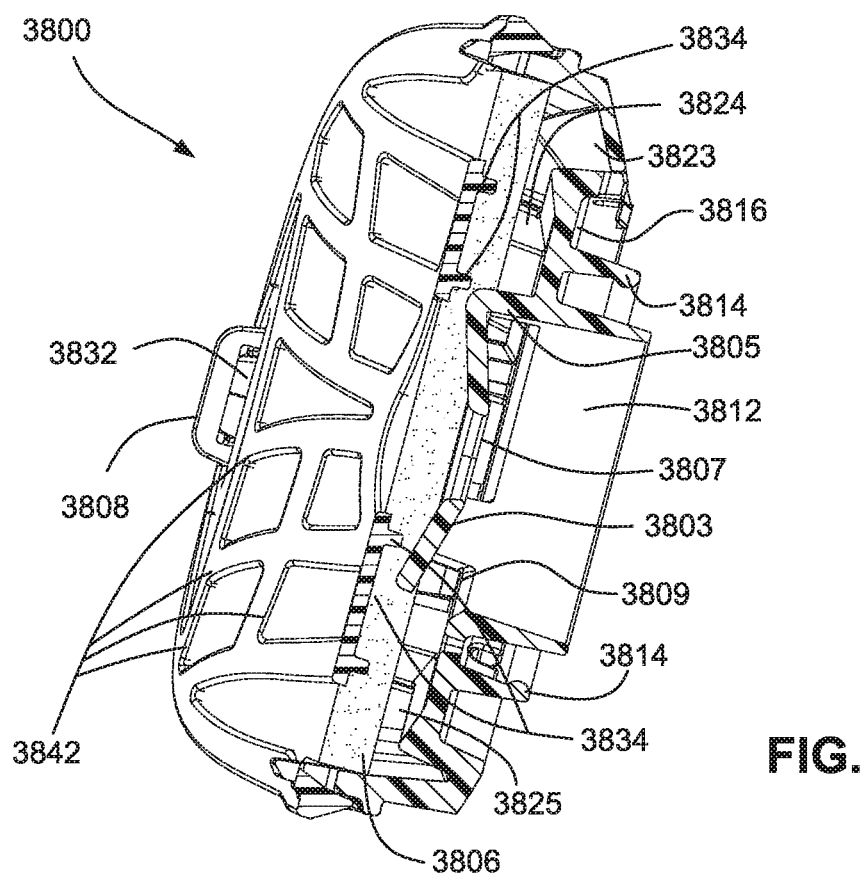

FIG. 67 is a cross-sectional view of a plenum chamber insert taken through line 67-67 of FIG. 64 according to an example of the present technology.

Figure 68:
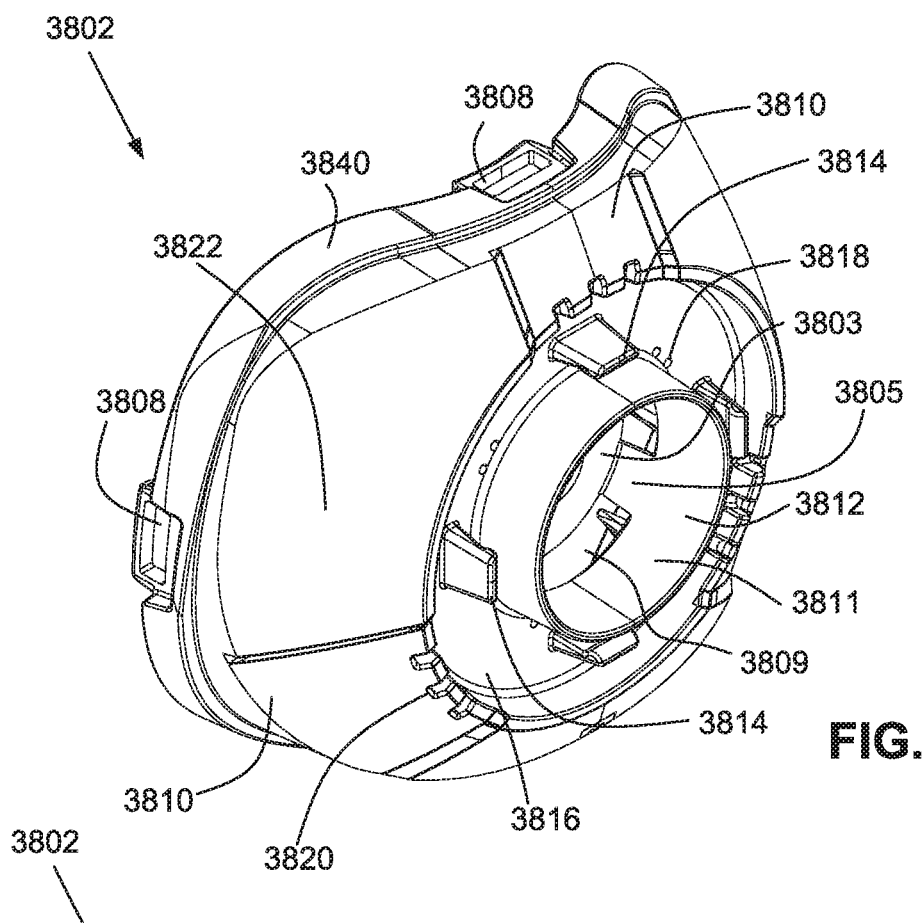

FIG. 68 is an anterior perspective view of an anterior insert frame of a plenum chamber insert according to an example of the present technology.

Figure 69:
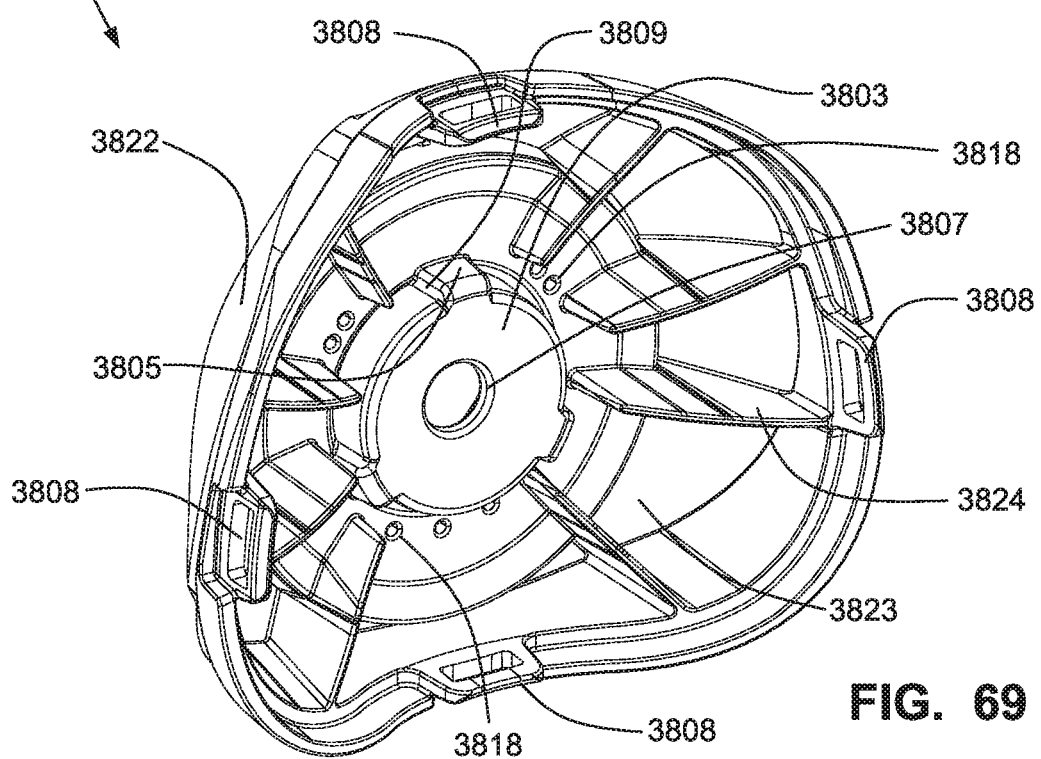

FIG. 69 is a posterior perspective view of an anterior insert frame of a plenum chamber insert according to an example of the present technology.

Figure 70:
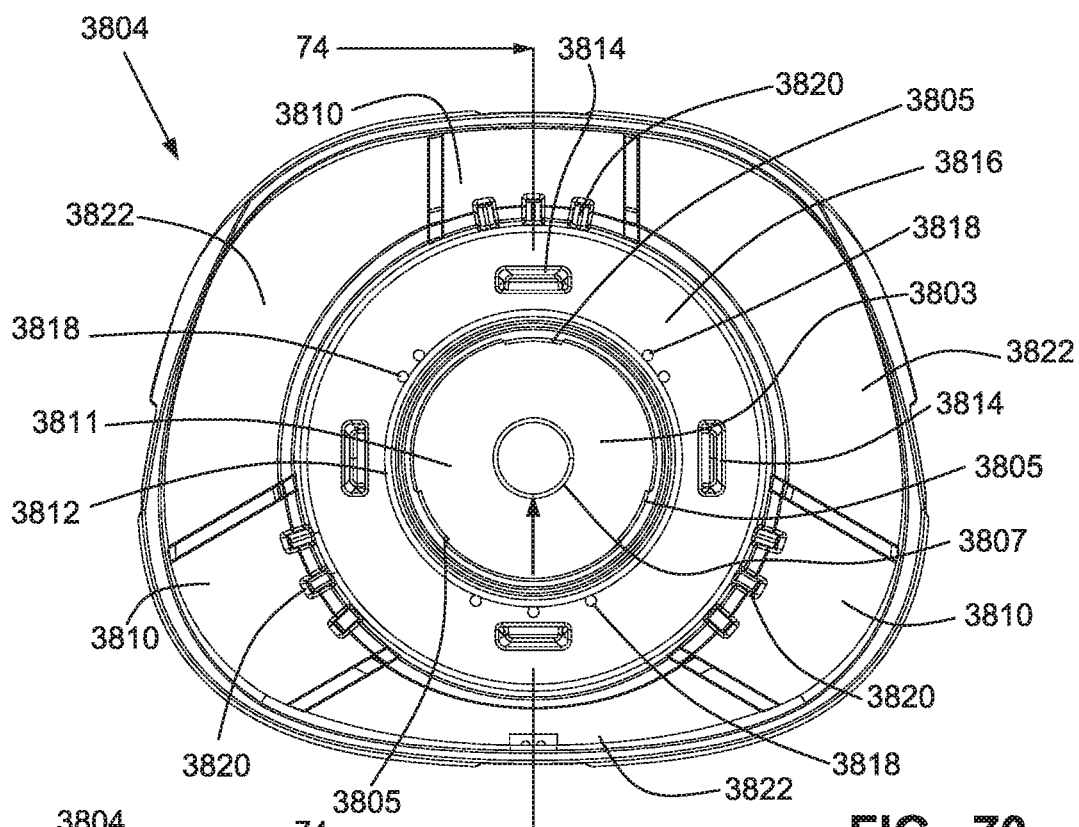

FIG. 70 is an anterior view of an anterior insert frame of a plenum chamber insert according to an example of the present technology.

Figure 71:
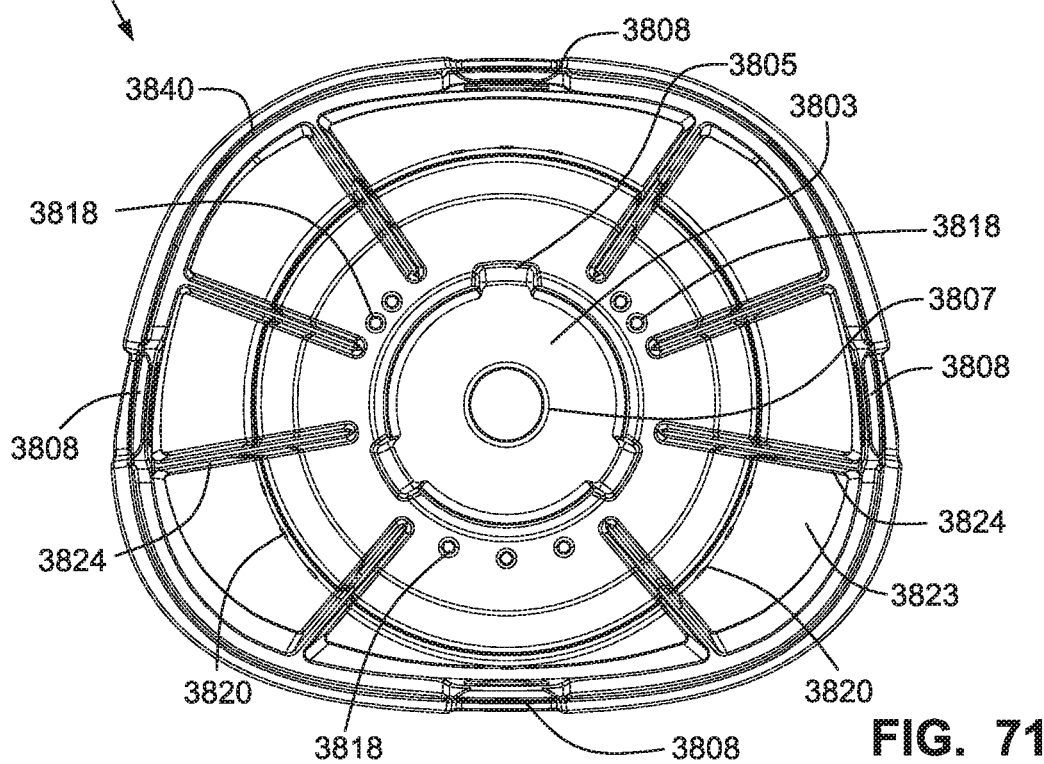

FIG. 71 is a posterior view of an anterior insert frame of a plenum chamber insert according to an example of the present technology.

Figure 72:
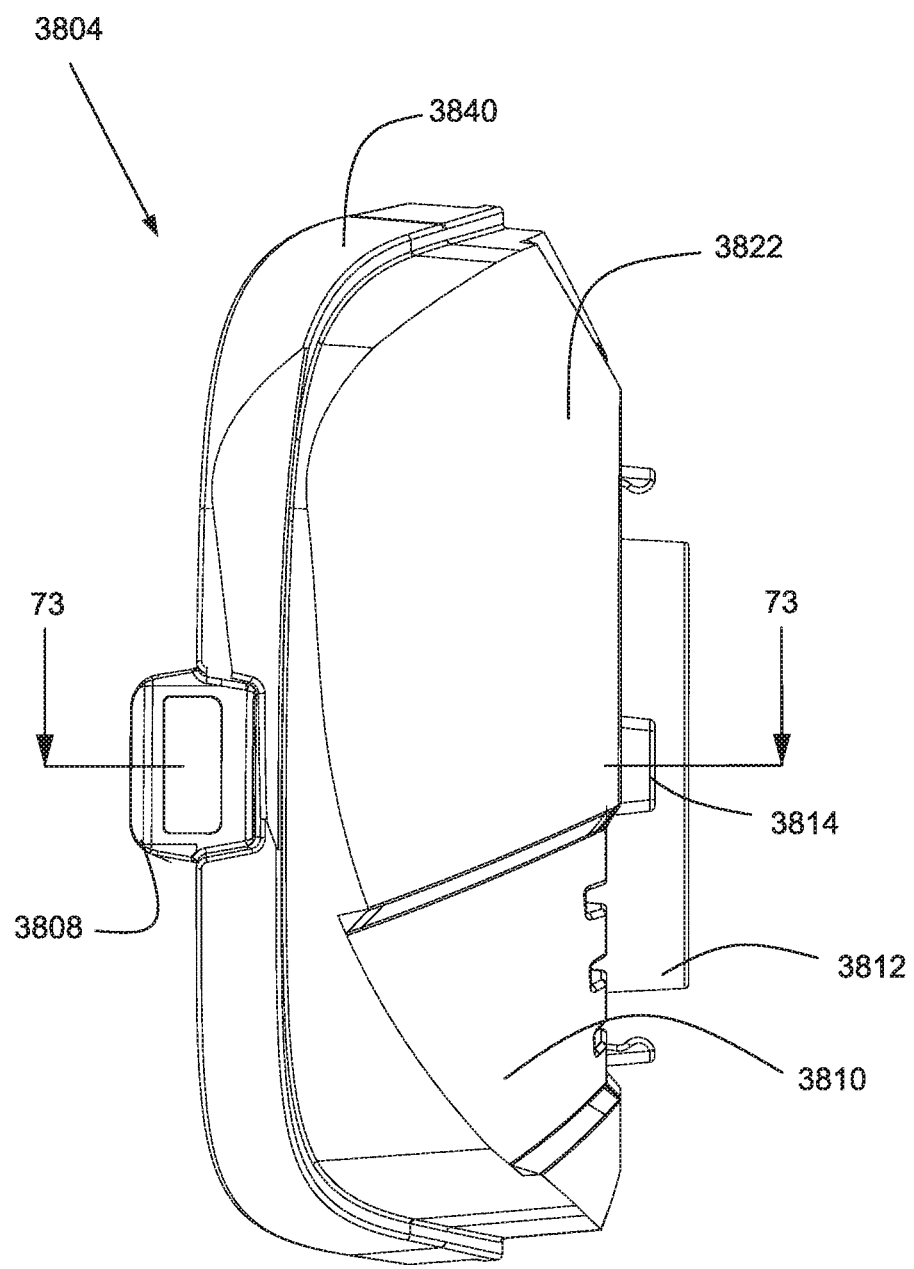

FIG. 72 is a lateral view of an anterior insert frame of a plenum chamber insert according to an example of the present technology.

Figure 73:
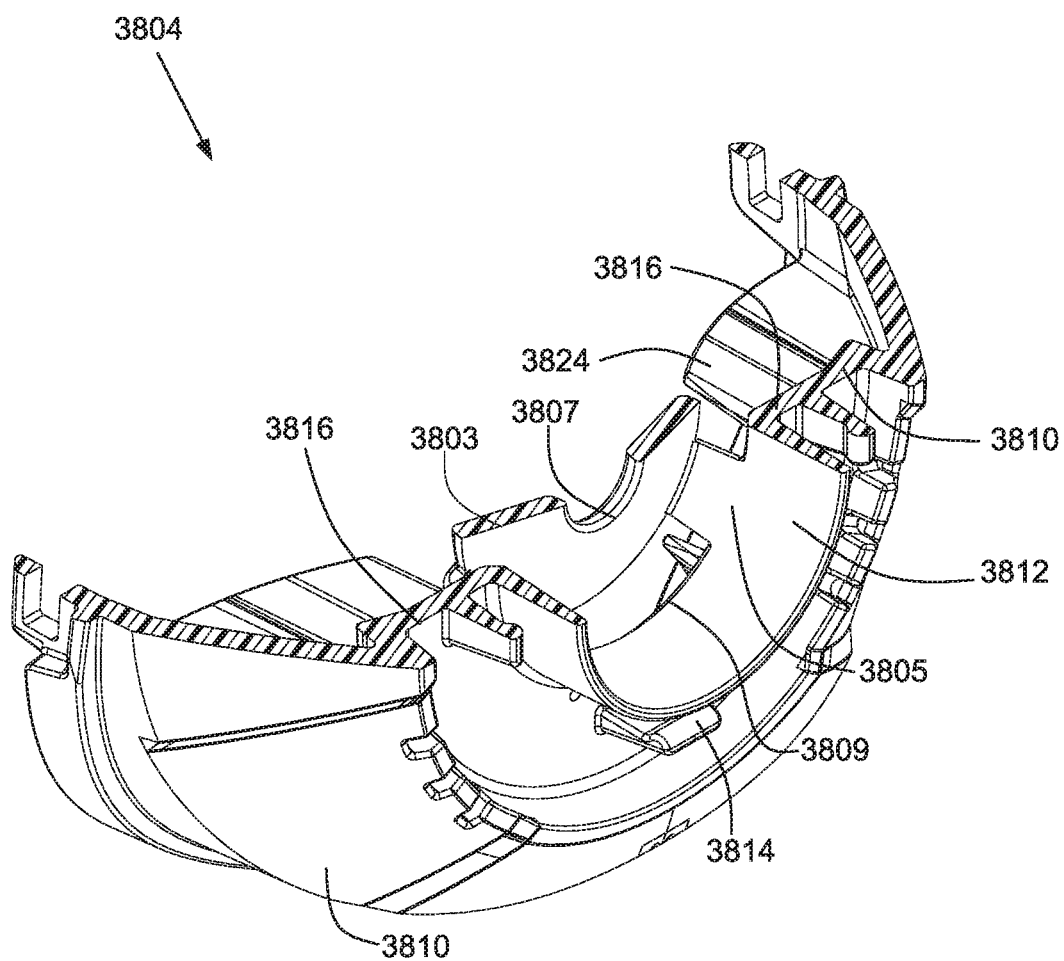

FIG. 73 is a cross-sectional view of an anterior insert frame of a plenum chamber insert taken through line 73-73 of FIG. 72 according to an example of the present technology.

Figure 74:
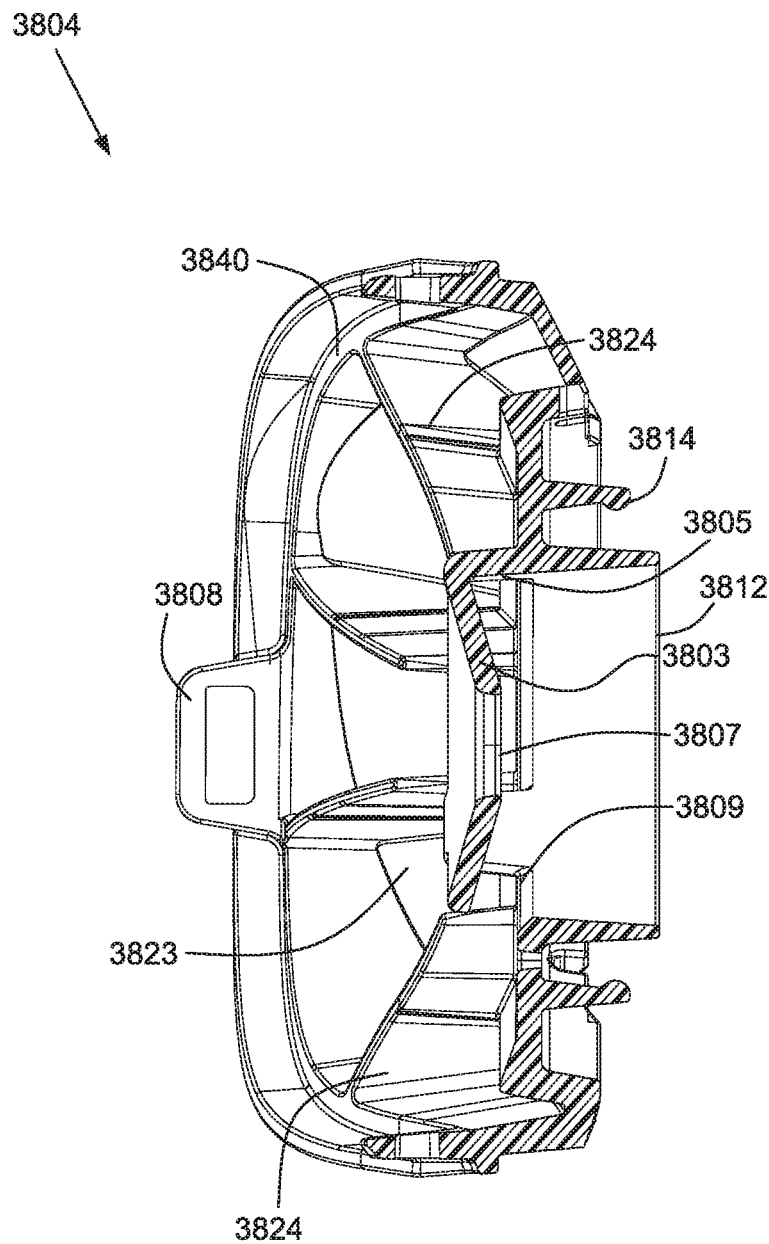

FIG. 74 is a cross-sectional view of an anterior insert frame of a plenum chamber insert taken through line 74-74 of FIG. 70 according to an example of the present technology.

Figure 75:
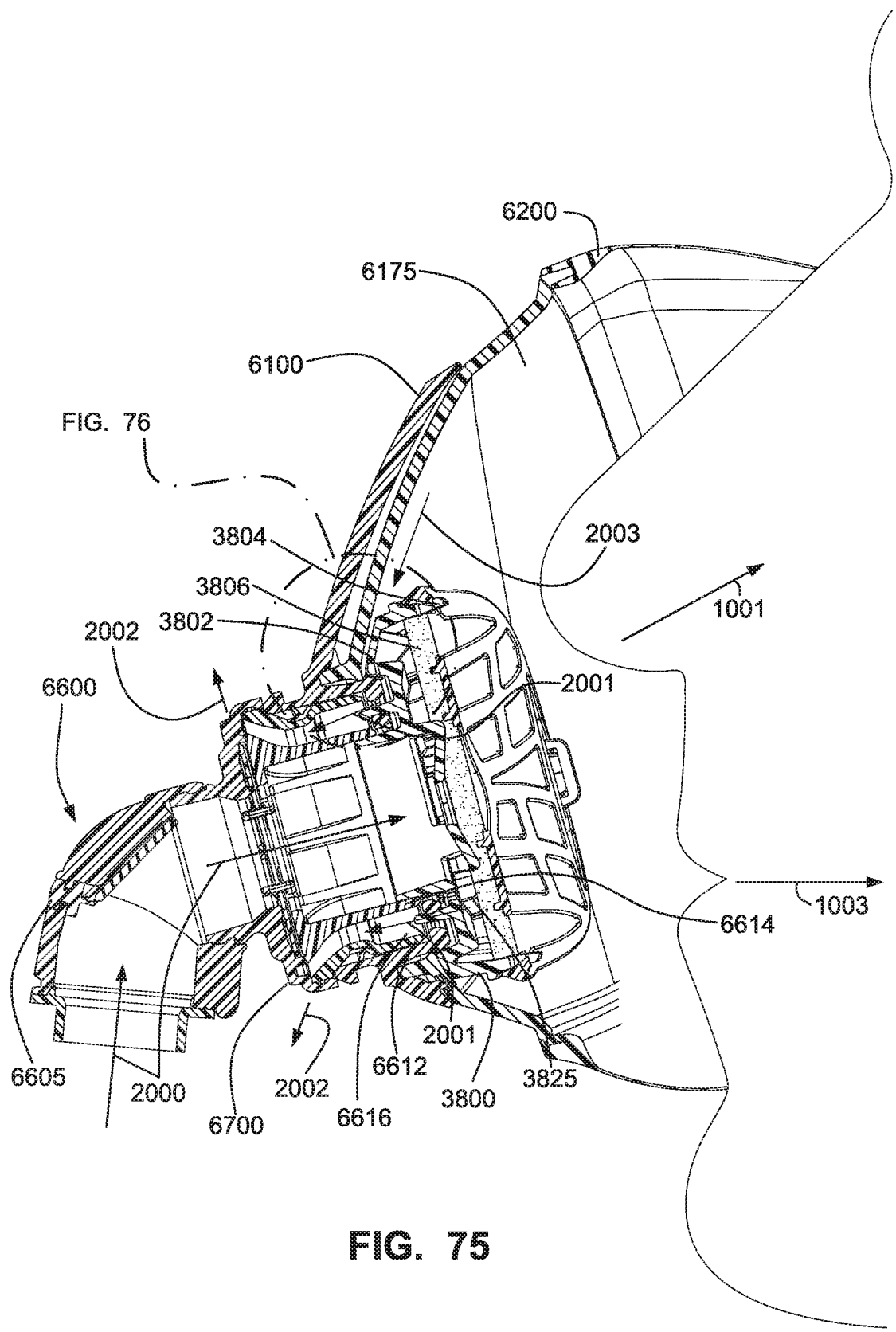

FIG. 75 shows a cross-sectional view of a patient interface based on FIG. 53, including a plenum chamber insert, against a patient's face during an inhalation phase according to an example of the present technology.

Figure 76:
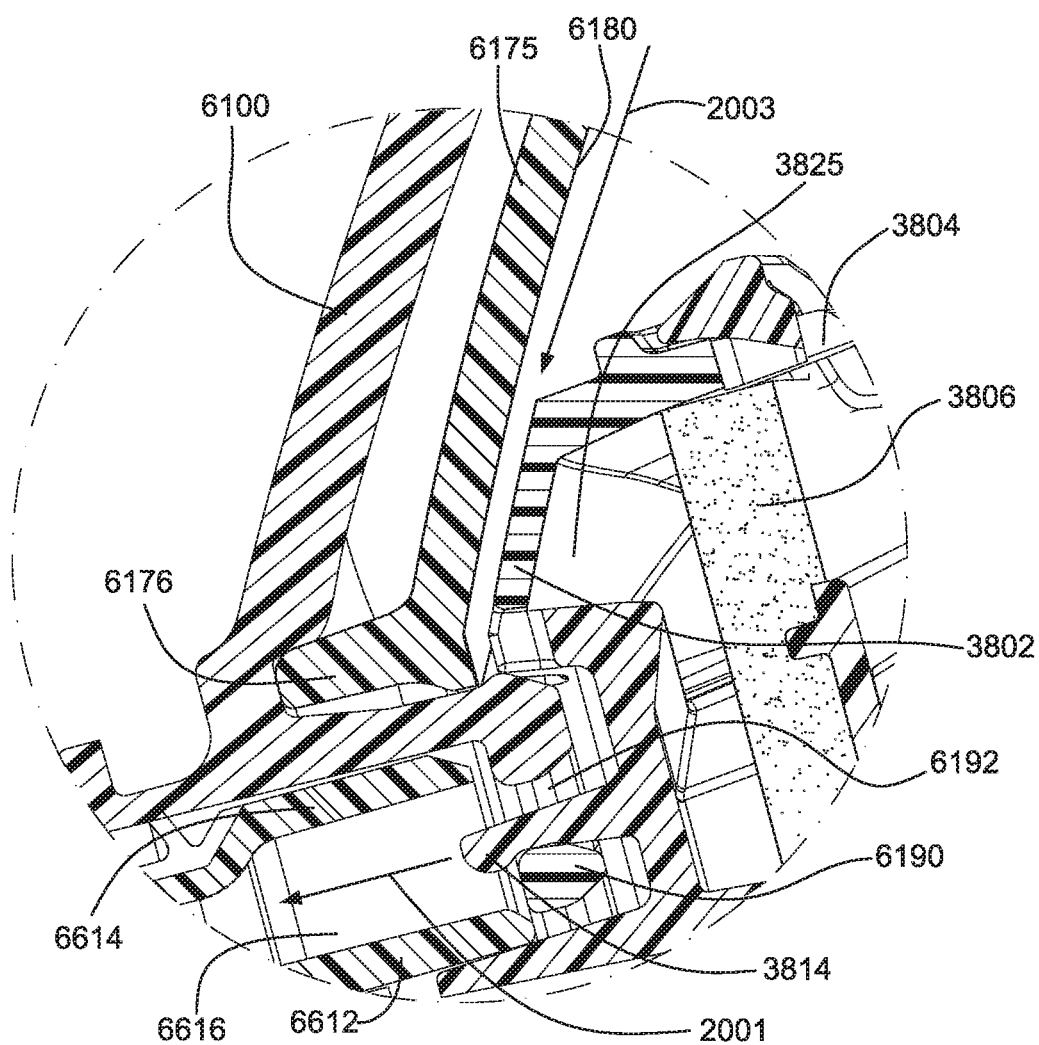

FIG. 76 shows a detailed view of FIG. 75.

Figure 77:
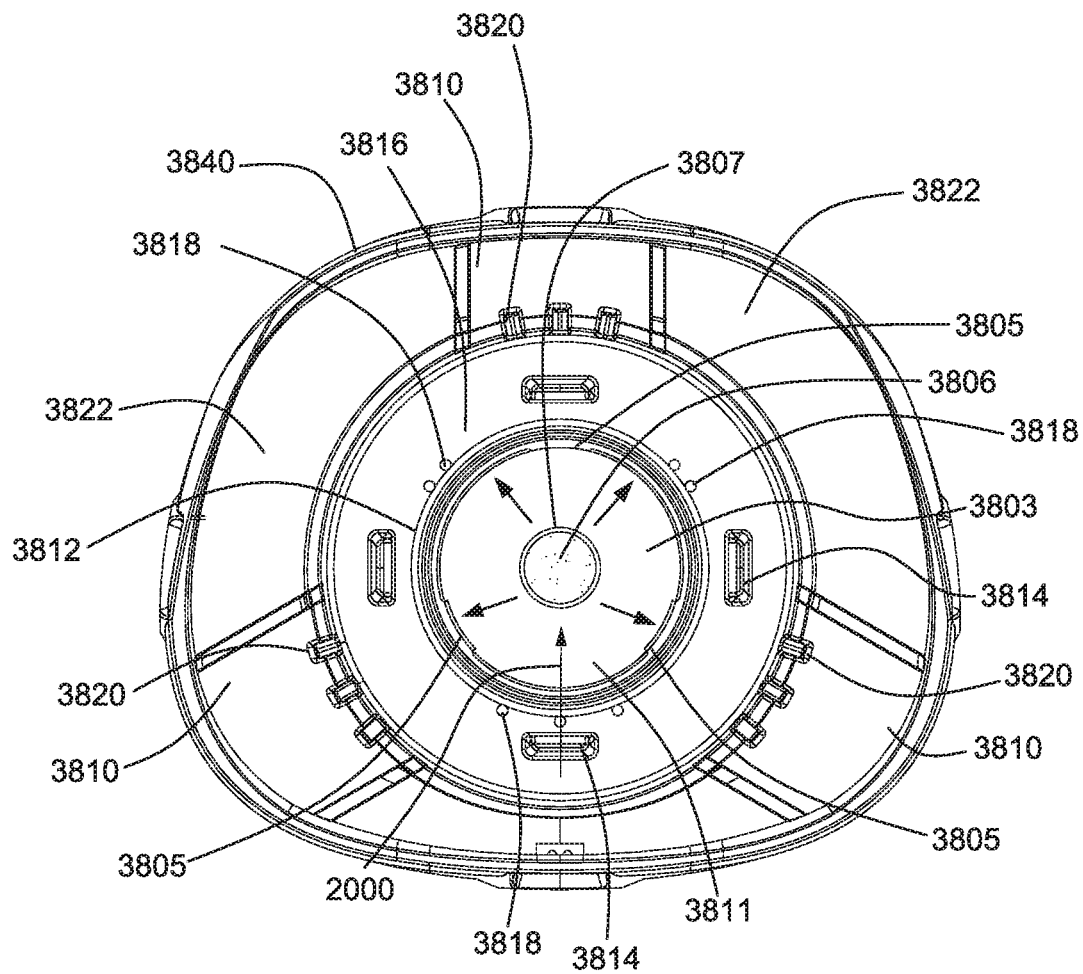

FIG. 77 shows an anterior view of a plenum chamber insert during an inhalation phase according to an example of the present technology.

Figure 78:
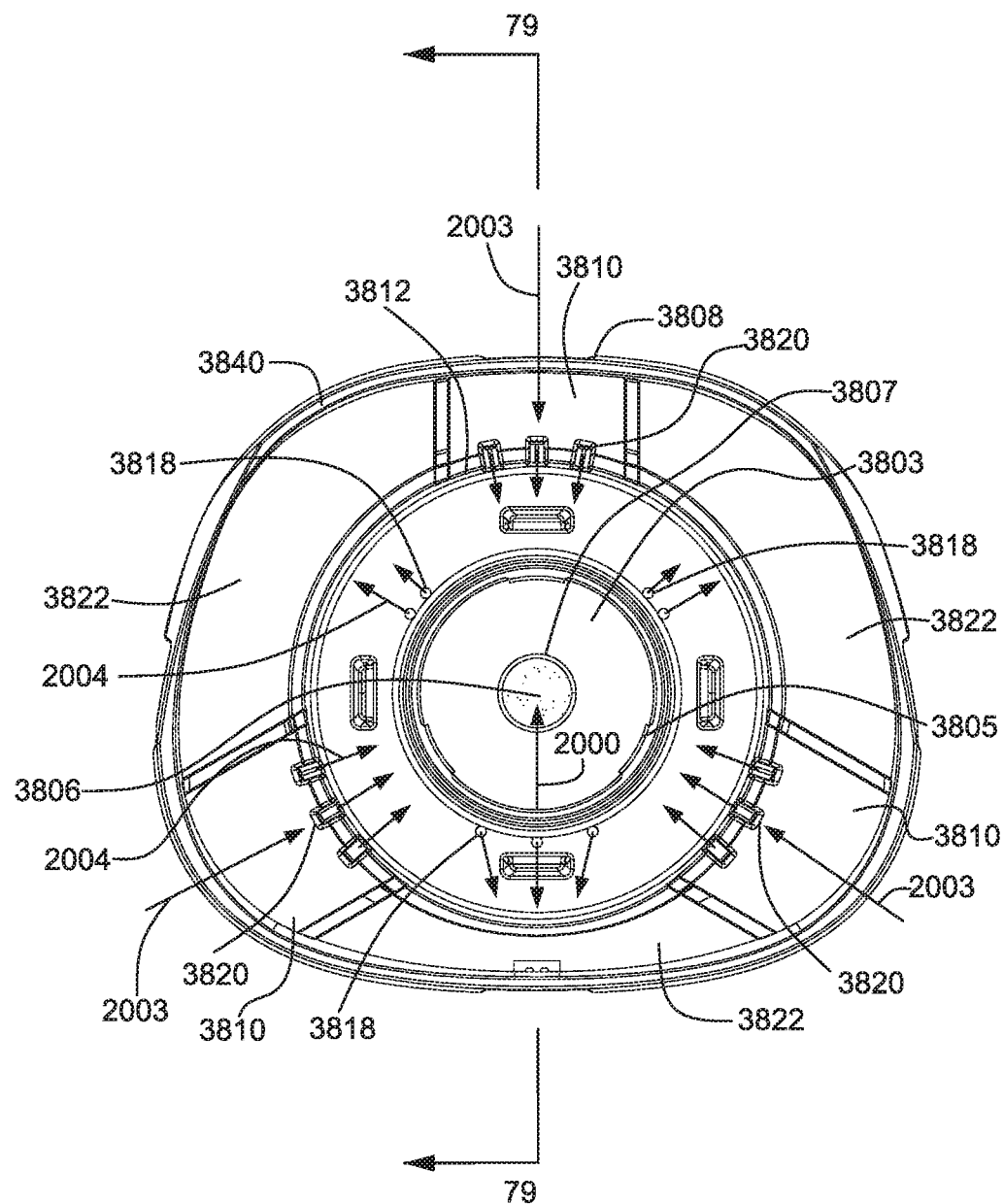

FIG. 78 shows an anterior view of a plenum chamber insert during breath pause according to an example of the present technology.

Figure 79:
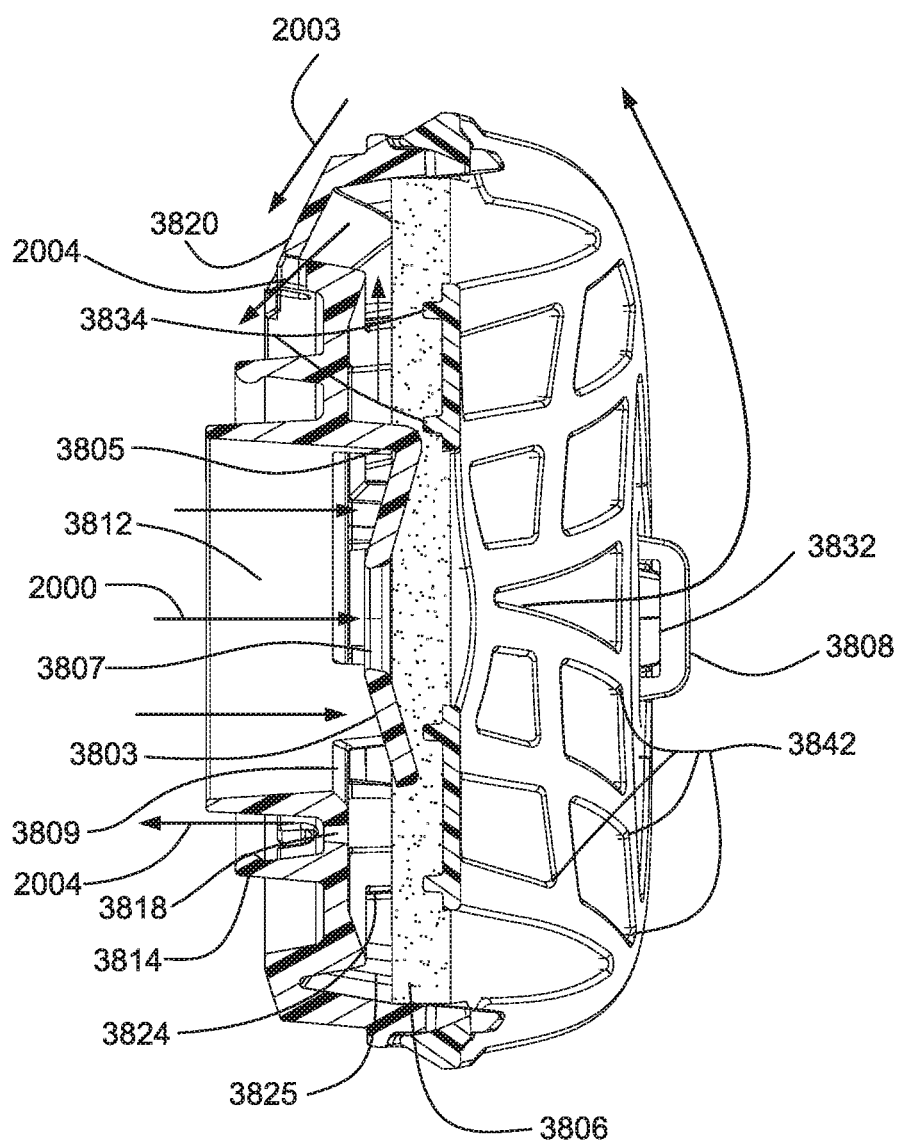

FIG. 79 shows a cross-sectional view of a plenum chamber insert taken through line 79-79 of FIG. 78 during breath pause according to an example of the present technology.

Figure 80:
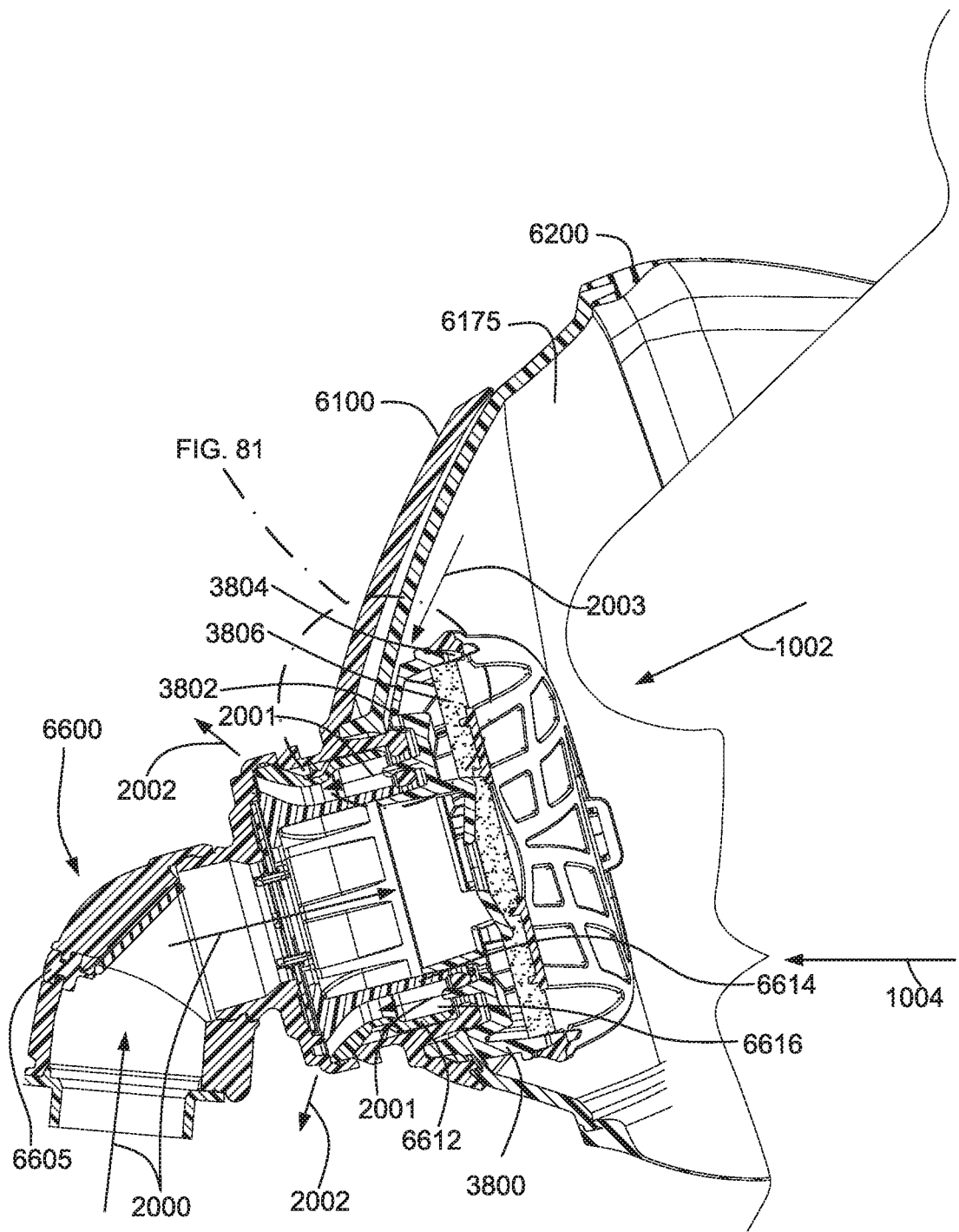

FIG. 80 shows a cross-sectional view of a patient interface based on FIG. 53, including a plenum chamber insert, against a patient's face during an exhalation phase according to an example of the present technology.

Figure 81:
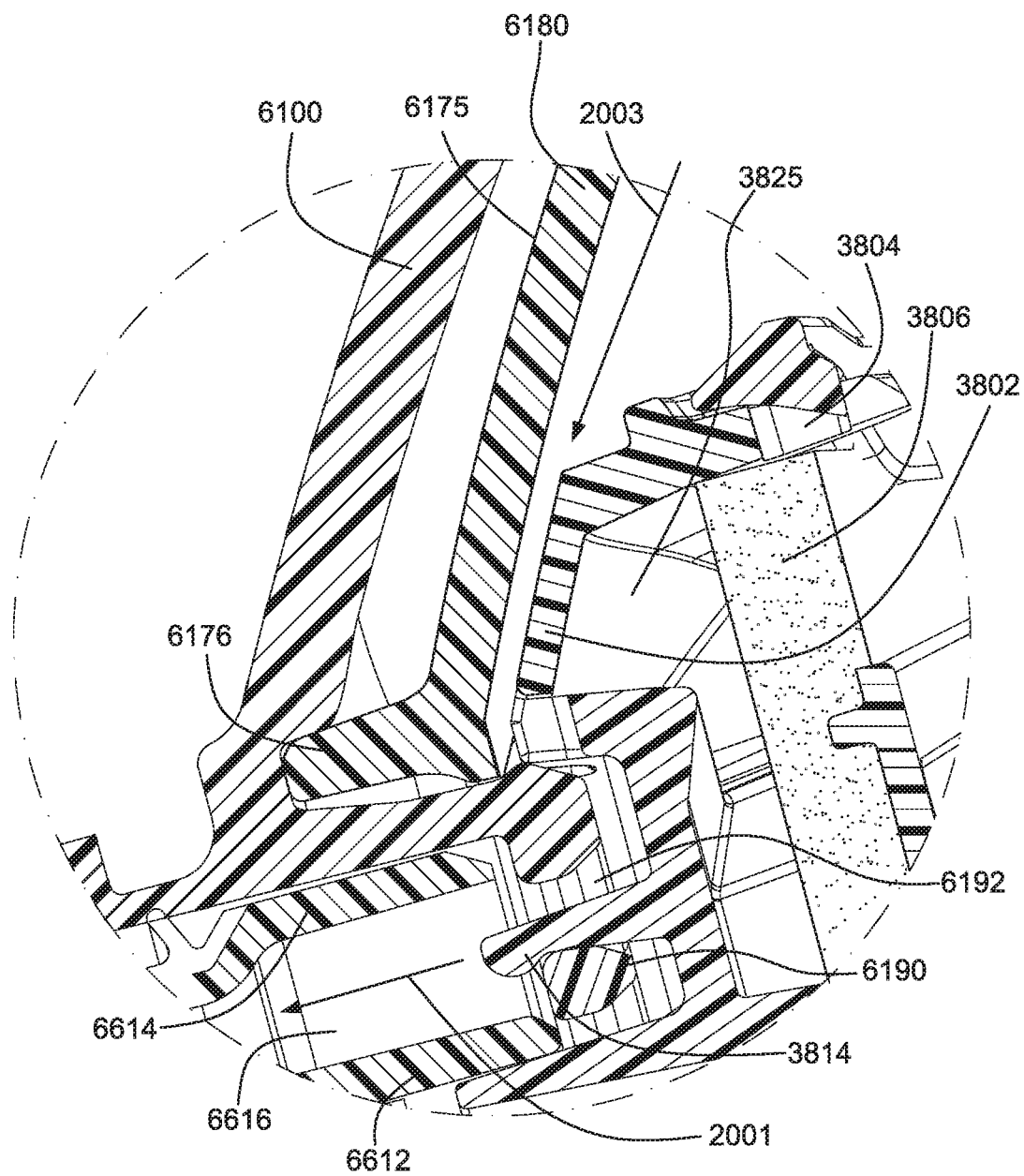

FIG. 81 shows a detailed view of FIG. 80.

Figure 82:
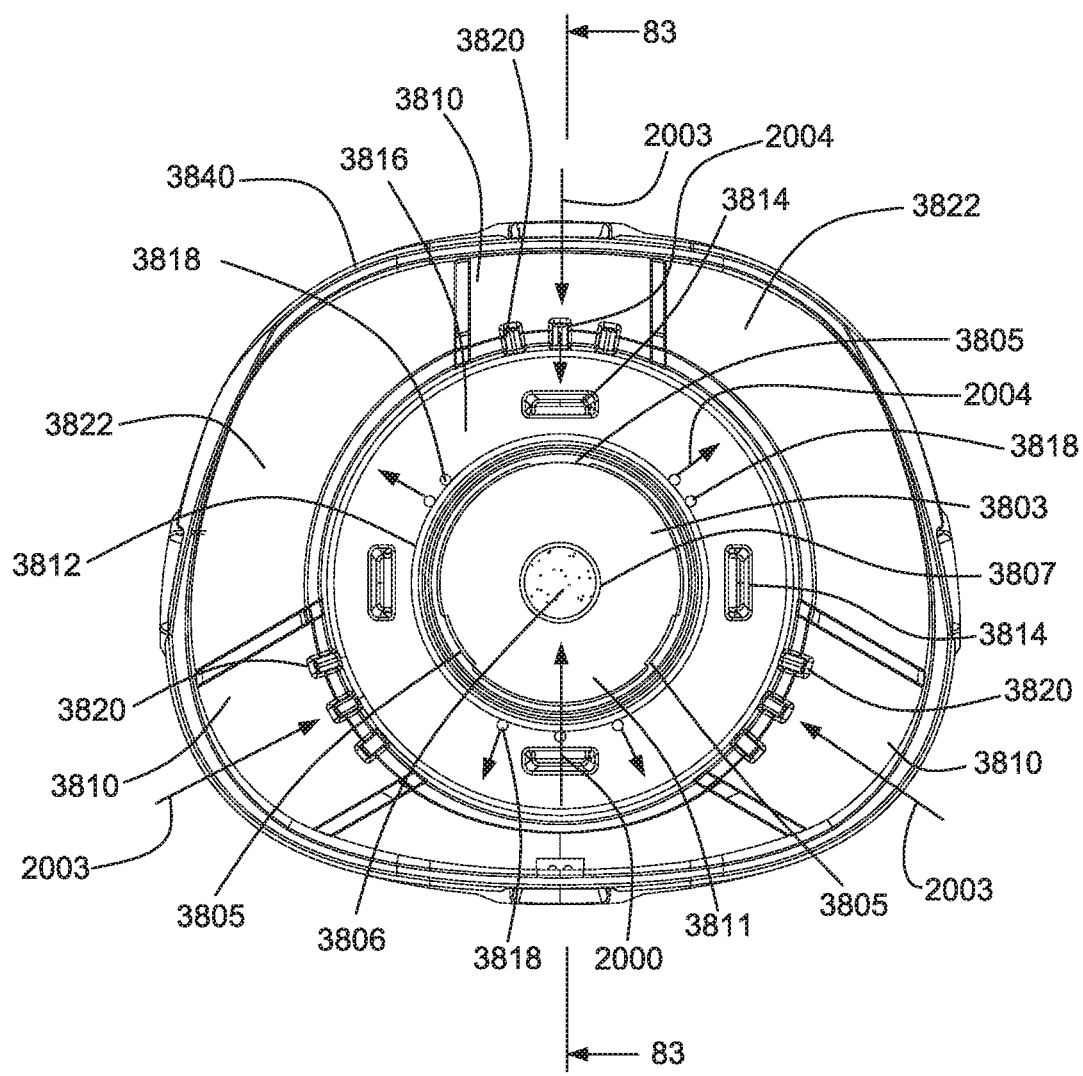

FIG. 82 shows an anterior view of a plenum chamber insert during an exhalation phase according to an example of the present technology.

Figure 83:
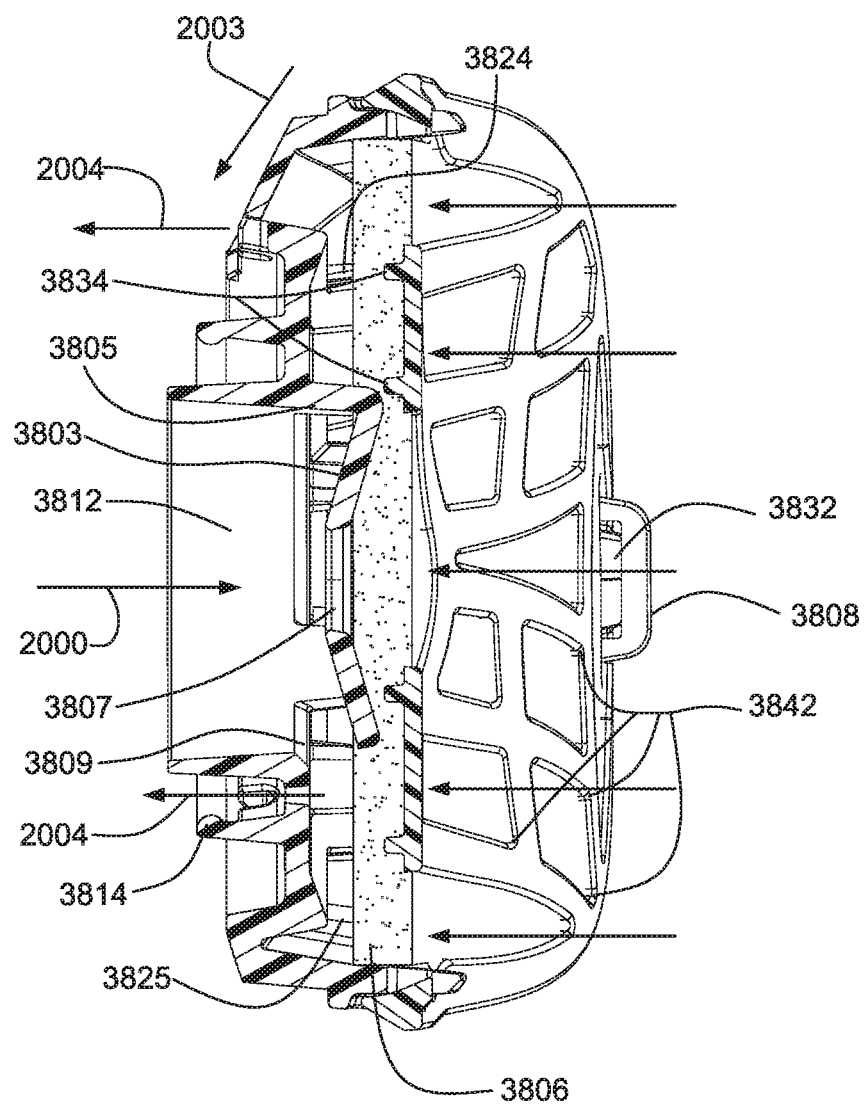

FIG. 83 shows a cross-sectional view of a plenum chamber insert taken through line 83-83 of FIG. 82 during an exhalation phase according to an example of the present technology.

Figure 84:
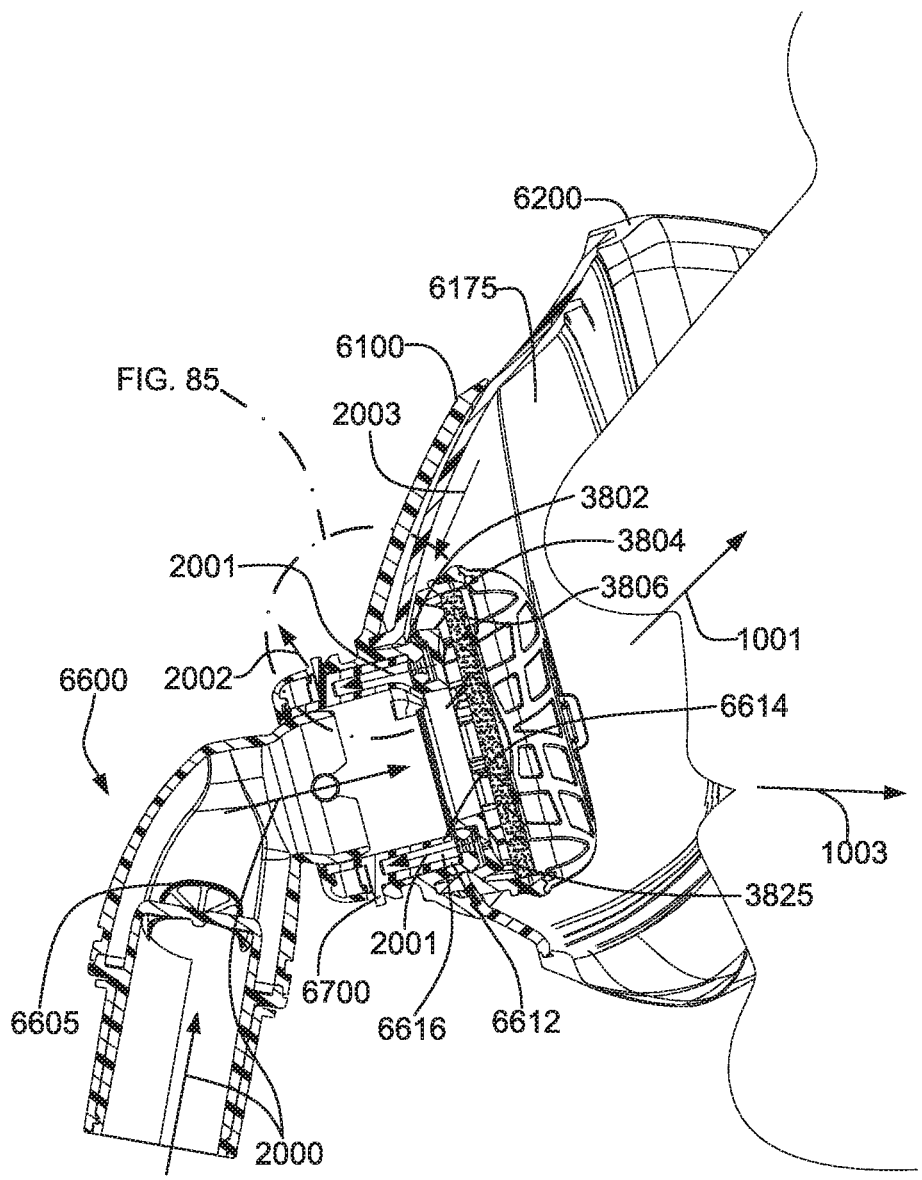

FIG. 84 shows a cross-sectional view of a patient interface based on FIG. 22, including a plenum chamber insert, against a patient's face during an inhalation phase according to an example of the present technology.

Figure 85:
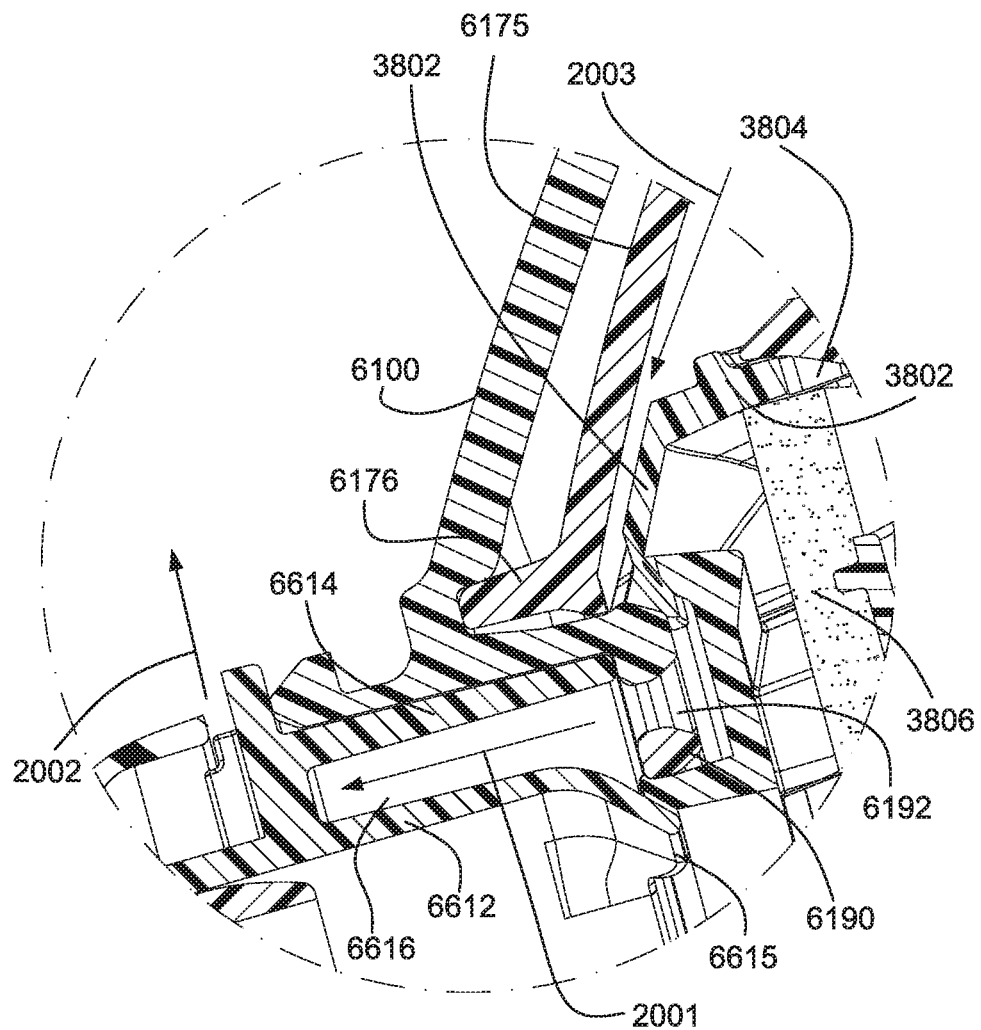

FIG. 85 shows a detailed view of FIG. 84.

Figure 86:
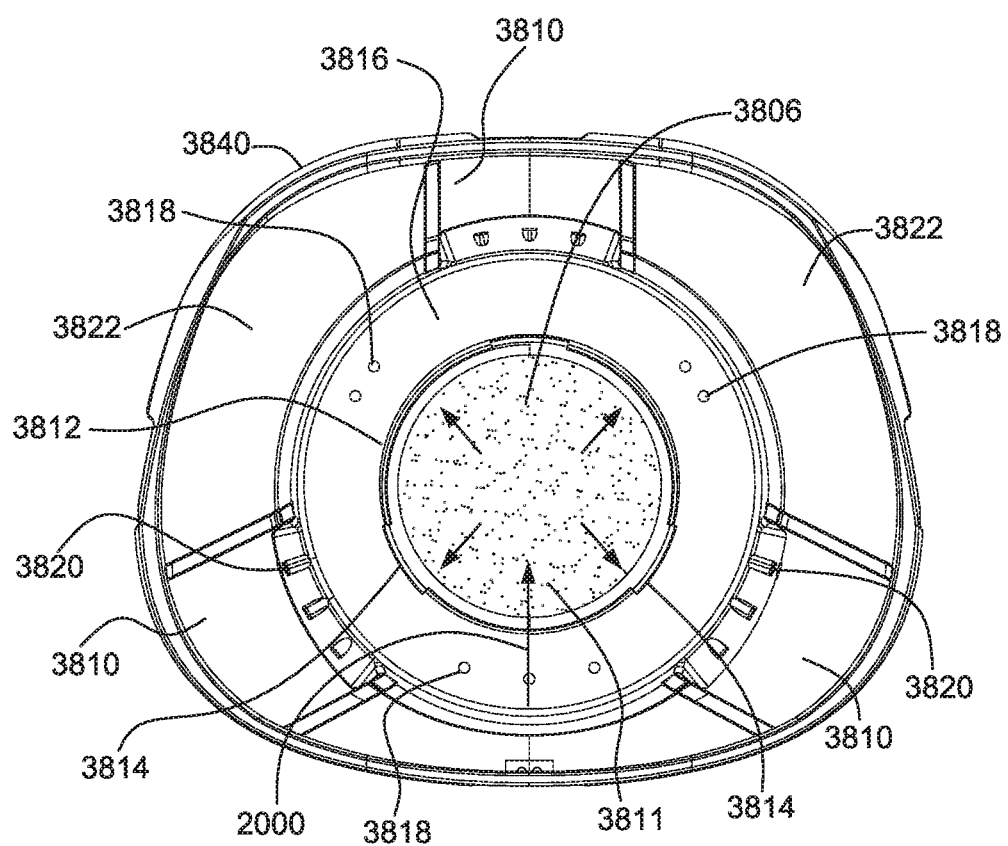

FIG. 86 shows an anterior view of a plenum chamber insert during an inhalation phase according to an example of the present technology.

Figure 87:
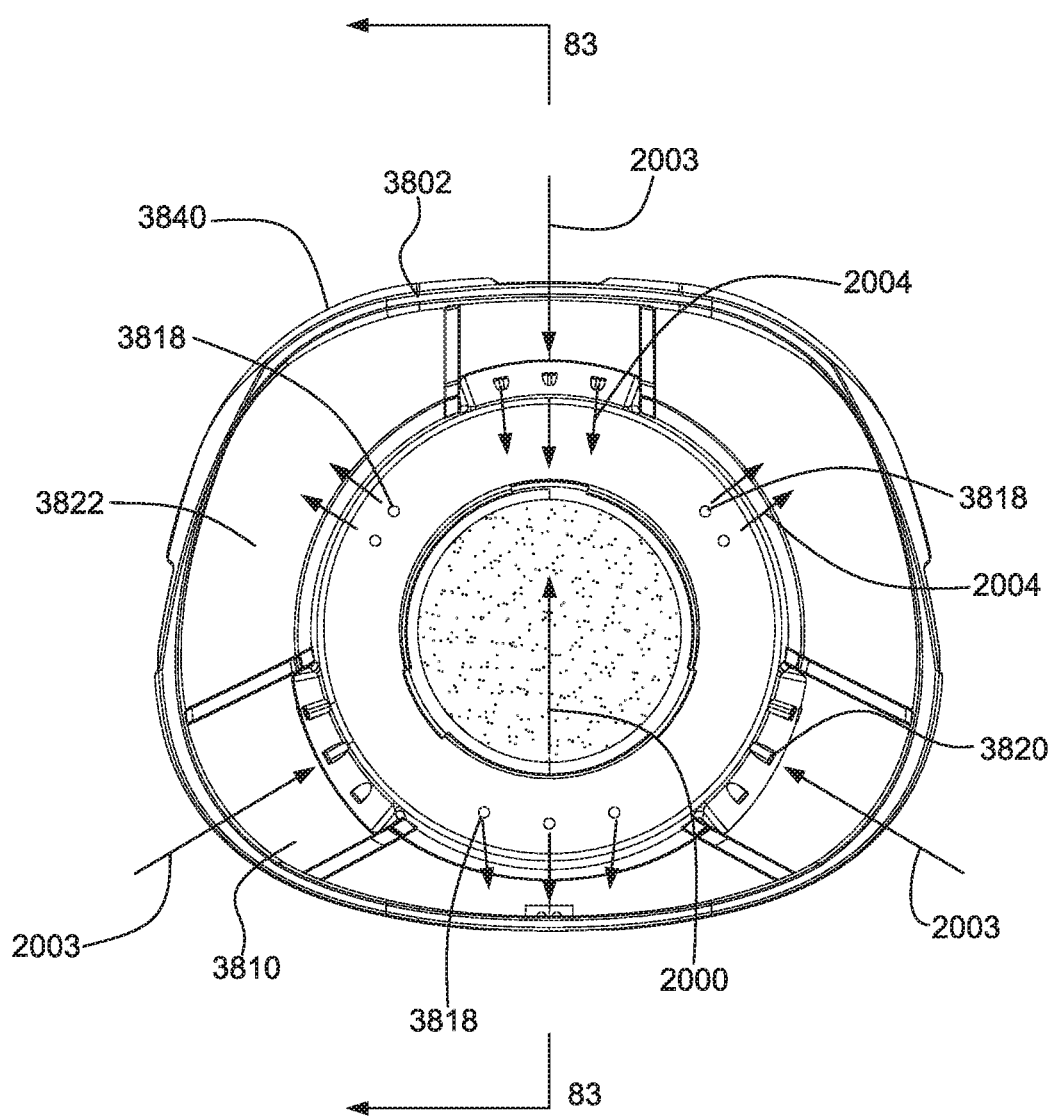

FIG. 87 shows an anterior view of a plenum chamber insert during breath pause according to an example of the present technology.

Figure 88:
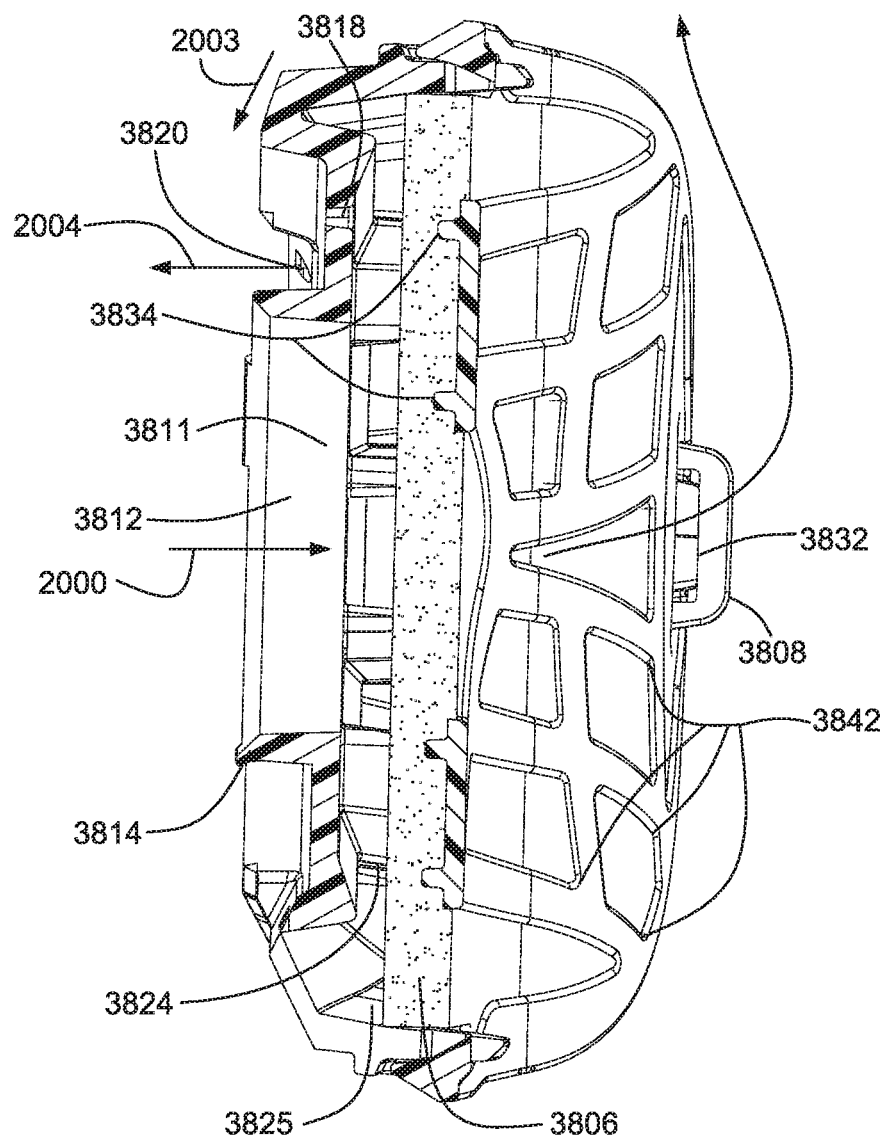

FIG. 88 shows a cross-sectional view of a plenum chamber insert taken through line 88-88 of FIG. 87 during breath pause according to an example of the present technology.

Figure 89:
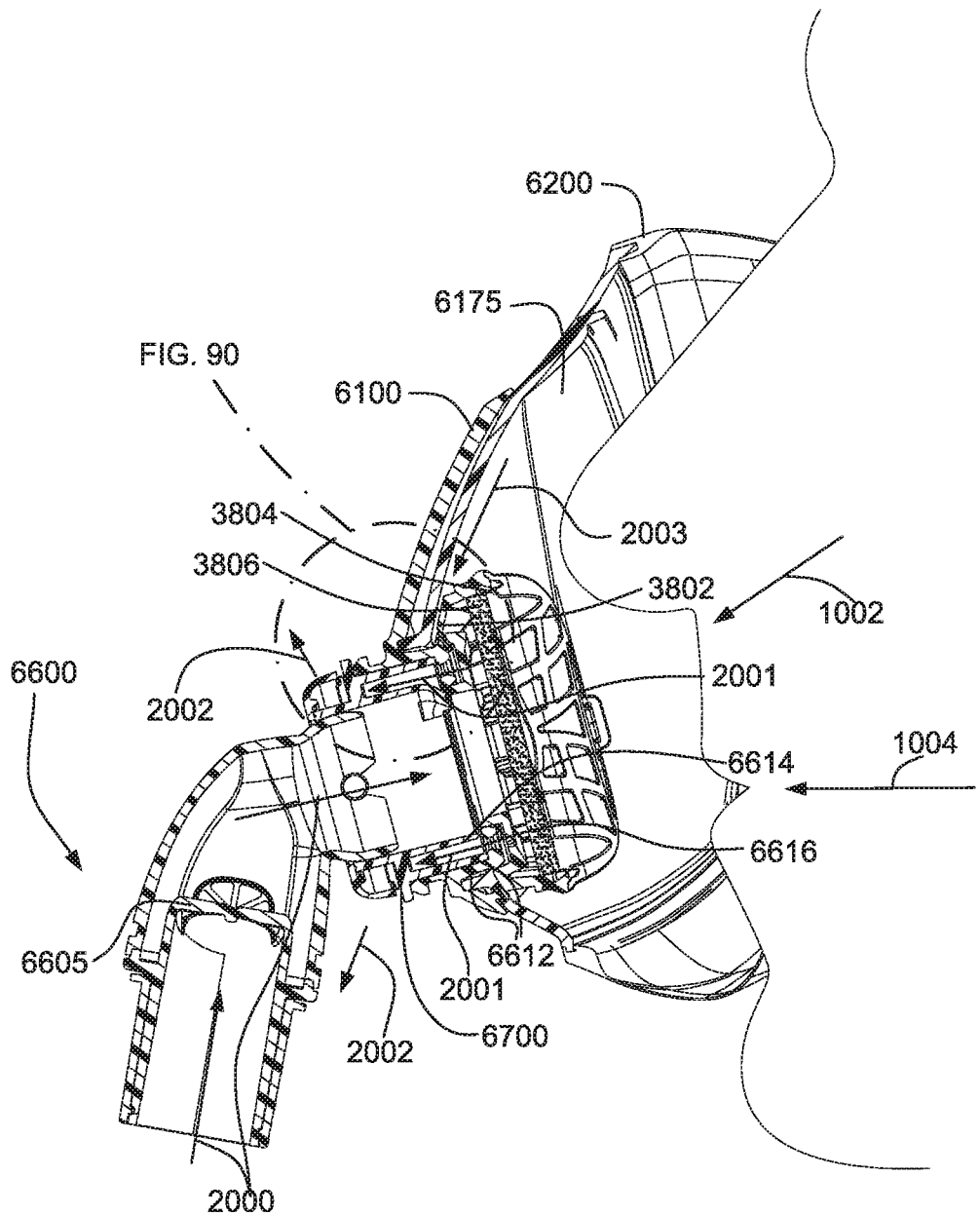

FIG. 89 shows a cross-sectional view of a patient interface based on FIG. 22, including a plenum chamber insert, against a patient's face during an exhalation phase according to an example of the present technology.

Figure 90:
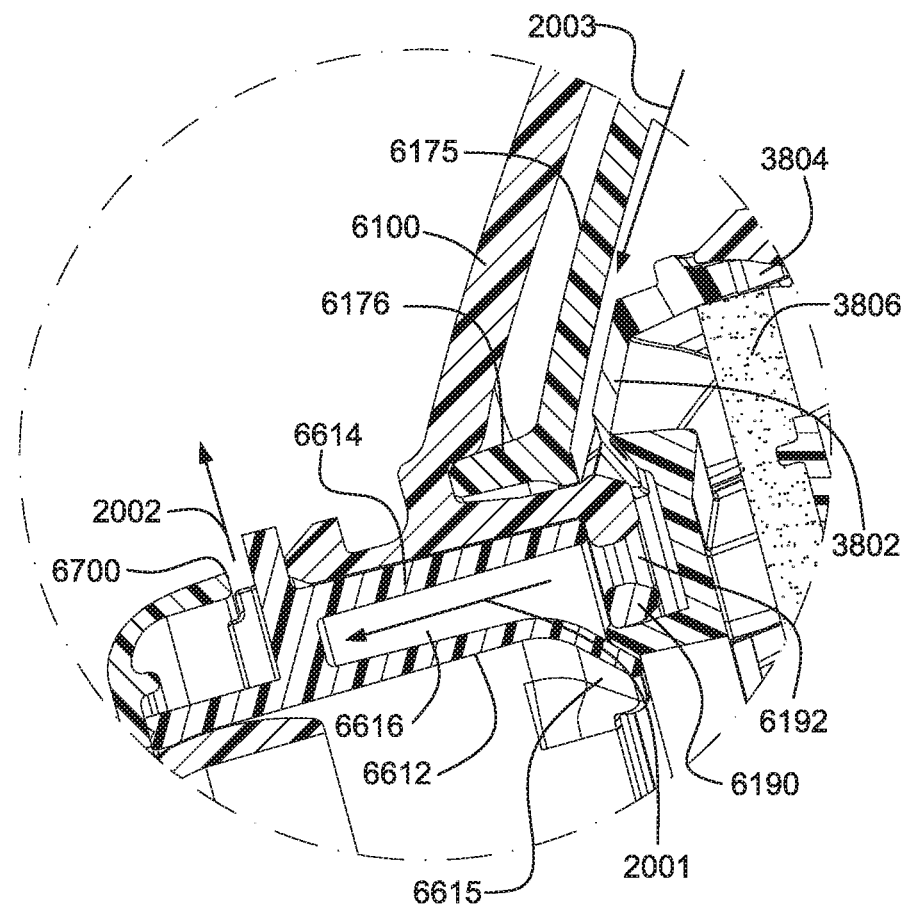

FIG. 90 shows a detailed view of FIG. 89.

Figure 91:
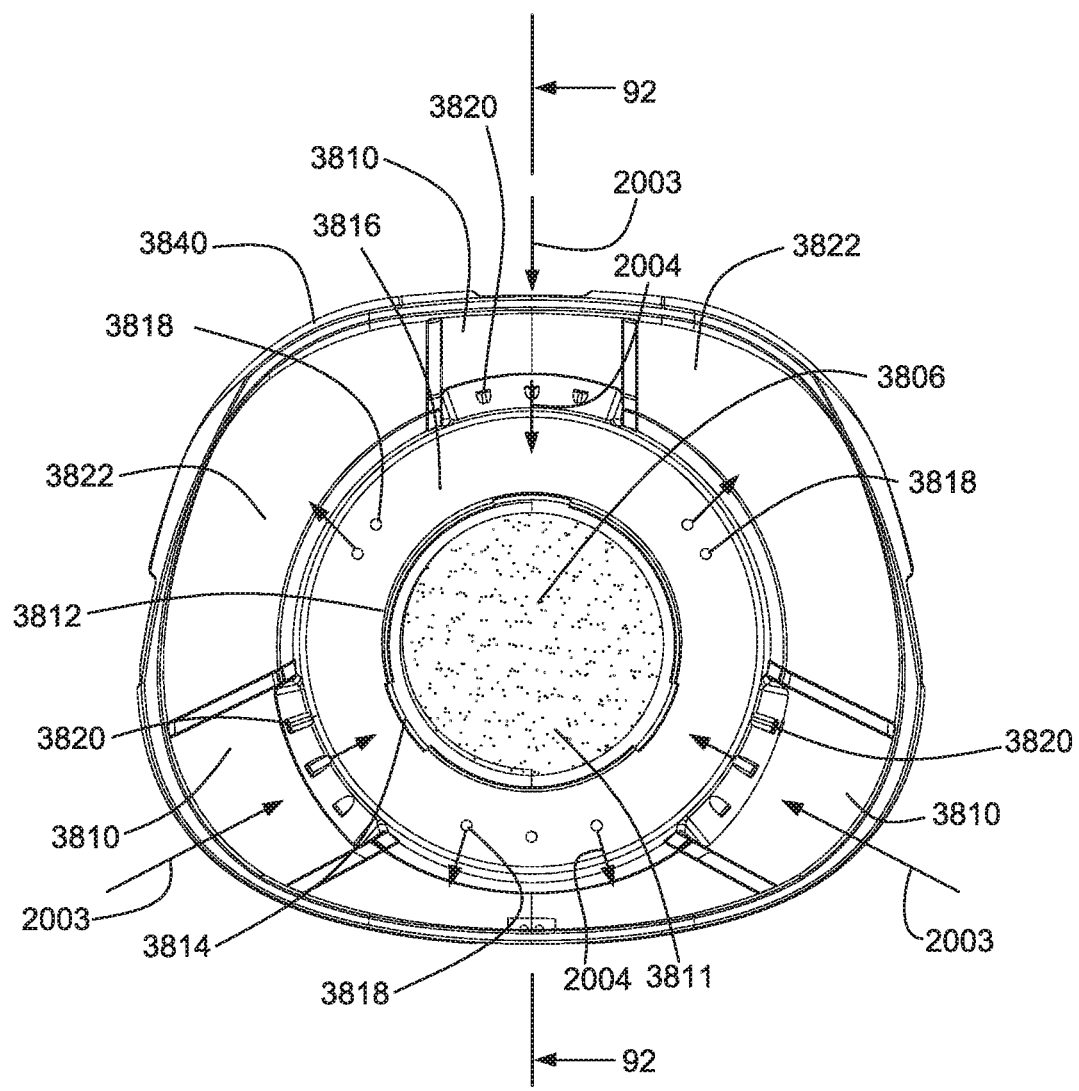

FIG. 91 shows an anterior view of a plenum chamber insert during an exhalation phase according to an example of the present technology.

Figure 92:
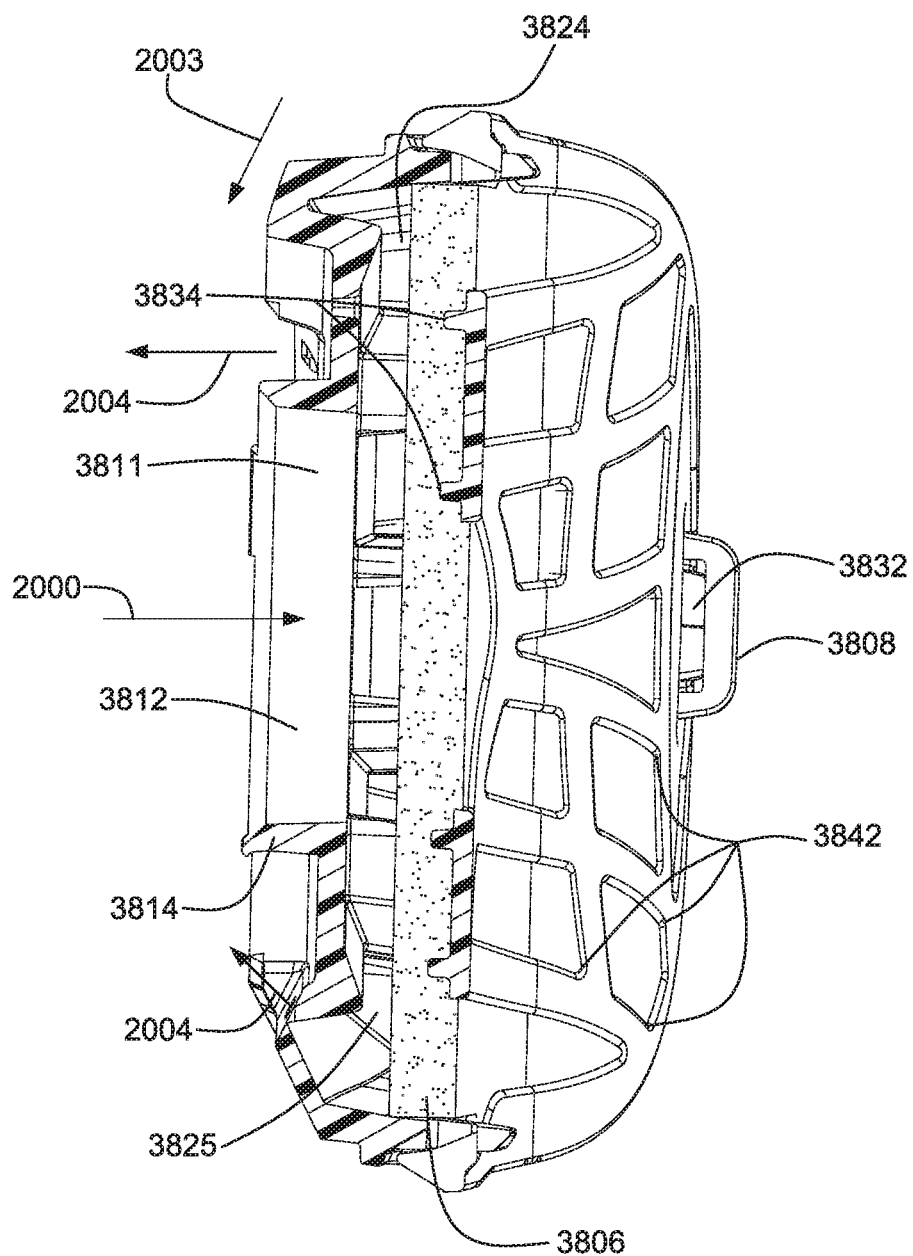

FIG. 92 shows a cross-sectional view of a plenum chamber insert taken through line 92-92 of FIG. 91 during an exhalation phase according to an example of the present technology.

Figure 93:
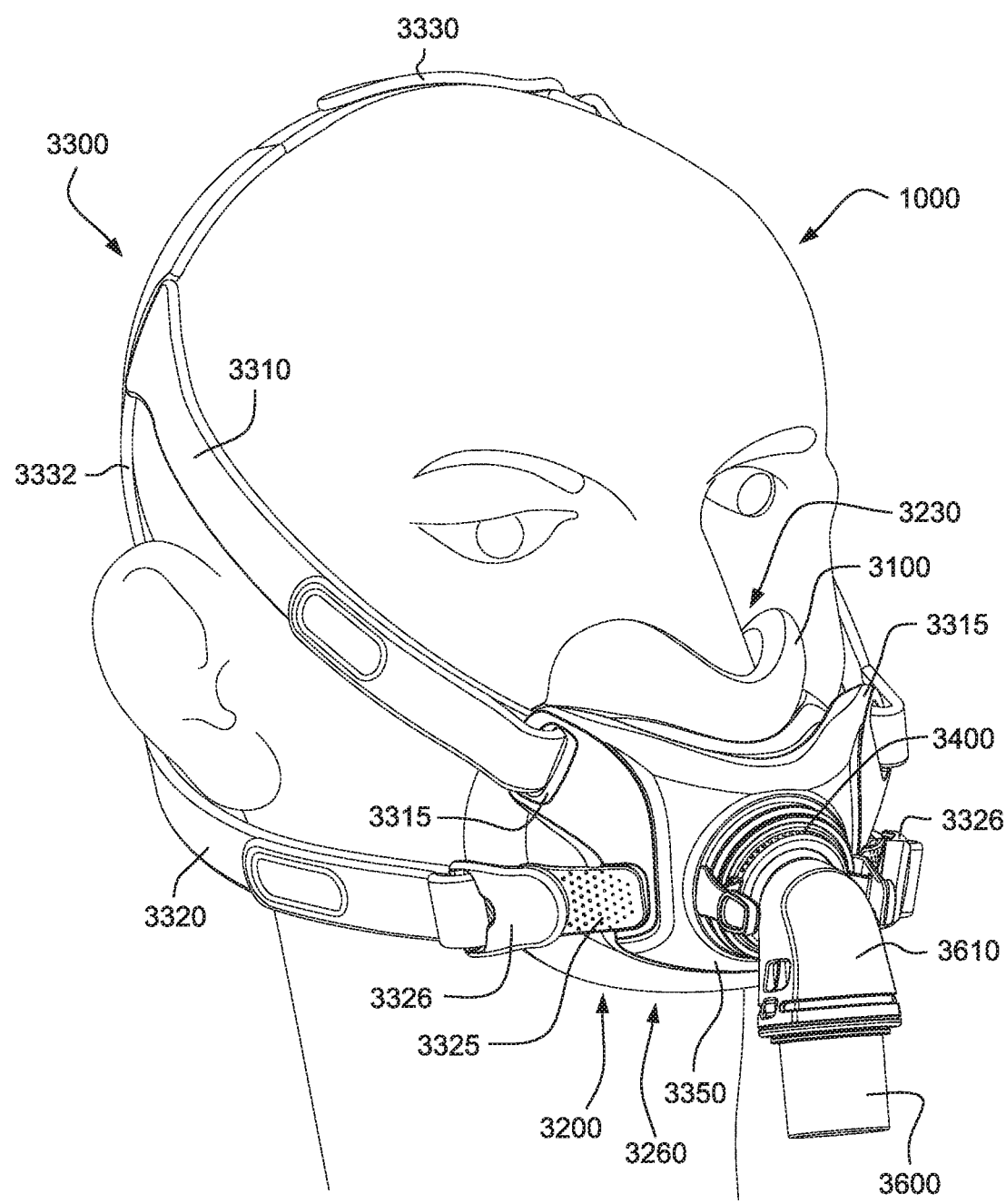

FIG. 93 is a perspective view of a patient interface 3000 according to one example of the present technology while worn by a patient.

Figure 94:
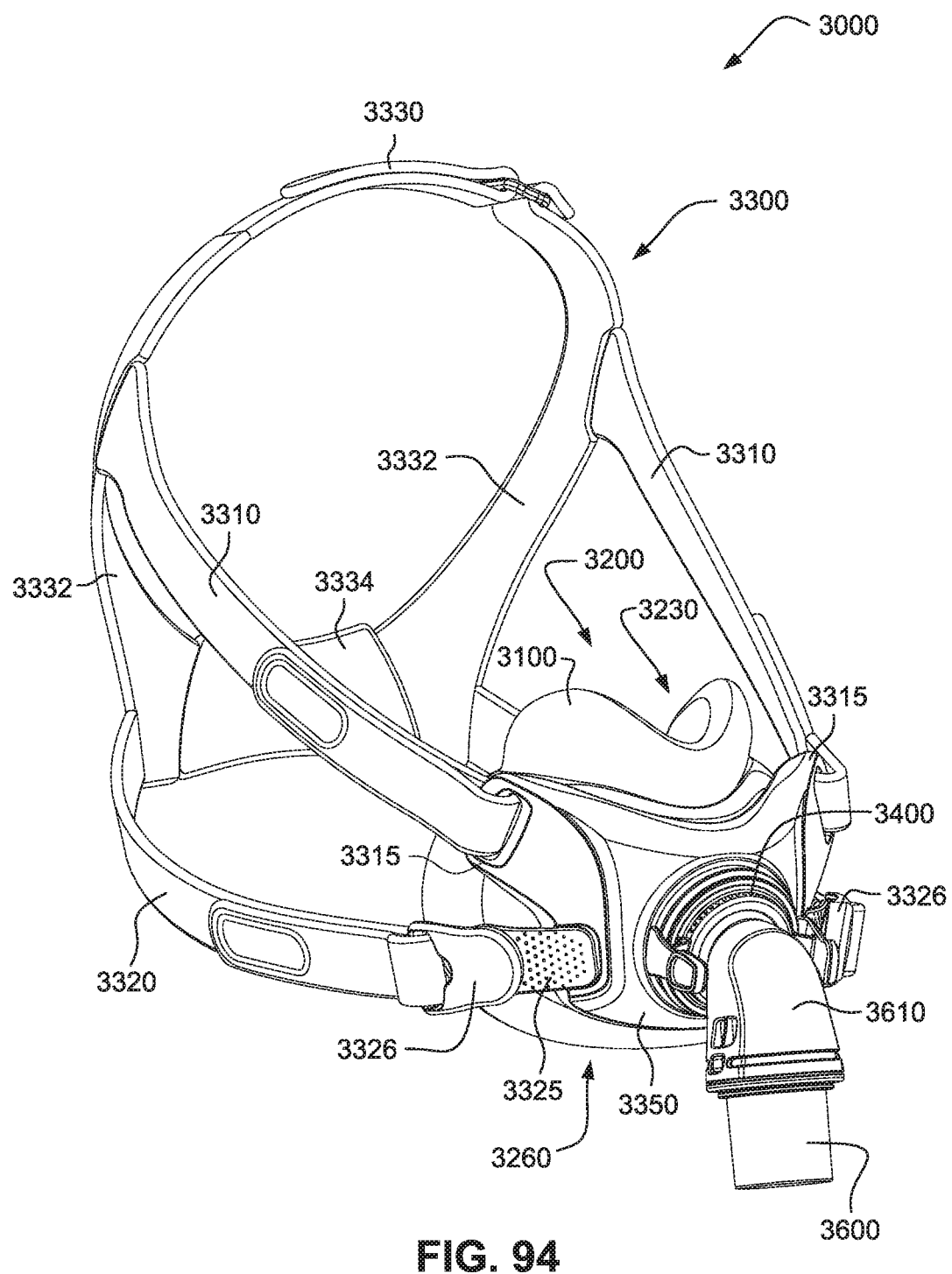

FIG. 94 is a perspective view of a patient interface 3000 according to one example of the present technology.

Figure 95:
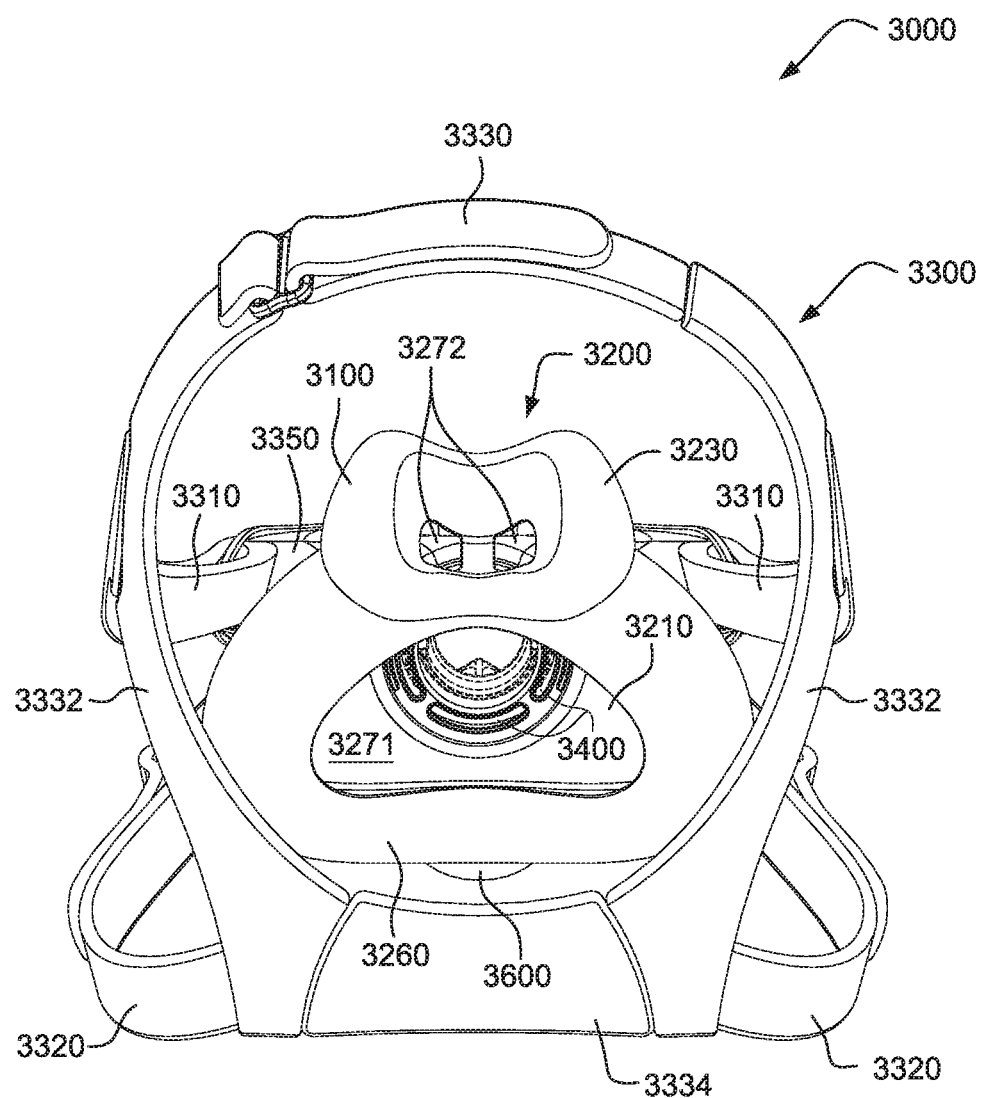

FIG. 95 is a posterior view of a patient interface 3000 according to one example of the present technology.

Figure 96:
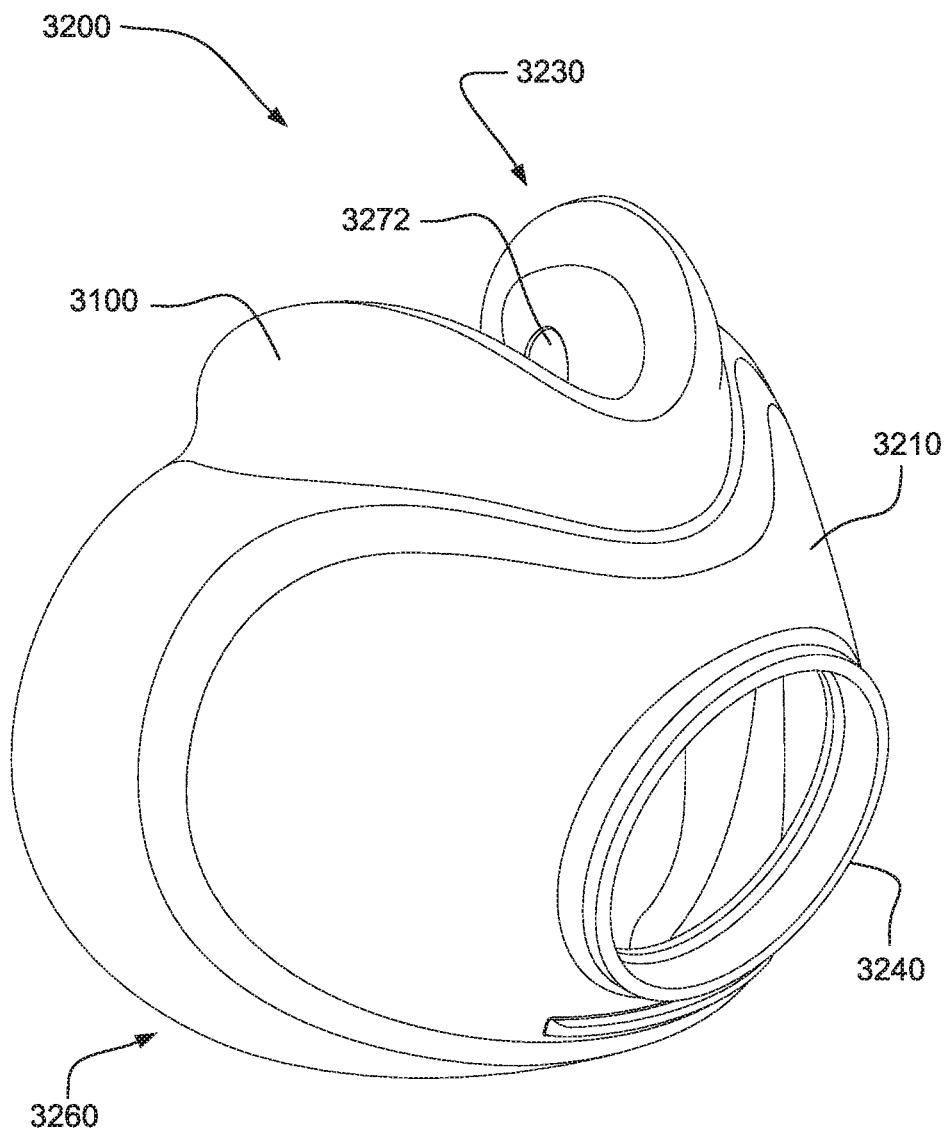

FIG. 96 is a perspective view of a seal-forming structure 3100 and a plenum chamber 3200 according to one example of the present technology.

Figure 97:
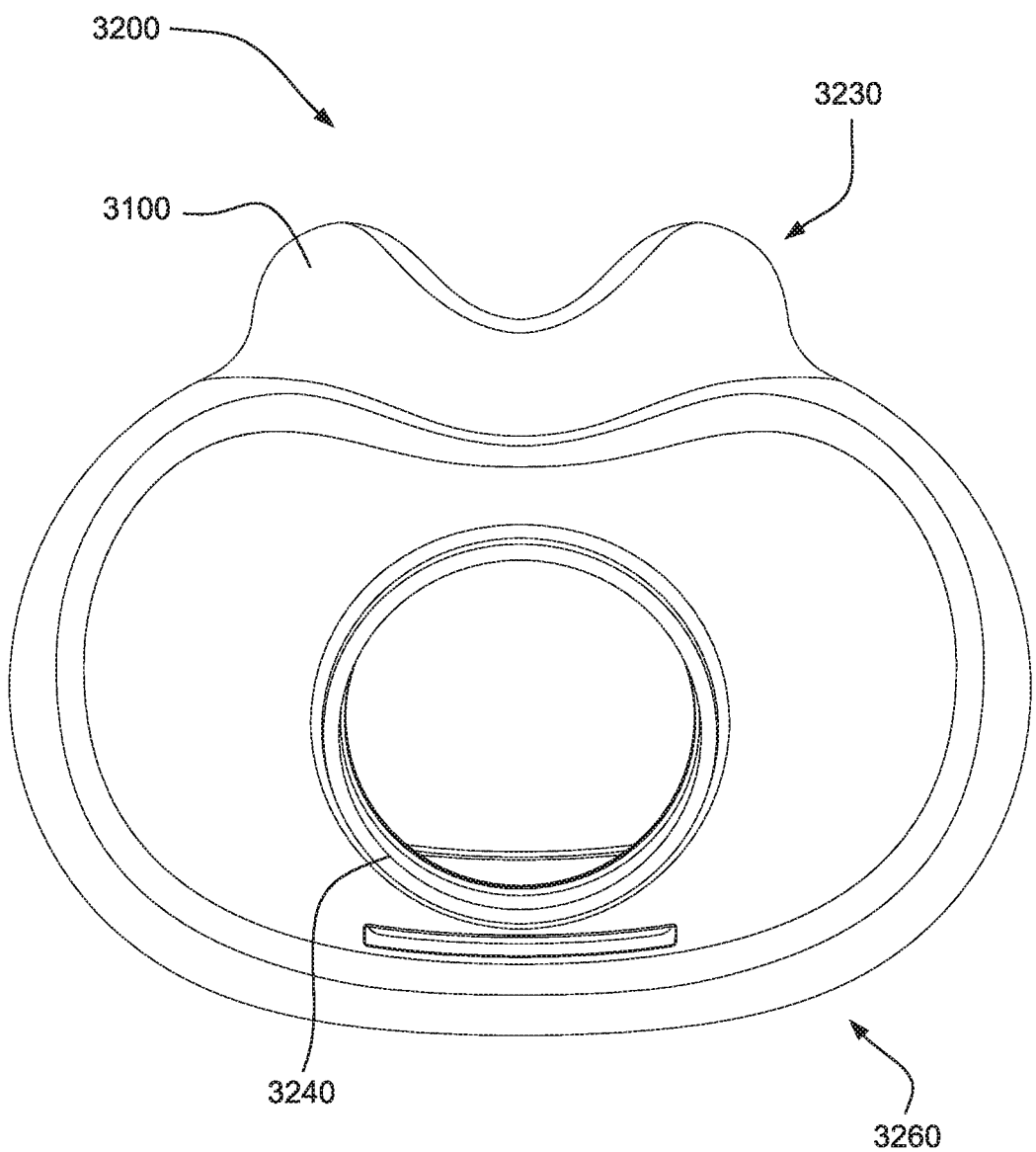

FIG. 97 is an anterior view of a seal-forming structure 3100 and a plenum chamber 3200 according to one example of the present technology.

Figure 98:
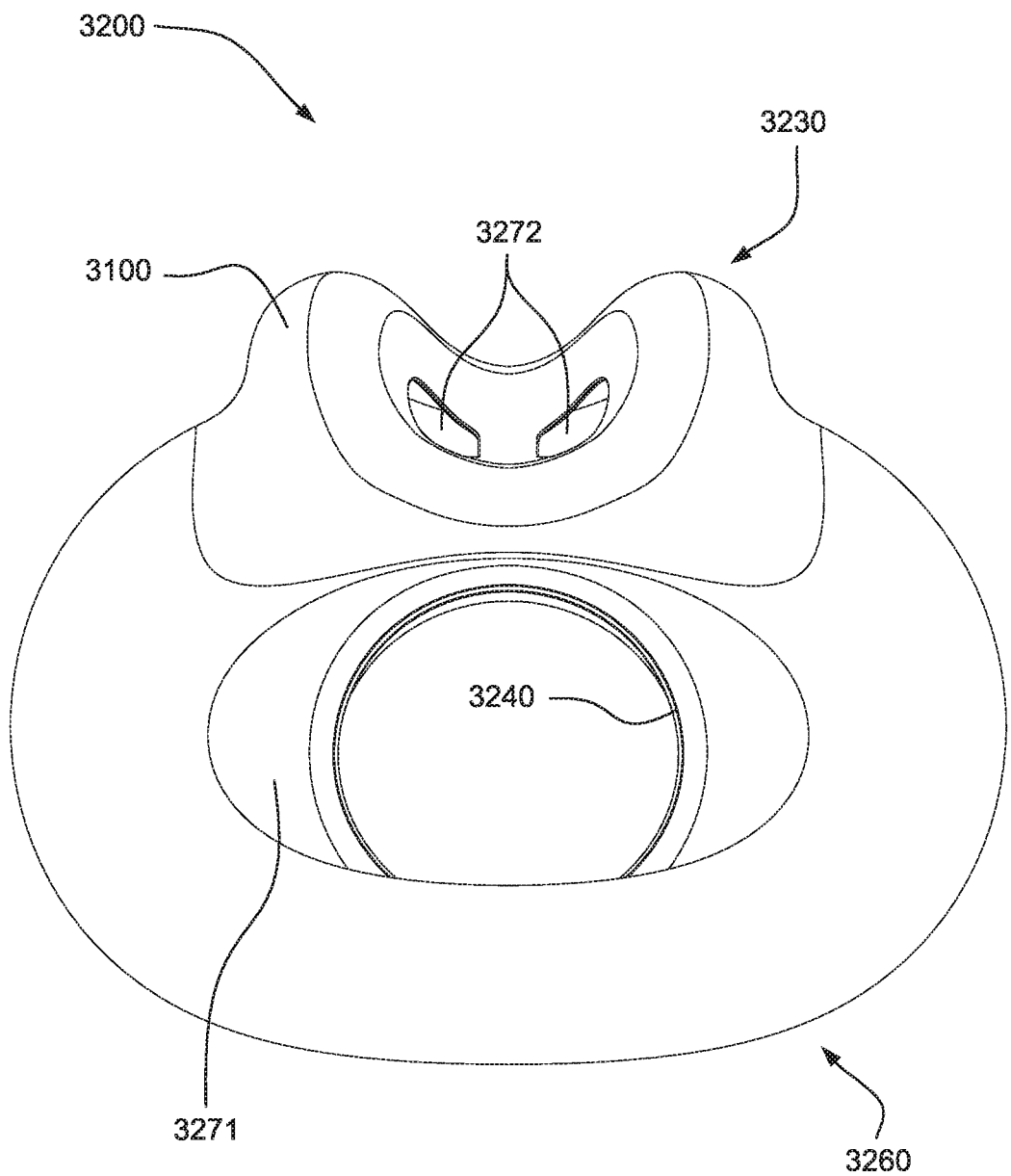

FIG. 98 is a posterior view of a seal-forming structure 3100 and a plenum chamber 3200 according to one example of the present technology.

Figure 99:
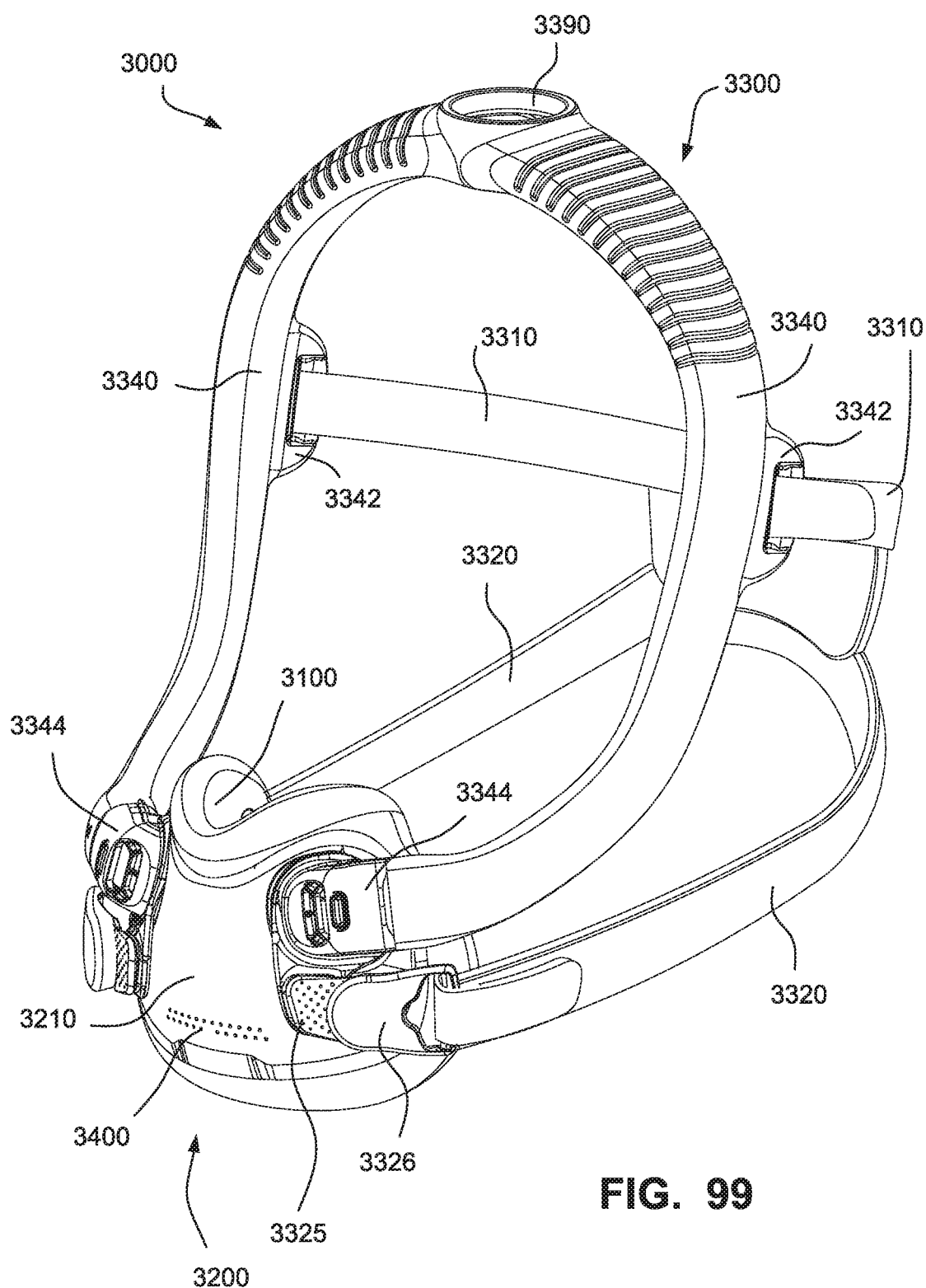

FIG. 99 is a perspective view of a patient interface 3000 according to another example of the present technology.

Figure 100:
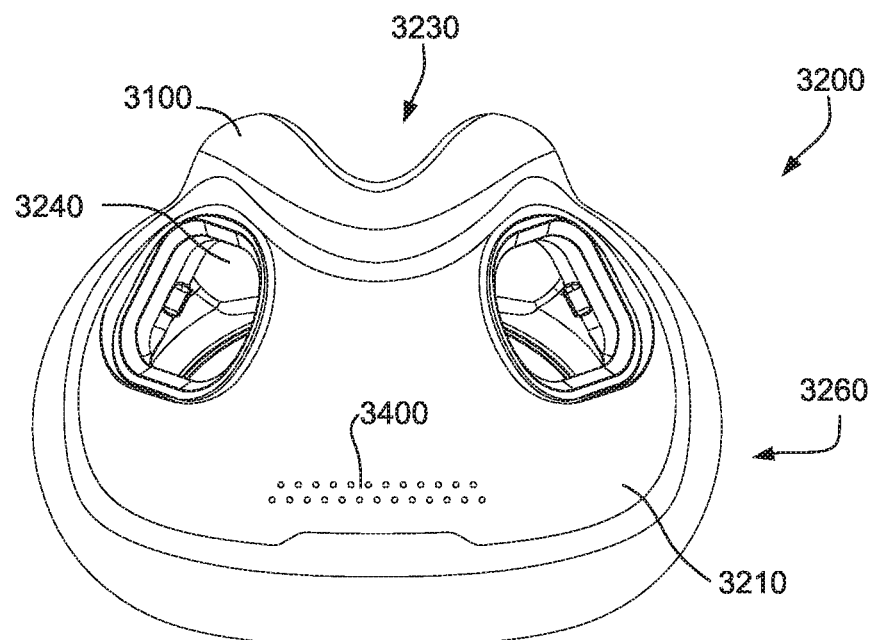

FIG. 100 is an anterior view of a seal-forming structure 3100 and a plenum chamber 3200 according to one example of the present technology.

Figure 101:
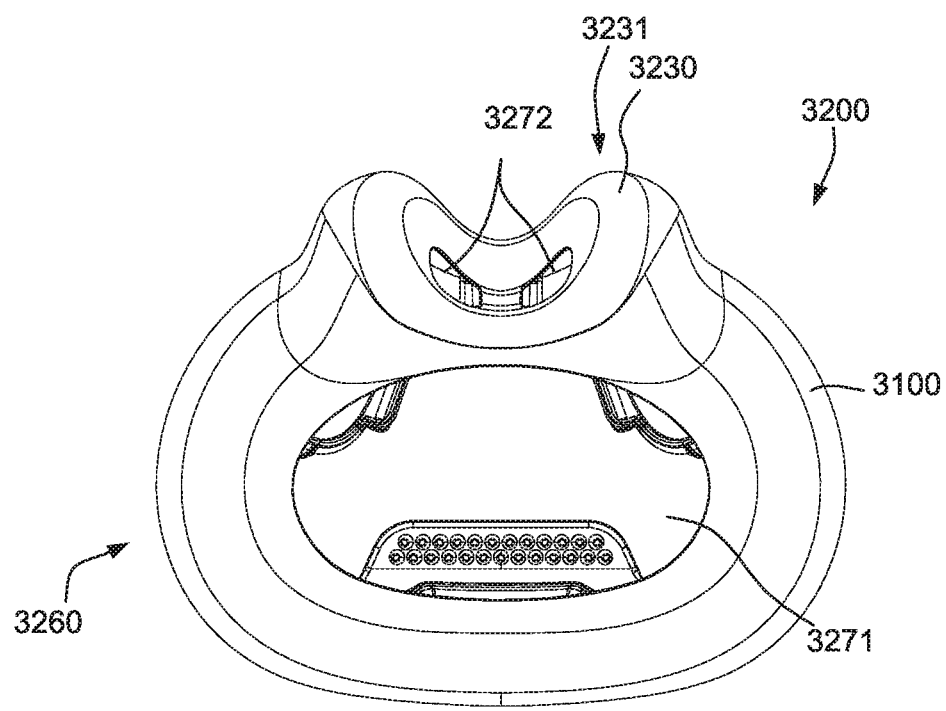

FIG. 101 is a posterior view of a seal-forming structure 3100 and a plenum chamber 3200 according to one example of the present technology.

Figure 102:
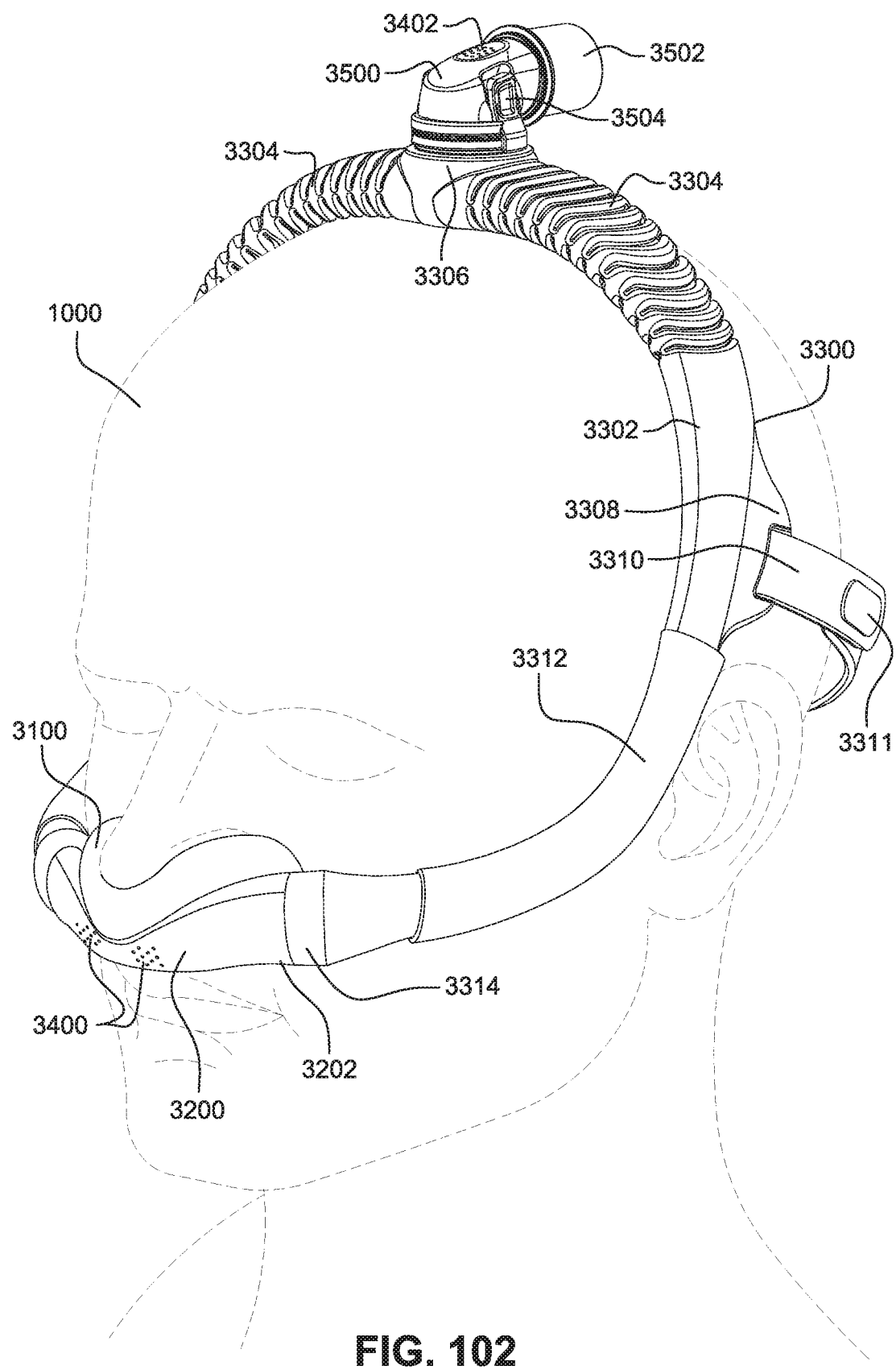

FIG. 102 is an anterolateral view from a superior position of a patient interface according to an example of the present technology worn by a patient.

Figure 103:
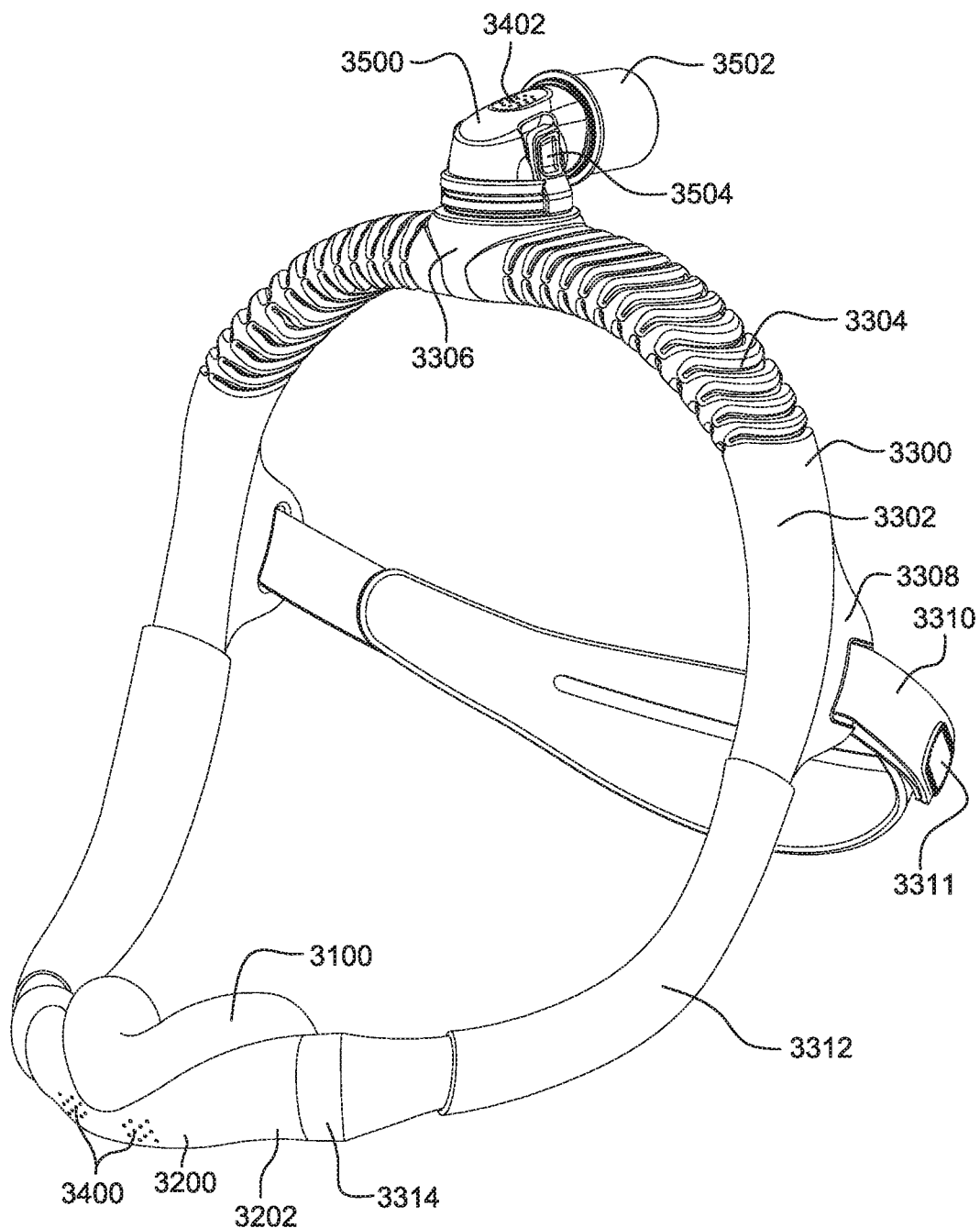

FIG. 103 is an anterolateral view from a superior position of a patient interface according to an example of the present technology.

Figure 104:
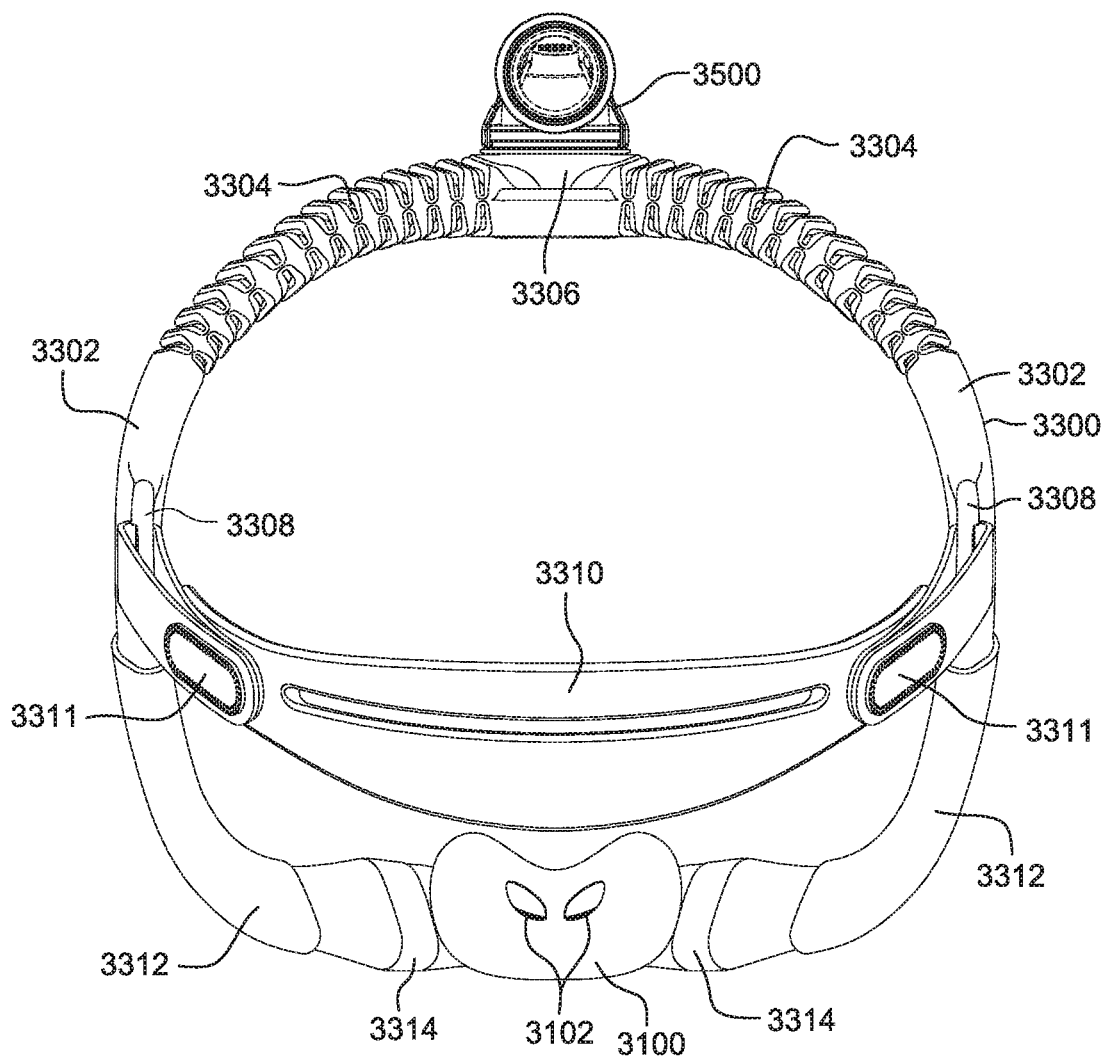

FIG. 104 is a posterior view of a patient interface according to an example of the present technology.

Figure 105:
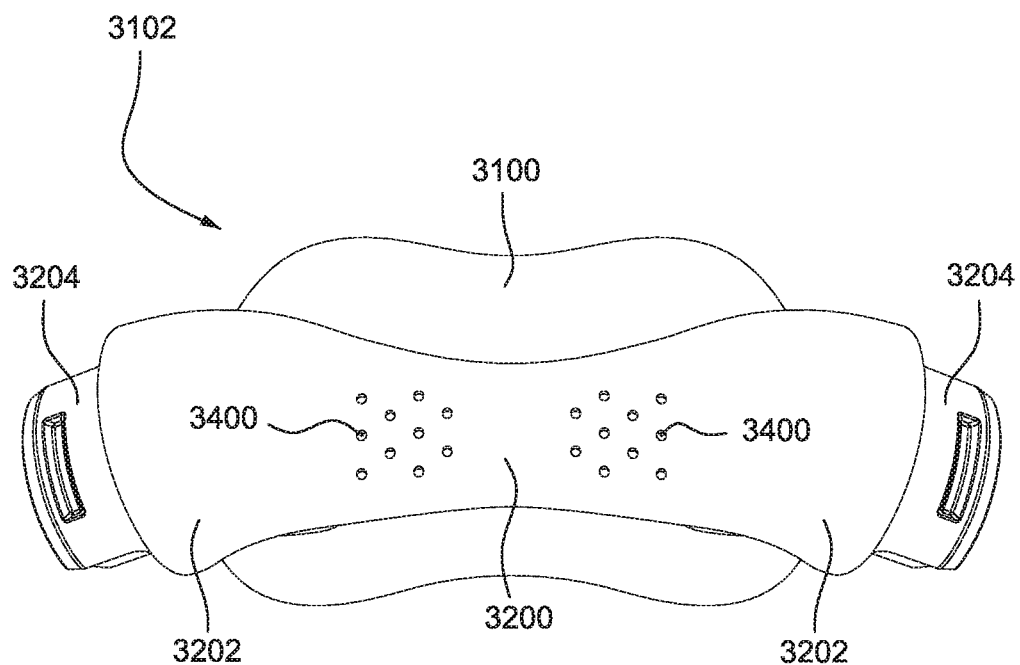

FIG. 105 is an anterior view of a seal-forming structure and a plenum chamber for a patient interface according to an example of the present technology.

Figure 106:
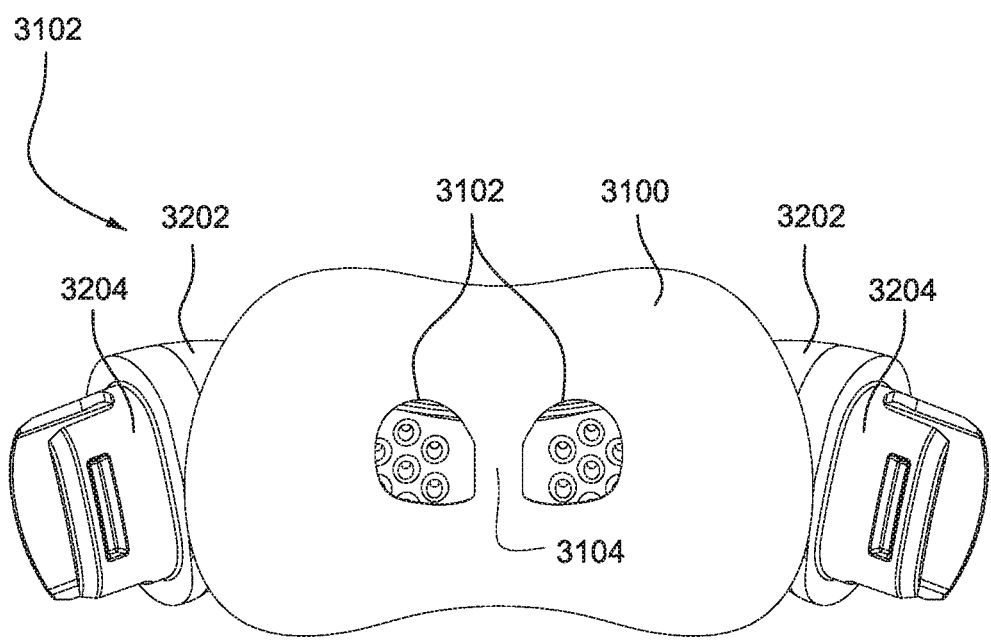

FIG. 106 is a posterior view of a seal-forming structure and a plenum chamber for a patient interface according to an example of the present technology.

Figure 107:
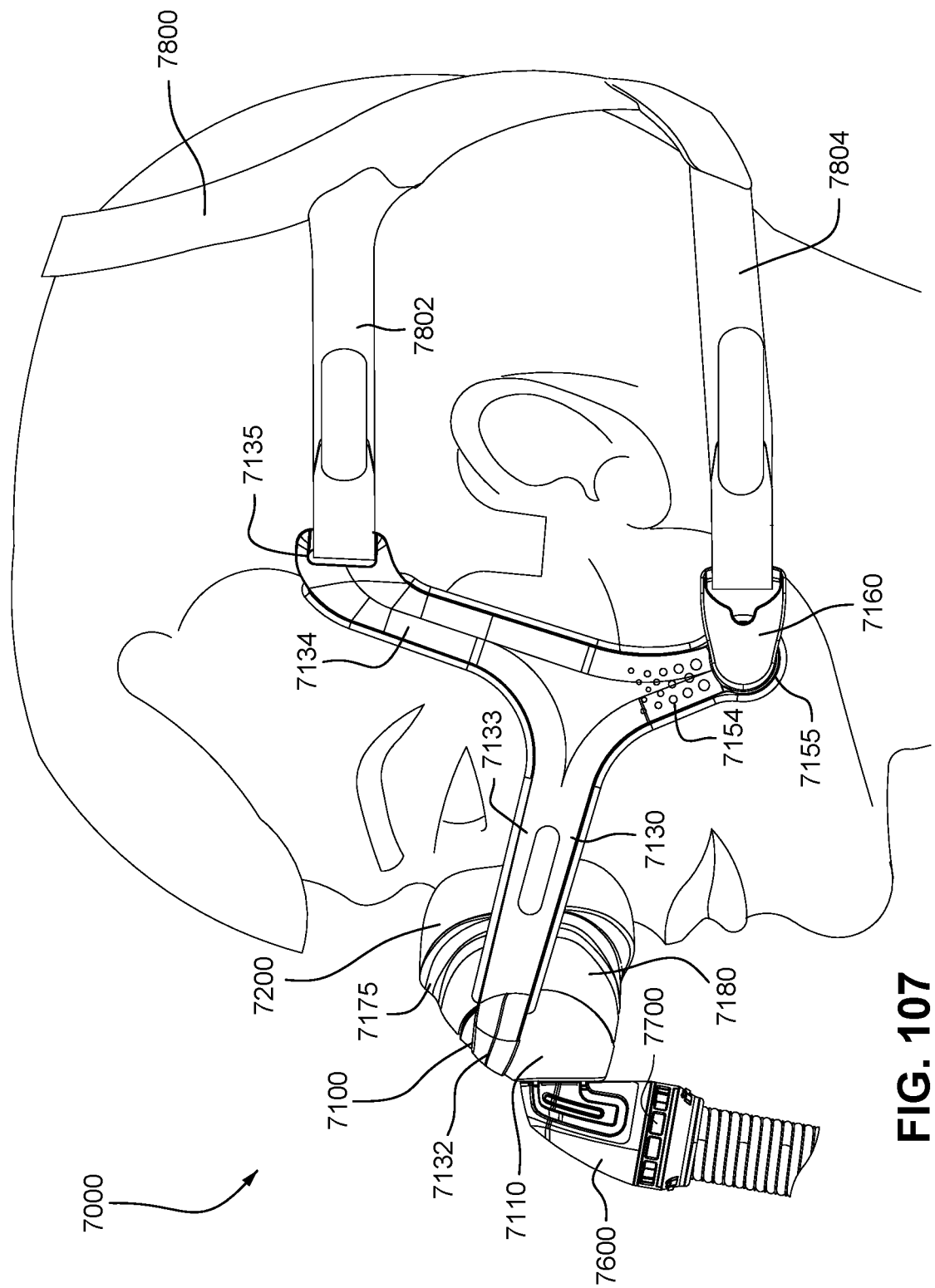

FIG. 107 is a lateral view from a superior position of a patient interface according to an example of the present technology worn by a patient.

Figure 108:
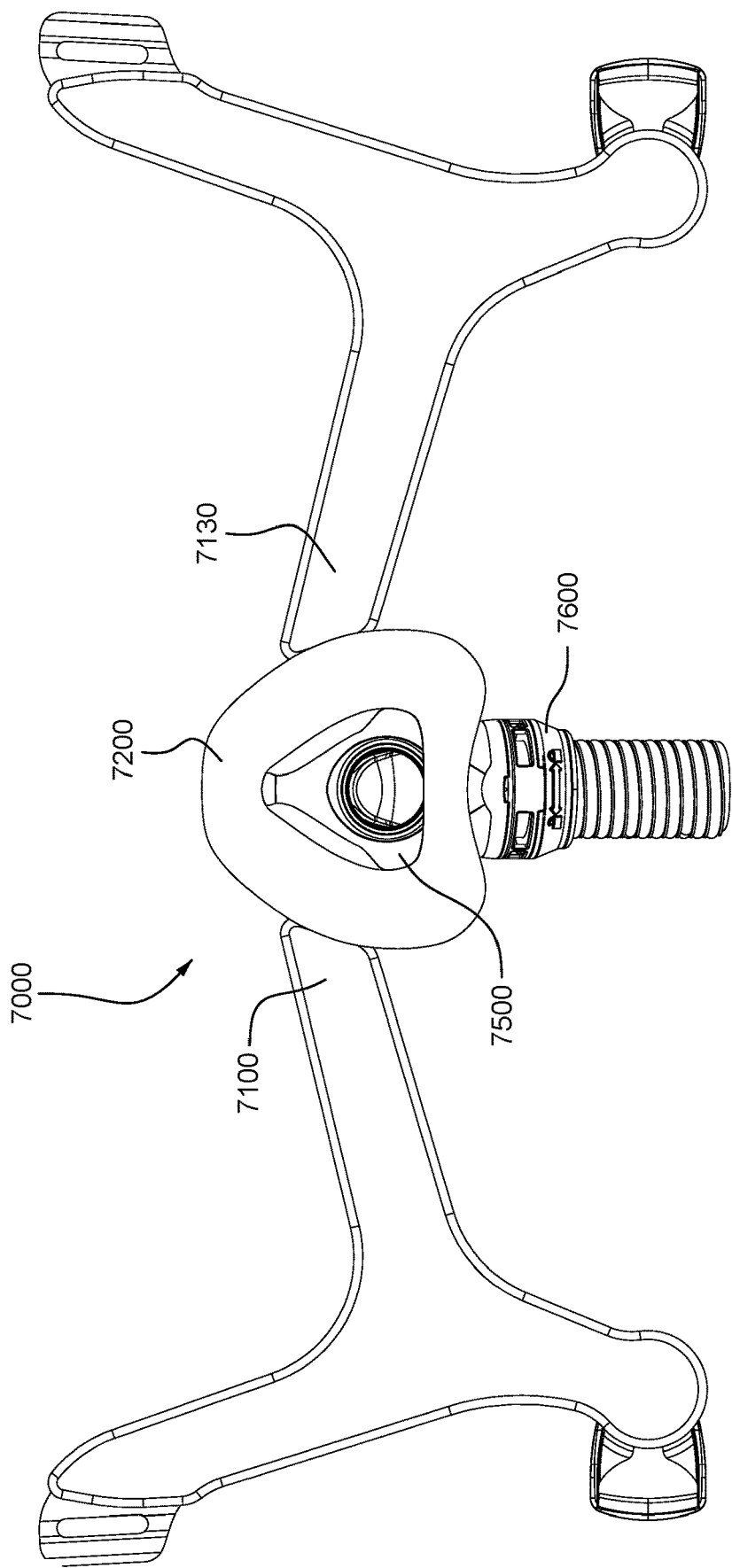

FIG. 108 is a posterior view of a patient interface according to an example of the present technology.

Figure 109:
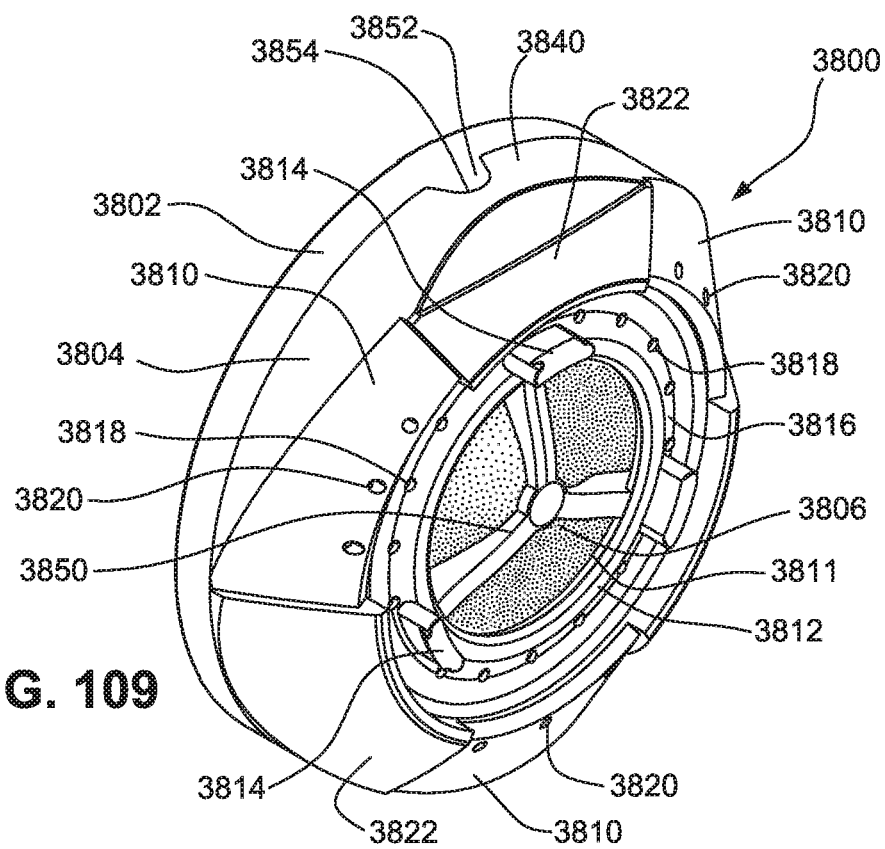

FIG. 109 is an anterior perspective view of a plenum chamber insert according to an example of the present technology.

Figure 110:
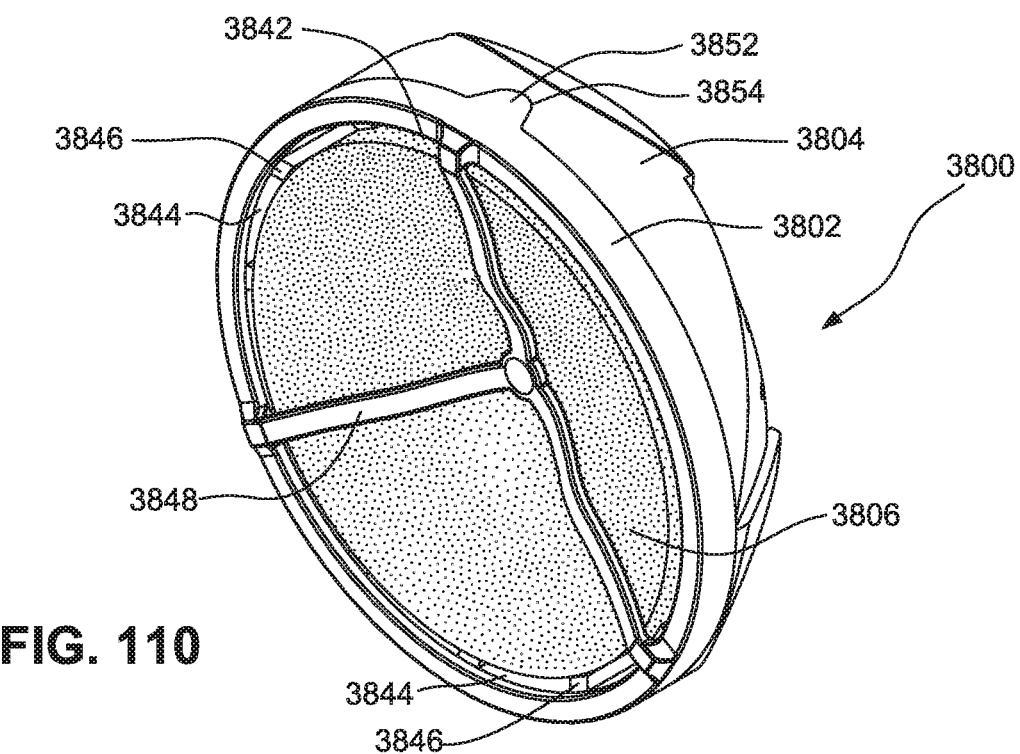

FIG. 110 is a posterior perspective view of a plenum chamber insert according to an example of the present technology.

Figure 111:
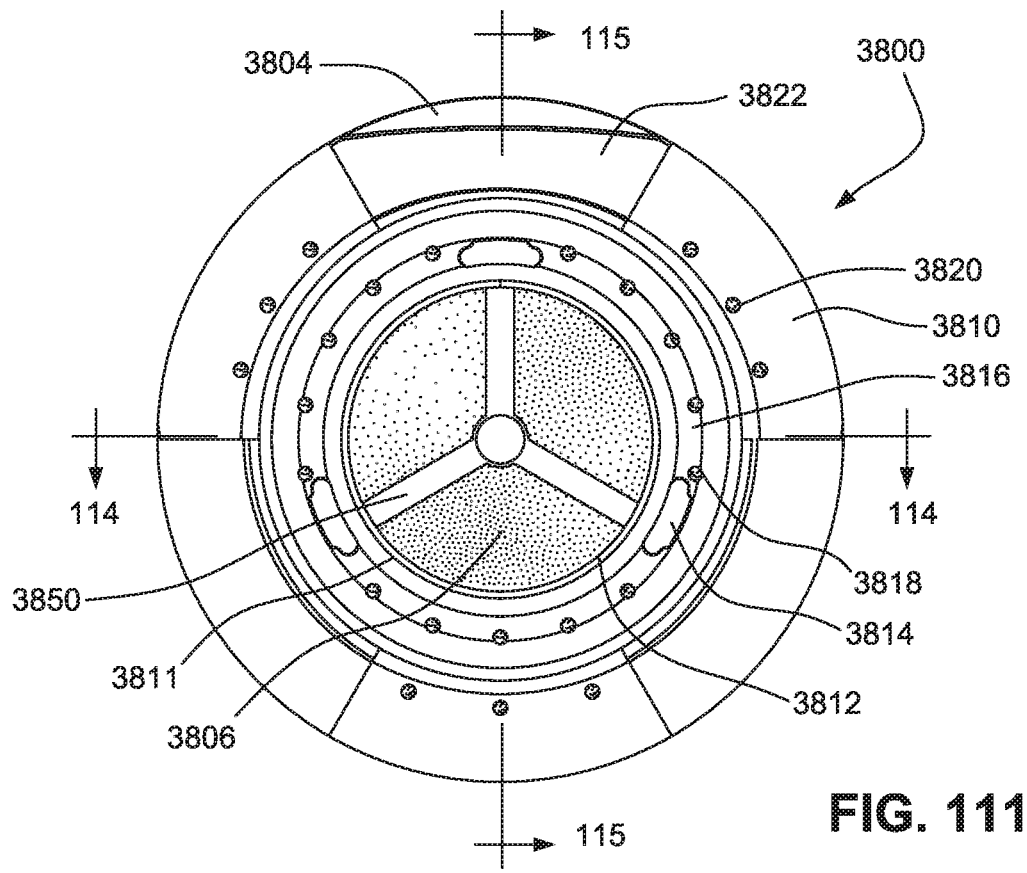

FIG. 111 is an anterior view of a plenum chamber insert according to an example of the present technology.

Figure 112:
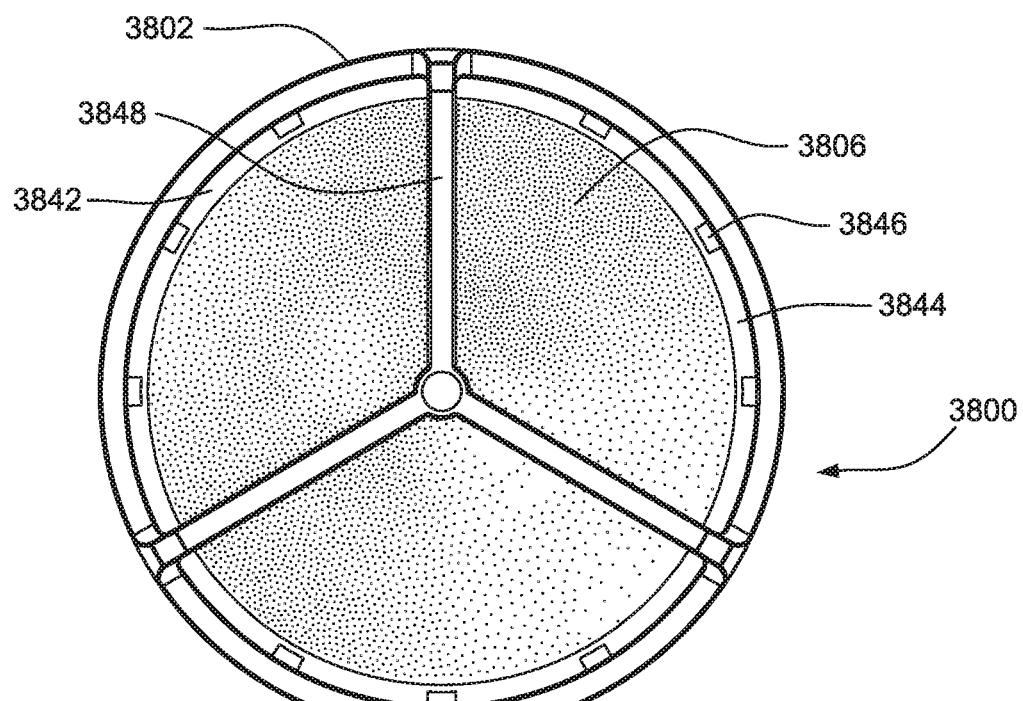

FIG. 112 is a posterior view of a plenum chamber insert according to an example of the present technology.

Figure 113:
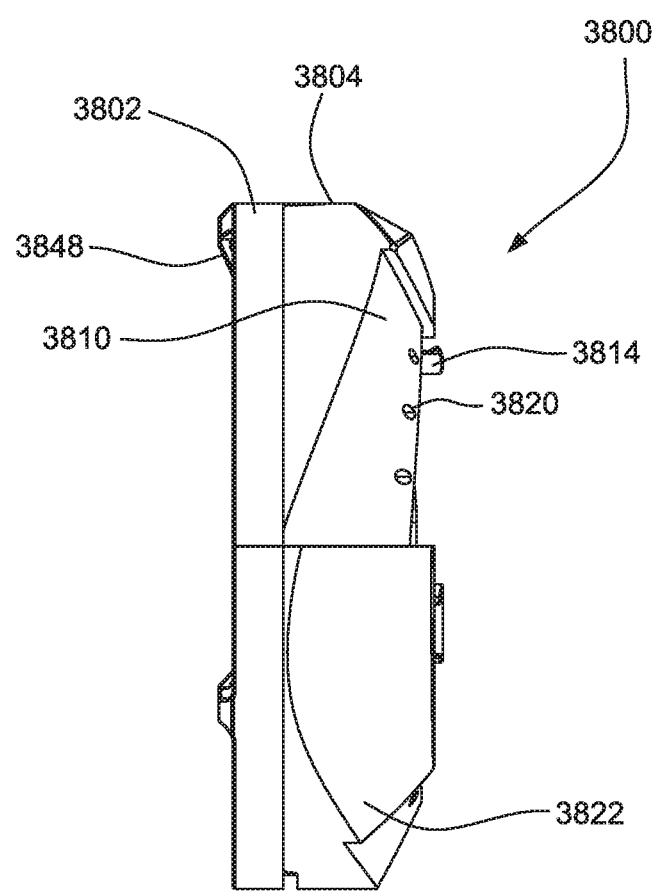

FIG. 113 is a lateral view of a plenum chamber insert according to an example of the present technology.

Figure 114:
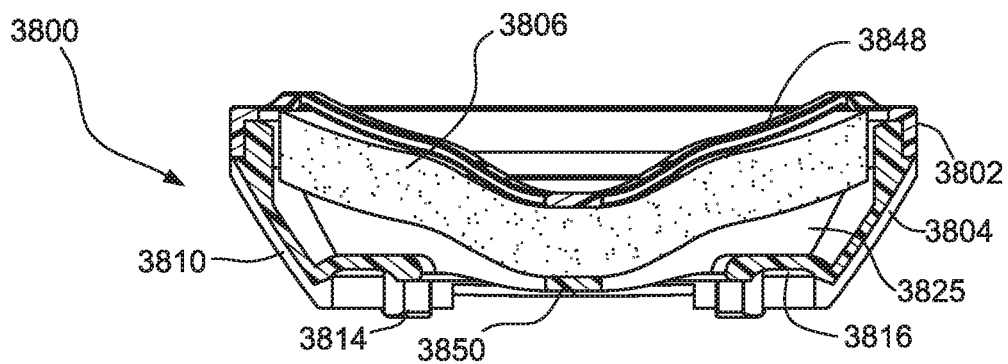

FIG. 114 is a cross-sectional view of a plenum chamber insert according to an example of the present technology taken through line 114-114 of FIG. 111.

Figure 115:
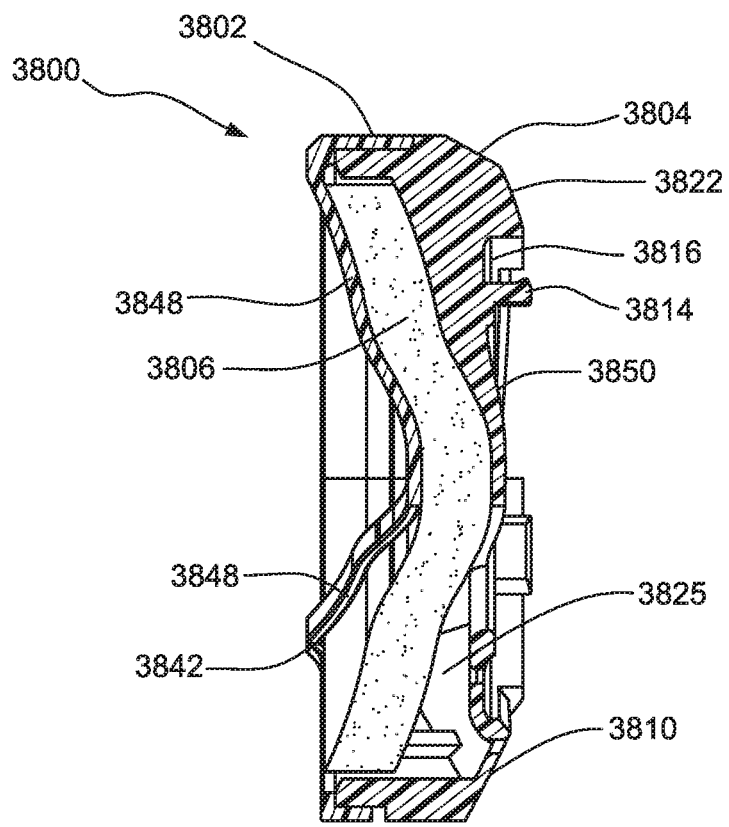

FIG. 115 is a cross-sectional view of a plenum chamber insert according to an example of the present technology taken through line 115-115 of FIG. 111.

Figure 116:
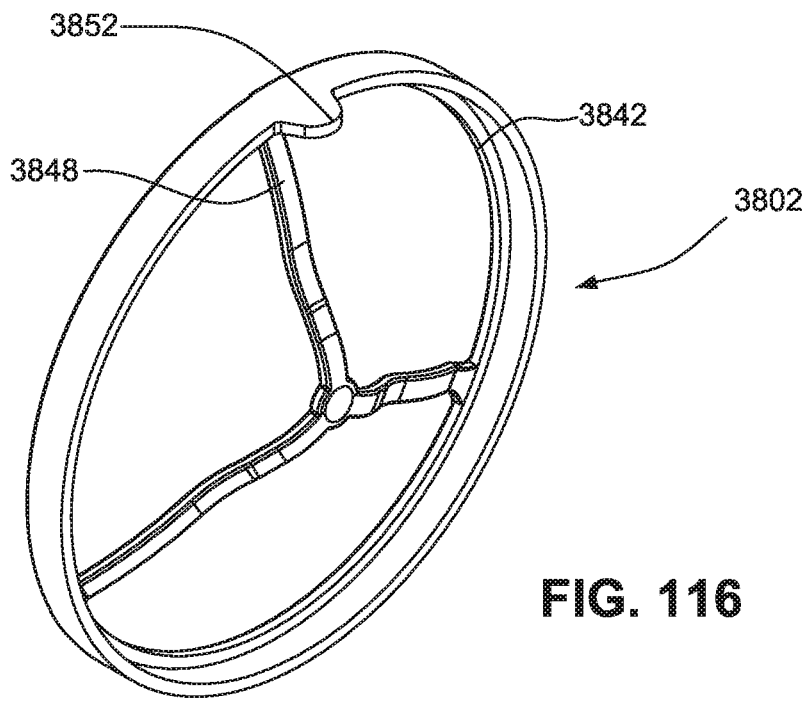

FIG. 116 is an anterior perspective view of a posterior insert frame of a plenum chamber insert according to an example of the present technology.

Figure 117:
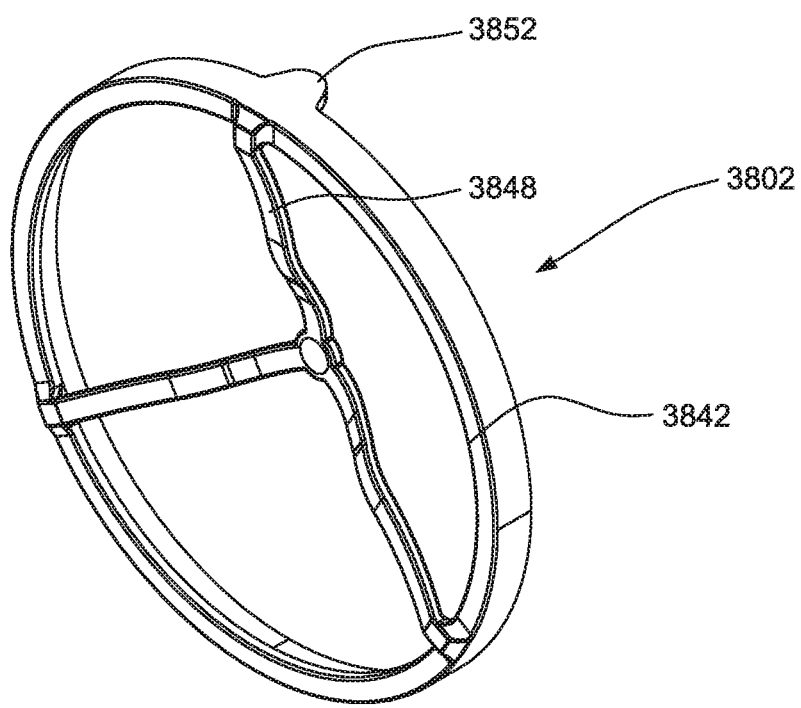

FIG. 117 is a posterior perspective view of a posterior insert frame of a plenum chamber insert according to an example of the present technology.

Figure 118:
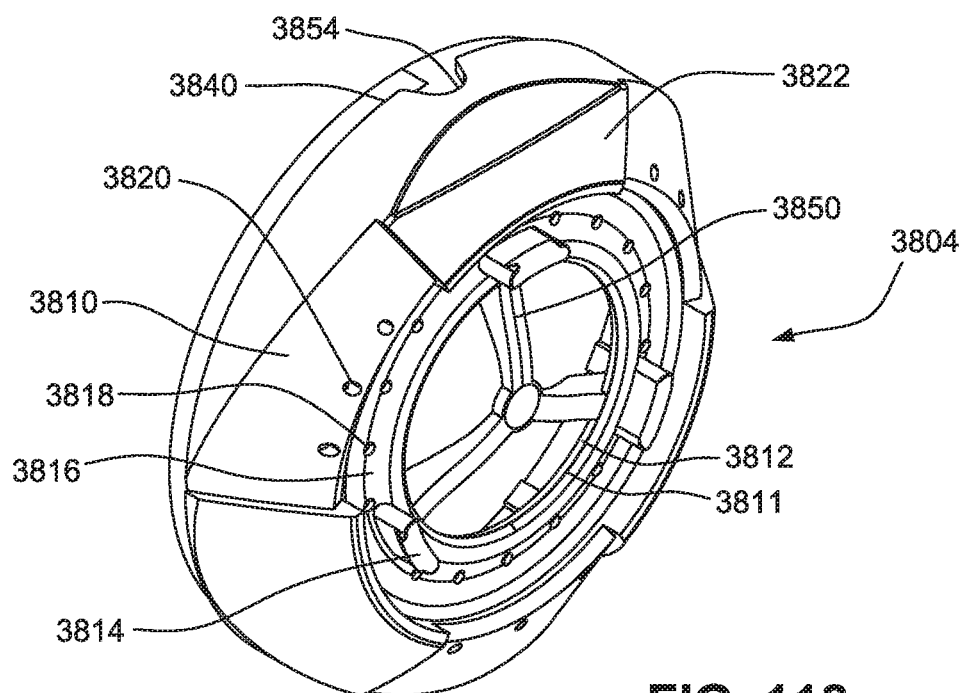

FIG. 118 is an anterior perspective view of an anterior insert frame of a plenum chamber insert according to an example of the present technology.

Figure 119:
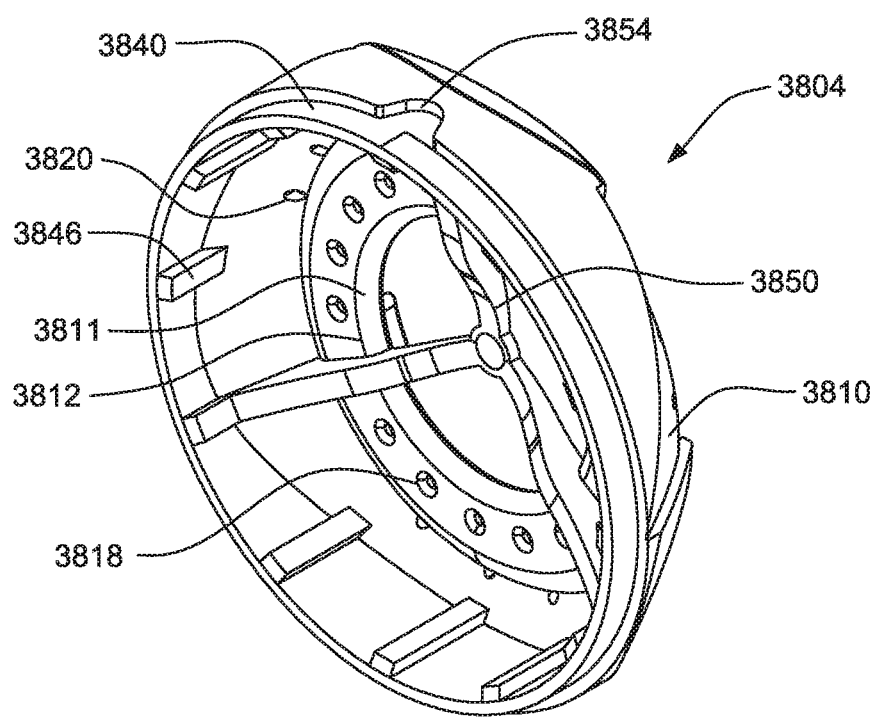

FIG. 119 is a posterior perspective view of an anterior insert frame of a plenum chamber insert according to an example of the present technology.

Figure 120:
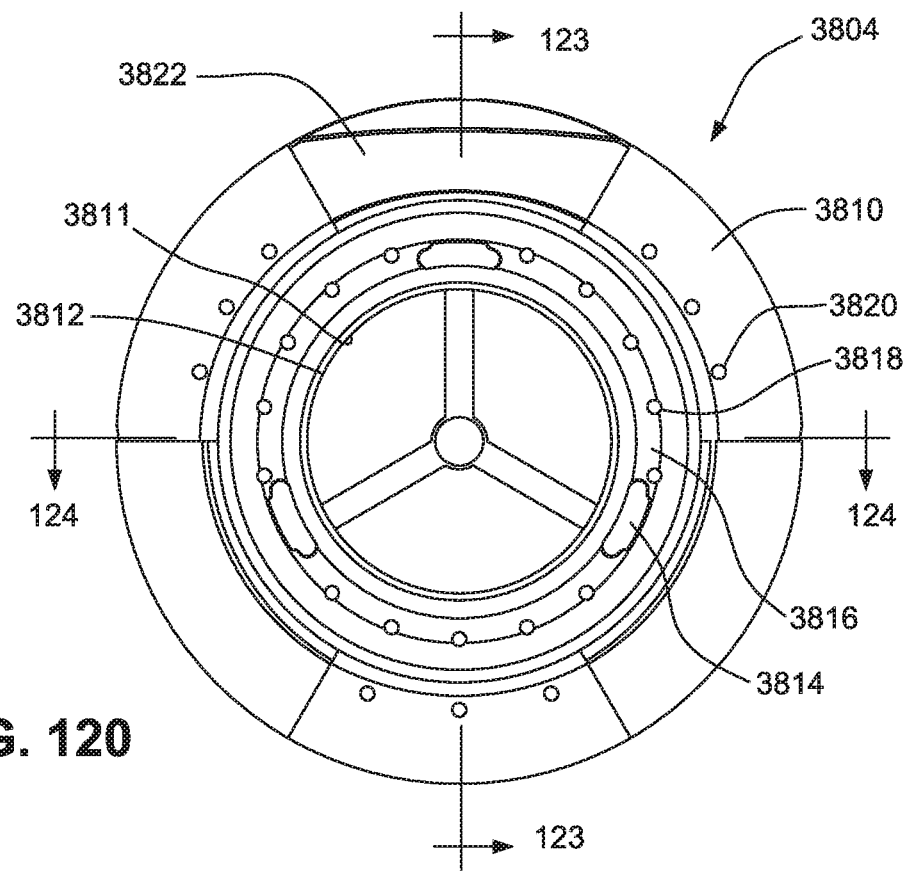

FIG. 120 is an anterior view of an anterior insert frame of a plenum chamber insert according to an example of the present technology.

Figure 121:
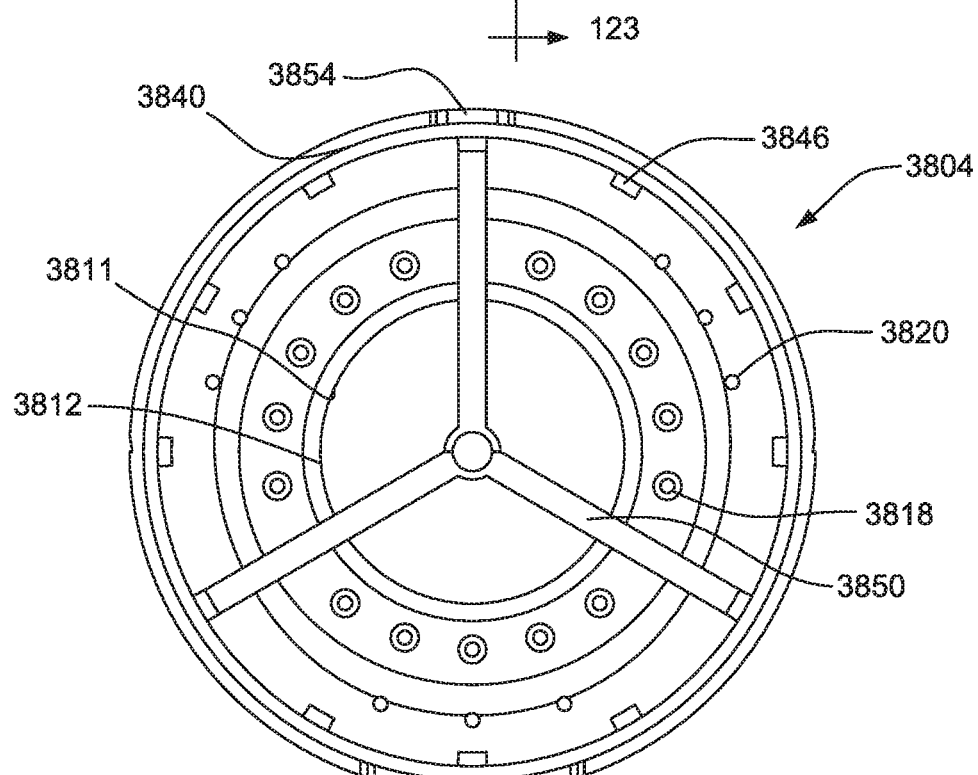

FIG. 121 is a posterior view of an anterior insert frame of a plenum chamber insert according to an example of the present technology.

Figure 122:
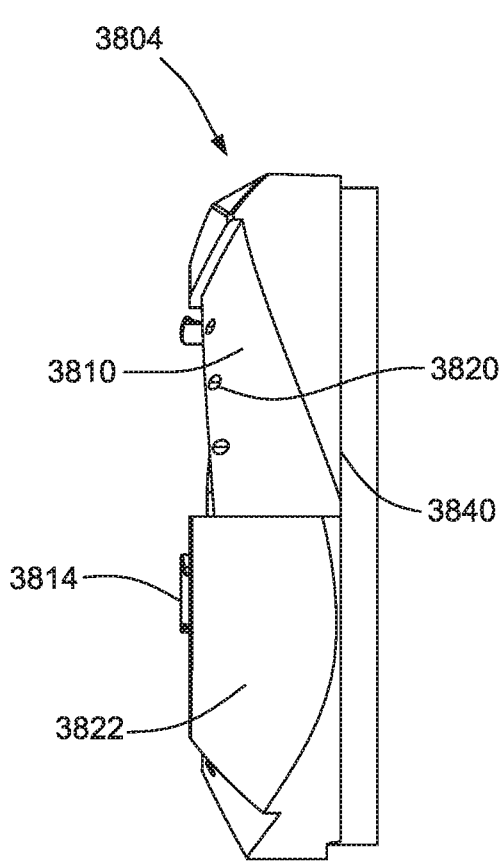

FIG. 122 is a lateral view of an anterior insert frame of a plenum chamber insert according to an example of the present technology.

Figure 123:
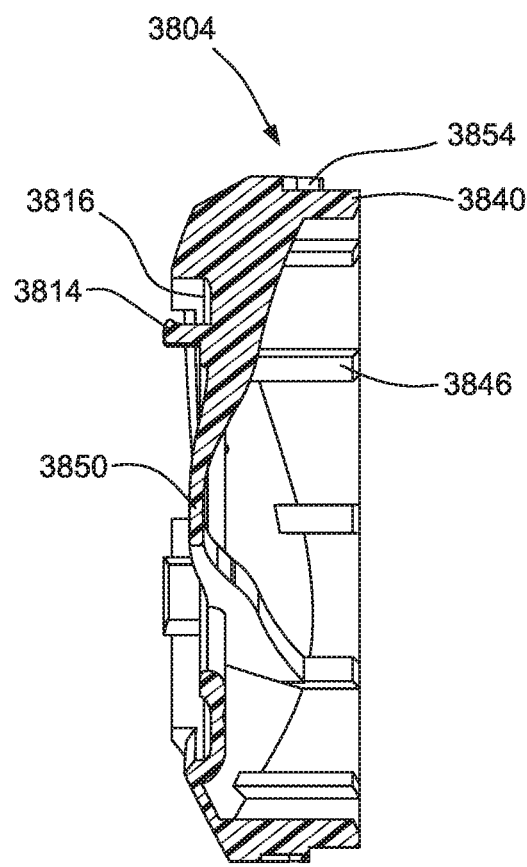

FIG. 123 is a cross-sectional view of an anterior insert frame of a plenum chamber insert according to an example of the present technology taken through line 123-123 of FIG. 120.

Figure 124:
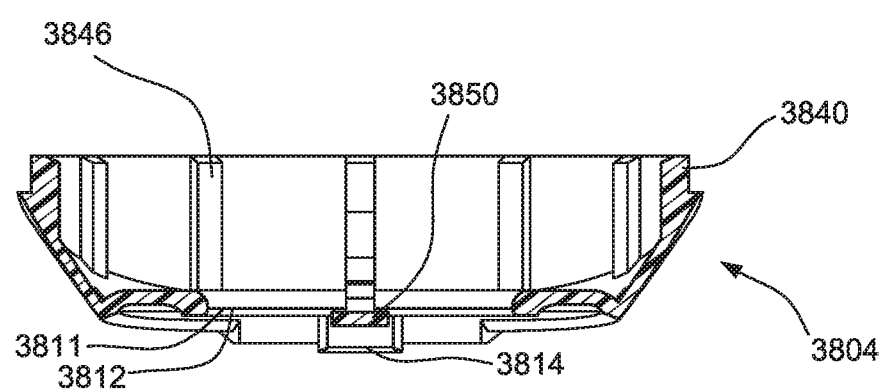

FIG. 124 is a cross-sectional view of an anterior insert frame of a plenum chamber insert according to an example of the present technology taken through line 124-124 of FIG. 120.

Figure 125:
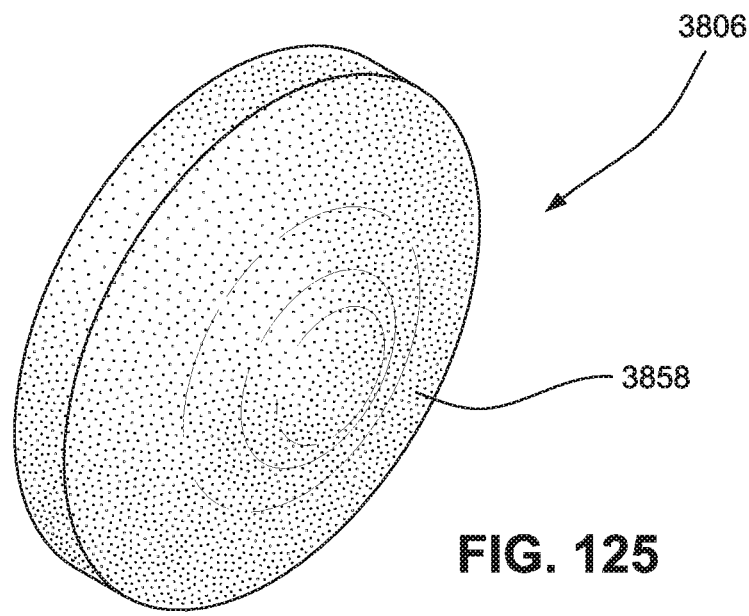

FIG. 125 is an anterior perspective view of heat and moisture exchanger (HMX) material of a plenum chamber insert according to an example of the present technology.

Figure 126:
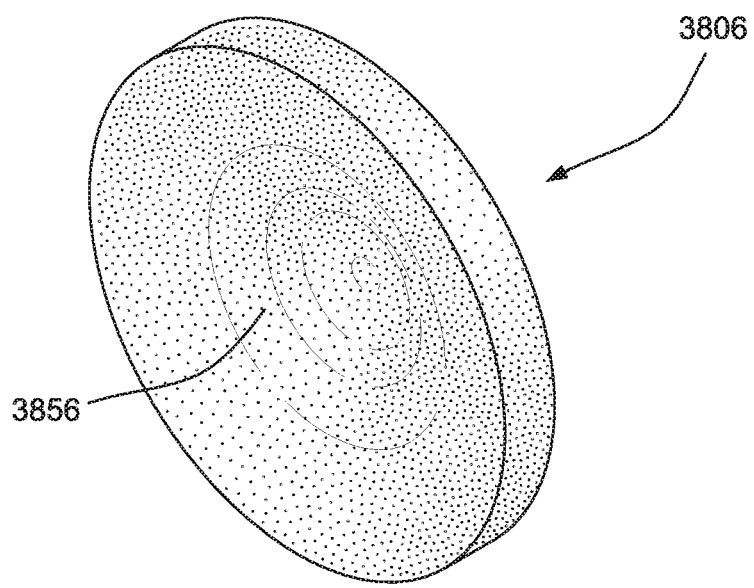

FIG. 126 is a posterior perspective view of heat and moisture exchanger (HMX) material of a plenum chamber insert according to an example of the present technology.

Figure 127:
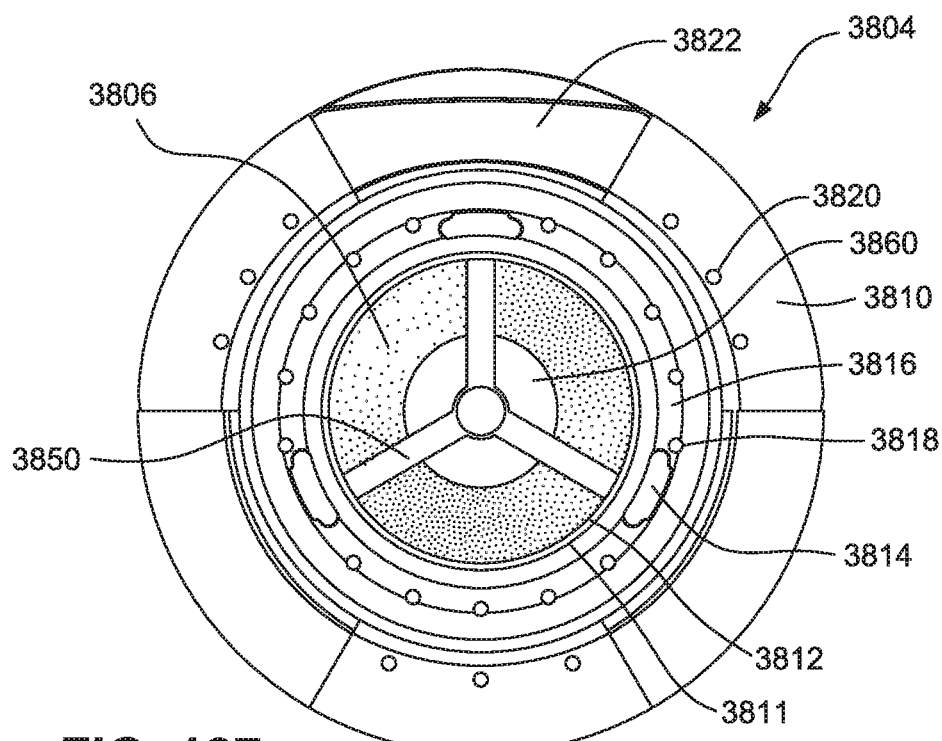

FIG. 127 is an anterior view of a plenum chamber insert according to an example of the present technology.

Figure 128:
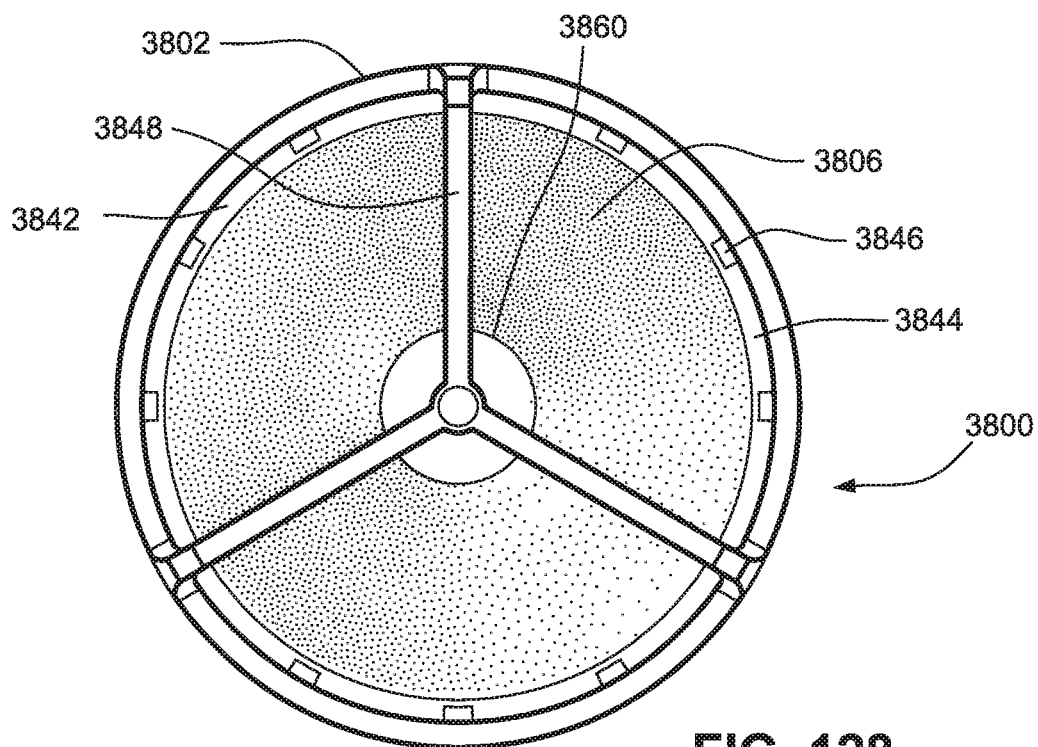

FIG. 128 is a posterior view of a plenum chamber insert according to an example of the present technology.

Figure 129:
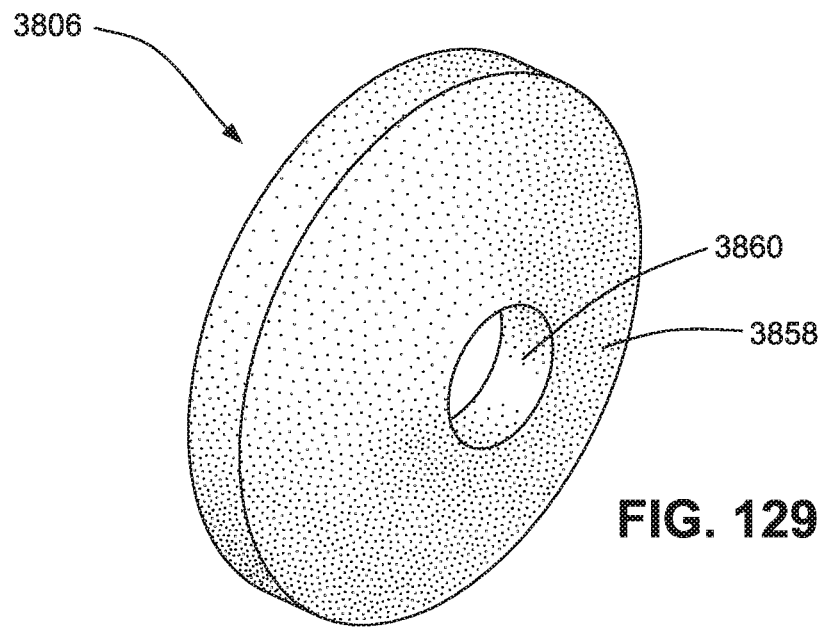

FIG. 129 is an anterior perspective view of heat and moisture exchanger (HMX) material of a plenum chamber insert according to an example of the present technology.

Figure 130:
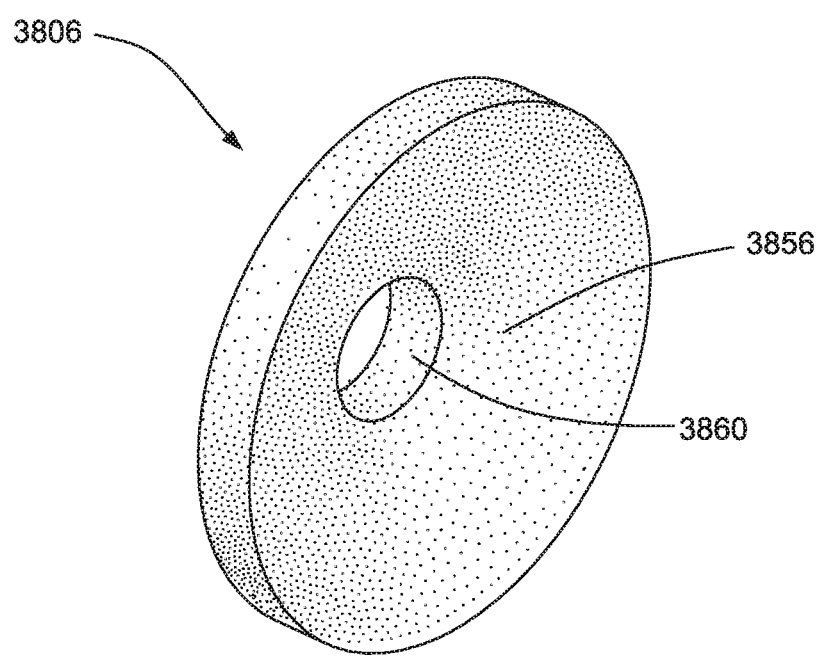

FIG. 130 is a posterior perspective view of heat and moisture exchanger (HMX) material of a plenum chamber insert according to an example of the present technology.

FIGS. 131-138 show a posterior view of a posterior insert frame of a plenum chamber insert with an orientation indicator according to examples of the present technology.

Figure 139:
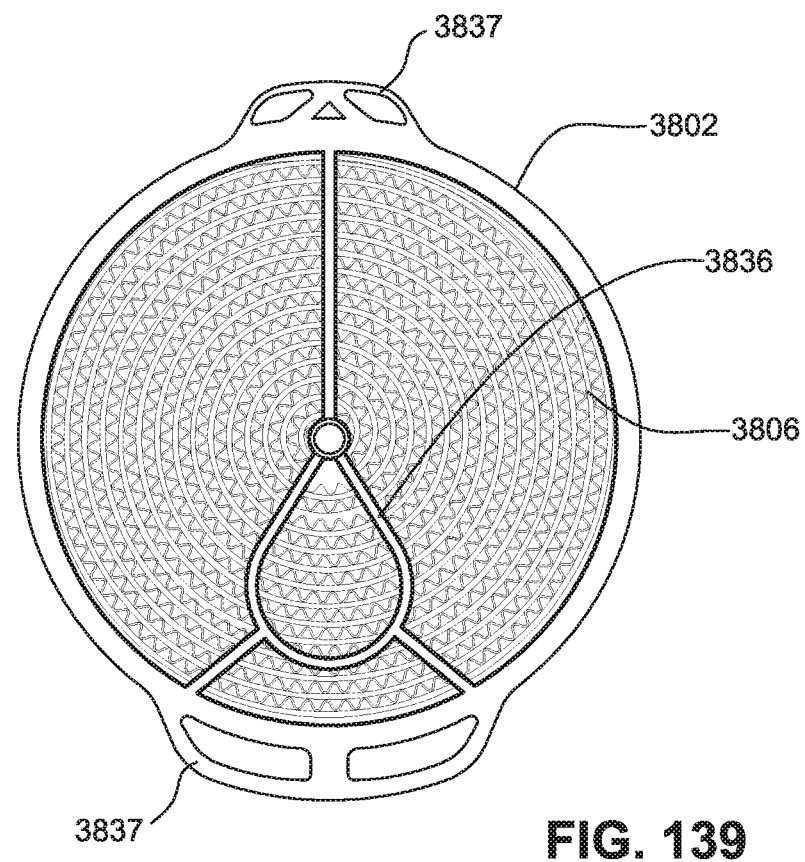

FIG. 139 shows a posterior view of a plenum chamber insert with an orientation indicator and heat and moisture exchanger (HMX) material according to example of the present technology.

Figure 140:
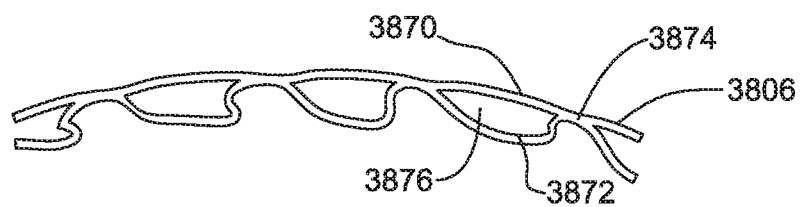

FIG. 140 shows a side view of an example of heat and moisture exchanger (HMX) material.

Figure 141:
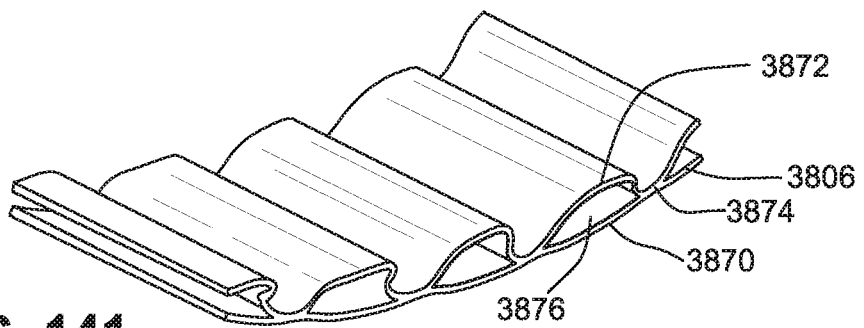

FIG. 141 shows a top perspective view of an example of heat and moisture exchanger (HMX) material.

Figure 142:
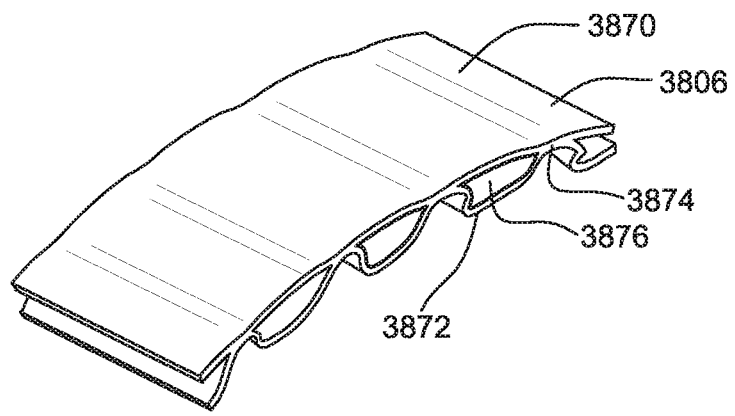

FIG. 142 shows a bottom perspective view of an example of heat and moisture exchanger (HMX) material.

Figure 143:
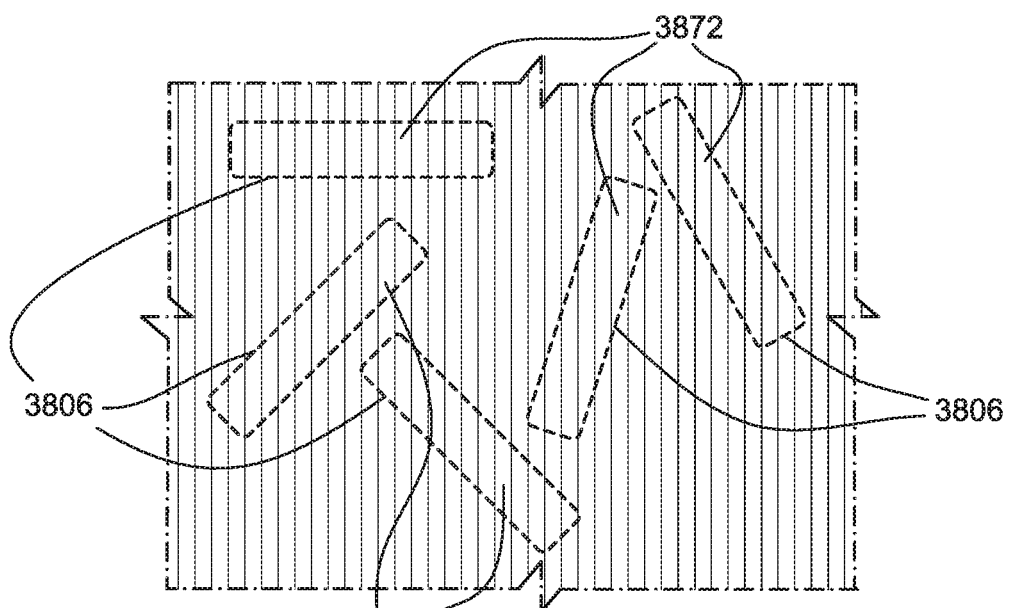

FIG. 143 shows a top view of a bulk sheet of heat and moisture exchanger (HMX) material according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cm $H_2O$ with respect to ambient.

The patient interface 3000 in accordance with one form of the present technology is constructed and arranged to be able to provide a supply of air at a positive pressure of at least 10 cm H₂O with respect to ambient.

The patient interface 3000 in accordance with one form of the present technology is constructed and arranged to be able to provide a supply of air at a positive pressure of at least 20 cm H₂O with respect to ambient.

FIGS. 7-16 show a patient interface that may be provided with the plenum chamber insert according to examples of the present technology. Description of this patient interface follows below, and further details are provided in U.S. Patent Application Publication No. US 2018/0250486 A1, which is incorporated herein by reference in its entirety. The patient interface includes a frame assembly 6100, a chassis 6175 including a seal-forming structure 6200, an air delivery connector (e.g., elbow assembly 6600), and a positioning and stabilising structure (e.g., headgear 6800 including upper side straps 6802, lower side straps 6804, and crown strap 6806). FIGS. 7 to 9 are exemplary views of the patient interface 6000 with arm covers 6750 for upper arms 6134 of the frame assembly 6100 attached, and FIGS. 10 to 16 are exemplary views of the patient interface 6000 with the headgear 6800 and the arm covers 6750 removed.

Similar to the example described above, the chassis 6175 connects to the frame assembly 6100 (via a first retention feature on the frame assembly) independently of the elbow assembly 6600, and the elbow assembly 6600 connects to the frame assembly 6100 (via a second retention feature on the frame assembly) independently of the cushion assembly 6175. That is, the retention connections of the chassis 6175 and the elbow assembly 6600 to the frame assembly 6100 are separate and distinct from one another and allow independent engagement/disengagement.

In the example of patient interface 6000, a first seal for the air flow path is formed between the elbow assembly 6600 and the frame assembly 6100, and a separate second seal is formed between the frame assembly 6100 and the cushion assembly 6175. In this example, the frame assembly 6100 is provided in the air flow path. That is, the elbow assembly 6600 is structured to establish a hard-to-hard connection and dynamic seal with the frame assembly 6100, and the chassis 6175 is structured to establish a separate hard-to-hard connection and static seal with the frame assembly 6100.

In this example, the first end portion 6610 includes a plurality of vent holes 6700 to permit the exit of exhausted gases from the patient interface.

Also, in the example of patient interface 6000, the frame assembly 6100 includes a lockout feature along the opening 6105 that is structured and arranged to prevent direct connection or insertion of the air circuit 4170, e.g., air delivery tube. This arrangement requires use of the elbow assembly 6600 to interconnect the frame assembly 6100 and the air circuit 4170, thereby ensuring that the elbow assembly 6600 (and its vent and anti-asphyxia valve (AAV)) are present in the system.

In an example, the frame assembly 6100 includes a shroud or wall member 6110, a pair (i.e., right and left) of upper headgear connector arms 6134 (each comprising two flexible portions 6140, 6145) extending from respective sides of an upper portion of the shroud 6110, and a pair (i.e., right and left) of lower headgear connector arms 6154 extending from respective sides of a lower portion of the shroud 6110.

In the illustrated example, each upper headgear connector arm 6134 includes an upper headgear connection point in the form of a slot 6135 structured to receive a respective upper headgear strap 6802 of the headgear.

In the illustrated example, the central flexible portion 6140 of each arm 6134 comprises a single slot 6141 (on a posterior side) forming a hinge. In the illustrated example, the peripheral flexible portion 6145 of each arm 6134 comprises a plurality of slots 6146 (on each side of the arm, i.e., slots on anterior and/or posterior sides of the arm) forming a plurality of hinges over the cheek region.

In examples, the peripheral flexible portion 6145 of each arm need not include slots on the anterior or posterior sides. Instead, or in addition, the flexible portion may include one or more interconnecting elastomeric (e.g., silicone) sections that may form a flush or smooth transition between relatively harder plastic sections, but allow flexing, bending and/or pivoting. These can be made via insert or over molding, where the harder plastic sections are placed in the mold and the interconnecting sections are molded over the harder plastic sections.

Each lower headgear connector arm 6154 comprises the magnetic connector 6155 (including encased magnet 6155B) structured to locate and connect to the headgear clip 6160 provided to the respective lower headgear strap of the headgear. In the illustrated example, the end of each lower arm 6154 includes a magnet receiving portion 6155A to receive and align a magnet 6155B and a cap 6155C to enclose and retain the magnet 6155B to the magnet receiving portion 6155A. As illustrated, the magnetic connector 6155 provides a protrusion which allows it to be inserted and retained within a corresponding receptacle provided by the headgear clip 6160.

In an example, the upper arms 6134 and/or the lower arms 6154 may be covered by a textile, e.g., for aesthetics, increase perception of softness/comfort, provide comfort on the face and minimise marking. For example, a textile arm cover or sock 6750 is provided to the upper arms 6134, while the upper arms 6134 have the arm covers 6750 removed. The cover 6750 conceals the upper arms 6134 making the outer surface smooth to increase comfort on the face, e.g., no marking and easier to slide over the facial surface. The cover 6750 may be optionally removable.

In an example, at least a portion of the upper arms 6134 and/or the lower arms 16154 may include dimples or a gold ball pattern, e.g., for aesthetics.

In an example, the elbow assembly 6600 includes a first end portion 6610 with pinch arms 6650 to releasably engage with the frame assembly 6100 and a second end portion 6620 adapted to connect to the air circuit 4170, e.g., via a swivel connector 6625.

In addition, the elbow assembly 6600 is structured to house an AAV assembly including AAVs structured to allow the patient to breathe through ports if pressurized gas is not of sufficient magnitude or not delivered.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700. In other forms, the patient interface 3000 may not include a forehead support.

5.3.8 Anti-Asphyxia Valve

In one form, the patient interface 3000 includes an anti-asphyxia valve 6605. The anti-asphyxia valve 6605 may be located in the elbow 6600.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.3.10 In-Mask HMX and Plenum Chamber Insert

The present technology envisions providing water vapour to the flow of air before it reaches the patient's airways without including a pre-filled water reservoir in the overall RPT system. Water vapour from ambient air and/or the patient's exhalation may be instead harvested/captured and then supplied back to the patient in the form of humidified air having increased absolute humidity. The water vapour content from one or both of these sources may be sufficient for the patient's airways to remain sufficiently moist so as to avoid or minimize discomfort to the patient.

The present technology envisions the use of a heat and moisture exchanging (HMX) component to provide the moisture to the air that is supplied to the patient. Thus, the therapy system may be operated without a humidifier 5000, e.g., a reservoir of water heated to humidify air after passing the RPT device 4000. Additionally, since the HMX material is positioned within the patient interface, i.e., downstream of the incoming flow of pressurized air via the air circuit, it may be unnecessary to include a heated tube in the air circuit because the air traveling through the air circuit will not have had its humidity increased by a humidifier, which in turn increases the chances of rainout (condensation within the air circuit), or if a heated tube is included it may be left off during use. In an alternative, the heated tube may be included in the therapy system and operated during therapy because heating the incoming flow of pressurized air may allow it to receive more water as it passes through the HMX material.

HMX material(s) may be placed within the air path, and it may be advantageous to place the HMX material(s) as close as possible to the patient to ensure that the maximum amount of moisture is harvested or captured by the HMX material(s) for resupplying to the air respired by the patient. The inclusion of an HMX within the air path, however, may cause increased impedance to vent flow, which may reduce carbon dioxide washout to atmosphere. Thus, the present technology also envisions one or more channels that allow the flow of exhaled gas to bypass the high impedance of the HMX material.

FIGS. 17-47 depict components associated with one example of the present technology that provides a relatively high level of performance (i.e., sufficiently high humidification) and may also provide a level of impedance to the incoming flow of pressurized air that allows it to be used with a wider range of available RPT devices, such as an RPT device that is capable of higher therapy pressures and flow rates (e.g., ResMed's AirSense 10).

FIGS. 17-24 show a sub-assembly of a patient interface according to an example of the present technology. The components depicted include a seal-forming structure 6200, a plenum chamber insert 3800, a plenum chamber or chassis 6175, a frame assembly 6100, and an elbow assembly 6600.

FIGS. 25-29 show a further sub-assembly that includes the seal-forming structure 6200, the plenum chamber or chassis 6175, and the plenum chamber insert 3800.

FIGS. 30-36 show a further sub-assembly that includes the components of the plenum chamber insert 3800—an anterior insert frame 3804, a posterior insert frame 3802, and a heat and moisture exchanger (HMX) material 3806. FIGS. 37 and 38 show the posterior insert frame 3802, and FIGS. 46-47 show the HMX material 3806, which are the same in both the low impedance version and the high humidification version of the plenum chamber insert 3800. FIGS. 39-45 show the anterior insert frame 3804 in greater detail.

FIGS. 48-74 depict components associated with an example of the present technology that may provide a level of impedance to the incoming flow of pressurized air, which may be optimal for use with an RPT device that is more compact and travel-friendly, may be battery-powered, and may not be capable of as high of therapy pressures and flow rates, such as ResMed's AirMini. As will be explained, a baffle 3803 may help the incoming flow of pressurized air 2000, which may be at a comparatively lower pressure and/or flow rate as a result of the capabilities of the RPT device, to be spread out across the HMX material 3806 to enhance humidification performance when pressure and/or flow rate of the incoming flow of pressurized air 2000 is/are lower.

FIGS. 48-55 show a sub-assembly of a patient interface according to an example of the present technology. The components depicted include a seal-forming structure 6200, a plenum chamber insert 3800, a plenum chamber or chassis 6175, a frame assembly 6100, and an elbow assembly 6600.

FIGS. 56-60 show a further sub-assembly that includes the seal-forming structure 6200, the plenum chamber or chassis 6175, and the plenum chamber insert 3800.

FIGS. 61-67 show a further sub-assembly that includes the components of the plenum chamber insert 3800—an anterior insert frame 3804, a posterior insert frame 3802, and a heat and moisture exchanger (HMX) material 3806. FIGS. 68-74 show the anterior insert frame 3804 in greater detail.

FIGS. 37 and 38 show the posterior insert frame 3802, and FIGS. 46-47 show the HMX material 3806, which are the same in both the low impedance version and the high humidification version of the plenum chamber insert 3800.

5.3.10.1 HMX Material

The HMX material 3806 captures, retains, and distributes heat and moisture. Different HMX materials 3806 may be used, such as foam, cellulose-based materials such as paper, or textile, or a combination of two or more such materials. The paper form of the HMX material 3806 may be a corrugated structure that forms a plurality of channels allowing air to travel through the HMX material along the channels. The HMX material 3806 may also be treated with a hygroscopic substance, such as one or more salts, which may enhance the ability of the HMX material 3806 to receive water vapour. Depending on conditions in the plenum chamber insert 3800 (e.g., humidity and temperature), the moisture may be absorbed and/or adsorbed by the HMX material 3806, and the moisture may also condense on the HMX material 3806.

In an example of the present technology, the HMX material 3806 is a flexible, polyurethane foam that has been treated with calcium chloride. The purpose of using this material is the capture and release of water vapour to provide humidity. The base foam (flexible, polyurethane) may be reticulated (like a net) open cell foam. This material may be easy to cut and shape so that it can fit into a plenum chamber insert 3800, as will be described below. An open cell foam material may also perform well as a substrate to hold the salt because it has a surface area that is relatively large compared to its volume. An open cell foam material may also be advantageous due to its low pneumatic impedance (i.e., relatively low resistance to air flow) and low weight.

Calcium chloride is an example of a salt that may be used in the present technology, but other salts are possible. Calcium chloride may be suitable because it aggressively adsorbs moisture (water vapour) from the air causing a swelling of the salt crystal on the surface of the foam. This hygroscopic property of the salt makes it suitable for performing the function of capturing (adsorption) the patient's moisture from the air during exhalation and returning it (desorption) to the incoming air flow during inhalation. This function may balance the humidity of the mask volume by adsorbing moisture during high humidity and releasing it during low humidity.

FIGS. 139-143 show HMX material 3806 in the form of corrugated paper. The corrugated paper may include a base layer 3870, a corrugated layer 3872, joints 3874 where the base layer 3870 and the corrugated layer 3872 are joined, and flutes 3876 formed where the base layer 3870 and the corrugated layer 3872 are separated to allow air to flow therethrough. Thus, the corrugated paper HMX material 3806 may be oriented when installed in the plenum chamber insert 3800 so that the flutes 3876 are approximately parallel to the flow of air through the plenum chamber insert 3800. This may increase the surface area available for heat and moisture exchange between the HMX material 3806 and the air passing through it. The HMX material 3806 may be rolled into a coil as shown in FIG. 139, for example, to allow for this orientation. Alternatively, the HMX material 3806 may be formed by vertically stacking layers of corrugated paper (e.g., as described in US Application Publication No. US 2016/0175552 A1, which is incorporated herein by reference in its entirety).

FIG. 143 also shows outlines of strips of HMX material 3806 cut at different angles relative to the corrugated layer 3872. This allows different angles of paths through the flutes 3876 to be formed when the HMX material 3806 is assembled, e.g., coiled.

5.3.10.2 Frame and Positioning within the Plenum Chamber

The patient interface 6000 of the present technology may hold the HMX material 3806 in position within the plenum chamber 6175 with a plenum chamber insert 3800 so that incoming and outgoing air flows can pass through the HMX material 3806 for adsorption and desorption of moisture. Since the HMX material 3806 may be constructed of one or more of the materials discussed above, which may be relatively lightweight and may not be relatively rigid, the plenum chamber insert 3800 may help the HMX material 3806 retain its shape within the plenum chamber 6175 and remain in position during therapy.

In an example, the plenum chamber insert 3800 is a frame for the HMX material 3806. The plenum chamber insert 3800 may include a posterior insert frame 3802 and an anterior insert frame 3804, which may be releasably coupled together and which may releasably retain the HMX material 3806 therebetween. The anterior insert frame 3804 may be moulded, e.g., in one piece, from a relatively rigid plastic material, such as polycarbonate. The posterior insert frame 3802 may be moulded, e.g., in one piece, from a relatively flexible plastic material, such as polypropylene.

As can be seen in the cross-sectional views of FIGS. 23 and 54, for example, when the plenum chamber insert 3800 is inserted in the patient interface 6000 and the patient interface 6000 is worn by the patient 1000, the plenum chamber insert 3800 will be positioned between the entrance to the patient's 1000 airways and a plenum chamber port 6176. The plenum chamber insert 3800 may be inserted into the patient interface 6000, specifically the plenum chamber 6175, and retained therein. The plenum chamber insert 3800 may divide the plenum chamber 6175 into anterior and posterior regions, the posterior region being proximal to the patient during use. The plenum chamber insert 3800 may also be positioned within the plenum chamber 6175 sufficiently in an anterior direction so that contact with the patient's face is avoided when the patient interface 6000 is worn by the patient. Also, due to being positioned within the plenum chamber 6175, when the patient interface 6000 is worn by the patient, the plenum chamber insert 3800 may be located sufficiently close to the entrance to the patient's airways so that as much of the humidified, warmed air from the plenum chamber insert 3800 can reach the patient's airways as possible and so that as much of the humidified, warmed air from the patient's airways can reach the plenum chamber insert 3800 as possible. Thus, the components of the plenum chamber insert 3800, the posterior insert frame 3802, the anterior insert frame 3804, and the HMX material 3806 may have a concave shape on a posterior side thereof to avoid contact with the patient's face.

The plenum chamber insert 3800 may be releasably attached within the plenum chamber 6175, either by being attached to the plenum chamber 6175 or to another component. For example, the anterior insert frame 3804 may include tabs 3814 that clip, e.g., via a snap-fit, to the frame assembly 6100 through the plenum chamber port 6176 and into the port or opening 6105 of the frame assembly 6100. The frame assembly 6100 may include a retaining structure 6190 extending into the port 6105, e.g., as shown in FIG. 12, that receives the tabs 3814. The retaining structure 6190 may be constructed in one piece with the frame assembly 6100. The retaining structure 6190 may extend radially inward from the opening 6105.

FIGS. 21-23 and 52-54 show examples of how the plenum chamber insert 3800 may be connected to the frame assembly 6100 by tabs 3814 on the anterior insert frame 3804 connecting to the retaining structure 6190. In the former example, the tabs 3814 are formed on a rim 3812, which will be described in further detail below, and the tabs 3814 may extend radially outward from the rim 3812. The former example also includes three tabs 3814 formed on the rim 3812, but it should be understood that one tab 3814 may be sufficient for connection to the retaining structure 6190, and in other examples two tabs 3814 may be formed on the rim 3812, and in still further examples more than three tabs 3814 may be formed on the rim 3812. The latter example includes four tabs 3814 extending from an annular channel 3816 formed on the anterior insert frame 3804 and the tabs 3814 may extend parallel to but separately from the rim 3812. It should be understood that, in the latter example, one tab 3814 may be sufficient for connection to the retaining structure 6190, and in other examples two, three, or more than four tabs 3814 may also be formed on the rim 3812. In the latter example (FIGS. 52-54), the tabs 3814 can be seen extending through corresponding retaining structure hole 6192 formed through the retaining structure 6190. Accordingly, there may be a number of tabs 3814 that corresponds to the number of retaining structure holes 6192.

Alternatively, the plenum chamber insert 3800 may be joined to one or more structures formed on an interior surface 6180 of the plenum chamber 6175.

The plenum chamber insert 3800 may also include a plenum chamber insert port 3811 that receives the flow of pressurized air 2000 from the RPT device 4000 via the air circuit 4170 and the elbow assembly 6600. The cross-sectional views FIGS. 21-23 and 52-54 show that, when assembled, the plenum chamber port 6176, the opening 6105 in the frame assembly 6100, and the plenum chamber insert port 3811 may be arranged in pneumatic communication, e.g., substantially coaxially, as these components are also in line with the first end portion 6610 of the elbow assembly 6600 that connects to the frame assembly 6100 at the opening 6105. This arrangement permits the flow of pressurized air 2000 to pass through the plenum chamber insert 3800 to be heated and humidified during therapy, as explained above.

The cross-sectional views of FIGS. 21-23 and 52-54 also show how an exterior surface of the plenum chamber insert 3800, such as the exterior surface of the anterior insert frame 3804 (e.g., an anterior insert frame wall 3822) may be positioned adjacent to the interior surface 6180 of the plenum chamber 6175 to minimize the amount of air that can bypass the HMX material 3806 as it enters the plenum chamber 6175. For example, the anterior insert frame wall 3822 and the interior surface 6180 of the plenum chamber 6175 may either be in contact at at least some points, or the anterior insert frame wall 3822 may be fully in contact with the interior surface 6180 of the plenum chamber 6175 so that air cannot pass between these surfaces. Alternatively, these surfaces may not be in contact but may be so close together that resistance to air flow is so high that there is only a negligible amount of flow between the surfaces.

The anterior insert frame 3804 may also include the rim 3812, which may be positioned adjacent to or in contact with an inner wall 6614 of the first end portion 6610 of the elbow assembly 6600 such that the incoming flow of air 2000 passes from the elbow assembly 6600 and directly into the plenum chamber insert 3800, as can be seen in FIGS. 21-23 and 52-54. For example, the rim 3812 may have a smaller outer diameter than the inner diameter of the inner wall 6614 such that the rim 3812 extends into hole formed by the inner wall 6614 and the rim 3812 and the inner wall 6614 overlap, as shown in FIGS. 52-54. The opposite arrangement is also possible. In either arrangement, the elbow assembly 6600 may be free to rotate about its connection to the frame assembly 6100 at the lip 6106 without disrupting the connection between the plenum chamber insert 3800 and the frame assembly 6100 at the retaining structure 6190.

The example of FIGS. 21-23 show that the inner wall 6614 of the elbow assembly 6600 may include a deflecting structure 6615 that extends radially inward from the inner wall 6614. In this arrangement, the rim 3812 is spaced from but adjacent to the inner wall 6614 so that the deflecting structure 6615 has enough clearance so that the elbow assembly 6600 may be free to rotate about its connection to the frame assembly 6100 at the lip 6106 without disrupting the connection between the plenum chamber insert 3800 and the frame assembly 6100 at the retaining structure 6190.

It should also be understood that the elbow assembly 6600 shown in FIGS. 21-23 and the elbow assembly 6600 shown in FIGS. 52-54 are both compatible with the arrangement of the rim 3812 and the tabs 3814 in the former example. However, the elbow assembly 6600 shown in FIGS. 21-23 may be incompatible with the arrangement of the rim 3812 and the tabs 3814 of the example shown in FIGS. 52-54 because the rim 3812 is longer to engage the inner wall 6614 and as such the deflecting structure 6615 would contact the rim 3812 and dislodge the plenum chamber insert 3800 from its connection to the frame assembly 6100.

In both of these configurations, the elbow assembly 6600 may also include an outer wall 6612 that, along with the inner wall 6614, forms an elbow vent flow path 6616 to allow vent flow passing through the elbow 2001 to reach the vent holes 6700 without interference from the incoming flow of pressurized air 2000. Thus, the inner wall 6614 may be understood to separate incoming and outgoing flows of air, which prevents the incoming of pressurized air 2000 from being vented directly to atmosphere and prevents the outgoing vent flow through the elbow 2001 from being recirculated back to the patient.

The arrangement of the rim 3812 to pneumatically communicate with the elbow assembly 6600, as described above, may help to maximize the amount of air that passes through the plenum chamber insert 3800, and therefore the HMX material 3806, as air travels to the patient's airways from the elbow assembly 6600 to maximize humidification. By ensuring that as much of the incoming air flow passes through the HMX material 3806 as possible during use, heat and moisture exchange performance can be optimized. However, it should be understood that a certain amount of flow bypassing the HMX material 3806 may also be advantageous, as will be described below, to ensure that the HMX material 3806 is not dried out by air that reaches the HMX material 3806, receives moisture, and is then vented directly to ambient without reaching the patient 1000.

In addition to the concave shape of the posterior, patient-facing side of the plenum chamber insert 3800, the posterior insert frame 3802 may also prevent the patient's skin from contacting the HMX material 3806, in addition to helping retain the HMX material 3806 within the plenum chamber insert 3800. The posterior insert frame 3802 may have a generally open construction, i.e., including several posterior insert frame openings 3842. Numerous posterior insert frame openings 3842 provide a large, exposed surface area on the patient-proximal side of the HMX material 3806 for expired air to reach the HMX material 3806 so that it can receive moisture and heat. Depending on conditions in the plenum chamber insert 3800 (e.g., humidity and temperature), the moisture may be absorbed and/or adsorbed by the HMX material 3806, and the moisture may also condense on the HMX material 3806. Similarly, a large exposed surface area on the patient-proximal side of the HMX material 3806, a HMX material posterior surface 3830, allows the flow of pressurized air passing through the HMX material 3806 and into the plenum chamber 6175 to have minimal impedance from the posterior insert frame 3802.

The posterior insert frame 3802 may also include an orientation indicator 3836 to provide a visual and/or tactile indication of the orientation of the plenum chamber insert 3800. FIG. 38, for example, shows that the orientation indicator 3836 is shaped like a droplet with the pointed portion indicating the superior side and the rounded portion indicating the inferior side. Since the plenum chamber insert 3800, particularly the anterior insert frame 3804, is shaped to fit closely against the interior surface of the plenum chamber 6175 and the generally triangular shape of the plenum chamber 6175 is asymmetrical in at least one direction, the plenum chamber insert 3800 may be shaped such that it fits against the interior surface of the plenum chamber 6175 in only one orientation. Accordingly, an orientation indicator 3836 may assist the patient in determining the proper orientation of the plenum chamber insert 3800 for assembly.

FIGS. 131-139 show examples of orientation indicators 3836 that may be formed on the posterior insert frame 3802. In these examples, the posterior insert frame 3802 may be integrally formed (e.g., molded) with the orientation indicator 3836. Alternatively, the posterior insert frame 3802 and the orientation indicator 3836 may be formed (e.g., molded) separately and then fixed to one another. The outline of the shape of the orientation indicator 3836 may be solid material and may be otherwise open to allow air to pass through openings formed by the orientation indicator 3836. The orientation indicator 3836 may indicate for the patient the proper orientation of the plenum chamber insert 3800 into the patient interface 3000—when viewed as shown in these drawings, the upright orientation of the image formed by the orientation indicator 3836 can indicate to the patient that the plenum chamber insert 3800 is oriented properly for assembly to the patient interface 3000. Additionally, because the orientation indicator 3836 may be formed from solid material a patient that is visually impaired can determine proper orientation by touching the orientation indicator 3836 to determine orientation of the plenum chamber insert 3800. Also, when the plenum chamber insert 3800 has a circular shape, these orientation indicators 3836 may assist the patient in ascertaining the correct orientation when installing the plenum chamber insert 3800 in the patient interface 3000.

Figure 131:
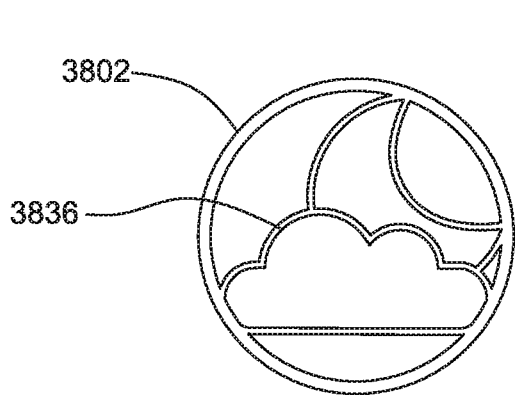
Figure 132:
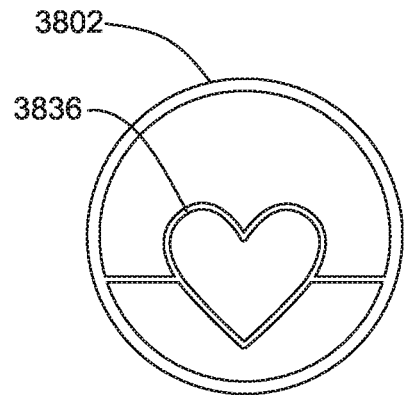
Figure 133:
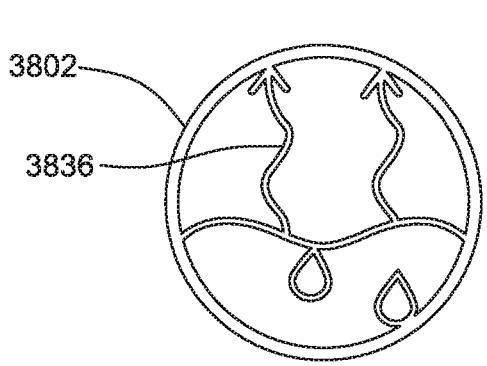
Figure 134:
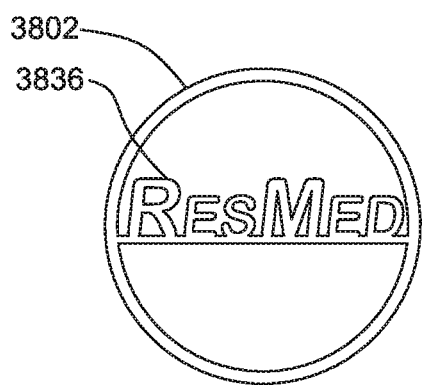
Figure 135:
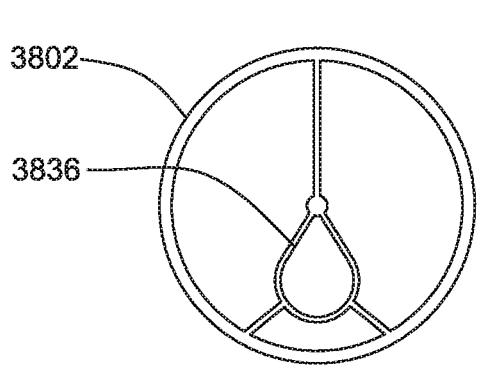
Figure 136:
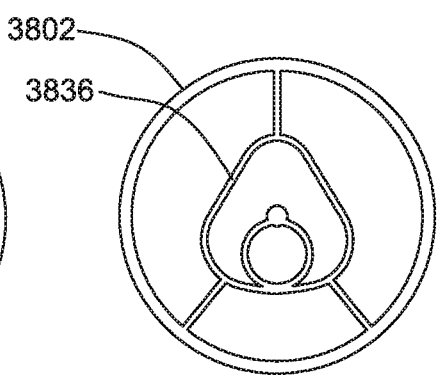
Figure 137:
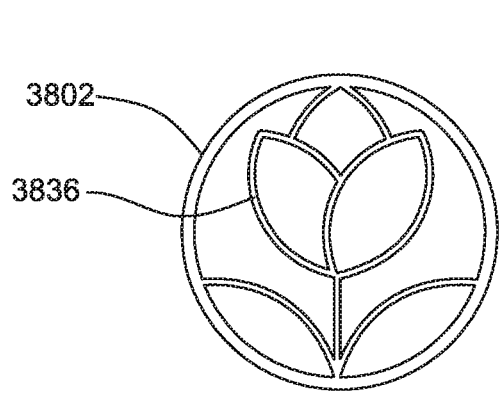
Figure 138:
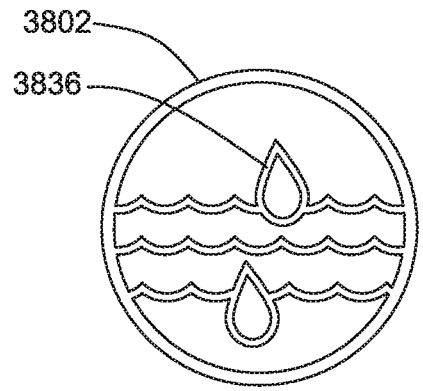

FIG. 131 shows the orientation indicator 3836 in the form of a crescent moon and a cloud. FIG. 132 shows the orientation indicator 3836 in the form of a heart. FIG. 133 shows the orientation indicator 3836 in the form of water droplets and wavy arrows indicating upward evaporation. FIG. 134 shows the orientation indicator 3836 in the form of text (numbers and/or letters of any language can be used). FIG. 135 shows the orientation indicator 3836 in the form of a single water droplet. FIG. 136 shows the orientation indicator 3836 in the form of an outline of a full-face patient interface (see FIG. 25). FIG. 137 shows the orientation indicator 3836 in the form of a flower with a stem and leaves. FIG. 138 shows the orientation indicator 3836 in the form of waves on the surface of water and water droplets. FIG. 139 shows the orientation indicator 3836 of FIG. 135 along with the HMX material 3806 in the form of corrugated paper rolled into a coil.

FIG. 139 also shows a pair of tabs 3837, positioned opposite one another on the posterior insert frame 3802. The tabs 3837 may improve usability for the patient by providing a gripping surface for installing and removing the plenum chamber insert 3800, when assembled, from the patient interface 3000. The tabs 3837 may also serve as an orientation indicator 3836. Also, in other examples there may be just one tab 3837 at either the top or the bottom of the posterior insert frame 3802.84520

The posterior insert frame 3802, as mentioned above, may also retain the HMX material 3806 within the plenum chamber insert 3800 by securing it against the anterior insert frame 3804. The posterior insert frame 3802 may include one or more posterior insert frame protrusions 3834 to engage the HMX material posterior surface 3830 of the HMX material 3806 and urge an HMX material anterior surface 3828 against anterior insert frame spacers 3824 on the patient-proximal side of the anterior insert frame 3804. Also, to ensure that the anterior insert frame 3804 and the posterior insert frame 3802 maintain a connection to retain the HMX material 3806, the anterior insert frame 3804 and the posterior insert frame 3802 may include one or more corresponding pairs of catches 3808 and detents 3832. Additionally, the HMX material 3806 may have notches 3826 corresponding to each of pair of catch 3808 and detent 3832 so that the HMX material 3806 does not interfere with engagement between the catches 3808 and detents 3832 while extending out to the perimeter of the plenum chamber insert 3800 as far as possible.

As noted above, the HMX material 3806 may be urged against anterior insert frame spacers 3824 to hold the HMX material 3806 in position within the plenum chamber insert 3800. The anterior insert frame spacers 3824 may also separate the HMX material 3806 from an anterior insert frame inner surface 3823 to form a void 3825 within the plenum chamber insert 3800. The anterior insert frame spacers 3824 and the void 3825 that they form within the plenum chamber insert 3800 may allow the incoming flow of pressurized air 2000 to spread across the anterior surface 3828 of the HMX material 3806 to ensure that as much of the incoming flow is heated and humidified by the HMX material 3806 as possible. Other the incoming flow of pressurized air 2000 entering the plenum chamber insert 3800 via the port 3811 might be focused on the immediate area of the HMX material 3806 while peripheral areas of the HMX material 3806 would receive less flow, which in turn may produce less than optimal performance in terms of heat and moisture exchange.

The anterior insert frame 3804 may also include a baffle 3803 extending from the rim 3812 into the port 3811 in the example shown in FIGS. 48-82, while the other version shown in the preceding drawings may not include the baffle 3803. The baffle 3803 may also help to diffuse and distribute the incoming flow of pressurized air 2000 from the port 3811 to be spread as evenly as possible across the anterior surface 3828 of the HMX material 3806. The baffle 3803 may include a baffle hole 3807 that allows the incoming flow of pressurized air 2000 to pass therethrough. Also, the baffle 3803 may be positioned within the port 3811 by baffle suspending tabs 3805 that form baffle bypass paths 3809 to allow the incoming flow of pressurized air 2000 to pass around the baffle and the rim 3812 to be spread across the HMX material 3806.

FIGS. 109-126 and FIGS. 127-130 show further examples of plenum chamber inserts 3800 according to the present technology. In these examples, the plenum chamber insert 3800 includes the posterior insert frame 3802, the anterior insert frame 3804, and the HMX material 3806 positioned between and held in place by the posterior insert frame 3802 and the anterior insert frame 3804. In the examples, the posterior insert frame 3802, the anterior insert frame 3804, and the HMX material 3806 have an approximately circular shape around their respective perimeters. The shape and dimensions of the components of the plenum chamber insert 3800 may be selected based on the shape and dimensions of the plenum chamber 3200 of the patient interface 3000 with which the plenum chamber insert 3800 is intended to be used. Thus, the plenum chamber insert 3800 may be designed to fit a specific patient interface(s) 3000, but not others. Also, the circular shape of the plenum chamber insert 3800 may allow the plenum chamber insert 3800 to be attached to a patient interface 3800 regardless of orientation.

The plenum chamber insert 3800 of these examples may also include a peripheral gap 3844 positioned between the outer periphery of the HMX material 3806 and the inner periphery of the posterior insert frame 3802 and the anterior insert frame 3804. The anterior insert frame 3804 may also include peripheral spacers 3846 that are spaced apart circumferentially around the interior periphery of the anterior insert frame 3804 to maintain the peripheral gap 3844 when the HMX material 3806 is installed. The peripheral gap 3844 may allow the incoming flow of pressurized gas to pass around the outer periphery of the HMX material 3806 so that it can spread across the anterior (i.e., facing away from the patient and towards to the direction of the incoming flow) surface of the HMX material 3806. Allow the flow of incoming pressurized air to spread more evenly across the anterior surface of the HMX material 3806 may improve heat and moisture exchange by ensuring that the incoming flow of pressurized air is not concentrated on any particular region of the HMX material 3806 and is more evenly dispersed across the HMX material 3806.

The posterior insert frame 3802 may also include a posterior HMX retainer 3848 that is shaped and dimensioned to be concave so as to hold the HMX material 3806 in a concave shape away from the patient's face in use. For example, FIGS. 125 and 126 show that the HMX material 3806 is shaped to have a concave side 3856 and a convex side 3858. The concave side 3856 may face the patient during use and this shape helps to avoid contact between the patient's facial features and the HMX material 3806, which may contaminate the HMX material 3806 and/or cause discomfort for the patient. The posterior insert frame 3802 may also include a projection 3852 that engages a corresponding indent 3854 in the anterior insert frame 3804 to indicate proper orientation of the anterior insert frame 3804 and the posterior insert frame 3802 relative to one another when assembling the plenum chamber insert 3800.

The anterior insert frame 3804 may also include an anterior HMX retainer 3850 to retain the HMX material 3806, prevent the HMX material 3806 from extending out through the plenum chamber insert port 3811, and prevent foreign objects from contacting the HMX material 3806 through the plenum chamber insert port 3811.

In the examples of FIGS. 127-130, the HMX material 3806 includes an HMX material hole 3860. The HMX material hole 3860 may allow more flow through the HMX material 3806 to reduce impedance while still maintaining adequate heat and moisture exchange during use. The HMX material 3806, whether formed from paper or foam, may include the HMX material hole 3860.

5.3.10.3 Venting and Carbon Dioxide Washout

While the plenum chamber insert 3800 and the HMX material 3806 may provide humidification during therapy, these structures may also impede flow through the plenum chamber 6175. Forming the HMX material 3806 from an open cell foam or corrugated paper, as described above, may minimize impedance to the incoming flow of pressurized air that is directed through the HMX material 3806. However, the plenum chamber insert 3800 may also impede the outgoing flow of exhaled air that includes a relatively high concentration of carbon dioxide. As explained, minimizing rebreathing of carbon dioxide is advantageous and improves therapy. Thus, the plenum chamber insert 3800 includes features described below to improve venting of exhaled air.

The anterior insert frame 3804 may include one or more radial channels 3810. The depicted examples show three radial channels 3810 in the versions of the plenum chamber insert 3800 shown in FIGS. 30-45 and 61-74, but one radial channel 3810 may be sufficient depending on its location, size, and the configuration of the patient interface. In these examples, the plenum chamber insert 3800 is designed for a patient interface that has a generally triangular shape and the each of the radial channels 3810 roughly corresponds to one of the corners of the triangle because these corner regions may include higher concentrations of carbon dioxide due to stagnating flow in these regions. The depicted examples show the plenum chamber insert 3800 used with a compact full-face patient interface, i.e., the patient interface does not cover the patient's eyes, but encloses both the nose and the mouth for delivering the flow of pressurized air to the patient's airways. Accordingly, the patient interface may have a generally triangular shape in that it is wide enough to span the patient's mouth at a lower portion, but not so wide at the upper portion that it will interfere with the patient's eyes. While this shape may adequately cover and seal around the entrances to the patient's airways, the corners of this triangular shape may create dead space, which are regions where circulation and mixing of exhaled air and the flow of pressurized air are suboptimal. Thus, exhaled gas, particularly carbon dioxide, may stagnate and collect in these areas, rather than being vented to atmosphere, which may leave an excessive quantity of carbon dioxide within the patient interface for rebreathing by the patient.

Thus, the radial channels 3810 may provide a pathway for the exhaled air that collects in these corner regions to more easily pass to the vents and escape from the patient interface to ambient.

The radial channels 3810 may be recessed from adjacent portions of the anterior insert frame wall 3822 at three locations that generally correspond to the three corner regions of the generally triangular patient interface. These radial channels 3810 may provide a flow path for exhaled air, such as carbon dioxide, to bypass the plenum chamber insert 3800 and the HMX material 3806 to reach the vent structure 3400, e.g., the vent holes 6700 in the elbow assembly 6600, for venting to atmosphere. Thus, when the plenum chamber insert 3800 is inserted into the plenum chamber 6175 and adjacent to the interior surface 6180 of the plenum chamber 6175, the interior surface 6180 of the plenum chamber 6175, the anterior insert frame wall 3822, and the radial channels 3810 that are recessed from the anterior insert frame wall 3822 may form bypass passages 2010 for a bypass flow 2003 of exhaled air to more easily reach the vent holes 6700. By targeting the corner regions of the patient interface with this configuration of radial channels 3810, flow impedance may be reduced, which allows the incoming flow of pressurized air to circulate with and force out the exhaled air to reduce the carbon dioxide available within the patient interface for rebreathing.

The plenum chamber insert 3800 and the radial channels 3810 may be sized to provide the exhaled air bypass functionality for similar patient interfaces of different sizes within a given configuration, e.g., compact full-face. Thus, this arrangement may be provided to any of the patient interface configurations described further below.

The anterior insert frame 3804 may also include an annular channel 3816 radially outward of the rim 3812. The annular channel 3816 may also be recessed from the anterior insert frame wall 3822 so that the retaining structure 6190 of the frame assembly 6100 can extend into the annular channel 3816 and allow the tabs 3814 to attach to the retaining structure 6190 on the frame assembly 6100.

Additionally, the anterior insert frame 3804 may include a plurality of radial channel vent holes 3820 and annular channel vent holes 3818. These vent holes may improve the flow of air into and out of the interior of the plenum chamber insert 3800. The radial channel vent holes 3820 and annular channel vent holes 3818 may allow a portion of the incoming flow of pressurized air 2000, the flow of which is impeded by the HMX material 3806, to change directions and pass to atmosphere without being humidified and warmed by the HMX material 3806. This arrangement may reduce the amount of heat and moisture lost to atmosphere by such flows by ensuring that the excess incoming flow of pressurized air 2000 can pass directly to the atmosphere more easily and without having an opportunity to cool and dry the HMX material 3806 without having benefitted the patient.

It has been described above that the radial channels 3810 may assist with evacuating carbon dioxide from dead space regions within the patient interface where flow circulation may be limited. This may be particularly advantageous when a plenum chamber insert 3800 is used for heat and moisture exchange because the plenum chamber insert 3800 may increase impedance to the outgoing flow of exhaled gas, as well as to the incoming flow of pressurized air. However, it should be understood that the radial channels 3810 may improve carbon dioxide washout regardless of the presence of the HMX material 3806 because the radial channels 3806 may provide a path for exhaled gases, such as carbon dioxide, that may accumulate in dead space regions that exist as a result of the shape and configuration of the patient interface, not necessarily as a result of the vent flow impedance caused by the HMX material 3806. Thus, it should be understood that a plenum chamber insert 3800 with radial channels 3810, but without the HMX material 3806, may be incorporated into a patient interface when the functions of the HMX material 3806 may not be desired.

5.3.10.4 RPT Device Compatibility and Patient Interface Configurations

The different arrangements of the plenum chamber insert 3800, i.e., with and without the baffle 3803, may provide better overall performance for different configurations of therapy system, e.g., different types of RPT device. Also, it should be understood that the plenum chamber insert 3800 features described herein may be used with a wide range of patient interface configurations, including those described in the following subsections. For example, the shape and the dimensions of the plenum chamber insert 3800, the presence or absence of the baffle 3803, the number, shape, and dimensions of radial channels 3810, and any other relevant aspects may vary depending upon the intended patient interface configuration, but the principles of operation will be similar such that the various plenum chamber insert 3800 versions disclosed herein can be used with various patient interface configurations.

5.3.10.4.1 Plenum Chamber Insert with and without Baffle

FIGS. 17-47 depict components associated with an example of the present technology that provides a relatively high level of performance (i.e., high humidification) and may also provide a level of impedance to the incoming flow of pressurized air that allows it to be used with wider range of available RPT devices, such as an RPT device that is capable of higher therapy pressures and flow rates (e.g., ResMed's AirSense 10). FIGS. 48-74 depict components associated with an example of the present technology that may provide a level of impedance to the incoming flow of pressurized air, which may be optimal for use with an RPT device that is more compact and travel-friendly, may be battery-powered, and may not be capable of as high of therapy pressures and flow rates, such as ResMed's AirMini. As will be explained in Section 5.3.10.5 "Therapy with Plenum Chamber Insert," the version in FIGS. 48-74 includes a baffle 3803, for example, while the version in FIGS. 17-47 does not.

Due to the wider range of elbow assembly 6600 and RPT device 4000 compatibility of the version of the plenum chamber insert 3800 shown in FIGS. 17-47, the plenum chamber insert 3800 is designed to allow greater air flow therethrough and minimize impedance to account for losses that may result from certain elbow assemblies 6600 that may allow for some amount of leakage of the incoming flow of pressurized air directly to the vent structure 3400 without interacting with the HMX material 3806.

Impedance and flow paths through the plenum chamber insert 3800 were optimized by removing the baffle 3803 from within the rim 3812 around the plenum chamber inlet port 3811. Also, the annular channel vent holes 3818 and the radial channel vent holes 3820 were repositioned, as can be seen by comparison of FIGS. 41 and 70, for example. Also, moving the annular channel vent holes 3818 radially outward (shown in FIG. 41 as compared with FIG. 70) may reduce impedance and improve venting through the annular channel vent holes 3818, 5.3.10.4.2 Tube-Down, Ultra-Compact Full-Face Patient Interface FIGS. 93-98 show a patient interface 3000 according to one example of the present technology having a positioning and stabilising structure 3300, a plenum chamber 3200, and a seal forming structure 3100. The patient interface 3000 may also comprise a frame 3350 and the positioning and stabilising structure 3300 may also include a plurality of headgear straps connected to the frame 3350. The example of the patient interface shown in FIGS. 93-98 may be understood to be a tube-down arrangement in that the air circuit 4170 is connected to the frame 3350 opposite the patient's face such that in use the air circuit 4170 can be directed in a downward or inferior direction relative to the patient so that the air circuit 4170 avoids overlaying the patient's face, which may be bothersome. Additionally, the sealing arrangement of the seal-forming structure 3100 may be understood to be an ultra-compact full-face or oro-nasal arrangement. Full-face may be understood to mean that the patient's nose and mouth are sealed from atmosphere by the seal-forming structure 3100. Ultra-compact may be understood to mean that the seal-forming structure 3100 does not engage the patient's face above the bridge of the nose or above the pronasale. In an ultra-compact full-face arrangement, at least a portion of the patient's pronasale may remain uncovered. As will be described below, the seal-forming structure 3100 may have an opening that corresponds to the patient's mouth. The seal-forming structure 3100 may have another opening that corresponds to the patient's nose, and that opening may be further divided into separate openings for each naris. Also, this example of patient interface 3000 may not include a forehead support.

In some examples of the present technology, the plenum chamber 3200 is at least partially formed by a shell 3210 and the seal-forming structure 3100. The plenum chamber 3200 may comprise a cushion module or cushion assembly, for example. The shell 3210 may function as a chassis for the seal-forming structure 3100.

As explained above, the patient interface 3000 may seal separately around the nasal airways and the oral airway. The patient interface 3000 may comprise a plenum chamber 3200 having a nasal portion 3230 and an oral portion 3260. The seal forming structure may be configured to surround the nasal airways at the nasal portion 3230 and to seal around the patient's mouth at the oral portion 3260.

As explained above, the seal-forming structure 3100 at the nasal portion 3230 may not lie over a nose bridge region or nose ridge region of the patient's face and instead may seal against inferior surfaces of the patient's nose. The nasal portion 3230 may seal against the lip superior, the ala, and the anterior surface of the pronasale and/or the inferior surface of the pronasale. The actual sealing locations may differ between patients due to differences in shapes and sizes of the patient's facial features. The nasal portion 3230 may also be configured to contact and/or seal to a region of the patient's face between the ala and the nasolabial sulcus and at the lateral portions of the lip superior proximate the nasolabial sulcus.

The seal-forming structure 3100 of the oral portion 3260 may be configured to seal around a periphery of the patient's mouth in use. The oral portion 3260 may be configured to seal around the patient's face at the lip superior, nasolabial sulcus, cheeks, lip inferior, supramenton, for example.

The plenum chamber 3200 comprises a seal-forming structure 3100 comprising an oral hole 3271 and two nasal holes 3272. Each of the nasal holes 3272 may be positioned on the seal-forming structure 3100 to be substantially aligned with a naris of the patient in order to deliver a flow of air thereto in use.

The plenum chamber 3200 of the patient interface 3000 may be connected to the frame 3350. The plenum chamber 3200 may connect to the frame 3350 via a snap fit connection. In other examples, the plenum chamber 3200 may form a different type of removable connection to the frame 3350, e.g., a removable press fit or may be permanently connected to the frame 3350.

The positioning and stabilising structure 3300 may comprise a plurality of straps or strap portions connecting to the frame 3350 and passing around the patient's head in order to support the plenum chamber 3200 in sealing position against the patient's face. A single strap may be formed by multiple lengths of material(s) that have been cut or formed separately and then joined together at their ends to create a longer length or single strap may be a single length of material(s).

In the example illustrated in FIGS. 93-85, the positioning and stabilising structure 3300 comprises a pair of upper straps 3310. Each upper strap 3310 is configured to pass between a respective eye and ear of the patient. Additionally, the positioning and stabilising structure 3300 comprises a pair of lower straps 3320 configured to lie over the patient's cheeks below the patient's cheekbones. In this example, the plenum chamber 3200 is held in position with headgear straps via a four-point connection to the frame 3350.

In one example, the frame 3350 may be configured to enable connection to a swivel elbow assembly 3610 which provides a connection port 3600 for connection with an air circuit 4170. The swivel elbow assembly 3610 may form a releaseable snap-fit with the frame 3350, creating a fluid connection between the swivel elbow assembly 3610 and the frame 3350. The frame 3350 therefore enables a fluid connection between the swivel elbow assembly 3610 and the interior of the plenum chamber 3200.

The frame 3350 also comprises a pair of upper strap connection points 3315 to which the upper straps 3310 connect. In this example, each upper strap connection point 3315 comprises an aperture formed in the frame 3350. Each upper strap 3310 is able to connect to a respective upper strap connection point 3315 by passing through the aperture, looping back onto itself and securing to itself. Each upper strap 3310 may secured to itself via hook and loop materials configured to releasably bind to each other upon contact. In alternative examples, each upper strap 3310 may pass through a respective aperture, loop back onto itself and be secured onto itself with a band, clip or the like. In further alternative examples, the upper straps 3310 may connect to the frame 3350 via side release buckle connections.

The frame 3350 also comprises a pair of lower strap connection points 3325 to which the lower straps 3320 connect. In this example, each lower strap connection point 3325 comprises a magnet. Each lower strap 3320 comprises a lower strap clip 3326 comprising a magnet or material that is attracted to the magnet at the lower strap connection point 3325. In this example, each lower strap clip 3326 comprises an aperture through which the end of a respective lower strap 3320 and is able to pass and then loop back and be secured onto itself, for example with hook and loop material, a band, a clip or the like. In alternative examples, the lower straps 3320 may connect to the frame 3350 via side release buckle connections, onto hooks or via any other suitable connection.

The positioning and stabilising structure 3300 may also comprise one or more of a top crown strap 3330, a pair of lateral crown straps 3332 and a neck strap 3334. In the example illustrated in FIGS. 93-95, the upper straps 3310 and lower straps 3320 are connected to ends of a top crown strap 3330. The top crown strap 3330 is configured to pass around the patient's head and lie against superiorly and posteriorly facing surfaces. The top crown strap 3330 may be configured to overlie the parietal bone of the patient's skull. Each end of the top crown strap 3330 connects to a respective one of the upper straps 3310 and also to a respective one of a pair of lateral crown straps 3332. Each one of the lateral crown straps 3332 connects between the upper strap 3310 and the lower strap 3320 on a respective side of the patient's head. The inferior ends of the lateral crown straps 3332 are connected to each other by a neck strap 3334. The neck strap 3334 may be configured to pass across the sagittal plane and lie against inferior and/or posterior facing surfaces of the patient's head or lie against the back of the patient's neck. The neck strap 3334 may overlie, or lie inferior to, the occipital bone of the patient's skull.

In the example illustrated in FIGS. 93-95, the patient interface 3000 comprises a vent 3400. The vent 3400 in this example comprises passages within the frame 3350 and swivel elbow assembly 3610 through which air can flow from the interior of the plenum chamber 3200 to atmosphere. Air can flow into the swivel elbow assembly 3610 and then out to atmosphere through exterior holes of the swivel elbow assembly 3610 forming part of the vent 3400.

5.3.10.4.3 Tube-Up, Ultra-Compact Full-Face Patient Interface

FIG. 99 shows a patient interface 3000 comprising the plenum chamber 3200 shown in FIGS. 100 and 101. The patient interface 3000 in this example also comprises a positioning and stabilising structure 3300 to hold the seal-forming structure 3100 in sealing position on the patient's face in use. The positioning and stabilising structure 3300 in this example comprises a pair of headgear tubes 3340. This arrangement of the patient interface 3000 may also be understood to be an ultra-compact full-face arrangement, similar to the arrangement of FIGS. 93-98 with regard to how it contacts and seals against the patient's face in use. This arrangement may also be understood to be a tube-up system in that the headgear tubes 4170 are in pneumatic communication with the air circuit 4170 above or superior to the patient's head so that the air circuit 4170 avoids overlaying the patient's face during use, which may be bothersome.

The pair of headgear tubes 3340 are connected to each other at their superior ends and are each configured to lie against superior and lateral surfaces of the patient's head in use. Each of the headgear tubes 3340 may be configured to lie between a corresponding eye and ear of the patient in use. The inferior end of each headgear tube 3340 is configured to fluidly connect to the plenum chamber 3200. In this example, the inferior end of each headgear tube 3340 connects to a headgear tube connector 3344 configured to connect to the shell 3210 of the plenum chamber 3200. The positioning and stabilising structure 3300 comprises a conduit headgear inlet 3390 at the junction of the two headgear tubes 3340. The conduit headgear inlet 3390 is configured to receive a pressurised flow of gas, for example via an elbow comprising a connection port 3600, and allow the flow of gas into the headgear tubes 3340. The headgear tubes 3340 supply the pressurised flow of gas to the plenum chamber 3200.

The positioning and stabilising structure 3300 may comprise one or more straps in addition to the headgear tubes 3340. In this example the positioning and stabilising structure 3300 comprises a pair of upper straps 3310 and a pair of lower straps 3320. The posterior ends of the upper straps 3310 and lower straps 3320 are joined together. The junction between the upper straps 3310 and lower strap 3320 is configured to lie against a posterior surface of the patient's head in use, providing an anchor for the upper strap 3310 and lower straps 3320. Anterior ends of the upper straps 3310 connect to the headgear tubes 3340. In this example each headgear tube 3340 comprises a tab 3342 having an opening through which a respective upper strap 3310 can be passed through and then looped back and secured onto itself to secure the upper headgear strap 3310 to the headgear tube 3340. The positioning and stabilising structure 3300 also comprises a lower strap clip 3326 provided to the anterior end of each of the lower straps 3320. Each of the lower strap clip 3326 is configured to connect to a lower connection point 3325 on the plenum chamber 3200. In this example, the lower strap clips 3326 are secured magnetically to the lower connection points 3325. In some examples, there is also a mechanical engagement between the lower strap clips 3326 and the lower connection points 3325.

The headgear tube connectors 3344 may be configured to allow the patient to breathe ambient air in the absence of pressure within the plenum chamber 3200. Each headgear tube connector 3344 may comprise an anti-asphyxia valve (AAV). The AAV in each headgear tube connector 3344 may be configured to open in the absence of pressure within the plenum chamber 3200 in order to allow a flow of air between the interior of the plenum chamber 3200 and ambient. Each AAV may be biased into a configuration which blocks the flow of air from the interior of the plenum chamber 3200 into a respective headgear tube 3340 but allows for the exchange of air between the plenum chamber 3200 and ambient. When the headgear tubes 3340 are pressurised, the AAV in each headgear tube connector 3344 may prevent the exchange of air between the interior of the plenum chamber 3200 and ambient but allow for a flow of air from the respective headgear tube 3340 into the plenum chamber 3204 breathing by the patient.

The plenum chamber 3200 shown in FIGS. 99-101 comprise a vent 3400. In this example, the vent 3400 comprises a plurality of holes. In these examples, the vent 3400 is provided to the shell 3210. In other examples of the present technology the patient interface 3000 may comprises a vent module, either permanently or detachably connected to the plenum chamber 3200. In some examples of the present technology the patient interface 3000 comprises a diffuser configured to diffuse air flowing though the vent 3400. The vent 3400 may be positioned centrally on the shell 3210 to avoid being covered by the patient's bed or bed clothes during side sleeping. Additionally, the vent 3400 in these examples may be positioned relatively inferiorly on the shell 3210 such that the vent 3400 is aligned approximately with the patient's mouth to ensure that effective gas washout of exhaled carbon dioxide from the patient's mouth. Furthermore, since the inlet ports 3240 of the plenum chamber 3200 are provided at a relatively superior location on the plenum chamber 3200, a bias flow of air received at the inlet ports 3240 may flow through a relatively large volume (e.g., from a superior location to an inferior location), which may provide for efficient gas washout and may reduce the likelihood of stagnant air pockets bypassed by the bias flow.

5.3.10.4.4 Tube-Up, Nasal Cradle Patient Interface

FIGS. 102-106 depict an example of a tube-up, nasal cradle patient interface. Similar to the example shown in FIGS. 99-101, the tube-up aspect may be understood to describe conduits of the positioning and stabilising structure 3300 that pass along corresponding lateral sides of the patient's head between the corresponding eye and ear to be connected to the air circuit. The nasal cradle aspect may be understood to describe the sealing and face contacting arrangement in which the seal-forming structure 3100 is shaped and dimensioned to contact and seal against the patient's face around the inferior periphery of the patient's nose. The seal-forming structure 3100 may contact the patient's face at the lip superior or above the upper vermilion, along the alae, at or below the pronasale, and at or proximate to the patient's nasolabial sulcus. In a nasal cradle sealing arrangement, the seal-forming structure 3100 does not extend beyond the pronasale or does not extend to the nasal bridge. In a nasal cradle arrangement, at least a portion of the patient's pronasale may remain uncovered.

In the example depicted in FIGS. 102-106, the seal-forming structure 3100 includes naris openings 3102 that may be formed through the medial region. The naris openings 3102 are positioned to generally align with patient's corresponding naris to provide the flow of pressurised gas to the patient's nares for inhalation and for exhaled gas to be passed back into the seal-forming structure 3100 for discharge to atmosphere via the plenum chamber vent 3400, as described further below. There may also be a bridge portion 3104 positioned between the naris openings 3102. The bridge portion 3104 may be long enough to be slack in an undeformed state such that when the patient's nose contacts the medial region, the bridge portion 3104 can accommodate deformation of the seal-forming structure 3100 without stretching. Additionally, the bridge portion 3104 may prevent user set up error by preventing the patient's nose from being inserted into what would otherwise be a single hole.

At each lateral side of the plenum chamber 3200 there may be a plenum chamber lateral end 3202 in the form of a hollow passageway. A plenum chamber connector 3204 may also be provided at each lateral side of the plenum chamber 3200 laterally outward of the plenum chamber lateral end 3202. The plenum chamber connectors 3204 may connect to respective ends 3314 of the positioning and stabilising structure 3300. The connection between the plenum chamber connectors 3204 and respective ends 3314 of the positioning and stabilising structure 3300 may be releasable at both sides. In other examples, one side may have a permanent connection while the other side has a releasable connection. In still further examples, both connections between the plenum chamber connectors 3204 and respective ends 3314 of the positioning and stabilising structure 3300 may be permanent.

The positioning and stabilising structure 3300 in this example includes lateral portions 3302 and superior portions 3304 in the form of conduits that direct a flow pressurised gas from a hub 3306 to ends 3314. The positioning and stabilising structure 3300 may be arranged such that the hub 3306 and the decoupling structure 3500 are positioned superior to the patient's head in use. As described below, the decoupling structure 3500 may be rotatable within the hub 3306 and when the patient is wearing the patient interface 3000, e.g., during therapy, the location of the hub 3306 and the decoupling structure 3500 superior to the patient's head allows the patient to move more freely without becoming entangled with the air circuit 4170.

The positioning and stabilising structure 3300 may be constructed of silicone. For example, the lateral portions 3302, the superior portions 3304, the hub 3306, and the lateral ends 3314 may able constructed or molded from a single piece of silicone.

The superior portions 3304 of the positioning and stabilising structure 3300 have ridges and valleys (or concertina sections) that allow the superior portions 3304 to conform to the shape of the corresponding portion of the patient's head in use. The ridges and valleys of the superior portions 3304 allow the superior portions 3304 to be extended and contracted along the longitudinal axis to accommodate larger or smaller heads. The ridges and valleys of the superior portions 3304 allow the superior portions 3304 to be flexed to different radii of curvature to accommodate patient heads of different shapes and sizes.

The lateral portions 3302 portions of the positioning and stabilising structure 3300 may not be formed with the ridges and valleys of the superior portions 3304. Therefore, the lateral portions 3302 may be less extensible and flexible than the superior portions 3304, which may be advantageous because there is less variability in the shape and size of the lateral sides of a patient's head.

The ends 3314 may connect to respective plenum chamber lateral ends 3202. As described above, the plenum chamber lateral ends 3202 receive the flow of pressurised gas from the positioning and stabilising structure 3300, which passes through the plenum chamber 3200, through the seal-forming structure 3100, and on to the patient's airways.

The lateral portions 3302 may also each include a tab 3308 that receives a posterior strap end portion 3311 of a posterior strap 3310. The posterior strap 3310 may be length-adjustable, e.g., with a hook and loop material arrangement whereby one of the posterior strap end portion 3311 and the remainder of the posterior strap 3310 includes hook material on its exterior while the other includes loop material on its exterior. The length adjustability of the posterior strap 3310 allows tension on the lateral portions 3302 to be increased to pull the seal-forming structure 3100 into sealing engagement with the patient's face at a desired amount of pressure (i.e., sufficiently tight to avoid leaks while not so tight as to cause discomfort).

The lateral portions 3302 may also be provided with sleeves 3312 that cushion the patient's face against the lateral portions 3302. The sleeves 3312 may be constructed of a breathable textile material that has a soft feel.

The size of each vent hole and the number of vent holes may be optimised to achieve a balance between noise reduction while achieving the necessary carbon dioxide washout, even at extreme humidification. In the depicted examples, the vent holes of the plenum chamber vent 3400 may not provide the total amount of venting for the system. The decoupling structure 3500 may include a decoupling structure vent 3402. The decoupling structure vent 3402 may include one hole or a plurality of holes through the decoupling structure 3500. The decoupling structure vent 3402 may function to bleed off excess pressure generated by the RPT device 4000 before reaching the patient, while the plenum chamber vent 3400 may function to washout carbon dioxide exhaled by the patient during therapy.

The decoupling structure 3500 may also include a swivel 3502 that allows for rotatable connection to an air circuit 4170.

The rotatability of the decoupling structure 3500, the decoupling structure 3500 being in the form of an elbow, and the rotatability of the swivel 3502 on the decoupling structure 3500 may all increased the degrees of freedom, which in turn reduces tube drag and torque on the patient interface 3000 caused by the connection to the air circuit 4170.

The hub 3306, described above, is connected to a decoupling structure 3500, which is a rotatable elbow in these examples. The decoupling structure 3500 may be rotatable 360° within the hub 3306 in use. The decoupling structure 3500 may be removable from the hub 3306 by manually depressing buttons 3504 to release catches (not shown) from within the hub 3306.

5.3.10.4.5 Nasal Patient Interface

FIGS. 107 and 108 show a patient interface 7000 in accordance with another aspect of the present technology. In this example, the patient interface is a nasal interface type including a seal-forming structure 7200 structured to form a seal around the patient's nose. The seal-forming structure 7200 may seal at or above the patient's pronasale. The patient interface 7000 leaves the patient's mouth uncovered. The patient interface 7000 comprises a frame assembly 7100, a cushion assembly 7175 including the seal-forming structure 7200, an elbow assembly 7600, and a positioning and stabilising structure (e.g., headgear 7800). The cushion assembly 7175 may connect to the frame assembly 7100 independently of the elbow assembly 7600, and the elbow assembly 7600 may connect to the frame assembly 7100 independently of the cushion assembly 7175. The elbow assembly 7600 may includes a vent assembly 7700 to allow for the washout of exhaled air to atmosphere.

In this example, the frame assembly 7100 may include a shroud 7110 and a headgear connector 7130 provided to the shroud 7110 to provide a 4-point connection to the headgear 7800. The cushion assembly 7175 may include a shell 7180 that is permanently (e.g., co-molded, overmolded) connected to the seal-forming structure or cushion 7200. In an example, the cushion 7200 is constructed of a relatively flexible or pliable material (e.g., silicone) and the shell 7180 is constructed of a relatively rigid material (e.g., polycarbonate). The shell 7180 and the cushion 7200 cooperate to form the plenum chamber 7500.

In this example, the headgear connector 7130 includes a shroud connection portion 7132 connected to the shroud 7110, a pair (i.e., right and left) of upper headgear connector arms 7134 structured to connect to respective upper headgear straps 7802 of the headgear 7800, a pair (i.e., right and left) of lower headgear connector arms 7154 structured to connect to respective lower headgear straps 7804 of the headgear 7800, and intermediate portions 7133 to interconnect the upper and lower arms 7134, 7154 with the shroud connection portion 7132.

In this example, each upper headgear connector arm 7134 includes an upper headgear connection point in the form of a slot 7135 structured to receive a respective upper headgear strap 7802 of the headgear 7800. In this example, each lower headgear connector arm 7154 includes a lower headgear connection point in the form of a magnetic connector 7155 structured to locate and connect to a magnet associated with a headgear clip 7160 provided to a respective lower headgear strap 7804 of the headgear 7800.

5.3.10.5 Therapy with Plenum Chamber Insert

FIGS. 75-92 show operational phases of an exemplary RPT system that includes a plenum chamber insert 3800. The plenum chamber insert 3800 and patient interface 6000 of FIGS. 48-74, i.e., the baffled version, is used to demonstrate operation of the system with the plenum chamber insert 3800 in FIGS. 75-83. Operation of the plenum chamber insert 3800 and patient interface 6000 of FIGS. 17-47, i.e., without the baffle, will be substantially similar, with the exception of the flow distributing effect of the baffle 3803 that is omitted from this version, which is shown in FIGS. 84-92. Also, it should be understood that while the various stages of breathing are shown in which the patient inhales, exhales, and pauses breathing, the flow of pressurized air 2000 will continue uninterrupted, as will the vent flow, throughout the patient's breathing cycle. Furthermore, the flow of pressurized air 2000 and the vent flow may be understood to pass through the plenum chamber insert 3800 in opposite directions simultaneously throughout the patient's breathing cycle.

FIGS. 75-77 and 84-86 show the flow of pressurized air 2000 during inhalation. The patient is seen breathing, with the nose 1001 and mouth 1003, in air from the RPT device after it has passed through the plenum chamber insert 3800 to be heated and humidified. FIG. 76 also shows how the baffle 3803 spreads the flow of air upon entry into the void 3825 after passing through the port 3811, which distributes the air across the anterior surface 3828 of the HMX material 3806 so that the air collects as much humidity and heat as possible from the HMX material 3806 for transfer to the patient upon inhalation. Also, a portion of the flow 2002 within the patient interface may be vented to atmosphere— although this is the inhalation phase, at least some venting may be desired at all times to ensure that adequate carbon dioxide washout occurs throughout the respiratory cycle. The flow of air bypassing the HMX material 3806 can be seen at 2003 through the bypass passage 2010 formed by the radial channel 3810 and the interior surface 6180 of the plenum chamber 6175. Vent flow through the elbow assembly 6600 can be seen at 2001, which then passes to ambient at 2002, and it should be understood that this flow may include the bypass flow 2003 and return flows of air 2004 that did not pass through the HMX material 3806 but were discharged through the radial channel vent holes 3820 and annular channel vent holes 3818 as well as flows from the patient-side of the HMX material 3806 that did pass through the HMX material 3806, e.g., after exhalation.

FIGS. 78, 79, 87, and 88 show the flow of pressurized air 2000 passing through the plenum chamber insert 3800 during breath pause, i.e., the cessation of expansion or contraction of the lungs that occurs between inhalation and exhalation phases. Since the patient is not inhaling the air that passes through the HMX material 3806, the pressure of the flow within the plenum chamber 6175 causes that flow to recirculate past the plenum chamber insert 3800 in the opposite direction. Some of the flow may return through the HMX material 3806, while some of the flow may return 2004 via the radials channels 3810 and bypass the HMX material 3806 at 2003. Additionally, some of the flow may not pass through the HMX material 3806. Instead, that portion of the flow may be recirculated back out of the plenum chamber insert 3800 via the annular channel vent holes 3818 and the radial channel vent holes 3820.

FIGS. 80-83 and 89-92 show flow of air during the exhalation phase of the patient. The patient is breathing out through their nose 1002 and mouth 1004 and air is vented through the elbow 2001 to atmosphere 2002, although the flow of pressurized air 2000 into the patient interface may continue, if the patient is receiving CPAP therapy. As can be seen, a portion of the exhaled air will travel out of the patient interface by traveling through the HMX material 3806, which receives heat and moisture for the next inhalation phase. Depending on conditions in the plenum chamber insert 3800 (e.g., humidity and temperature), the moisture may be absorbed and/or adsorbed by the HMX material 3806, and the moisture may also condense on the HMX material 3806. Also, a portion of the exhaled air may bypass 2003 the HMX material 3806 by traveling along the radial channels 3810 to ensure that carbon dioxide is evacuated from dead space regions within the patient interface where flow circulation may be limited.

5.4 RPT Device

An RPT device 4000 in accordance with one aspect of the present technology comprises mechanical, pneumatic, and/ or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cm $H_2O$, or at least 10 cm $H_2O$, or at least 20 cm $H_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cm $H_2O$ to about 20 cm $H_2O$, or in other forms up to about 30 cm $H_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module that forms part of the algorithms executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components

5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor 4272 provided in the RPT device 4000.

5.6.2.5.2 Flow Rate Transducer

One or more flow rate transducers 5214 may be provided to the humidifier 5000 in addition to, or instead of, a flow rate sensor 4274 provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.6.2.7 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including cm $H_2O$, g-f/cm$^2$ and hectopascal. 1 cm $H_2O$ is equal to 1 g-f/cm$^2$ and is approximately 0.98 hectopascal. In this specification, unless otherwise stated, pressure is given in units of cm $H_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240. (Year? Required?)

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cm $H_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\emptyset(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.8.4 Anatomy 5.8.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion

5.8.4.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.10 REFERENCE SIGNS LIST | |
|---|---|
| patient | 1000 |
| nasal inhalation | 1001 |
| nasal exhalation | 1002 |
| oral inhalation | 1003 |
| oral exhalation | 1004 |
| bed partner | 1100 |
| flow of air at therapeutic pressure | 2000 |
| vent flow through elbow | 2001 |
| vent flow of air to ambient | 2002 |
| bypass flow | 2003 |
| return flow | 2004 |
| bypass passage | 2010 |
| patient interface | 3000 |
| seal - forming structure | 3100 |
| plenum chamber | 3200 |
| chord | 3210 |
| superior point | 3220 |
| inferior point | 3230 |
| positioning and stabilising structure | 3300 |
| vent | 3400 |
| connection port | 3600 |
| forehead support | 3700 |
| plenum chamber insert | 3800 |
| posterior insert frame | 3802 |
| baffle | 3803 |
| anterior insert frame | 3804 |
| baffle suspending tabs | 3805 |
| heat and moisture exchanger (HMX) material | 3806 |
| baffle hole | 3807 |
| catch | 3808 |
| baffle bypass path | 3809 |
| radial channel | 3810 |
| plenum chamber insert port | 3811 |

| 5.10 REFERENCE SIGNS LIST -continued | |
|---|---|
| rim | 3812 |
| tab | 3814 |
| annular channel | 3816 |
| annular channel vent hole | 3818 |
| radial channel vent hole | 3820 |
| anterior insert frame wall | 3822 |
| anterior insert frame inner surface | 3823 |
| anterior insert frame spacer | 3824 |
| void | 3825 |
| notch | 3826 |
| HMX material anterior surface | 3828 |
| HMX material posterior surface | 3830 |
| posterior insert frame detent | 3832 |
| posterior insert frame protrusion | 3834 |
| orientation indicator | 3836 |
| tab | 3837 |
| posterior insert frame peripheral edge | 3838 |
| anterior insert frame peripheral shoulder | 3840 |
| posterior insert frame opening | 3842 |
| peripheral gap | 3844 |
| peripheral spacer | 3846 |
| posterior HMX retainer | 3848 |
| anterior HMX retainer | 3850 |
| projection | 3852 |
| indent | 3854 |
| concave side | 3856 |
| convex side | 3858 |
| HMX material hole | 3860 |
| base layer | 3870 |
| corrugated layer | 3872 |
| joint | 3874 |
| flute | 3876 |
| RPT device | 4000 |
| external housing | 4010 |
| upper portion | 4012 |
| portion | 4014 |
| panel | 4015 |
| RPT device chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| heated air circuit | 4171 |
| supplemental oxygen | 4180 |
| electrical components | 4200 |
| Printed Circuit Board Assembly (PCBA) | 4202 |
| power supply | 4210 |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| humidifier | 5000 |
| humidifier inlet | 5002 |
| humidifier outlet | 5004 |

5.10 REFERENCE SIGNS LIST

| | |
|---|---|
| humidifier base | 5006 |
| reservoir | 5110 |
| conductive portion | 5120 |
| humidifier reservoir dock | 5130 |
| locking lever | 5135 |
| water level indicator | 5150 |
| humidifier transducer | 5210 |
| air pressure sensor | 5212 |
| air flow rate transducer | 5214 |
| temperature sensor | 5216 |
| humidity sensor | 5218 |
| heating element | 5240 |
| humidifier controller | 5250 |
| central humidifier controller | 5251 |
| heating element controller | 5252 |
| air circuit controller | 5254 |
| patient interface | 6000 |
| frame assembly | 6100 |
| opening | 6105 |
| lip | 6106 |
| shroud | 6110 |
| upper headgear connector arm | 6134 |
| slot | 6135 |
| central flexible portion | 6140 |
| single slot | 6141 |
| peripheral flexible portion | 6145 |
| slots | 6146 |
| lower headgear connector arm | 6154 |
| magnetic connector | 6155 |
| magnet receiving portion | 6155A |
| magnet | 6155B |
| cap | 6155C |
| headgear clip | 6160 |
| plenum chamber | 6175 |
| port | 6176 |
| interior surface | 6180 |
| retaining structure | 6190 |
| retaining structure hole | 6192 |
| seal - forming structure | 6200 |
| elbow assembly | 6600 |
| anti-asphyxia valve | 6605 |
| first end portion | 6610 |
| outer wall | 6612 |
| inner wall | 6614 |
| deflecting structure | 6615 |
| elbow vent flow path | 6616 |
| second end portion | 6620 |
| swivel connector | 6625 |
| pinch arms | 6650 |
| vent holes | 6700 |
| arm covers | 6750 |
| headgear | 6800 |
| upper side straps | 6802 |
| side straps | 6804 |
| crown strap | 6806 |

The invention claimed is:

1. A patient interface comprising:
a plenum chamber pressurisable to a therapeutic pressure of at least 4 cm $H_2O$ greater than ambient air pressure, said plenum chamber including a plenum chamber port sized and structured to receive a flow of air at the therapeutic pressure for breathing by a patient;
a seal-forming structure constructed and arranged to contact and seal against a region of the patient's face surrounding an entrance to the patient's airways, said seal-forming structure having a hole therein such that the flow of air at said therapeutic pressure is delivered to at least the patient's nares, the seal-forming structure constructed and arranged to maintain said therapeutic pressure in the plenum chamber throughout the patient's respiratory cycle in use;
a positioning and stabilising structure configured to hold the seal-forming structure in a therapeutically effective position on the patient's head, the positioning and stabilising structure comprising a tie, the tie being constructed and arranged so that at least a portion of the tie overlies a region of the patient's head superior to the patient's corresponding otobasion superior in use;
a plenum chamber insert configured to be positioned and retained within the plenum chamber and between the entrance to the patient's airways and the plenum chamber port, the plenum chamber insert further comprising an insert frame; and
a vent structure comprising a plurality of holes configured to allow a continuous flow of gases exhaled by the patient from an interior of the plenum chamber to ambient, said vent structure being sized and shaped to maintain the therapeutic pressure in the plenum chamber in use;
wherein the plenum chamber insert has a plenum chamber insert port positioned in pneumatic communication with the plenum chamber port such that the flow of air at the therapeutic pressure passes through the plenum chamber insert port after passing through the plenum chamber port;
wherein the plenum chamber insert has an exterior surface configured to be positioned adjacent to an interior surface of the plenum chamber when the plenum chamber insert is positioned and retained within the plenum chamber;
wherein when the plenum chamber insert is positioned and retained within the plenum chamber, a radial channel is formed between the interior surface of the plenum chamber and the exterior surface of the plenum chamber insert, the radial channel extending along the exterior surface of the insert frame from a radially outward edge of the insert frame to the plenum chamber port such that gas is able to pass between a patient-proximal side of the plenum chamber insert and a patient-distal side of the plenum chamber insert via the radial channel during use; and
wherein the patient interface is configured to allow the patient to breathe from ambient through their mouth in the absence of a flow of pressurised air through the plenum chamber port, or the patient interface is configured to leave the patient's mouth uncovered.

2. The patient interface of claim 1, wherein the seal-forming structure is constructed and arranged to be positioned against the patient's face and surround the patient's nares and mouth in use such that the flow of air at said therapeutic pressure is delivered to the patient's nares and mouth through the hole, and
wherein the patient interface is configured to allow the patient to breathe from ambient through their mouth in the absence of a flow of pressurised air through the plenum chamber inlet port.

3. The patient interface of claim 1, wherein the seal-forming structure and the plenum chamber have a generally triangular profile to cover the patient's nose and mouth while not covering the patient's eyes in use.

4. The patient interface of claim 3, wherein the plenum chamber insert further comprises three radial channels positioned circumferentially around the plenum chamber insert port and oriented to direct air inside of the seal-forming structure and the plenum chamber from a corresponding corner region of the generally triangular profile of the seal-forming structure and the plenum chamber from the patient-proximal side of the plenum chamber insert to the patient-distal side of the plenum chamber insert.

5. The patient interface of claim 1, wherein the plenum chamber insert further comprises a plurality of radial channels positioned circumferentially around the plenum chamber insert port and oriented to direct air inside of the seal-forming structure and the plenum chamber from the patient-proximal side of the plenum chamber insert to the patient-distal side of the plenum chamber insert.

6. The patient interface of claim 1, wherein the plenum chamber insert is permanently connected to the plenum chamber.

7. The patient interface of claim 1, wherein the plenum chamber insert is removably connected to the plenum chamber.

8. The patient interface of claim 1, wherein the plenum chamber insert further comprises a heat and moisture exchanger (HMX) material, the HMX material configured to receive and retain water from gas exhaled by the patient and to desorb the retained water into the flow of air at the therapeutic pressure passing through the HMX material, while the flow of air at the therapeutic pressure is provided to the plenum chamber port.

9. The patient interface of claim 8, wherein the HMX material comprises foam.

10. The patient interface of claim 8, wherein the HMX material comprises open-cell foam having a salt applied thereto.

11. The patient interface of claim 8, wherein the HMX material comprises paper.

12. The patient interface of claim 8, wherein the HMX material comprises a corrugated structure constructed from paper, the corrugated structure forming flow channels through the HMX material.

13. The patient interface of claim 12, wherein the flow channels are oriented to allow air to flow therethrough in a generally anterior-posterior direction during use.

14. The patient interface of claim 8, wherein the HMX material has a substantially consistent thickness.

15. The patient interface of claim 8, wherein the HMX material has a thickness that varies in at least one direction.

16. The patient interface of claim 8, wherein the insert frame is configured to secure the HMX material in an operable position within the plenum chamber.

17. The patient interface of claim 16, wherein the HMX material is shaped to substantially correspond to a shape of the insert frame.

18. The patient interface of claim 16, wherein the HMX material is configured to be deformed to substantially correspond to a shape of the interior of the insert frame.

19. The patient interface of claim 16, wherein the insert frame is permanently connected to the plenum chamber.

20. The patient interface of claim 16, wherein the insert frame is removably connected to the plenum chamber.

21. The patient interface of claim 16, wherein the insert frame further comprises an anterior insert frame and a posterior insert frame configured to be attached to one another, and
wherein the HMX material is secured between the anterior insert frame and the posterior insert frame when the anterior insert frame and the posterior insert frame are attached together.

22. The patient interface of claim 21, wherein the plenum chamber insert port is formed through the anterior insert frame.

23. The patient interface of claim 21, wherein the anterior insert frame further comprises an anterior insert frame wall, and
wherein the radial channel is recessed into the anterior insert frame wall.

24. The patient interface of claim 23, wherein the anterior insert frame further comprises at least one anterior insert frame spacer extending from the anterior insert frame wall, the anterior insert frame spacer configured to contact and space the HMX material away from the anterior insert frame wall such that a gap is formed between the anterior insert frame wall and the HMX material.

25. The patient interface of claim 23, wherein the anterior insert frame further comprises a rim surrounding the plenum chamber insert port and extending in anterior direction therefrom.

26. The patient interface of claim 25, further comprising a frame assembly configured to attach to the plenum chamber and join the positioning and stabilising structure to the plenum chamber; and
wherein the rim further comprises one or more tabs to releasably connect the plenum chamber insert to the frame assembly through the plenum chamber port.

27. The patient interface of claim 25, wherein the anterior insert frame further comprises an annular channel surrounding the rim and recessed into the anterior insert frame wall.

28. The patient interface of claim 27, further comprising a frame assembly configured to attach to the plenum chamber and join the positioning and stabilising structure to the plenum chamber; and
wherein the anterior insert frame further comprises one or more tabs extending from the annular channel to releasably connect the plenum chamber insert to the frame assembly through the plenum chamber port.

29. The patient interface of claim 27, further comprising one or more annular channel vent holes formed through the anterior insert frame at the annular channel.

30. The patient interface of claim 21, wherein the posterior insert frame further comprises a plurality of posterior insert frame openings such that at least a portion of the HMX material is exposed in a posterior direction that faces the patient during use.

31. The patient interface of claim 21, wherein the posterior insert frame further comprises an orientation indicator configured to visually and/or tactilely indicate the orientation of the plenum chamber insert, when the plenum chamber insert is assembled and when the plenum chamber insert is positioned and retained within the plenum chamber.

32. The patient interface of claim 21, further comprising at least one posterior insert frame protrusion extending from the posterior insert frame, the posterior insert frame protrusion configured to contact and hold the HMX material in position between the anterior insert frame and the posterior insert frame.

33. The patient interface of claim 21, wherein the anterior insert frame further comprises a catch or a detent and the posterior insert frame further comprises the other of the catch or the detent, the catch and the detent configured to retain the anterior insert frame and the posterior insert frame together.

34. The patient interface of claim 21, wherein the anterior insert frame further comprises a plurality of catches or a plurality of detents and the posterior insert frame further comprises an equal number of corresponding catches or detents.

35. The patient interface of claim 21, further comprising one or more radial channel vent holes formed through the anterior insert frame at the radial channel.

36. The patient interface of claim 1, further comprising an elbow assembly having a first end configured to be releasably attached to the plenum chamber and a second end configured to be releasably attached to an air circuit to provide the flow of air at the therapeutic pressure to the plenum chamber, the elbow assembly including the vent structure such that the vent structure is positioned opposite the patient's airways relative to the plenum chamber insert.

37. The patient interface claim 1, wherein the plenum chamber insert is concave on the patient-proximal side to avoid contact with the patient's face during use.

38. A patient interface system comprising:
the patient interface of claim 1;
a respiratory pressure therapy device configured to pressurize the flow of air at the therapeutic pressure; and
an air circuit configured to direct the flow of air from the respiratory pressure therapy device to the patient interface.

39. The patient interface system of claim 38, wherein a humidifier is not included.

40. The patient interface system of claim 38, wherein the air circuit includes a tube that does not include a heating element having a heated wire circuit.

* * * * *